United States Patent
Babu et al.

(10) Patent No.: US 6,936,719 B2
(45) Date of Patent: *Aug. 30, 2005

(54) BIARYL COMPOUNDS AS SERINE PROTEASE INHIBITORS

(75) Inventors: Yarlagadda S. Babu, Birmingham, AL (US); R. Scott Rowland, Hoover, AL (US); Pooran Chand, Birmingham, AL (US); Pravin L. Kotian, Birmingham, AL (US); Yahya El-Kattan, Birmingham, AL (US); Shri Niwas, Birmingham, AL (US)

(73) Assignee: BioCryst Pharmaceuticals, Inc., Birmingham, AL (US)

(*) Notice: Subject to any disclaimer, the term of this patent is extended or adjusted under 35 U.S.C. 154(b) by 26 days.

This patent is subject to a terminal disclaimer.

(21) Appl. No.: 10/738,027

(22) Filed: Dec. 18, 2003

(65) Prior Publication Data

US 2004/0162281 A1 Aug. 19, 2004

Related U.S. Application Data

(60) Division of application No. 10/127,460, filed on Apr. 23, 2002, now Pat. No. 6,699,994, which is a continuation-in-part of application No. PCT/US01/32582, filed on Oct. 22, 2001.
(60) Provisional application No. 60/281,735, filed on Apr. 6, 2001.

(51) Int. Cl.⁷ .................. C07D 213/81; A61K 31/44
(52) U.S. Cl. .................. 546/323; 546/306; 546/335; 546/337; 548/152; 548/204; 548/561; 548/567; 544/106; 544/335; 549/76; 549/273; 549/280; 549/496; 560/11; 560/12; 560/14; 560/35; 560/38; 560/39; 562/469; 564/246; 514/64; 514/538; 514/438; 514/517; 514/365; 514/472; 514/427; 514/428; 514/353; 514/563; 514/255; 514/455; 514/256; 514/235.2; 514/367; 514/403; 514/357; 514/354; 514/485; 514/637

(58) Field of Search .................. 546/306, 335, 546/337, 323; 544/106, 335; 548/152, 204, 561, 567; 549/76, 273, 280, 496; 560/11, 12, 14, 39, 38, 35; 562/469; 564/246; 514/64, 538, 438, 517, 472, 365, 427, 428, 353, 563, 255, 455, 256, 235.2, 367, 403, 357, 485, 637, 354

(56) References Cited

U.S. PATENT DOCUMENTS 6,699,994 B1 * 3/2004 Babu et al. .................. 546/306

FOREIGN PATENT DOCUMENTS

| EP | 911660 | 4/1999 |
|---|---|---|
| EP | 922973 | 6/1999 |
| EP | 1087246 | 3/2001 |
| WO | 9836299 | 8/1998 |
| WO | 9941231 | 8/1999 |

* cited by examiner

Primary Examiner—Shailendra Kumar
(74) Attorney, Agent, or Firm—Connolly, Bove, Lodge & Hutz, LLP

(57) ABSTRACT

Compounds of formula (I) are useful as inhibitors of trypsin like serine protease enzymes such as thrombin, factor VIIa, factor Xa, TF/FVIIa, and trypsin. These compounds could be useful to treat and/or prevent clotting disorders, and as anticoagulating agents.

18 Claims, No Drawings

BIARYL COMPOUNDS AS SERINE PROTEASE INHIBITORS

CROSS-REFERENCE TO RELATED APPLICATIONS

This application is a divisional of U.S. patent application Ser. No. 10/127,460, filed Apr. 23, 2002, now U.S. Pat. No. 6,699,994, which is a continuation-in-part of copending International Patent Application No. PCT/US01/32582 filed Oct. 22, 2001, which designated the United States and which claims priority from U.S. Patent Application Ser. No. 60/281,735 filed Apr. 6, 2001, the disclosures of which are incorporated herein by reference.

TECHNICAL FIELD

The present invention relates to the identification, through synthesis and testing, of heretofore unreported compounds which, in appropriate pharmaceutical compositions, exert a therapeutic effect through reversible inhibition of serine proteases.

BACKGROUND OF INVENTION

Serine proteases make up the largest and most extensively studied group of proteolytic enzymes. Their critical roles in physiological processes extend over such diverse areas as blood coagulation, fibrinolysis, complement activation, reproduction, digestion, and the release of physiologically active peptides. Many of these vital processes begin with cleavage of a single peptide bond or a few peptide bonds in precursor protein or peptides. Sequential limited proteolytic reactions or cascades are involved in blood clotting, fibrinolysis, and complement activation. The biological signals to start these cascades can be controlled and amplified as well. Similarly, controlled proteolysis can shut down or inactivate proteins or peptides through single bond cleavages.

While serine proteases are physiologically vital, they also can be hazardous. Their proteolytic action, if uncontrolled, can destroy cells and tissues through degradation of proteins. As a natural safeguard in normal plasma, 10% of the protein matter is composed of protease inhibitors. The major natural plasma inhibitors are specific for serine proteinases. Diseases (associated protease given in the parentheses) such as pulmonary emphysema (cathepsin G), adult respiratory distress syndrome (chymases), and pancreatitis (trypsin, chymotrypsin, and others) are characterized by uncontrolled serine proteases. Other proteases appear to be involved in tumor invasion (plasmin, plasminogen activator), viral transformation, and inflammation (kallikrein). Thus the design and synthesis of specific inhibitors for this class of proteinases could offer major therapeutic benefits.

Thrombus formation, that is blood coagulation, is normally initiated by tissue injury; its normal purpose is to slow or prevent blood loss and facilitate wound healing. There are other conditions, however, not directly connected with tissue injury that may promote the coagulation process and lead instead to harmful consequences; examples of such conditions are atherosclerosis and inflammation.

The complex pathways of blood coagulation involve a series of enzyme reactions in which plasma coagulation factors, actually enzyme precursors or zymogens, are sequentially activated by limited proteolysis. Blood coagulation, or the coagulation cascade, is viewed mechanistically as two pathways, the extrinsic and the intrinsic (FIG. 1). Each pathway proceeds through a sequence of the Roman-numeral-designated factors until they converge at the activation of factor X after merger of the pathways. Thrombin generation proceeds stepwise through a common pathway. Thrombin then acts on the solution plasma protein, fibrinogen, to convert it to stable insoluble fibrin clots, thus completing the coagulation cascade.

The extrinsic pathway is vital to the initiation phase of blood coagulation while the intrinsic pathway provides necessary factors in the maintenance and growth of fibrin. The initiation of the coagulation cascade involves the release of tissue factor (TF) from injured vessel endothelial cells and subendothelium. TF then acts upon factor VII to form the TF/FVIIa complex (where VIIa designates the activated factor rather than the zymogen form). This complex initiates coagulation by activating factors IX and X. The resulting factor Xa forms a prothrombinase complex that activates prothrombin to produce the thrombin that converts fibrinogen to insoluble fibrin. In contrast, the intrinsic system is activated in vivo when certain coagulation proteins contact subendothelial connective tissue. In the sequence that follows, contact factors XII and XI are activated. The resulting factor XIa activates factor IX; then factor IXa activates factor X thereby intersecting with the extrinsic pathway.

With time, the TF/FVIIIa complex (of the extrinsic pathway) loses activity due to the action of tissue factor pathway inhibitor (TFPI), a Kunitz-type protease inhibitor protein which, when complexed with factor Xa, can inhibit the proteolytic activity of TF/FVIIa. If the extrinsic system is inhibited, additional factor Xa is produced through the thrombin-mediated action in the intrinsic pathway. Thrombin, therefore, exerts a dual catalytic role in (a) the conversion of fibrinogen to fibrin and (b) mediating its own production. The autocatalytic aspect of thrombin production affords an important safeguard against excessive blood loss, and, assuming presence of a threshold level of prothrombinase, ensures that the blood coagulation process will go to completion.

While the ability to form blood clots is vital to survival, there are disease states wherein the formation of blood clots within the circulatory system can cause death. When patients are afflicted with such disease states, it is not desirable to completely inhibit the clotting system because life-threatening hemorrhage would follow. Thus, it is highly desirable to develop agents that inhibit coagulation by inhibition of factor VIIa without directly inhibiting thrombin.

Need for the prevention of intravascular blood clots or for anti-coagulant treatment in many clinical situations is well known. Drugs in use today are often not satisfactory. A high percentage of patients who suffer internal injuries or undergo certain surgical procedures develop intravascular blood clots which, if unchecked, cause death. In total hip replacement surgery, for example, it is reported that 50% of the patients develop deep vein thrombosis (DVT). Current approved therapies involve administration of heparin in various forms, but results are not entirely satisfactory; 10–20% of patients suffer DVT and 5–10% have bleeding complications. Along these lines, see International Publication No. WO 00/15658.

Other examples of clinical situations for which better anticoagulants would be of great value are when patients undergo transluminal coronary angioplasty and treatment for myocardial infarction or crescendo angina. The present therapy for these conditions is administration of heparin and aspirin, but this treatment is associated with a 6–8% abrupt vessel closure rate within 24 hours of the procedure. Transfusion therapy due to bleeding complications is required in approximately 7% of cases following the use of heparin. Occurrences of delayed vessel closures are also significant, but administration of heparin after termination of the procedure affords little beneficial effect and can be detrimental.

Heparin and certain derivatives thereof are the most commonly used anti-clotting agents. These substances exert their effects mainly through inactivation of thrombin, which is inactivated 100 times faster than factor Xa. Two other thrombin-specific anticoagulants, hirudin and hirulog, are in clinical trials (as of September 1999). However, bleeding complications are associated with these agents.

In preclinical studies in baboons and dogs, the targeting of enzymes involved in earlier stages of the coagulation cascade, such as factor VIIa or factor Xa, prevents clot formation and does not produce bleeding side effects observed with direct thrombin inhibitors.

Several preclinical studies reveal that inhibition of TF/FVIIa offers the widest window of therapeutic effectiveness and safety with respect to bleeding risk of any anticoagulant approach tested including thrombin, platelet, and factor Xa inhibition.

A specific inhibitor of factor VIIa would provide clinicians with a valuable and needed agent that would be safe and effective in situations where the present drugs of choice, heparin and related sulfated polysaccharides, are no better than marginally effective.

There exists a need for a low molecular weight specific serine protease inhibitors specific toward various enzymes, particularly for factor VIIa that does not cause unwanted side effects.

FIG. 1
Pathways of Coagulation

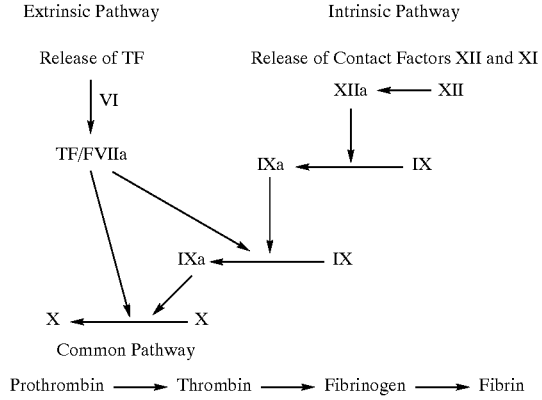

The FIGURE illustrates the extrinsic and intrinsic pathways of blood coagulation.

SUMMARY OF INVENTION

An aspect of the present invention relates to compounds represented by the formula:

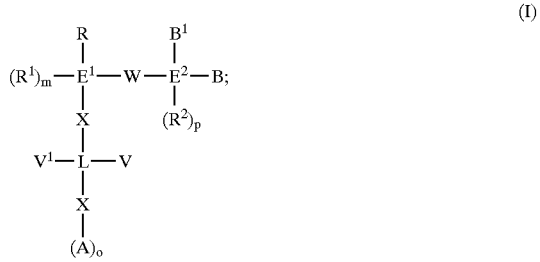

pharmaceutically acceptable salts thereof, and prodrugs thereof.

Each $E^1$ and L individually is a 5 to 7 membered saturated or unsaturated carbon ring, 5 to 7 membered saturated or unsaturated hetero ring, bicyclic saturated or unsaturated carbon ring, bicyclic saturated or unsaturated hetero ring, or 1–8 hydrocarbon chain which may be substituted with one or more hetero groups selected from N, O, S, S(O), and S(O$_2$) which may be saturated or unsaturated. The bicyclic rings typically contain 7–13 atoms in the ring.

R is —CH═CH—$R^2$, —C≡C—$R^2$, —C($R^2$)═CH$_2$, —C($R^2$)═C($R^3$), —CH═N$R^2$, —C($R^2$)═N—$R^3$, 4–7 membered saturated or unsaturated carbon ring system with or without substitution, 4–7 membered saturated or unsaturated hetero ring system with or without substitution, or chain of 2 to 8 carbon atoms having 1 to 5 double or triple bonds with substitutions selected from $R^1$, $R^2$, or $R^3$.

$R^1$ is H, —R, —NO$_2$, —CN, -halo, —N$_3$, —C$_{1-8}$ alkyl, —(CH$_2$)$_n$CO$_2R^2$, —C$_{2-8}$ alkenyl-CO$_2R^2$, —O(CH$_2$)$_n$CO$_2R^2$, —C(O)NR$^2$R$^3$, —P(O)(OR$^2$)$_2$, alkyl substituted tetrazol-5-yl, —(CH$_2$)$_n$O(CH$_2$)$_n$ aryl, —NR$^2$R$^3$, —(CH$_2$)$_n$ OR$^2$, —(CH$_2$)$_n$ SR$^2$, —N(R$^2$)C(O)R$^3$, —S(O$_2$)NR$^2$R$^3$, —N(R$^2$)S(O$_2$)R$^3$, —(CHR$^2$)$_n$NR$^2$R$^3$, —C(O)R$^3$, (CH$_2$)$_n$ N(R$^3$)C(O)R$^3$, —N(R$^2$)CR$^2$R$^3$ substituted or unsubstituted (CH$_2$)$_n$-cycloalkyl, substituted or unsubstituted (CH$_2$)$_n$-phenyl, or substituted or unsubstituted (CH$_2$)$_n$-heterocycle which may be saturated or unsaturated.

m is 1 except that when $E^1$ is a cyclic ring of more than 5 atoms, then m is 1 or higher, depending upon the size of the ring.

$R^2$ is H, -halo, -alkyl, -haloalkyl, —(CH$_2$)$_n$-phenyl, —(CH$_2$)$_{1-3}$-biphenyl, —(CH$_2$)$_{1-4}$-Ph-N(SO$_2$—C$_{1-2}$-alkyl)$_2$, —CO(CHR$^1$)$_n$—OR$^1$, —(CHR$^1$)$_n$-heterocycle, —(CHR$^1$)$_n$—NH—CO—R$^1$, —(CHR$^1$)$_n$—NH—SO$_2$R$^1$, —(CHR$^1$)$_n$-Ph-N(SO$_2$—C$_{1-2}$-alkyl)$_2$, —(CHR$^1$)$_n$—C(O) (CHR$^1$)—NHR$^1$, —(CHR$^1$)$_n$—C(S)(CHR$^1$)—NHR$^1$, —(CH$_2$)$_n$O(CH$_2$)$_n$CH$_3$, —CF$_3$, —C$_{2-5}$ acyl, —(CHR$^1$)$_n$ OH, —(CHR$^1$)$_n$CO$_2$R$^1$, —(CHR$^1$)$_n$—O-alkyl, —O(CHR$^1$)$_n$—O—(CH$_2$)$_n$—O-alkyl, —(CHR$^1$)$_n$—S-alkyl, —(CHR$^1$)$_n$—S(O)-alkyl, —(CHR$^1$)$_n$—S(O$_2$)-alkyl, —(CHR$^1$)$_n$—S(O$_2$)—NHR$^3$, —(CHR$^3$)$_n$—N$_3$, —(CHR$^3$)$_n$NHR$^4$, 2 to 8 carbon atom alkene chain having 1 to 5 double bonds, 2 to 8 carbon atom alkyne chain having 1 to 5 triple bonds, substituted or unsubstituted-(CHR$^3$)n heterocycle, or substituted or unsubstituted-(CHR$^3$)$_n$ cycloalkyl which may be saturated or unsaturated.

When n is more than 1, the substitutions $R^1$ and $R^3$ may be same or different.

$R^3$ is H, —OH, —CN, substituted alkyl, —C$_{2-8}$ alkenyl, substituted or unsubstituted cycloalkyl, —N(R$^1$)R$^2$, or 5–6 membered saturated substituted or unsubstituted hetero ring.

—NR²R³ may form a ring system having 4 to 7 atoms or may be bicyclic ring. The ring system may be of carbon or hetero atoms and further it may saturated or unsaturated and also may be substituted or unsubstituted.

W is a direct bond, —CHR²—, —CH=CR²—, —CR²=CH—, —CR²=CR²—, —C≡C—, —O—CHR²—, —CHR²—O—, —N(R²)—C(O)—, —C(O)—N(R)—, —N(R²)—CH—(R³)—, —CH₂—N(R²)—, —CH(R¹)—N(R²)—, —S—CHR²—, —CHR²—S—, —S(O₂)—N(R²)—, —C(O)N(R²)—(CHR²)n-, —C(R¹R²)n-NR²—, —N(R²)—S(O₂)—, —R²C(O)NR²—, —R²NC(O)NR²—, —CONR²CO—, —C(=NR²)NR²—, —NR²C(=NR²)NR²—, —NR²O—, —N=NCHR²—, or —C(O)NR²SO₂—.

E² is 5 to 7 membered saturated or unsaturated carbon ring, 5 to 7 membered saturated or unsaturated hetero ring, bicyclic ring system, $C_{1-8}$ alkyl, $C_{2-8}$ alkenyl, $C_{2-8}$ alkynyl, alkylaryl, aralkyl, aralkenyl, aralkynyl, alkoxy, alkylthio, or alkylamino.

each X individually is a direct bond, substituted or unsubstituted $C_{1-4}$ methylene chain; O, S, NR², S(O), S(O₂), or N(O) containing one or two $C_{1-4}$ substituted or unsubstituted methylene chains. X at different places may be same or different.

B is H, -halo, —CN, —NH₂, —(CH₂)$_n$—C(=NR⁴)NHR⁵, —(CH₂)$_n$—NHR⁴, —(CH₂)$_n$NHC(=NR⁴)NR⁵, —(CH₂)$_n$—OR⁴, $C_{1-8}$ substituted or unsubstituted alkyl, substituted or unsubstituted ring system having 4 to 7 carbon or hetero atoms which may be saturated or unsaturated.

B¹ is selected from B; B¹ and B may be same or different.

There may be more than one similar or different R² groups present on E², when E² is a cyclic group of more than 5 atoms. In particular, p is 1 except that when E² is a cyclic ring of more than 5 atoms, p is 1 or higher depending upon the size of the ring.

n is 0–4

A is selected from R¹.

o is 1 except that when L is a cyclic ring of more than 5 atoms, o is 1 or higher depending upon the size of the ring.

Each V and V¹ individually is selected from R¹ and N-alkyl substituted carboxamidyl (—CONHR) where the alkyl group may be straight, branched, cyclic, or bicyclic; N,N-disubstituted carboxamidyl (—CONR₁R₂ where R₁ and R₂ may be substituted or unsubstituted alkyl or aryl and may be the same or different); mono- or disubstituted sulfonamides (SO₂NHR or —SO₂NR₁R₂); and methylene- or polymethylene chain-extended variants thereof.

Each R⁴ and R⁵ individually is H, —(CH₂)$_n$OH, —C(O)OR⁶, —C(O)SR⁶, —(CH₂)$_n$ C(O)NR⁷R⁸, —O—C(O)—O—R⁷, an amino acid or a dipeptide, Each R⁶ is H, R⁷, —C(R⁷)(R⁸)—(CH₂)$_n$—O—C(O)—R⁹, —(CH₂)$_n$—C(R⁷)(R⁸)—O—C(O)R⁹, —(CH₂)$_n$—C(R⁷)(R⁸)—O—C(O)—O—R⁹, or —C(R⁷)(R⁸)—(CH₂)$_n$—O—C(O)—O—R⁹, Each R⁷, R⁸ and R⁹ individually is H, alkyl, substituted alkyl, aryl, substituted aryl, alkenyl, substituted alkenyl, alkynyl, substituted alkynyl, heterocycle, substituted heterocycle, alkylaryl, substituted alkylaryl, cycloalkyl, substituted cycloalkyl, or CH₂CO₂alkyl.

The present invention also relates to pharmaceutical compositions containing at least one of the above disclosed compounds and their prodrugs.

A further aspect of the present invention relates to a method for inhibiting trypsin-like serine protease enzymes, such as thrombin, factor Xa, factor VIIa, TF/VIIa, and trypsin in a patient which comprises administering to the patient an effective serine protease inhibiting amount of at least one of the above disclosed compounds.

Still other objects and advantages of the present invention will become readily apparent by those skilled in the art from the following detailed description, wherein it is shown and described preferred embodiments of the invention, simply by way of illustration of the best mode contemplated of carrying out the invention. As will be realized the invention is capable of other and different embodiments, and its several details are capable of modifications in various obvious respects, without departing from the invention. Accordingly, the description is to be regarded as illustrative in nature and not as restrictive.

BEST AND VARIOUS MODES FOR CARRYING OUT INVENTION

An aspect of the present invention relates to compounds represented by the formula:

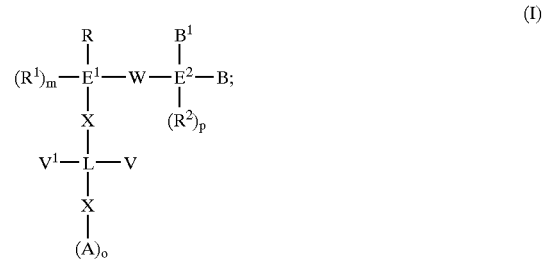

(I)

pharmaceutically acceptable salts thereof; and prodrugs thereof.

Each E¹ and L individually is a 5 to 7 membered saturated or unsaturated carbon ring, 5 to 7 membered saturated or unsaturated hetero ring, bicyclic saturated or unsaturated carbon ring, bicyclic saturated or unsaturated hetero ring, or 1–8 hydrocarbon chain which may be substituted with one or more hetero groups selected from N, O, S, S(O), and S(O₂) which may be saturated or unsaturated.

R is —CH=CH—R², —C≡C—R², —C(R²)=CH₂, —C(R²)=C(R³), —CH=NR², —C(R²)=N—R³, 4–7 membered saturated or unsaturated carbon ring system with or without substitution, 4–7 membered saturated or unsaturated hetero ring system with or without substitution, or chain of 2 to 8 carbon atoms having 1 to 5 double or triple bonds with substitutions selected from R¹, R², or R³. Preferably, these R, R¹, R², or R³ do not include —($C_{2-4}$ alkenyl)-CO₂—$C_{1-8}$ alkyl, —($C_{2-4}$ alkenyl)-CO₂—$C_{1-8}$ alkyl-phenyl, and —($C_{2-4}$ alkenyl)—CO₂—$C_{1-8}$ alkyl-O—$C_{1-4}$ alkyl.

R¹ is H, —R, —NO₂, —CN, -halo, —N₃, —$C_{1-8}$ alkyl, —(CH₂)$_n$CO₂R², —$C_{2-8}$ alkenyl-CO₂R², —O(CH₂)$_n$ CO₂R², —C(O)NR²R³, —P(O)(OR²)₂, alkyl substituted tetrazol-5-yl, —(CH₂)$_n$O(CH₂)$_n$ aryl, —NR²R³, —(CH₂)$_n$ OR², —(CH₂)$_n$ SR², —N(R²)C(O)R³, —S(O₂)NR²R³, —N(R²)S(O₂)R³, —(CHR²)$_n$ NR²R³, —C(O)R³, (CH₂)$_n$ N(R³)C(O)R³, —N(R²)CR²R³ substituted or unsubstituted (CH₂)$_n$-cycloalkyl, substituted or unsubstituted (CH₂)$_n$-phenyl, or substituted or unsubstituted (CH₂)$_n$-heterocycle which may be saturated or unsaturated.

m is 1 except that when E¹ is a cyclic ring of more than 5 atoms, then m is 1 or higher, depending upon the size of the ring. For instance if the ring is 6 atoms, m can be 1 or 2.

R² is H, -halo, -alkyl, -haloalkyl, —(CH₂)$_n$-phenyl, —(CH₂)$_{1-3}$-biphenyl, —(CH₂)$_{1-4}$-Ph-N(SO₂—$C_{1-2}$- alkyl)$_2$, —CO(CHR$^1$)$_n$—OR$^1$, —(CHR$^1$)$_n$-heterocycle, —(CHR$^1$)$_n$—NH—CO—R$^1$, —(CHR$^1$)n-NH—SO$_2$R$^1$, —(CHR$^1$)$_n$-Ph-N(SO$_2$—C$_{1-2}$-alkyl)$_2$, —(CHR$^1$)$_n$—C(O)(CHR$^1$)—NHR$^1$, —(CHR$^1$)$_n$—C(S)(CHR$^1$)—NHR$^1$, —(CH$_2$)$_n$O(CH$_2$)$_n$CH$_3$, —CF$_3$, —C$_{2-5}$ acyl, —(CHR$^1$)$_n$—OH, —(CHR$^1$)$_n$CO$_2$R$^1$, —(CHR$^1$)$_n$—O-alkyl, —(CHR$^1$)$_n$—O—(CH$_2$)$_n$—O-alkyl, —(CHR$^1$)$_n$—S-alkyl, —(CHR$^1$)$_n$—S(O)-alkyl, —(CHR$^1$)$_n$—S(O$_2$)-alkyl, —(CHR$^1$)$_n$—S(O$_2$)—NHR$_3$, —(CHR$^3$)$_n$—N$_3$, —(CHR$^3$)$_n$NHR$^4$, 2 to 8 carbon atom alkene chain having 1 to 5 double bonds, 2 to 8 carbon atom alkyne chain having 1 to 5 triple bonds, substituted or unsubstituted-(CHR$^3$)n heterocycle, or substituted or unsubstituted-(CHR$^3$)$_n$ cycloalkyl which may be saturated or unsaturated.

When n is more than 1, the substitutions R$^1$ and R$^3$ may be same or different.

R$^3$ is H, —OH, —CN, substituted alkyl, —C$_{2-8}$ alkenyl, substituted or unsubstituted cycloalkyl, —N(R$^1$)R$^2$, or 5–6 membered saturated substituted or unsubstituted hetero ring.

—NR$^2$R$^3$ may form a ring system having 4 to 7 atoms or may be bicyclic ring. The ring system may be of carbon or hetero atoms and further it may saturated or unsaturated and also may be substituted or unsubstituted.

W is a direct bond, —CHR$^2$—, —CH=CR$^2$—, —CR$^2$=CH—, —CR$^2$=CR$^2$—, —C≡C—, —O—CHR$^2$—, —CHR$^2$—O—, —N(R$^2$)—C(O)—, —C(O)—N(R$^2$)—, —N(R$^2$)—CH—(R$^3$)—, —CH$_2$—N(R$^2$)—, —CH(R$^1$)—N(R$^2$)—, —S—CHR$^2$—, —CHR$^2$—S—, —S(O$_2$)—N(R$^2$)—, —C(O)N(R$^2$)—(CHR$^2$)n-, —C(R$^1$R$^2$)n-NR$^2$—, —N(R$^2$)—S(O$_2$)—, —R$^2$C(O)NR$^2$—, —R$^2$NC(O)NR$^2$—, —CONR$^2$CO—, —C(=NR$^2$)NR$^2$—, —NR$^2$C(=NR$^2$)NR$^2$, —NR$^2$O—, —N=NCHR$^2$—, or —C(O)NR$^2$SO$_2$—.

E$^2$ is 5 to 7 membered saturated or unsaturated carbon ring, 5 to 7 membered saturated or unsaturated hetero ring, bicyclic ring system, C$_{1-8}$ alkyl, C$_{2-8}$ alkenyl, C$_{2-8}$ alkynyl, alkylaryl, aralkyl, aralkenyl, aralkynyl, alkoxy, alkylthio, or alkylamino.

each X individually is a direct bond, substituted or unsubstituted C$_{1-4}$ methylene chain; O, S, NR$^2$, S(O), S(O$_2$), or N(O) containing one or two C$_{1-4}$ substituted or unsubstituted methylene chains. X at different places may be same or different.

B is H, -halo, —CN, —NH$_2$, —(CH$_2$)$_n$—C(=NR$^4$)NHR$^5$, —(CH$_2$)$_n$—NHR$^4$, —(CH$_2$)$_n$NHC(=NR$^4$)NR$^5$, —(CH$_2$)$_n$—OR$^4$, C$_{1-8}$ substituted or unsubstituted alkyl, substituted or unsubstituted ring system having 4 to 7 carbon or hetero atoms which may be saturated or unsaturated.

B$^1$ is selected from B; B$^1$ and B may be same or different.

There may be more than one similar or different R$^2$ groups present on E$^2$, when E$^2$ is a cyclic system of more than 5 atoms. p is 1 or higher if E$^2$ is a cyclic ring of more than 5 atoms. For example, if the ring is 6 atoms, p can be 1 or 2.

n is 0–4

A is selected from R$^1$.

o is 1 except that when L is a cyclic ring of more than 5 atoms, o is 1 or higher depending upon the size of the ring. For instance, if the ring is 6 atoms, o can be 1 or 2.

Each V and V$^1$ individually is selected from R$^1$ and N-alkyl substituted carboxamidyl (—CONHR) where the alkyl group may be straight, branched, cyclic, or bicyclic; N,N-disubstituted carboxamidyl (—CONR$_1$R$_2$ where R$_1$ and R$_2$ may be substituted or unsubstituted alkyl or aryl and may be the same or different); mono- or disubstituted sulfonamides (SO$_2$NHR or —SO$_2$NR$_1$R$_2$); and methylene- or polymethylene chain-extended variants thereof.

Each R$^4$ and R$^5$ individually is H, —(CH$_2$)$_n$OH, —C(O)OR$^6$, —C(O)SR$^6$, —(CH$_2$), C(O)NR$^7$R$^8$, —O—C(O)—O—R$^7$, an amino acid or a dipeptide, Each R$^6$ is H, R$^7$, —C(R$^7$)(R$^8$)—(CH$_2$)$_n$—O—C(O)—R$^9$, —(CH$_2$)$_n$—C(R$^7$)(R$^8$)—O—C(O)R$^9$, —(CH$_2$)$_n$—C(R$^7$)(R$^8$)—O—C(O)—O—R$^9$, or —C(R$^7$)(R$^8$)—(CH$_2$)$_n$—O—C(O)—O—R$^9$, Each R$^7$, R$^8$ and R$^9$ individually is H, alkyl, substituted alkyl, aryl, substituted aryl, alkenyl, substituted alkenyl, alkynyl, substituted alkynyl, heterocycle, substituted heterocycle, alkylaryl, substituted alkylaryl, cycloalkyl, substituted cycloalkyl, or CH$_2$CO$_2$alkyl.

R substituent groups employed pursuant to the present invention contribute to significantly enhanced activity of the compounds of the present invention.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 8 carbon atoms. The expression "lower alkyl" refers to unsubstituted alkyl groups of 1 to 4 carbon atoms.

The terms "alkenyl" and "alkynyl" refer to straight or branched chain unsubstituted hydrocarbon groups typically having 2 to 8 carbon atoms.

The terms "substituted alkyl", "substituted alkenyl" or substituted alkynyl" refer to an alkyl, alkenyl or alkynyl group substituted by, for example, one to four substituents, such as halo, trifluoromethyl, trifluoromethoxy, hydroxy, alkoxy, cycloalkyloxy, heterocyclooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamine, aroylamino, aralkanoylamino, substituted alkanolamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. SO$_2$NH$_2$), substituted sulfonamido, nitro, cyano, carboxy, carbamyl (e.g. CONH$_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" or "alkylaryl" refers to an aryl group bonded directly through an alkyl group, such as benzyl or phenethyl.

The term "substituted aryl" or "substituted alkylaryl" refers to an aryl group or alkylaryl group substituted by, for example, one to four substituents such as alkyl; substituted alkyl, halo, trifluoromethoxy, trifluoromethyl, hydroxy, alkoxy, azido, cycloalkyloxy, heterocyclooxy, alkanoyl, alkanoyloxy, amino, alkylamino, aralkylamino, hydroxyalkyl, aminoalkyl, azidoalkyl, alkenyl, alkynyl, allenyl, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl. "Substituted benzyl" refers to a benzyl group substituted by, for example, any of the groups listed above for substituted aryl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl and adamantyl. Exemplary substituents include one or more alkyl groups as described above, or one or more groups described above as alkyl substituents.

The term "cycloalkenyl" refers to optionally substituted, unsaturated cyclic hydrocarbon ring systems, preferably containing 1 to 3 rings and 3–7 carbons per ring. Exemplary groups include cyclopentenyl and cyclohexenyl.

The terms "heterocycle", "heterocyclic" and "heterocyclo" refer to an optionally substituted, fully saturated or unsaturated, aromatic or nonaromatic cyclic group, for example, which is 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atoms.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuiryl, thienyl, thiophenyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, dihydropyridyl, N-oxopyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dixolane and tetrahydro-1,1-dioxothienyl, dioxanyl, isothiazolidinyl, thietanyl, thiiranyl, triazinyl and triazolyl and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, cournarinyl, cinnolinyl, quinoxalinyl, indazolyl, pyrrolapridyl, furopyridinyl (such as furo[2,3-c]pyridinyl, furo[3,1-b]pyridinyl, or furo[2,3-b]pyridinyl), dihydroisoindolyl, diyhydroquinazolinyl (such as 3,4-dihydro-4-oxo-quinazolinyl), benzisothiazolyl, benzisoxazolyl, benzodiazinyl, benzofurazanyl, benzothiopyranyl, benzothiazolyl, benzpyrasolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, theinofuryl, thienopyridyl, thienothienyl, and the like.

Exemplary substituents include one or more alkyl groups as described above or one or more groups described above as alkyl substituents.

Within the above-described definitions, certain embodiments are preferred. Preferred alkyl groups are lower alkyl groups containing 1 to about 8 carbon, and more preferably 1 to about 5 carbon atoms, and can be straight, branched-chain or cyclic saturated aliphatic hydrocarbon groups.

Examples of suitable alkyl groups include methyl, ethyl and propyl. Examples of branched alkyl groups include isopropyl and t-butyl. An example of a suitable alkylaryl group is phenethyl. Examples of suitable cycloalkyl groups typically contain 3–8 carbon atoms and include cyclopropyl, cyclobutyl, cyclopentyl and cyclohexyl. The aromatic or aryl groups are preferably phenyl or alkyl substituted aromatic groups (aralkyl) such as phenyl $C_{1-3}$ alkyl such as benzyl.

The N-heterocyclic rings preferably contain 3–7 atoms in the ring and a heteroatom such as N, S or O in the ring. Examples of suitable preferred heterocyclic groups are pyrrolidino, azetidino, piperidino, 3,4-didehydropiperidino, 2-methylpiperidino and 2-ethylpiperidino. In addition, the above substitutions can include halo such as F, Cl, Br, lower alkyl, lower alkoxy and halo substituted lower alkoxy.

Examples of some preferred B groups include —NHC(=NH)NH$_2$, —C(=NH)NH$_2$, NH$_2$, various N-substituted variants, and assorted prodrug derivatives.

Prodrug forms of the compounds bearing various nitrogen functions (amino, hydroxyamino, hydrazino, guanidino, amidino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl, or cycloalkenyl groups as defined beginning on page 7.

(a) Carboxamides, —NHC(O)R
(b) Carbamates, —NHC(O)OR
(c) (Acyloxy)alkyl carbamates, —NHC(O)OROC(O)R
(d) Enamines, —NHCR(=CHCR$O_2$R) or —NHCR(=CHCRONR$_2$)
(e) Schiff bases, —N=CR$_2$
(f) Mannich bases (from carboximide compounds), RCONHCH$_2$NR$_2$ Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the invention.

Prodrug forms of carboxyl-bearing compounds of the invention include esters (—CO$_2$R) where the R group corresponds to any alcohol whose release in the body through enzymatic or hydrolytic processes would be at pharmaceutically acceptable levels. Another prodrug derived from a carboxylic acid form of the invention may be a quaternary salt type

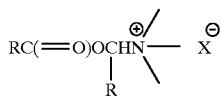

of structure described by Boder et al., J. Med. Chem. 1980, 23, 469.

Examples of some preferred groups for W are —$CH_2CH_2$—, —CH=CH—, —C≡C—, —$CH_2CH_2CH_2$—, —$CH_2$CH=CH—, —$CH_2$C≡C—, —CONH, —$CH_2$CONH—, —NHCONH—, —CONHCO—, —CONHCH$_2$—, —C(=NH)NH—, —$CH_2$C(=NH)NH—, —NHC(=NH)NH—, —NHNH—, —NHO—, —CONHSO$_2$—, —SO$_2$NH—, —NHSO$_2$CH$_2$—, —SO$_2$NHCH$_2$—, —CH$_2$O—, —CH$_2$OCH$_2$—, —OCH$_2$CH$_2$—, —CH$_2$NH—, —CH$_2$CH$_2$NH—, —CH$_2$NHCH$_2$—, —CH$_2$S—, —SCH$_2$CH$_2$, —CH$_2$SCH$_2$—, —CH$_2$SO$_2$CH$_2$—, —CH$_2$SOCH$_2$—, —CH(CO$_2$H)O and —CH(CO$_2$H)OCH$_2$.

Examples of some preferred groups for V and $V^1$ are N-alkyl substituted carboxamidyl (—CONHR) where the alkyl group may be straight, branched, cyclic, or bicyclic, and typically containing up to ten carbons; N,N-disubstituted carboxamidyl (—CONR$_1$R$_2$ where R$_1$ and R$_2$ may be substituted or unsubstituted alkyl or aryl and may be the same or different); mono- or disubstituted sulfonamides (SO$_2$NHR or —SO$_2$NR$_1$R$_2$); methylene- or polymethylene chain-extended variants thereof such as —(CH$_2$)$_n$CONHR$_1$, —(CH$_2$)$_n$CONR$_1$R$_2$, —(CH$_2$)$_n$SO$_2$NHR$_1$, —(CH$_2$)$_n$SO$_2$NR$_1$R$_2$ (where n=1–4), —NHC(O)R, N(R$_1$)C(O)R$_2$, NHSO$_2$R, CH$_2$NHR, CH$_2$NR$_1$R$_2$.

Pharmaceutically acceptable salts of the compounds of the present invention include those derived from pharmaceutically acceptable, inorganic and organic acids and bases. Examples of suitable acids include hydrochloric, hydrobromic, sulphuric, nitric, perchloric, fumaric, maleic, phosphoric, glycollic, lactic, salicyclic, succinic, toluene-p-sulphonic, tartaric, acetic, citric, methanesulphonic, formic, benzoic, malonic, naphthalene-2-sulphonic, trifluoroacetic and benzenesulphonic acids.

Salts derived from appropriate bases include alkali such as sodium and ammonia.

It is of course understood that the compounds of the present invention relate to all optical isomers and stereoisomers at the various possible atoms of the molecule.

The synthetic routes leading to the compounds in formula (I) are described in the following schemes.

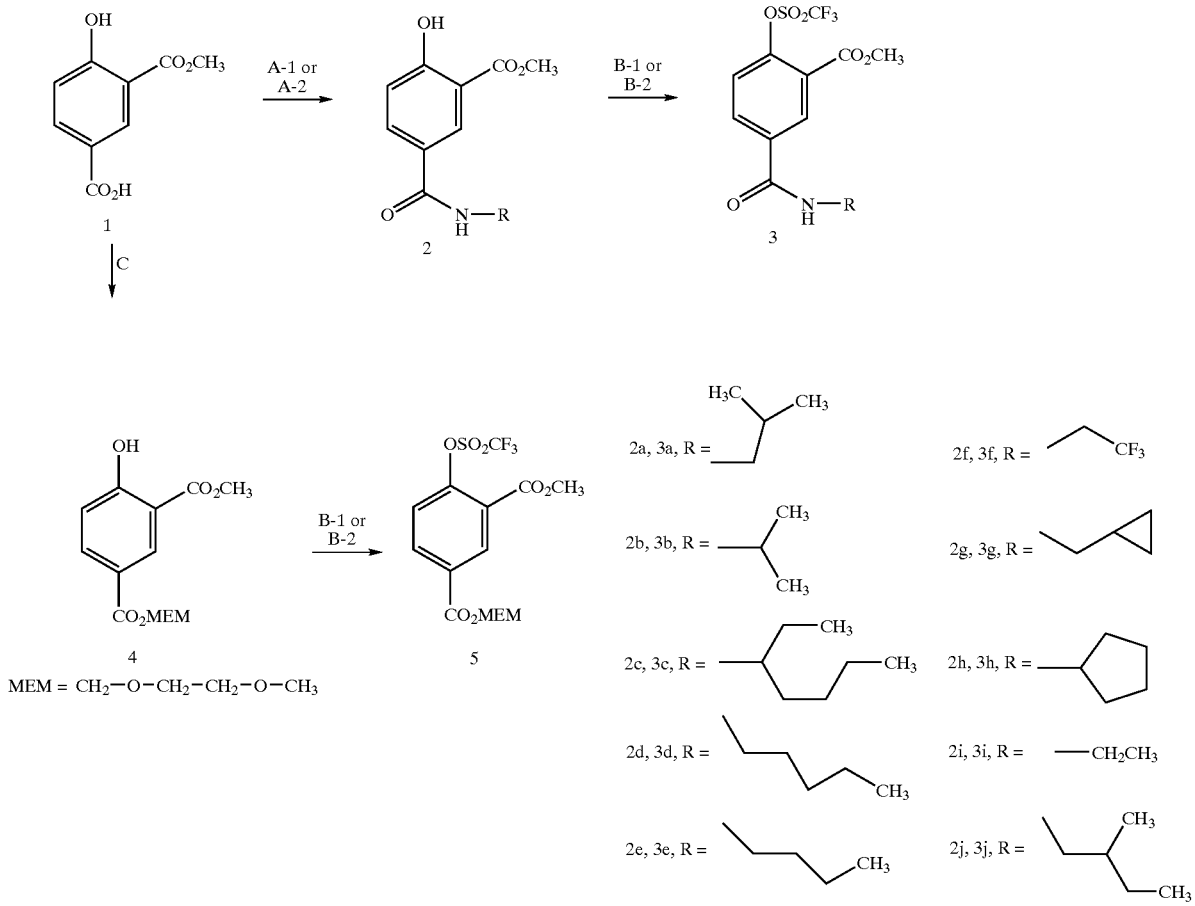

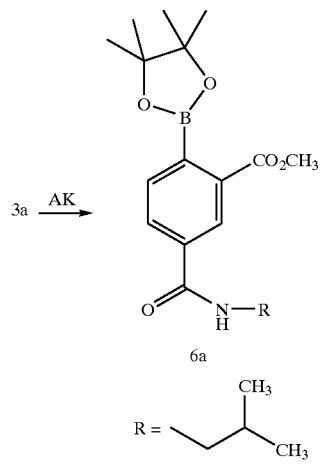
Scheme 2
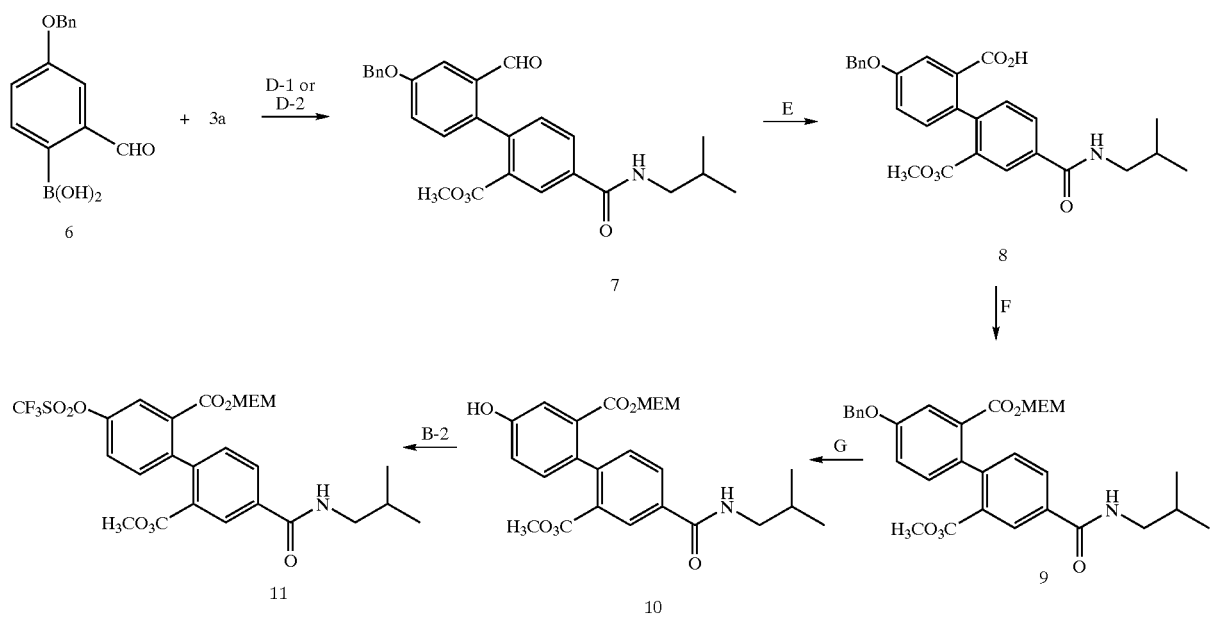
Scheme 3
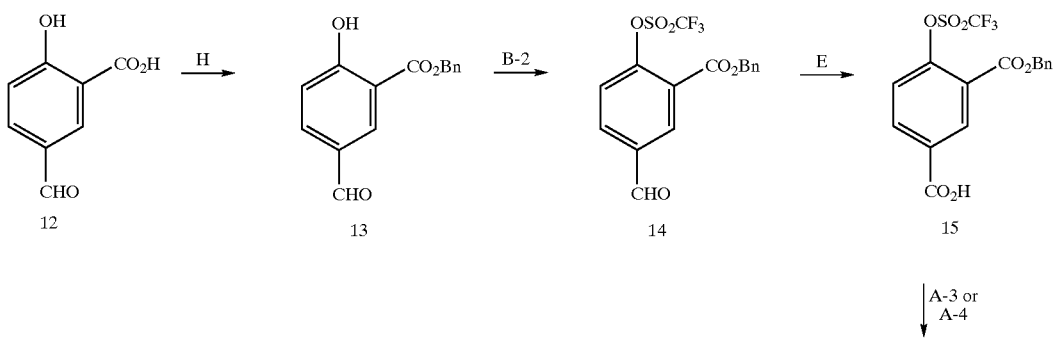

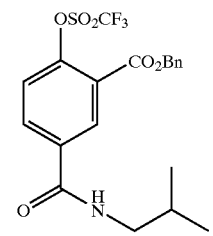
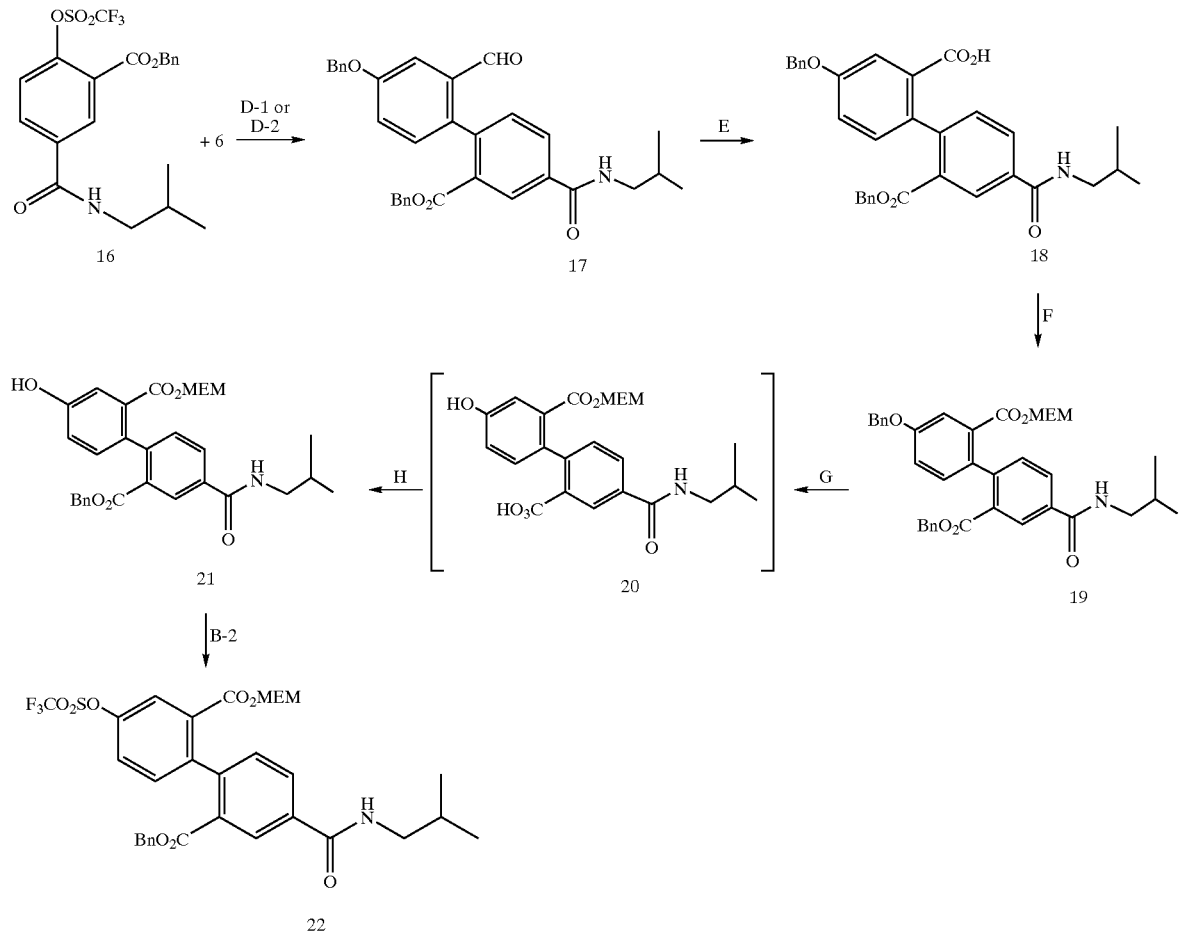
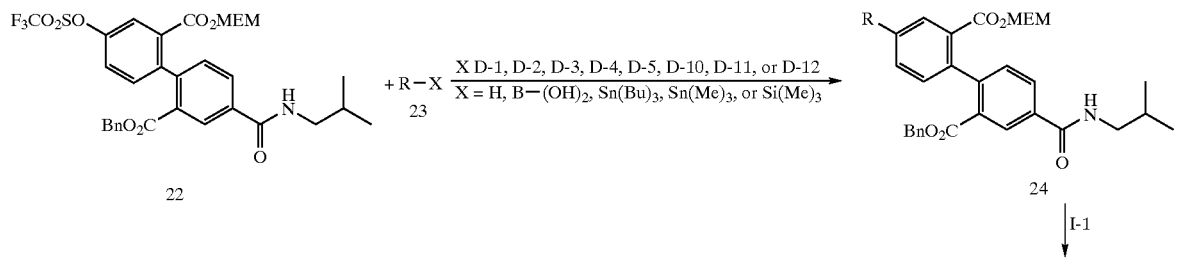

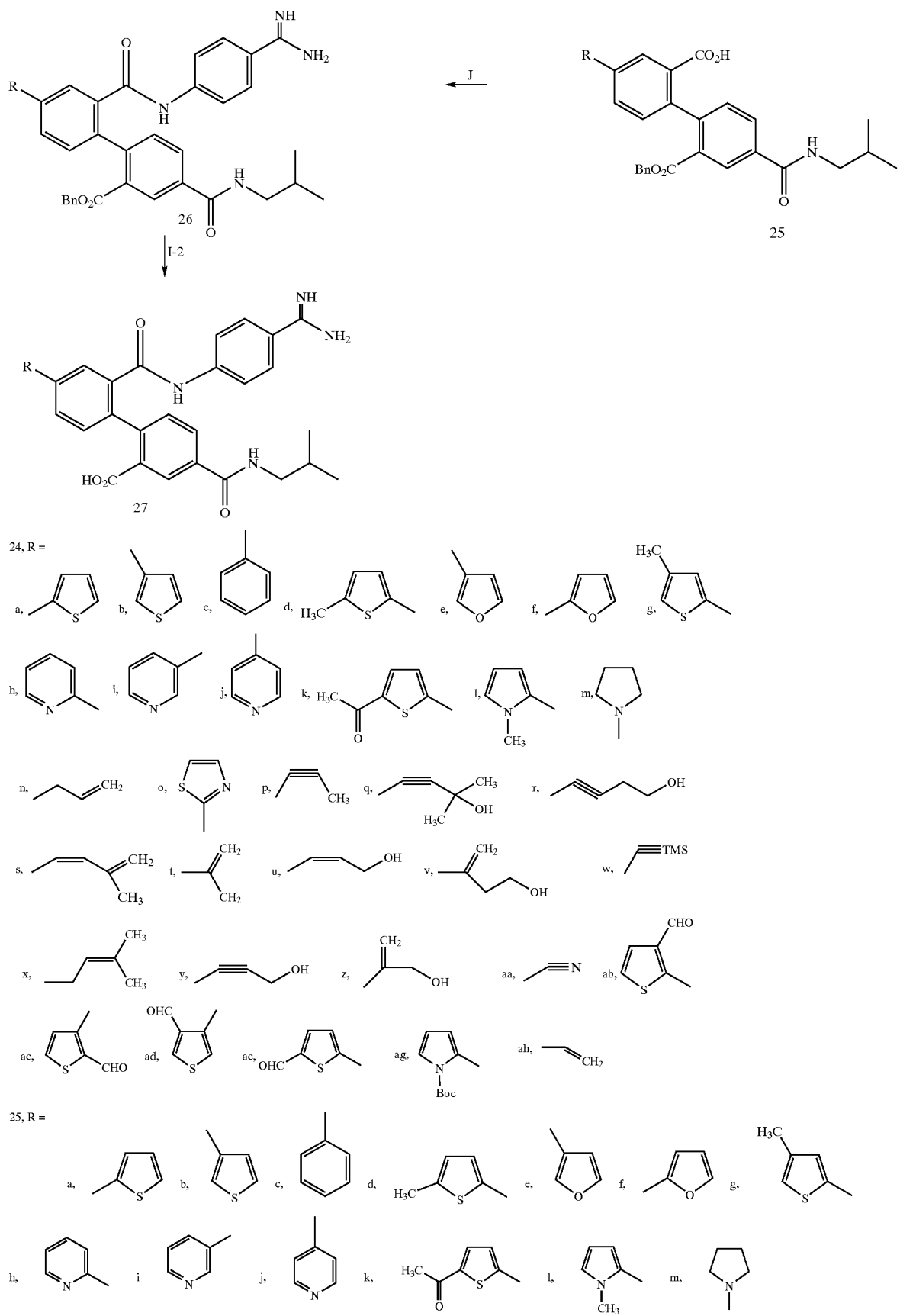

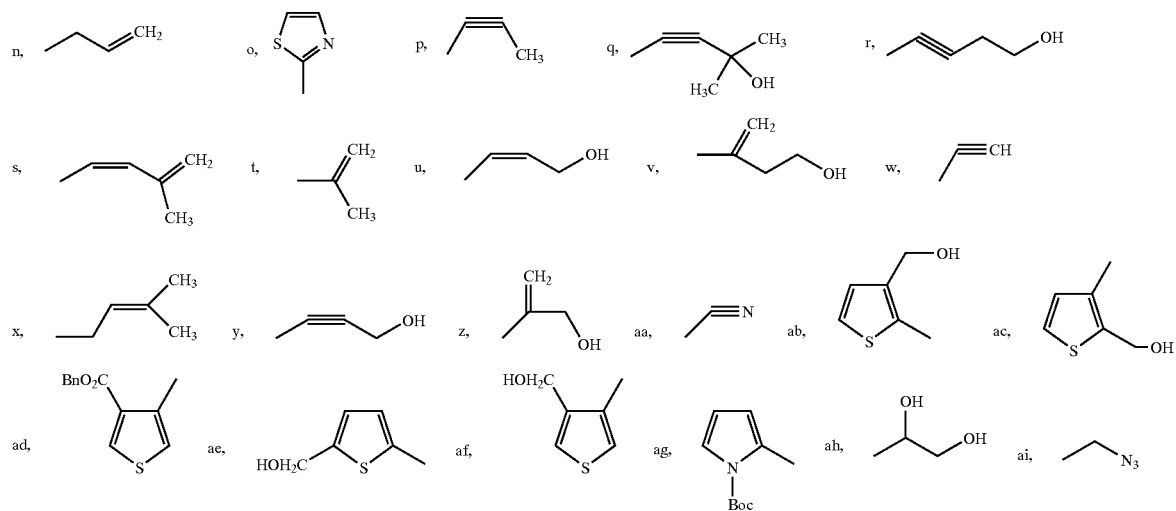
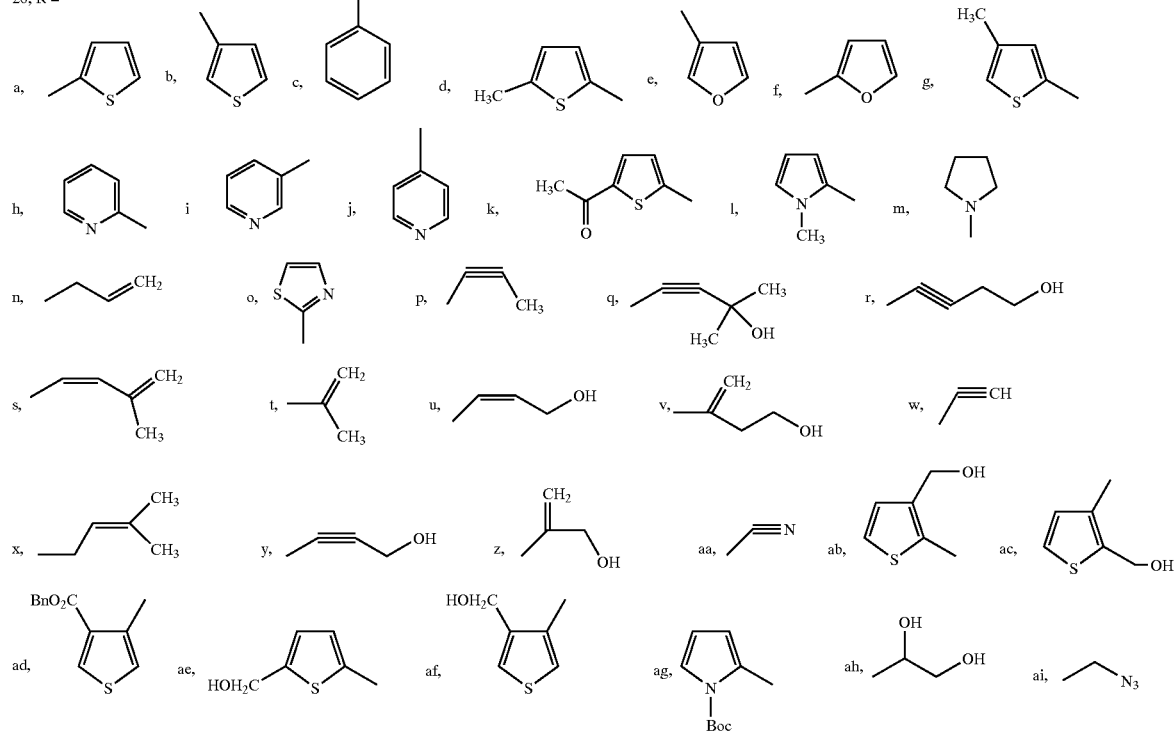
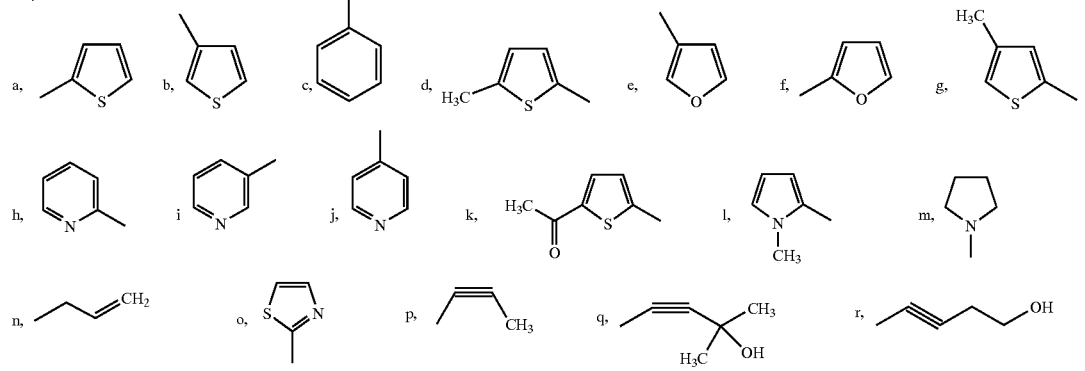

-continued

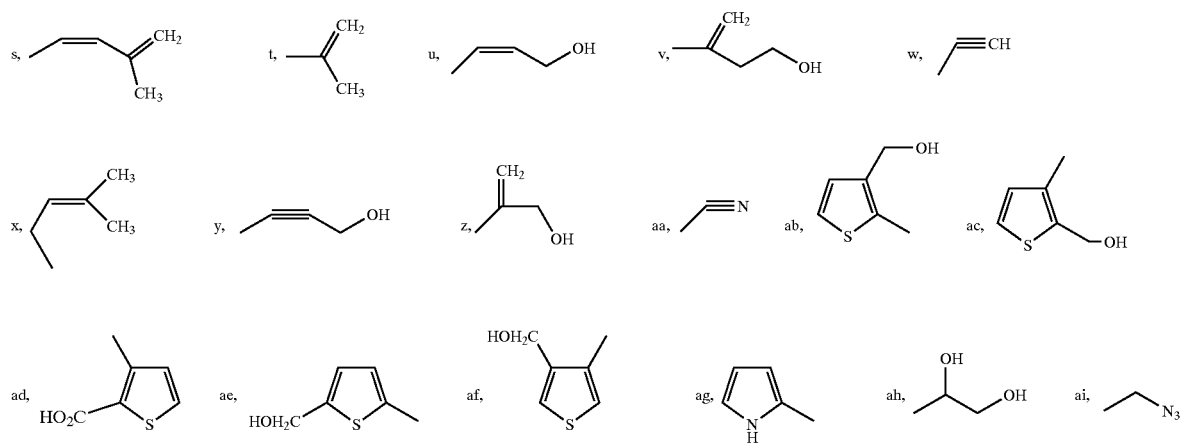

Conversion of

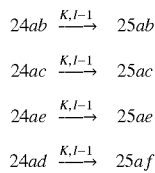

The reduction of the formyl group of 24ab, 24ac, 24ae, and 24ad was accomplished with NaBH$_4$ to give corresponding alcohols 24ab-i, 24ac-i, 24ae-i, and 24ad-i, respectively. Later, the MEM group was removed under acidic conditions to give 25ab, 25ac, 25ae, and 25af, respectively.

Conversion of

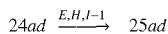

The aldehyde 24ad was oxidized to acid 24ad-i which was protected as benzyl ester to give 24ad-ii. MEM deprotection under acidic conditions produced 25ad.

Conversion of

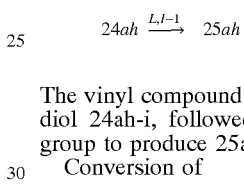

The vinyl compound 24ah was oxidized with OsO$_4$ to give diol 24ah-i, followed by acidic hydrolysis of the MEM group to produce 25ah.

Conversion of $$24ah \xrightarrow{L,M,K,N,O,I-1} 25ai$$

The vinyl compound 24ah on dihydroxylation with OsO$_4$ gave diol 24ah-i. Oxidative cleavage of the diol with NaIO$_4$ produced aldehyde 24ah-ii. The aldehyde on reduction gave alcohol 24ah-iii, which on further reaction with methane sulfonyl chloride yielded mesylate 24ah-iv. The mesylate on further reaction with sodium azide gave the corresponding azide 24ah-v, which on acidic hydrolysis produced 25ai.

Conversion of

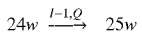

Scheme 6

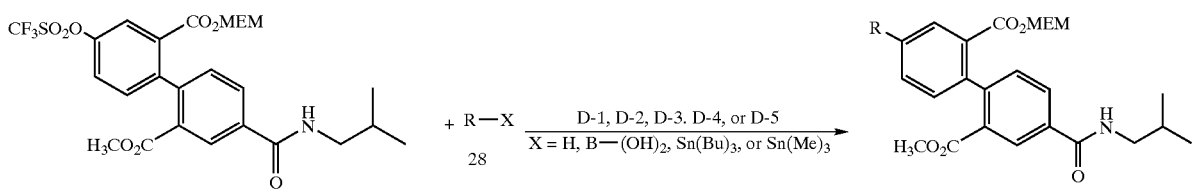

-continued
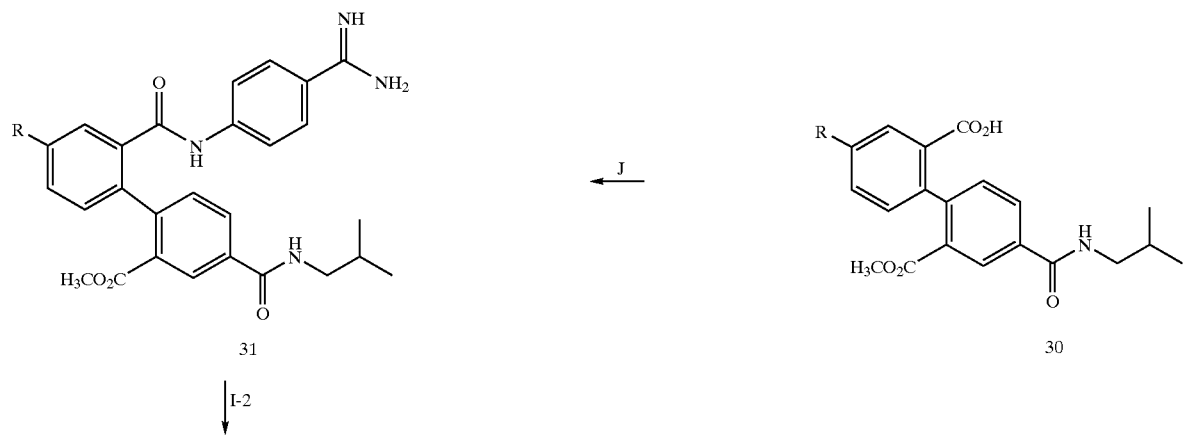
29, R =
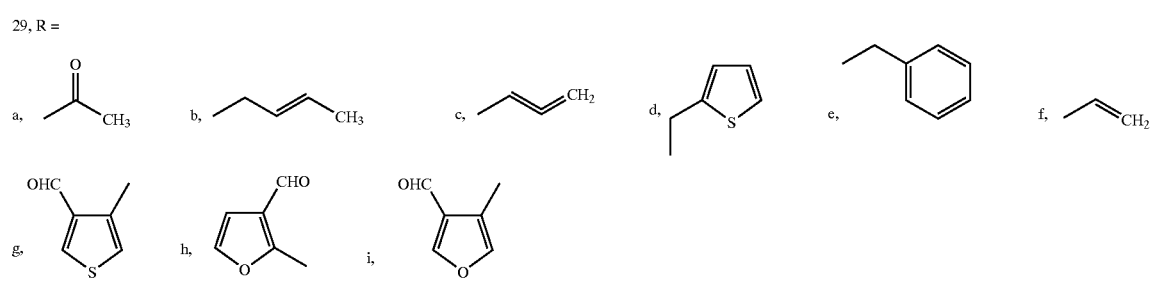
30, R =
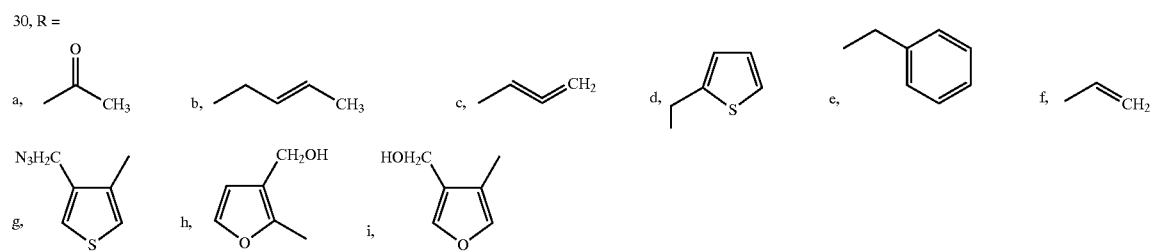
31, R =
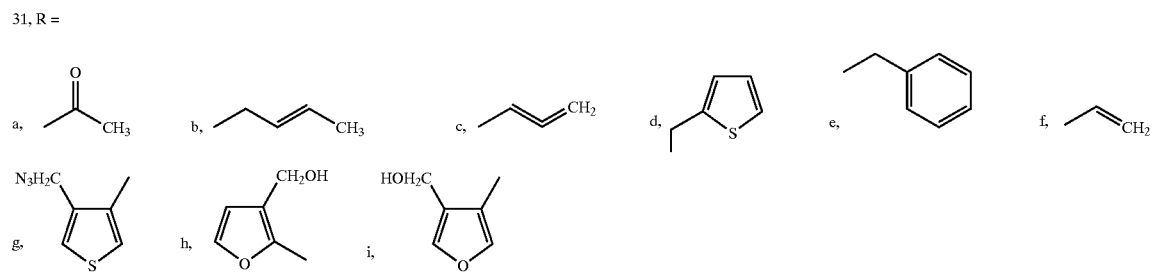

32, R =

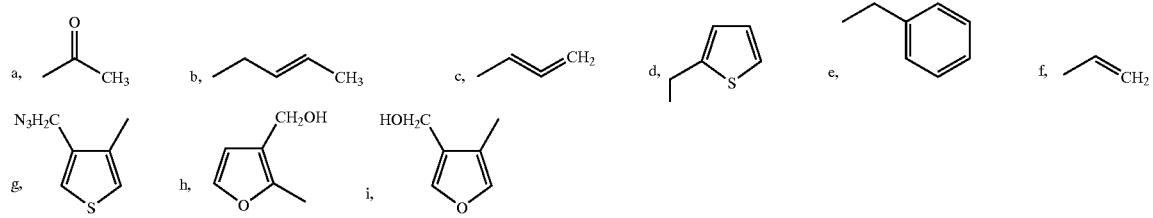

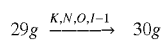

Conversion of $$29g \xrightarrow{K,N,O,I-1} 30g$$

Aldehyde 29g was converted to alcohol 29g-i by reduction with NaBH$_4$, followed by the reaction of methanesulfonyl chloride to give mesylate 29g-ii. The mesyl group was displaced with azide to give 29g-iii and finally, the MEM group was removed under acidic conditions to give 30g.

Conversion of

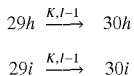

The reduction of the formyl group of 29h and 29i was accomplished with NaBH$_4$ to give corresponding alcohols 29h-i and 29i-i, respectively. Later, the MEM group was removed under acidic conditions to give 30h and 30i, respectively.

Compounds of the type 23 and 28, where X=—Sn(Bu)$_3$, are prepared using the methods AG-1 or AG-2

Scheme 7

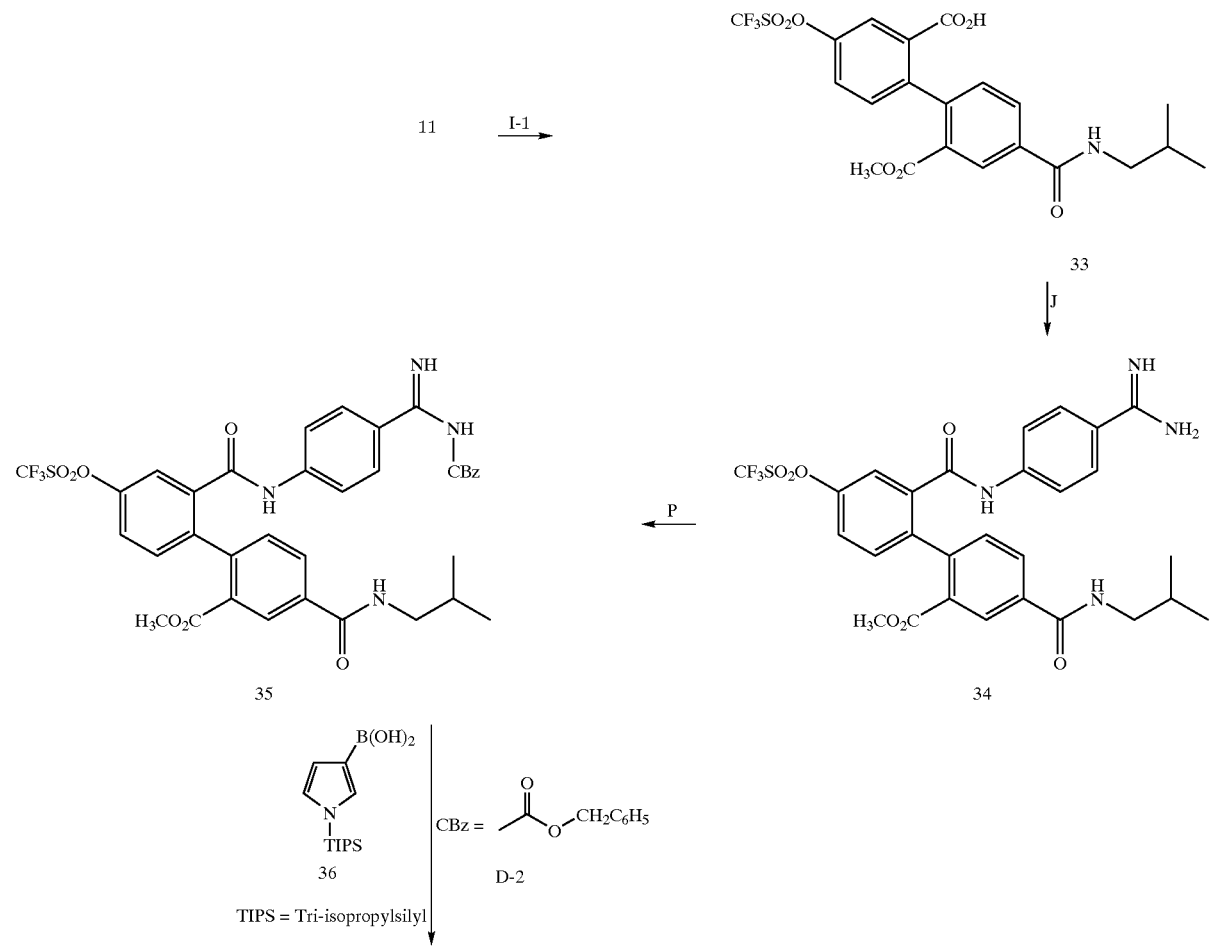

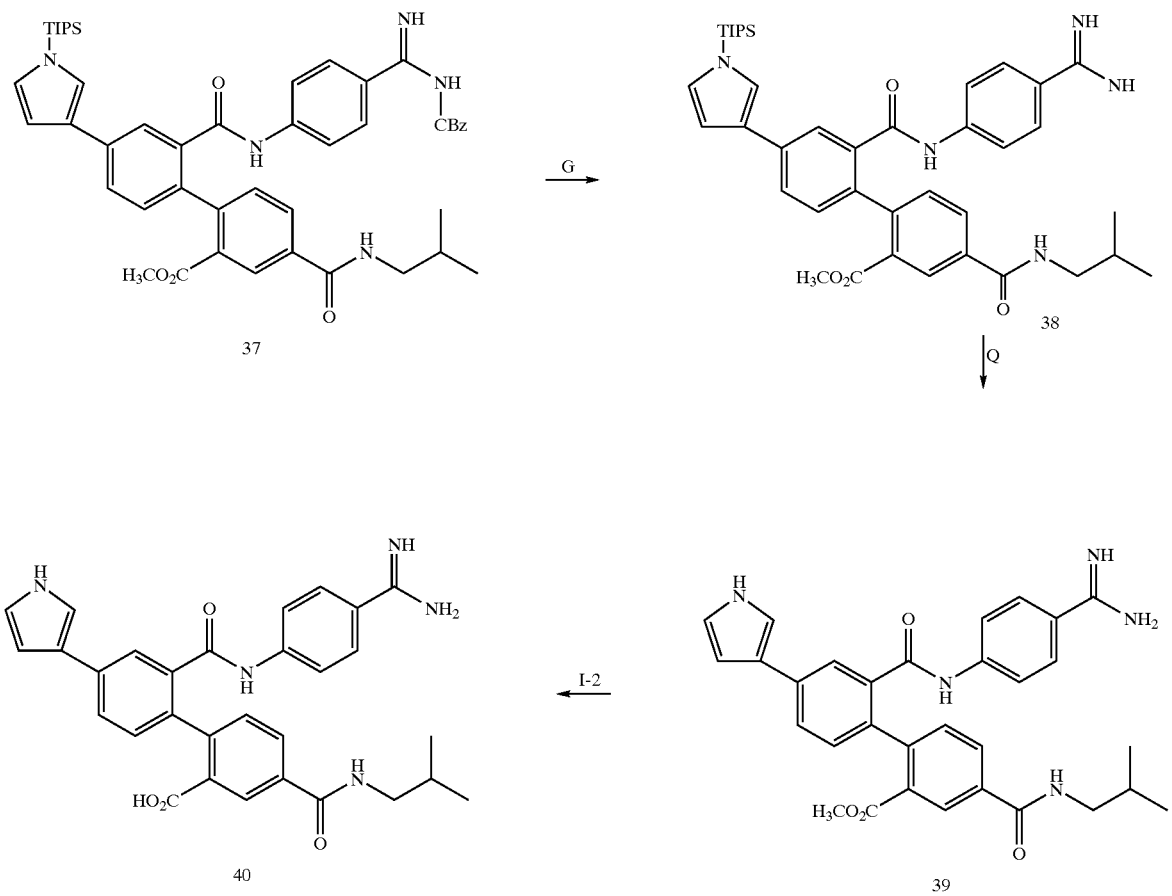
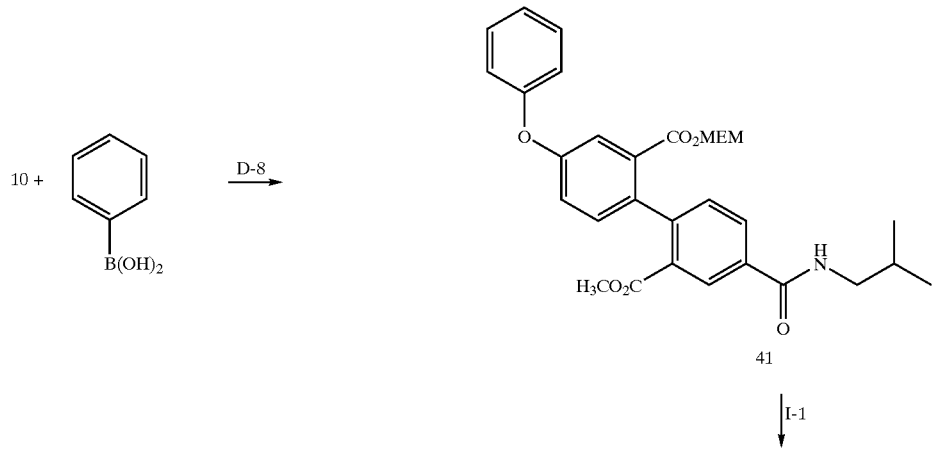
Scheme 8A

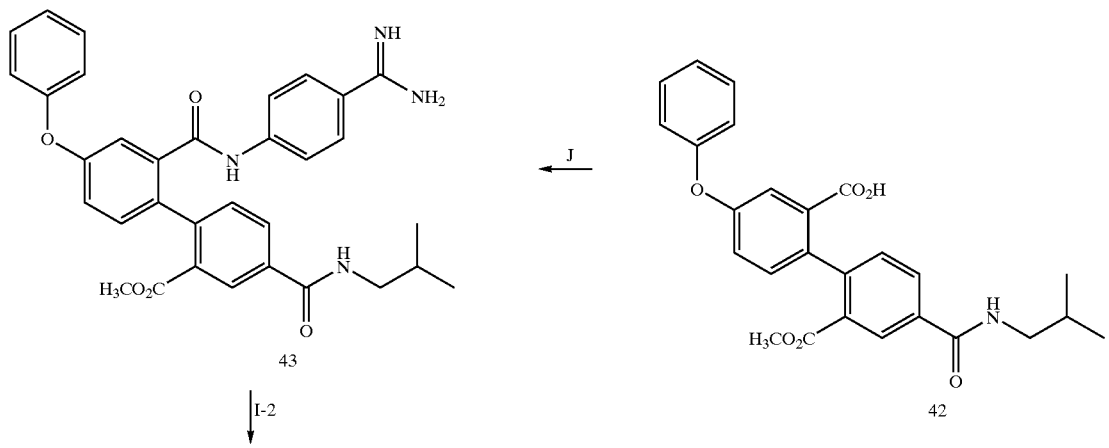
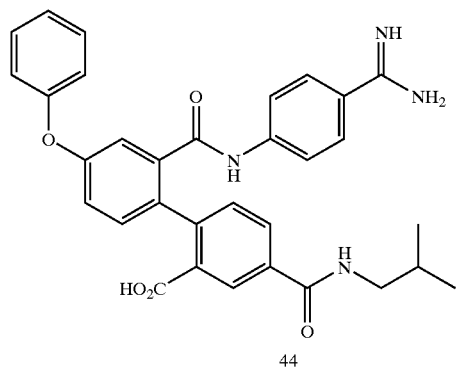
Scheme 8B
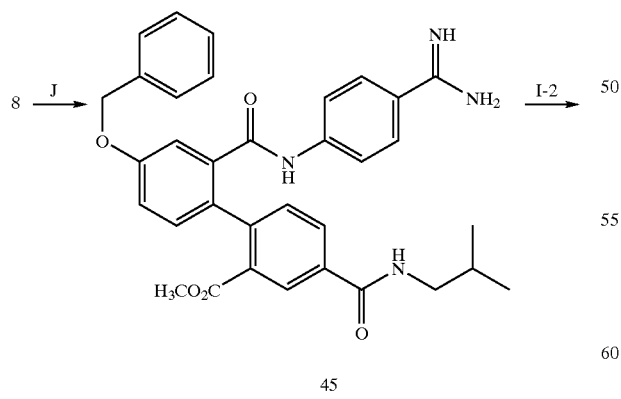
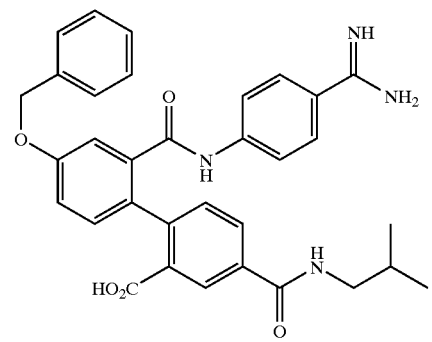

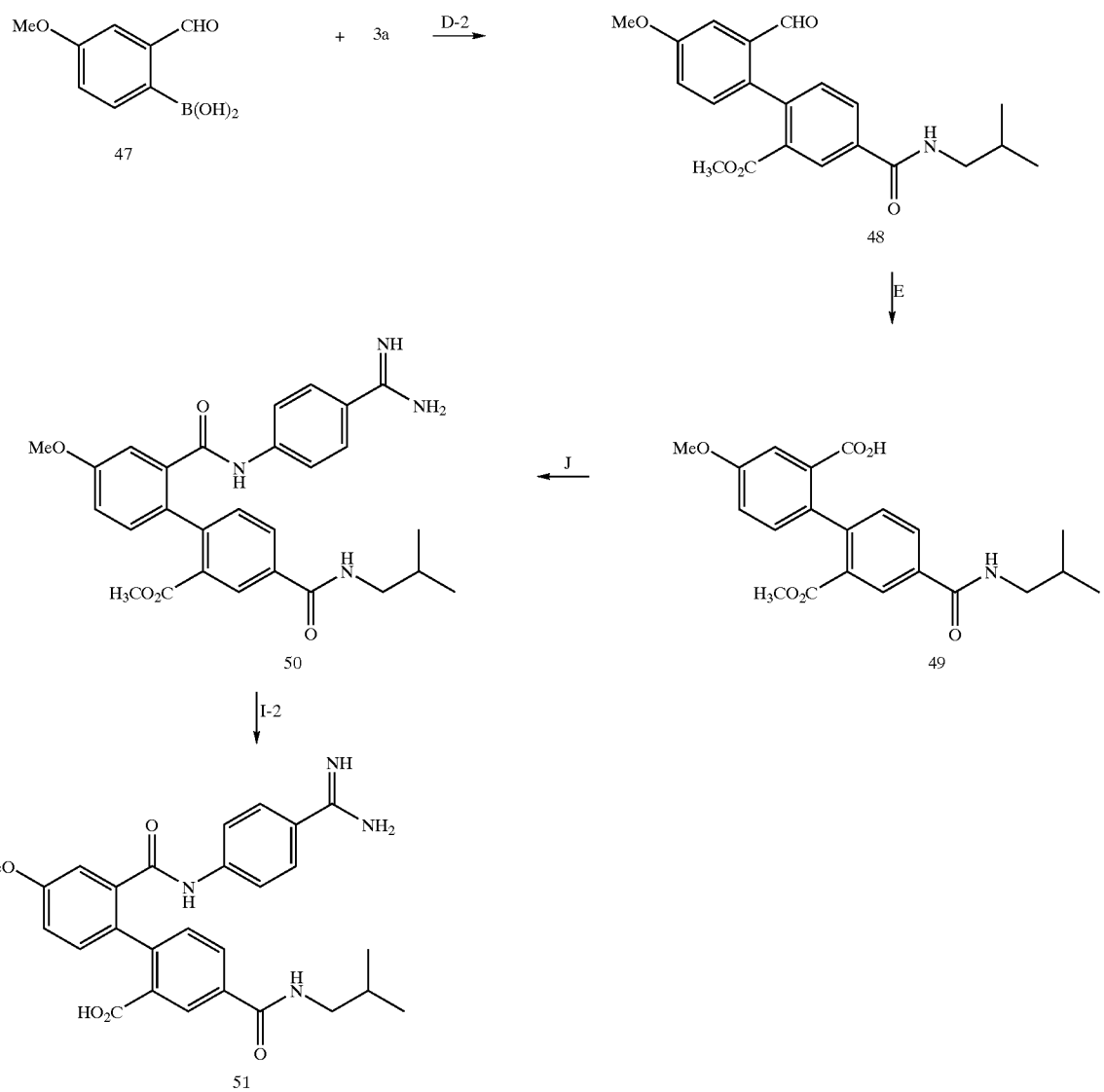
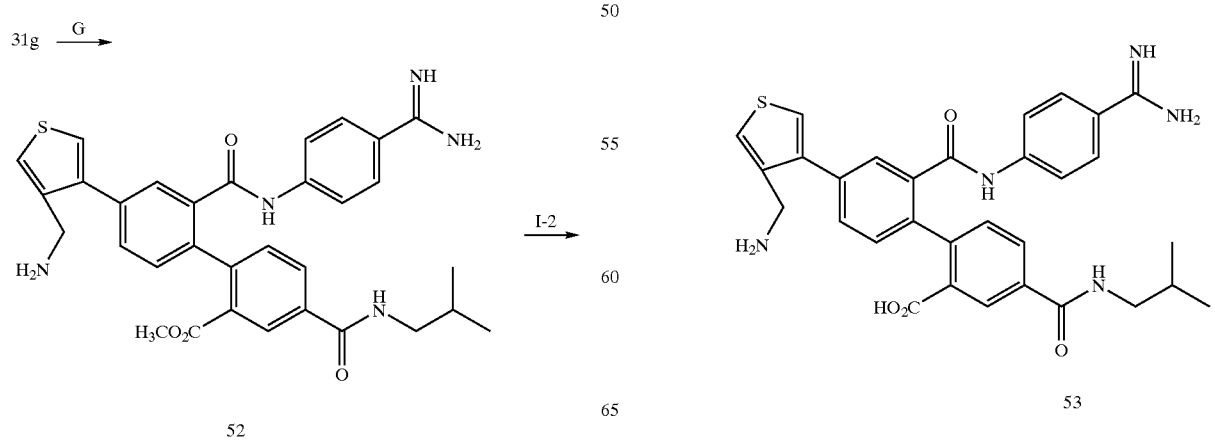
-continued

33
Scheme 8E
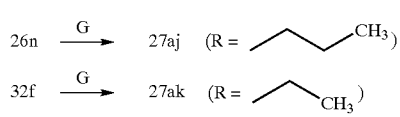
34
-continued
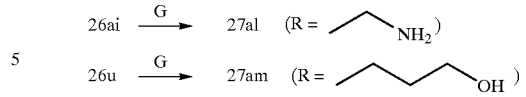
Scheme 9
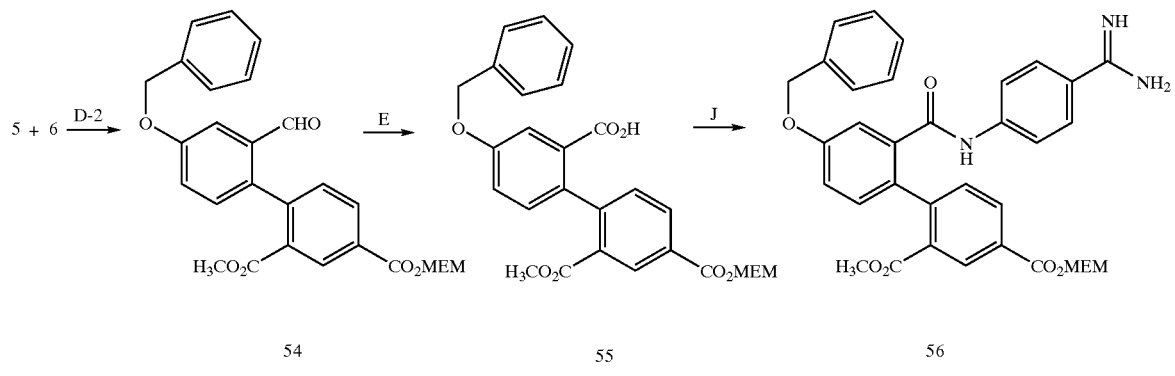
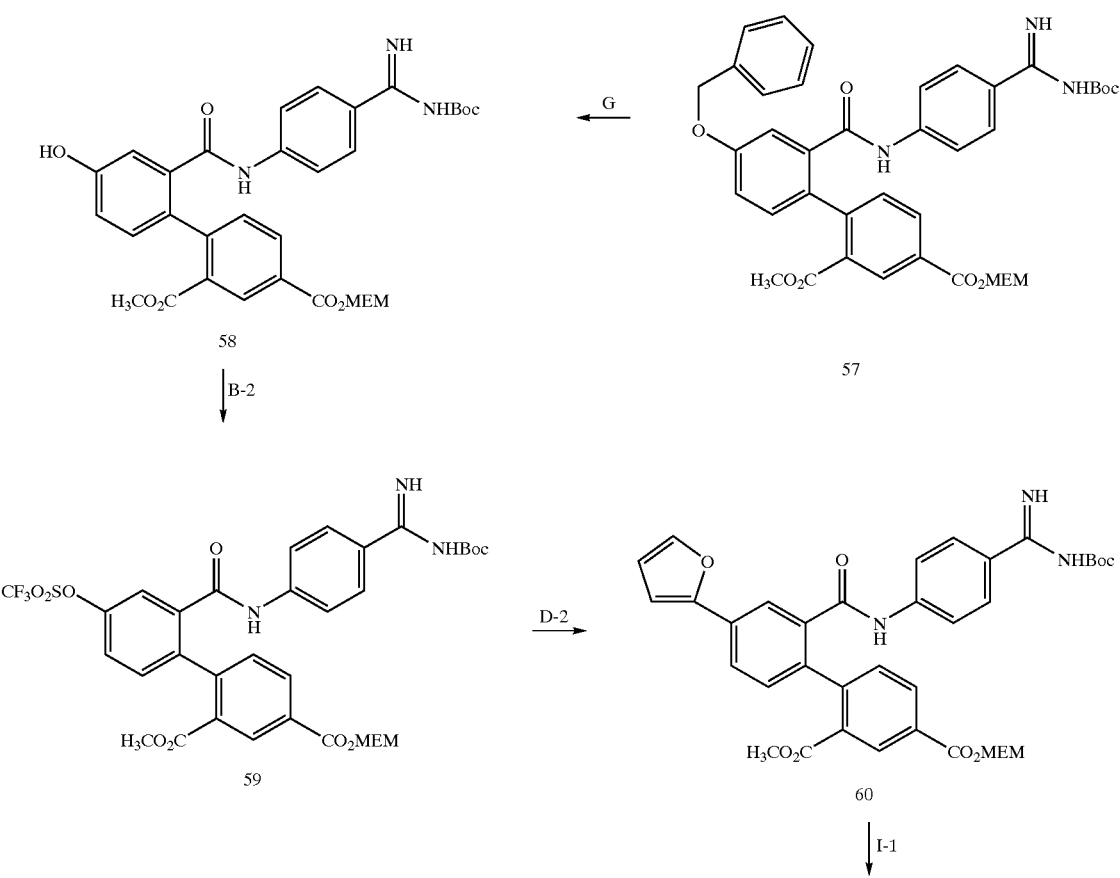

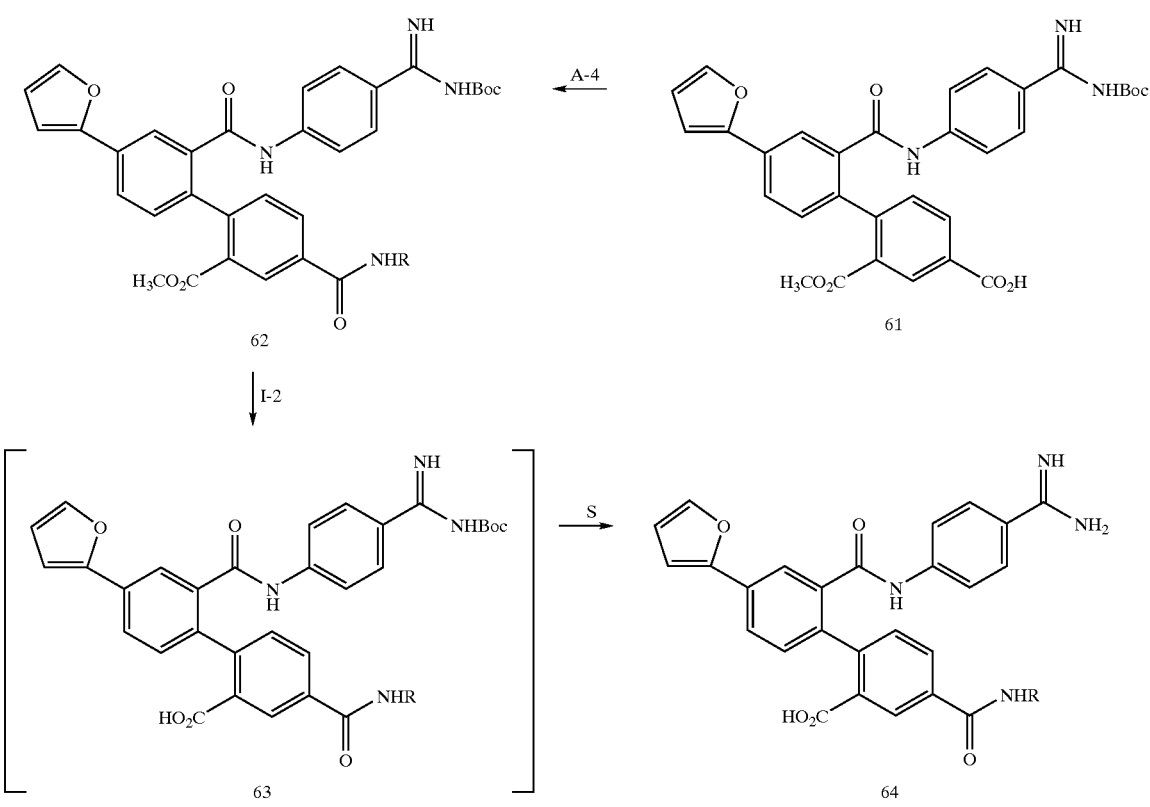
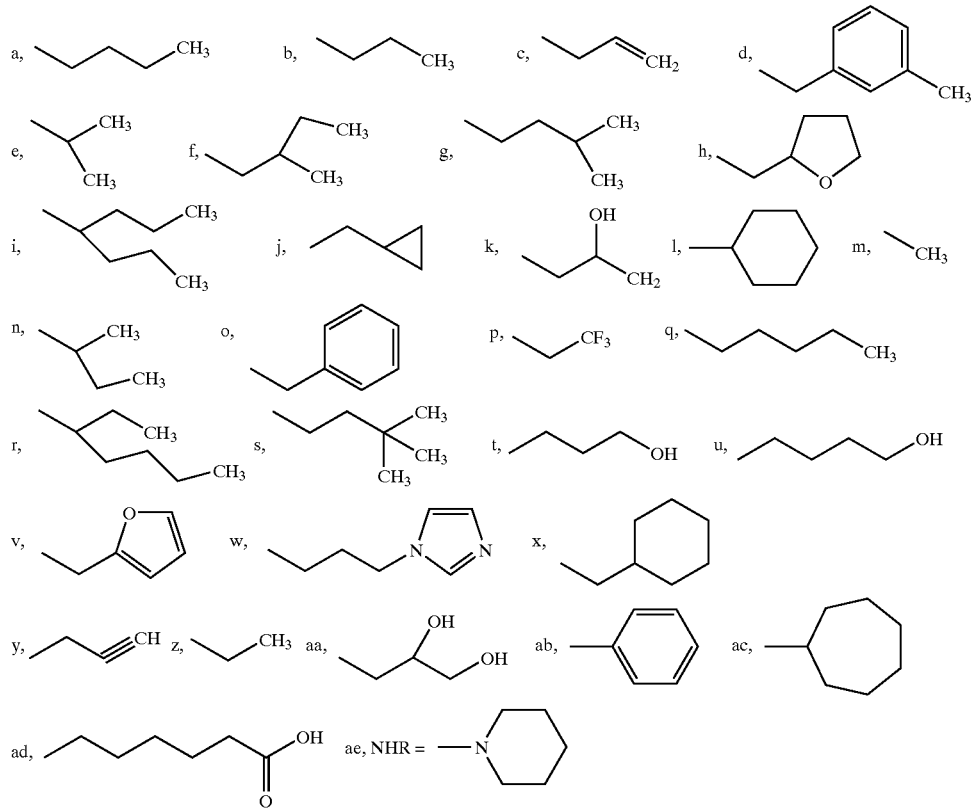

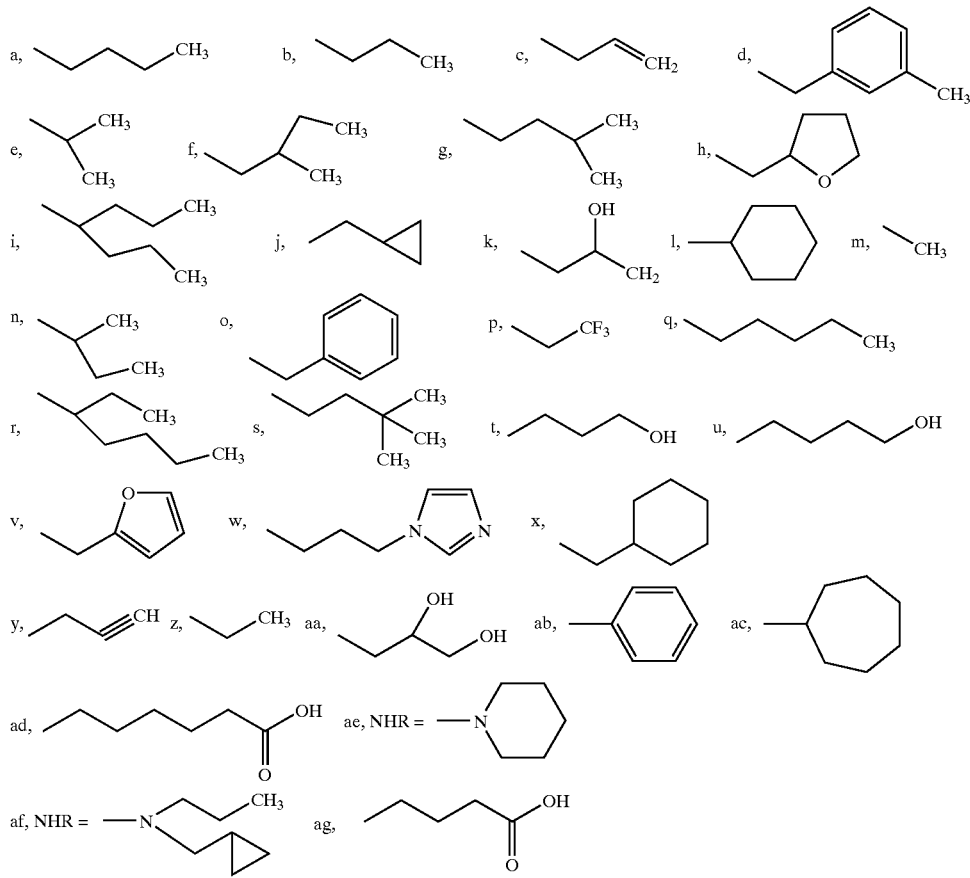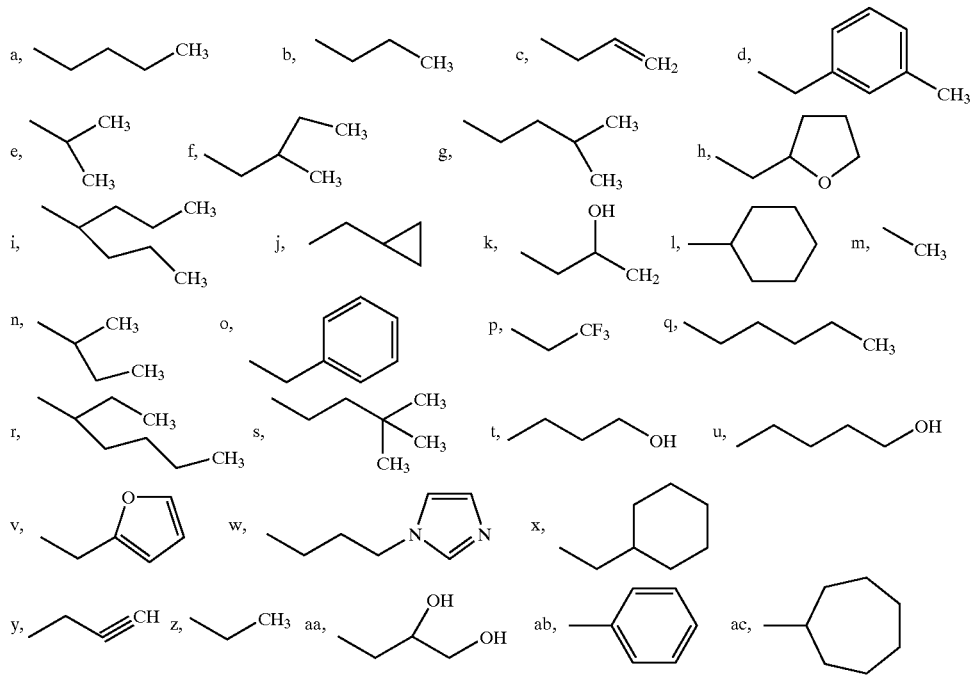

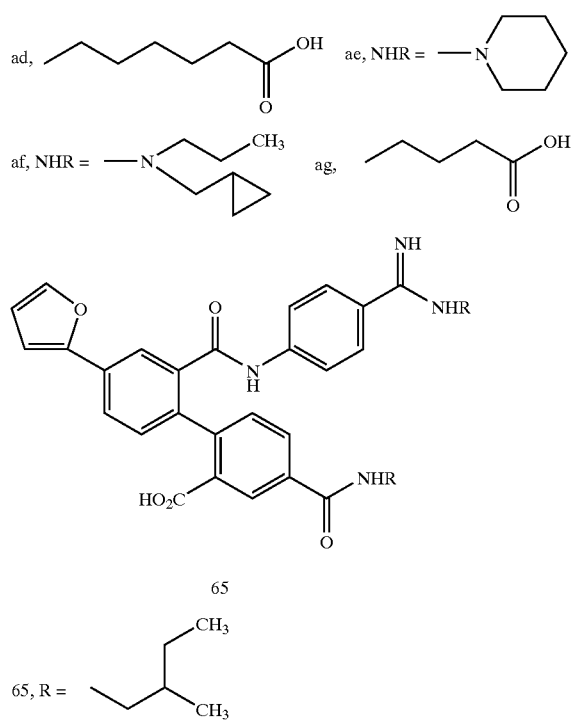
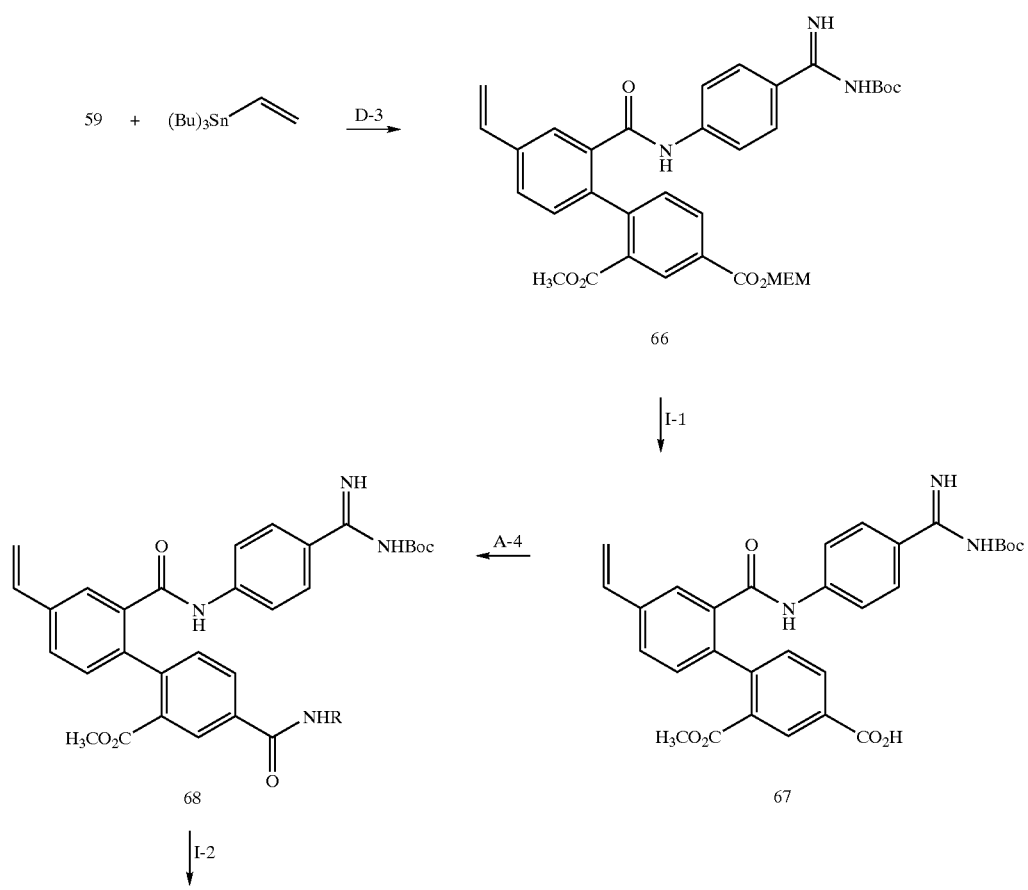

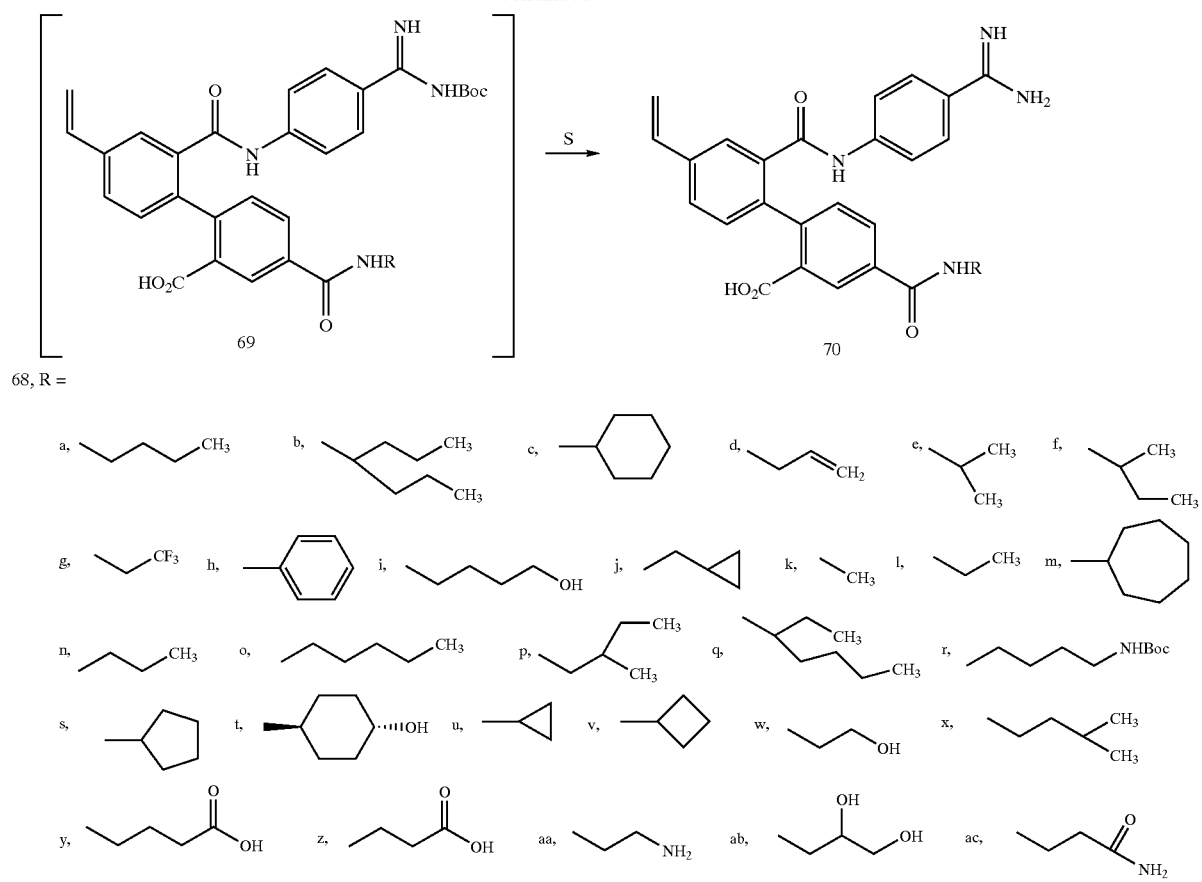
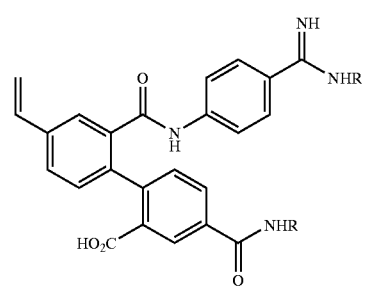

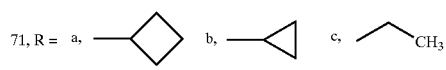
71, R = a, cyclobutyl  b, cyclopropyl  c, CH₃ (ethyl)
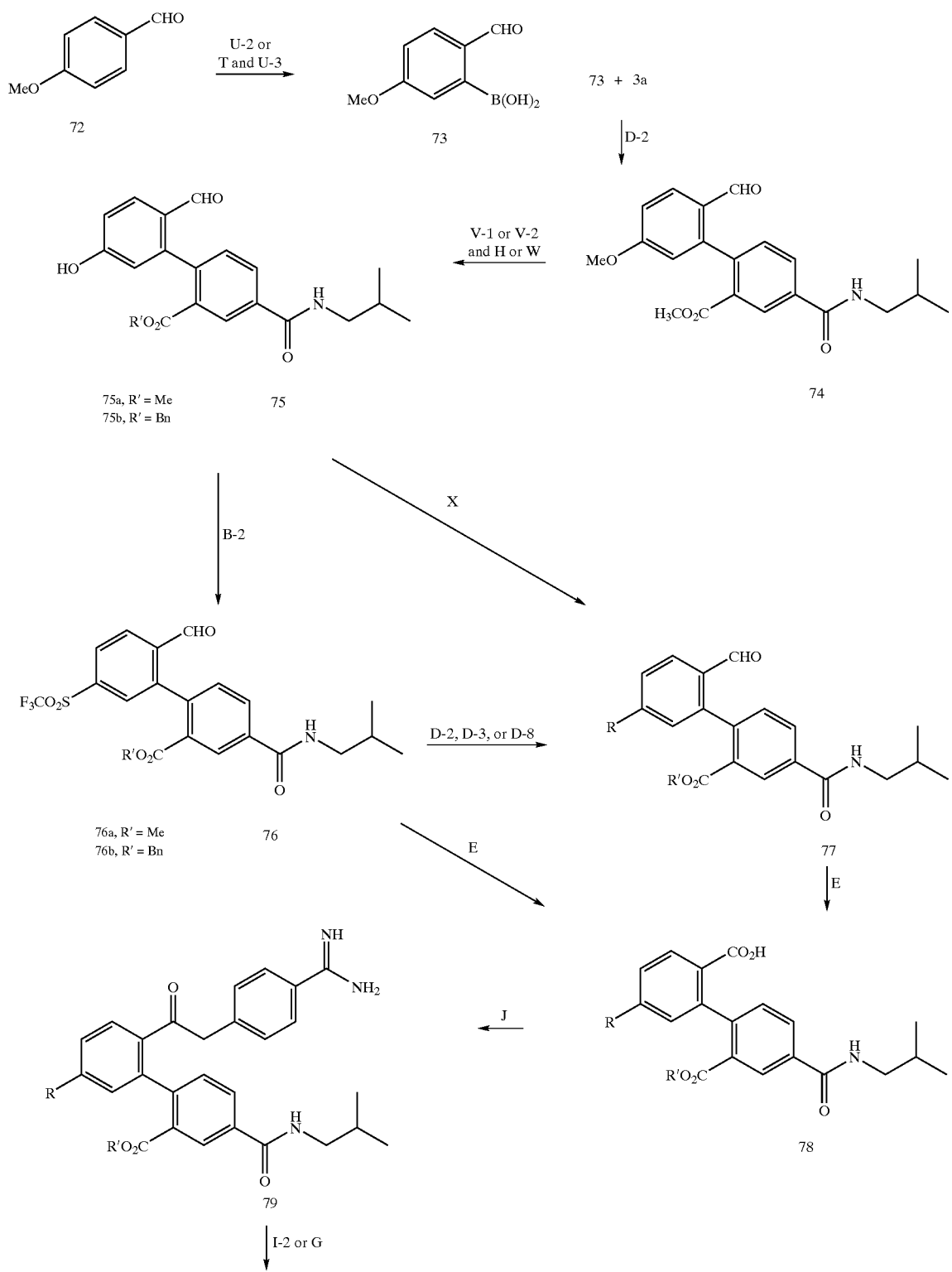
Scheme 11

-continued
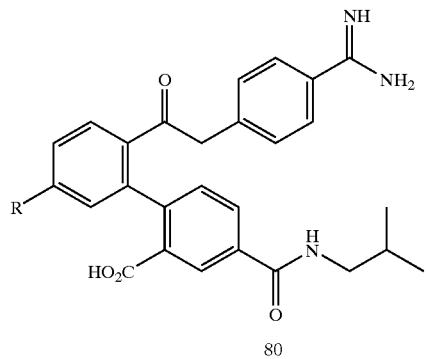
80
77a, 78a, 80a, R = —C(H)=CH₂; R' = CH₂    78b, 79b, R = OSO₂CF₃; R' = Bn; 80b, R = OH    77b, 78c, 79c, R = —O—CH₂CO₂C₂H₅; R' = Bn; 80c, R = —O—CH₂CO₂H
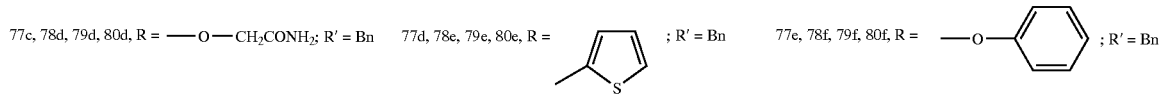
77c, 78d, 79d, 80d, R = —O—CH₂CONH₂; R' = Bn    77d, 78e, 79e, 80e, R = (2-methylthiophene); R' = Bn    77e, 78f, 79f, 80f, R = —O—Ph; R' = Bn
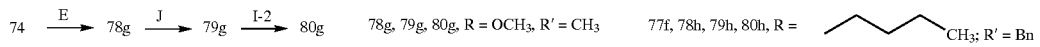
74 →E 78g →J 79g →I-2 80g    78g, 79g, 80g, R = OCH₃, R' = CH₃    77f, 78h, 79h, 80h, R = pentyl-CH₃; R' = Bn
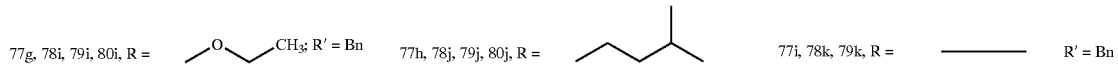
77g, 78i, 79i, 80i, R = —OCH₂CH₂OCH₃; R' = Bn    77h, 78j, 79j, 80j, R = isohexyl    77i, 78k, 79k, R = ethynyl; R' = Bn
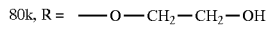
80k, R = —O—CH₂—CH₂—OH
Scheme 12
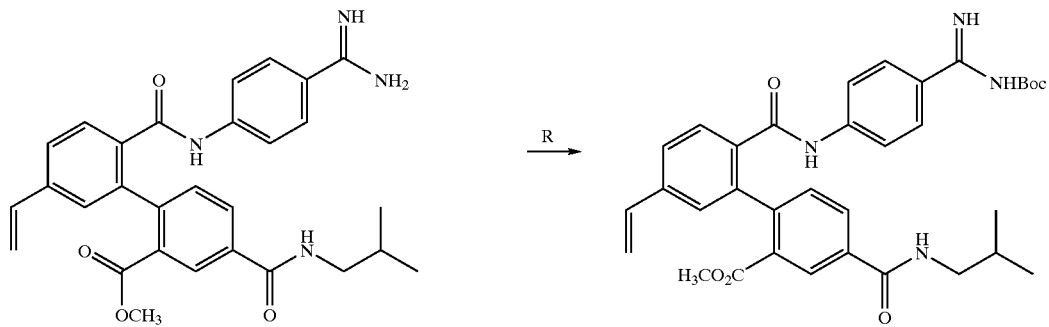
79a  →R  81  ↓L -continued
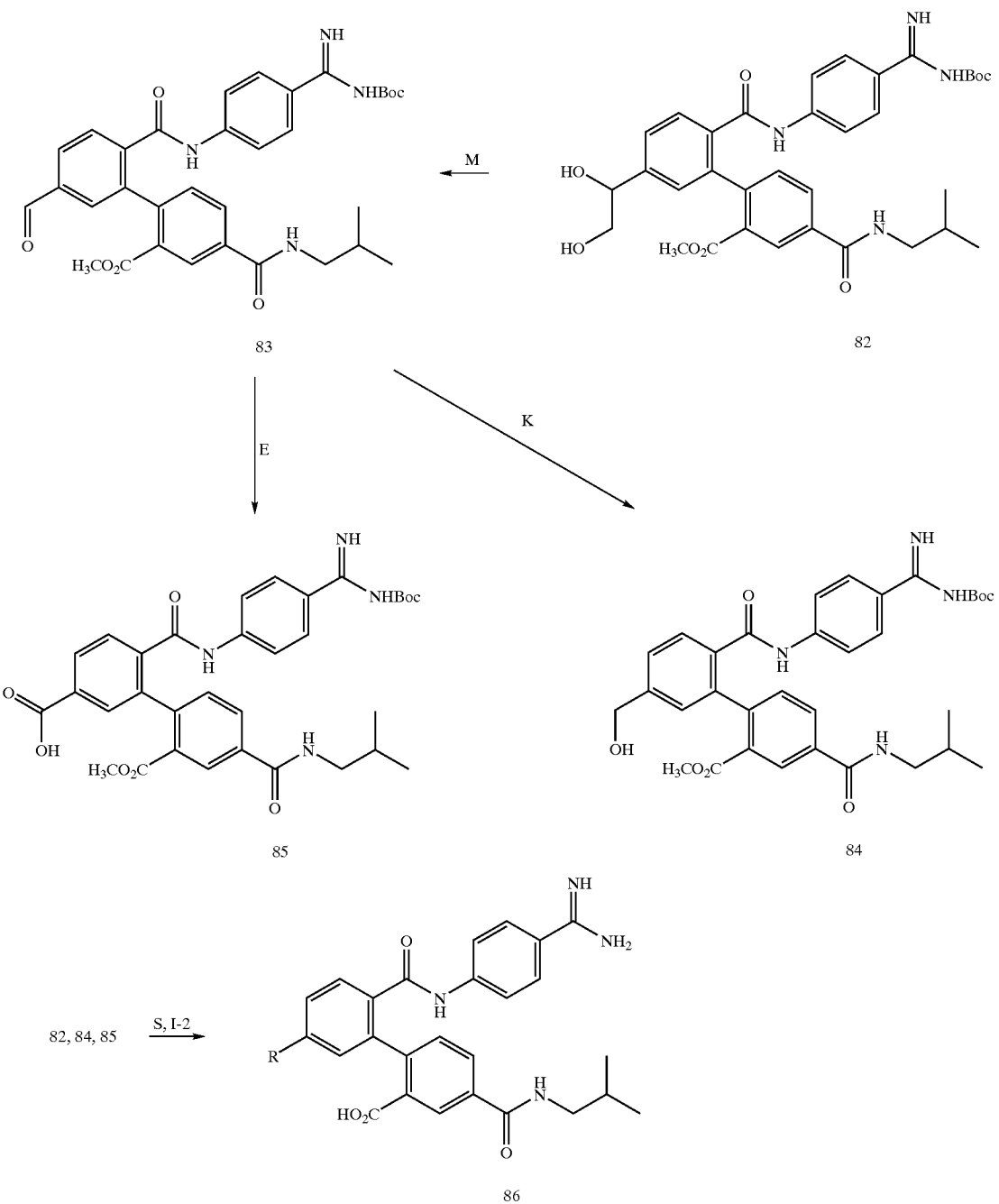
86a, R = CH(OH)CH₂OH
86b, R = CH₂OH
86c, R = CO₂H
Scheme 13
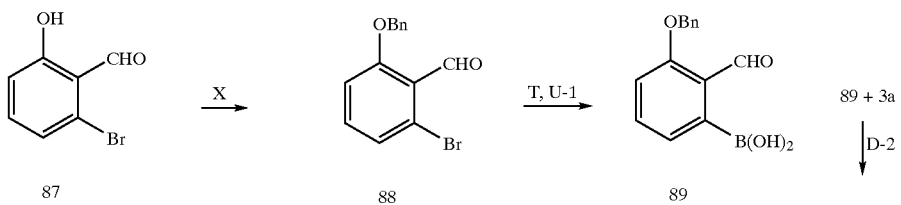

-continued
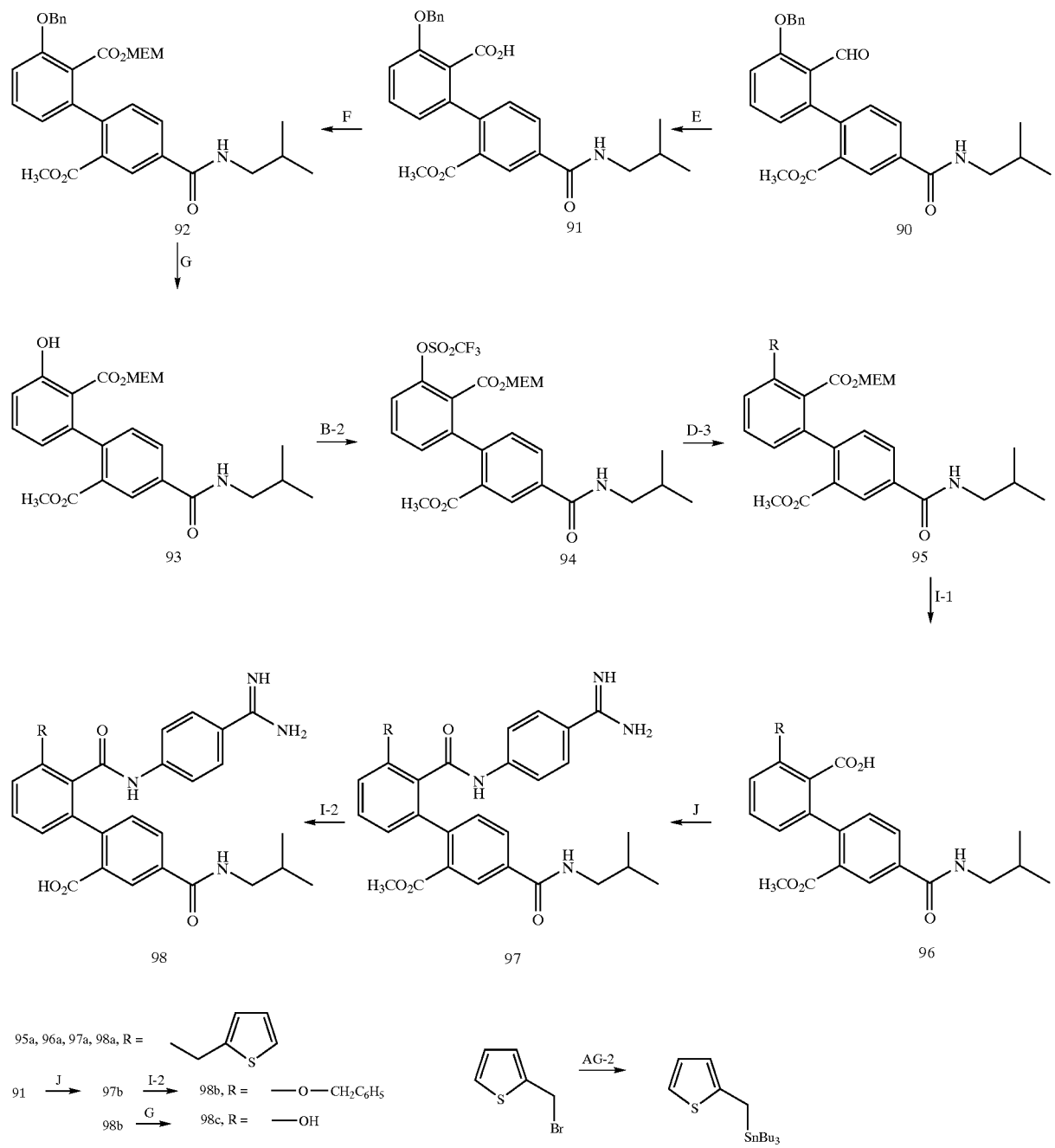
Scheme 14
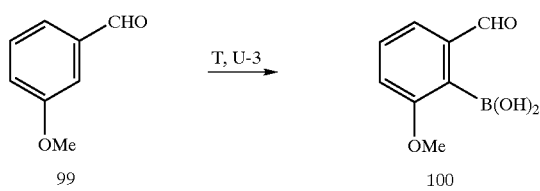

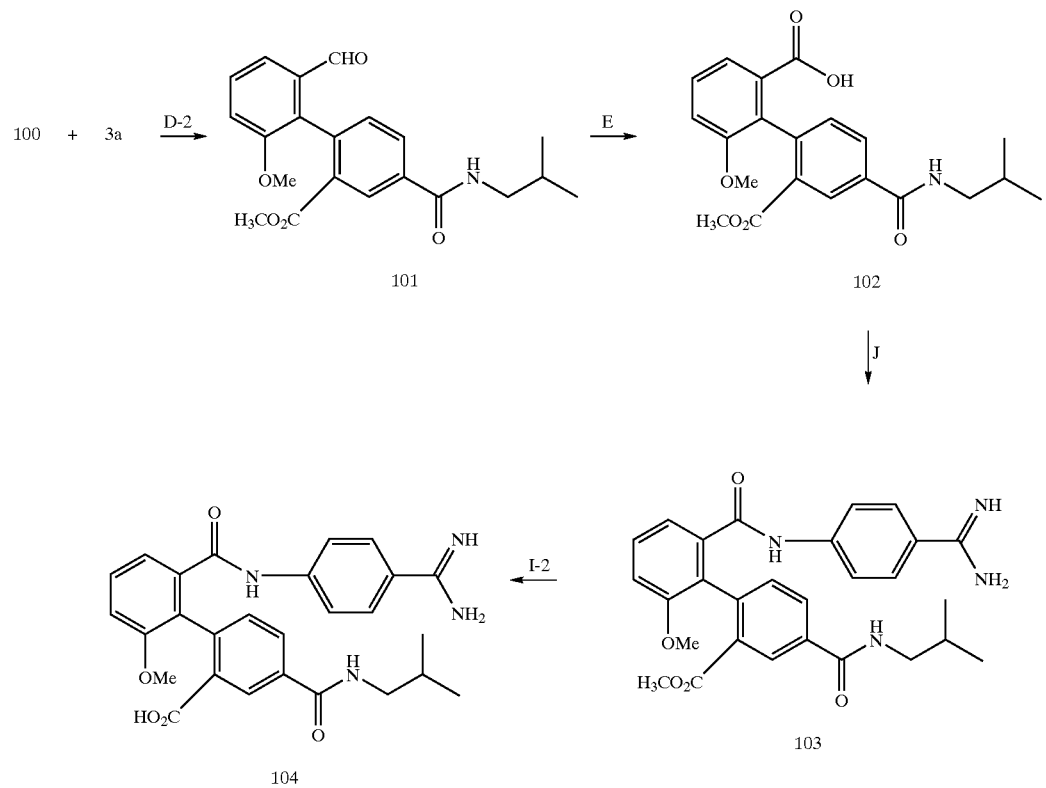
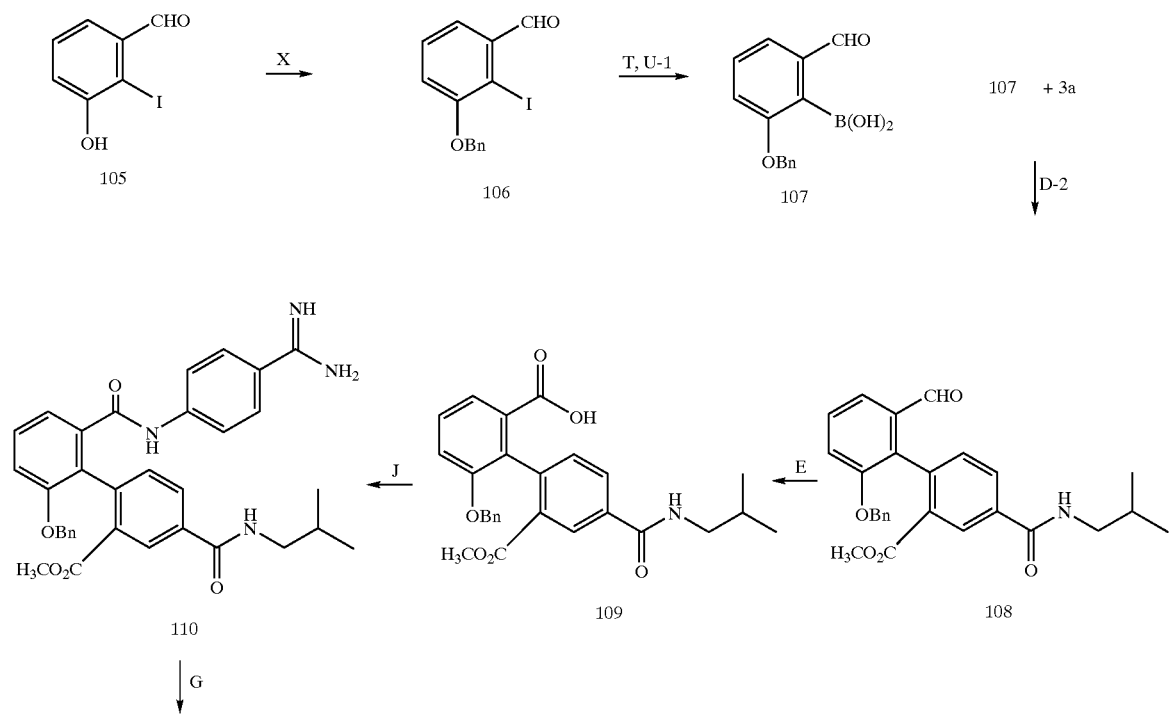

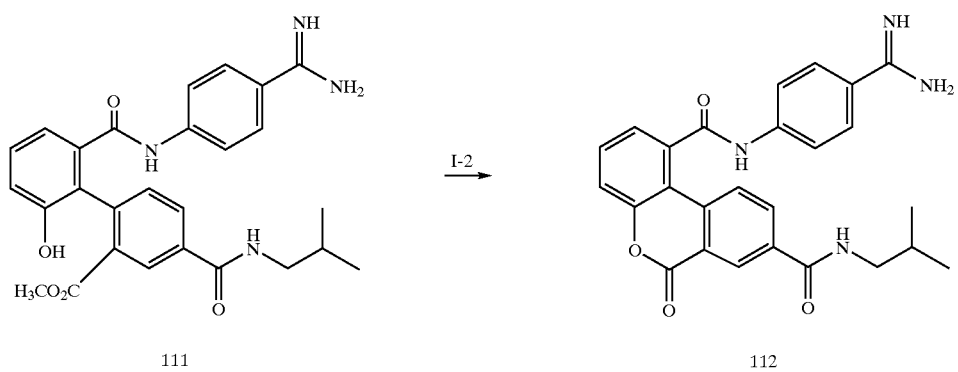
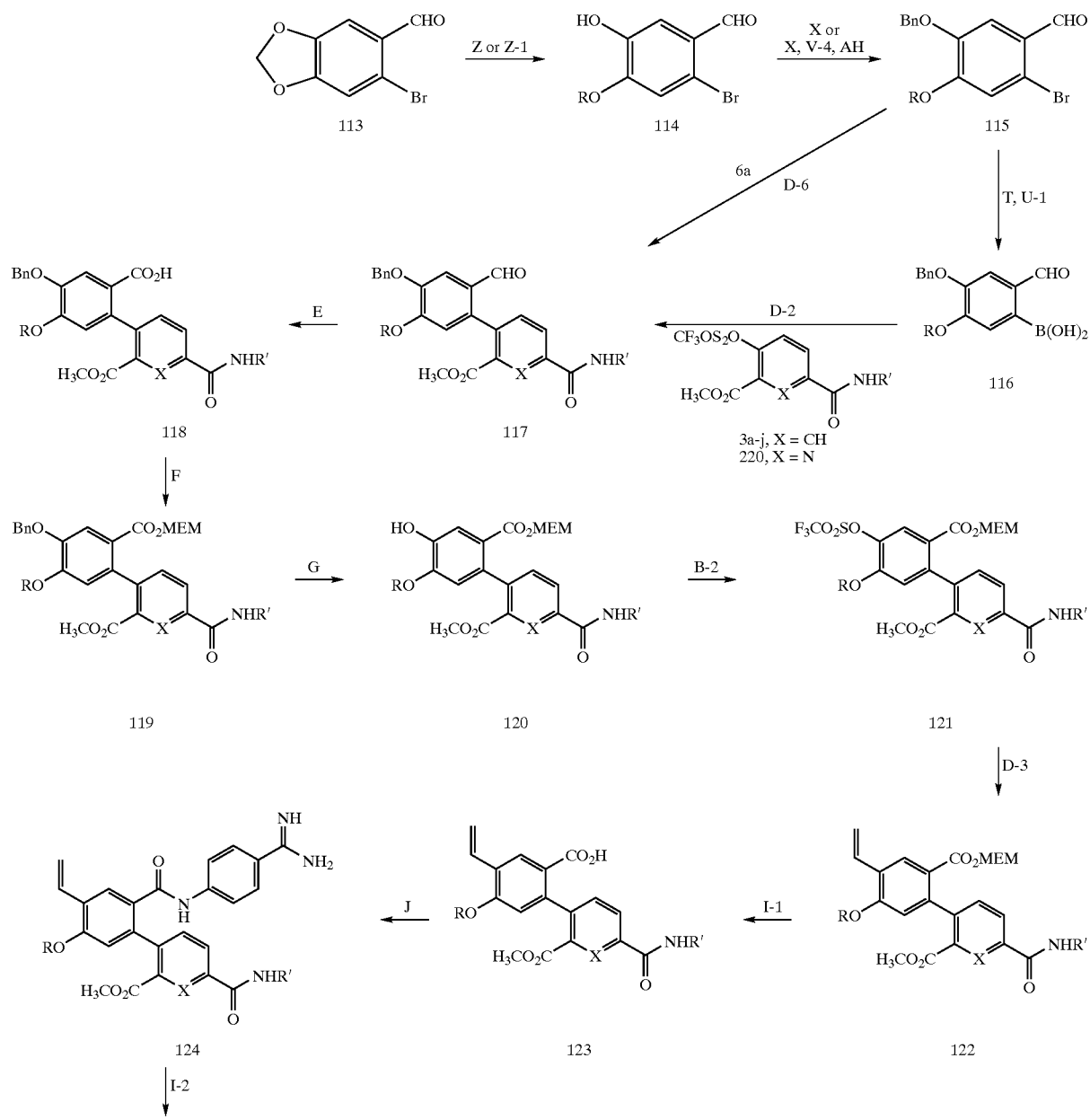
Scheme 16

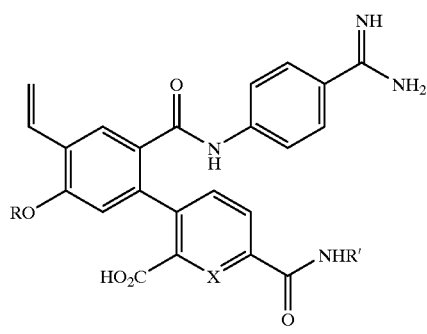

125

114a, 115a, 116a, R = CH₃;  114b, 115b, 116b, R = C₂H₅;  114c, 115c, 116c, R = —CH(CH₃)₂;  115d, R = —C(=O)—C(CH₃)₃

117a–125a, R = CH₃; R' = isobutyl; X = CH    117b–125b, R = C₂H₅; R' = isobutyl; X = CH    117c–125c, R = CH(CH₃)₂; R' = isobutyl; X = CH 117d–125d, R = CH₃; R' = isopropyl with CH₃; X = CH    117e–125e, R = CH₃; R' = 2-ethylpentyl; X = CH 117f–125f, R = CH₃; R' = n-pentyl; X = CH    117g–125g, R = CH₃; R' = CH₂CH₂CF₃; X = CH    117h–125h, R = CH₃; R' = n-hexyl; X = CH 117i–125i, R = CH₃; R' = cyclopropylmethyl; X = CH    117j–125j, R = CH₃; R' = cyclopentyl; X = CH    117k–125k, R = CH₃; R' = n-propyl; X = CH 117l–125l, R = CH₃; R' = 2-methylbutyl; X = CH    117m–124m, R = —C(=O)—C(CH₃)₃; R' = isobutyl; X = CH 125m, R = H; R' = isobutyl; X = CH    117n–125n, R = CH₃, X = N, R' = isobutyl Scheme 16a 118b $\xrightarrow{J}$

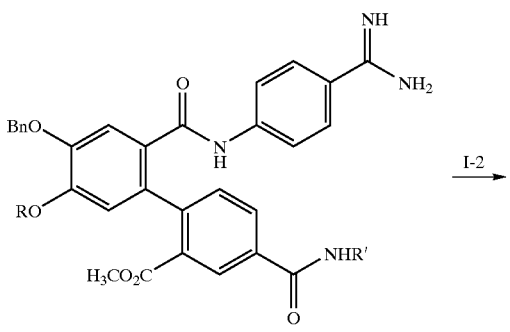

126

$\xrightarrow{I-2}$

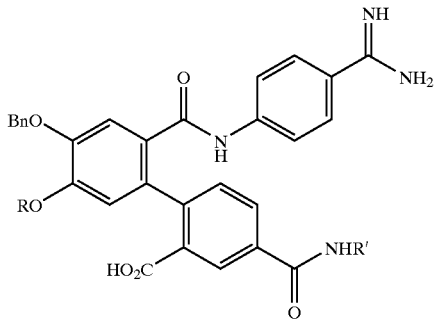

127

126, 127, R = C₂H₅; R' = isobutyl

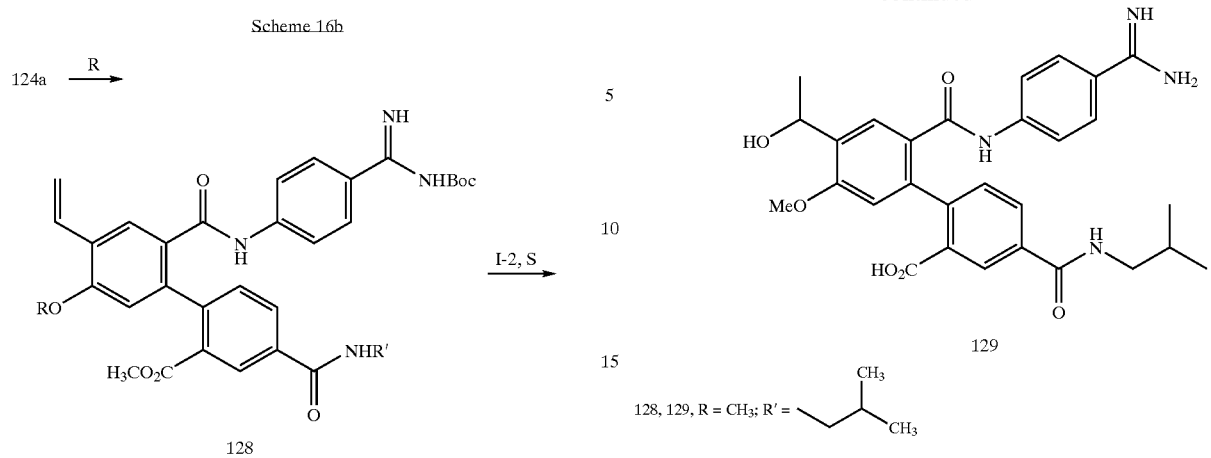
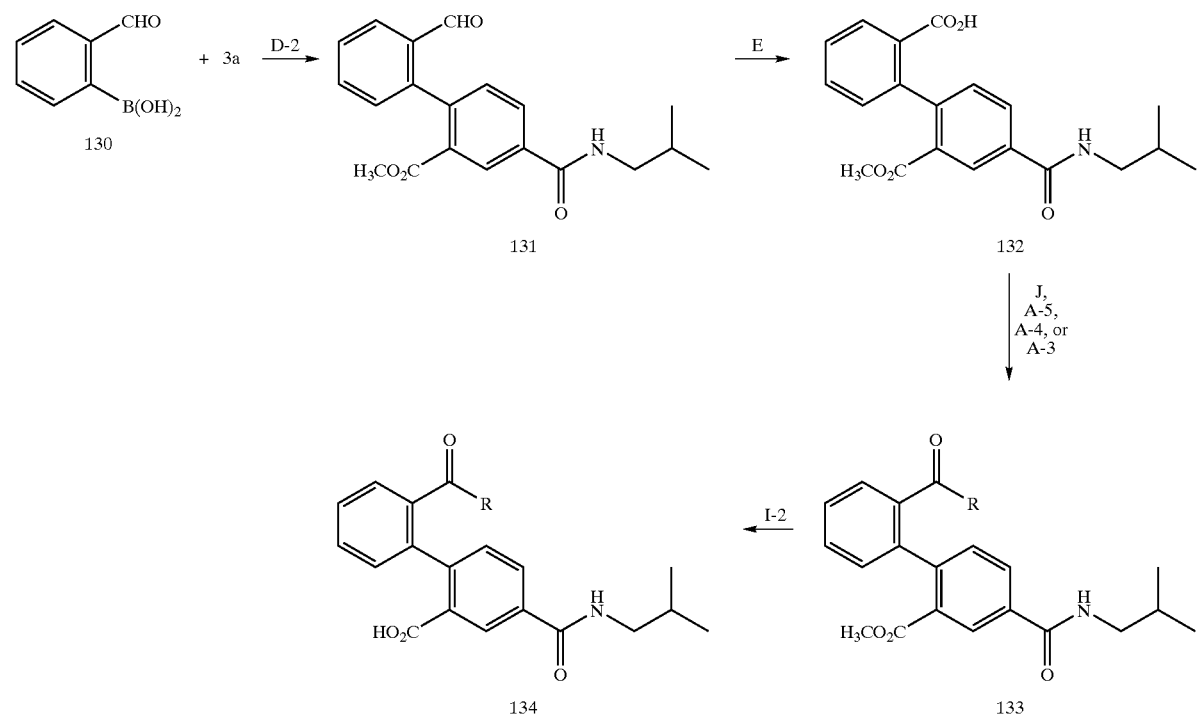
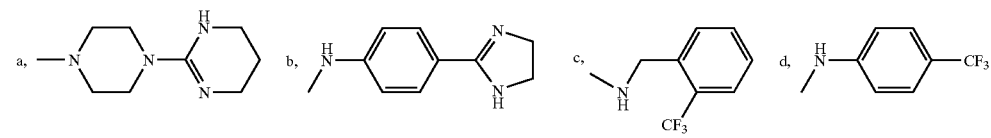
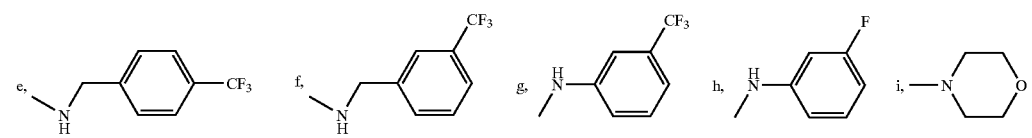

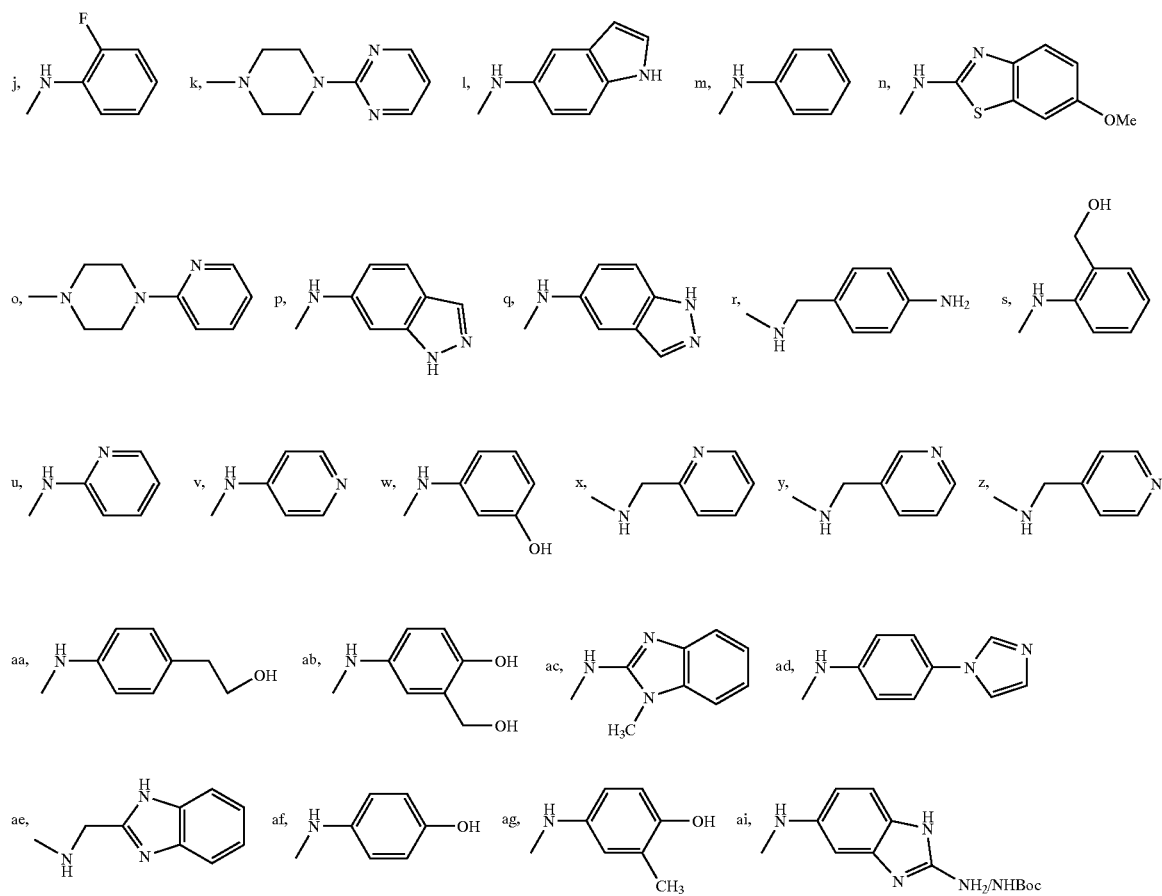
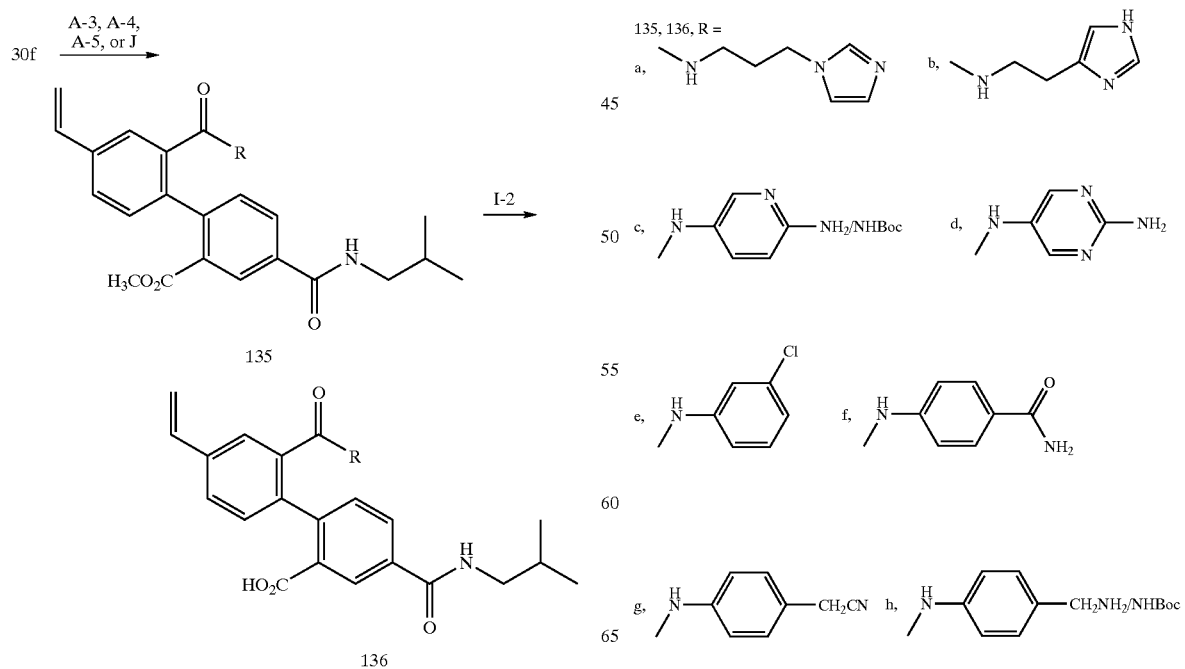

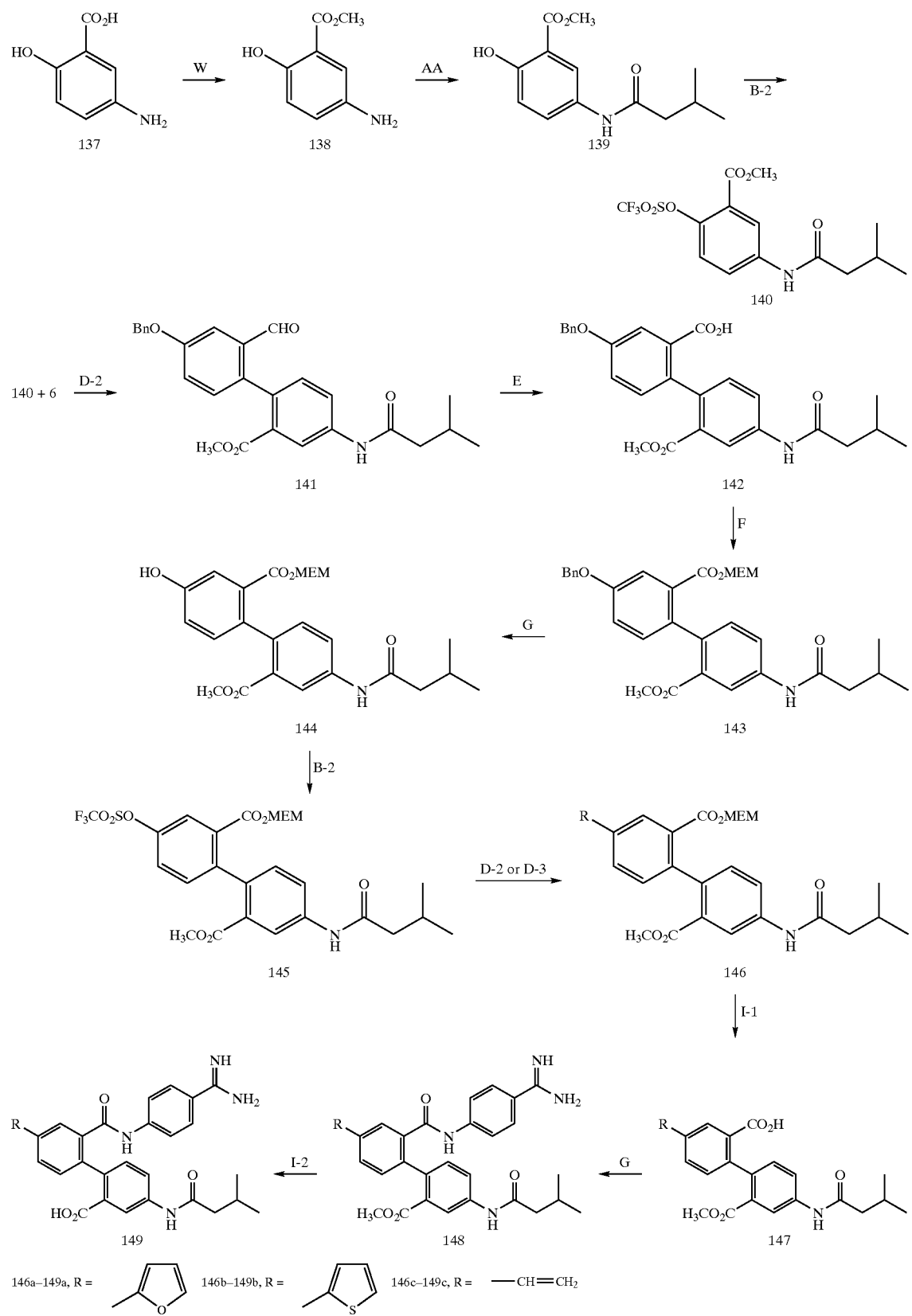

Scheme 19
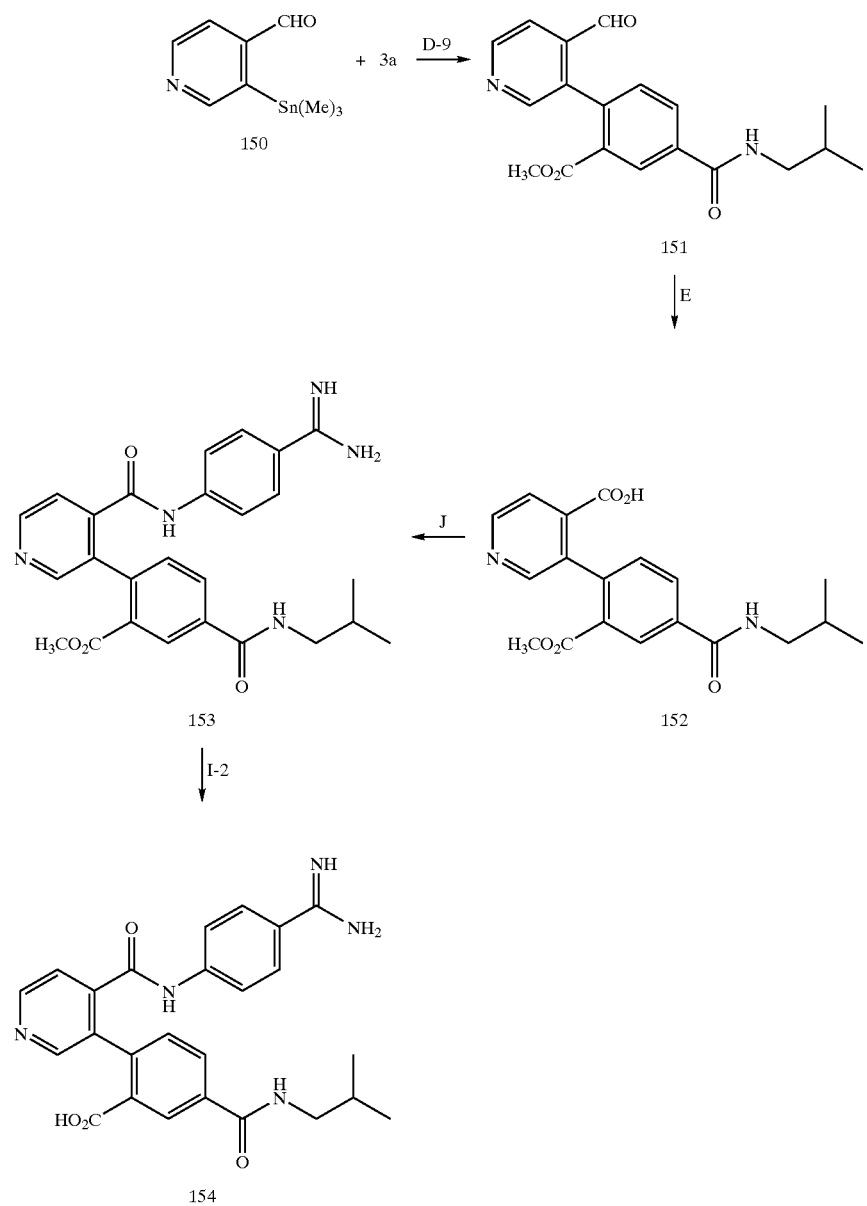
Scheme 19a
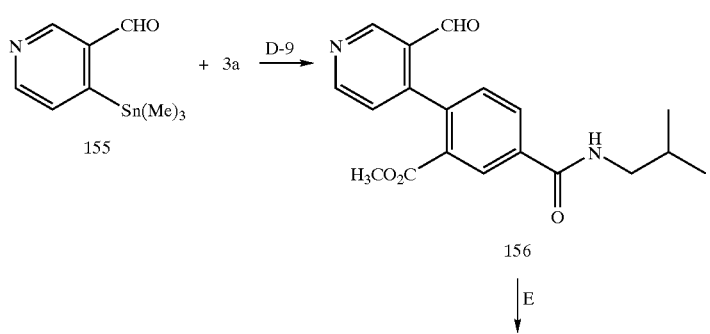

-continued
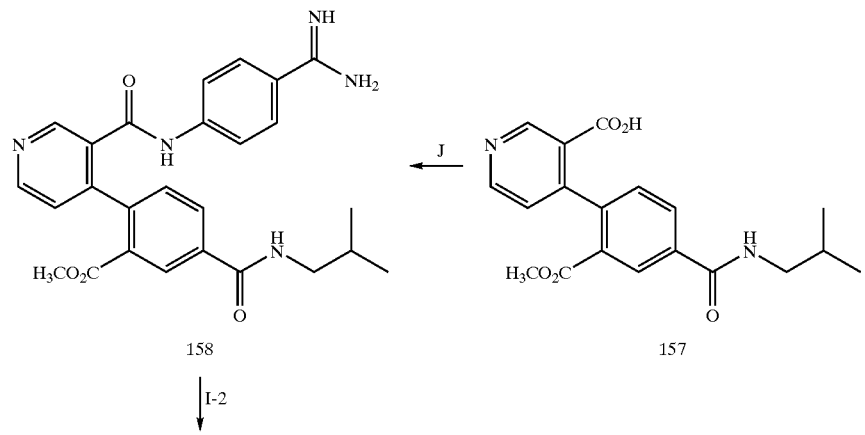
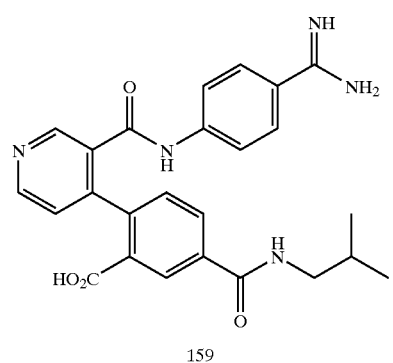
Scheme 20
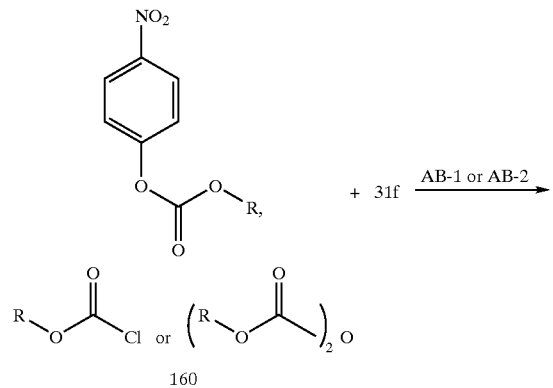
-continued
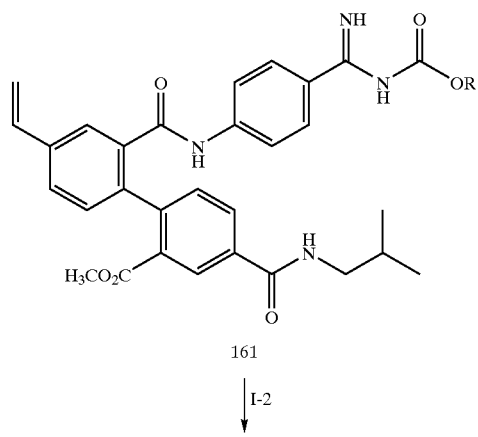

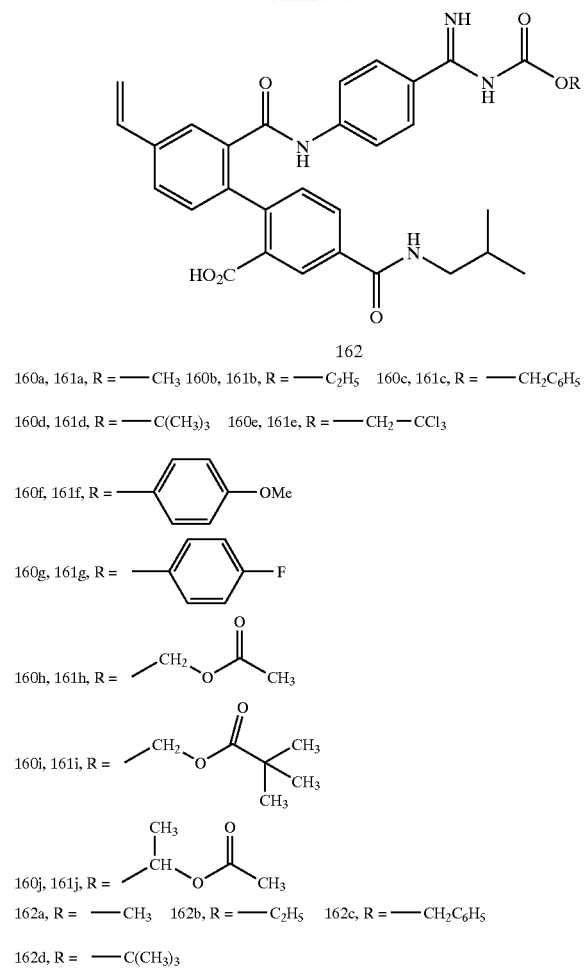
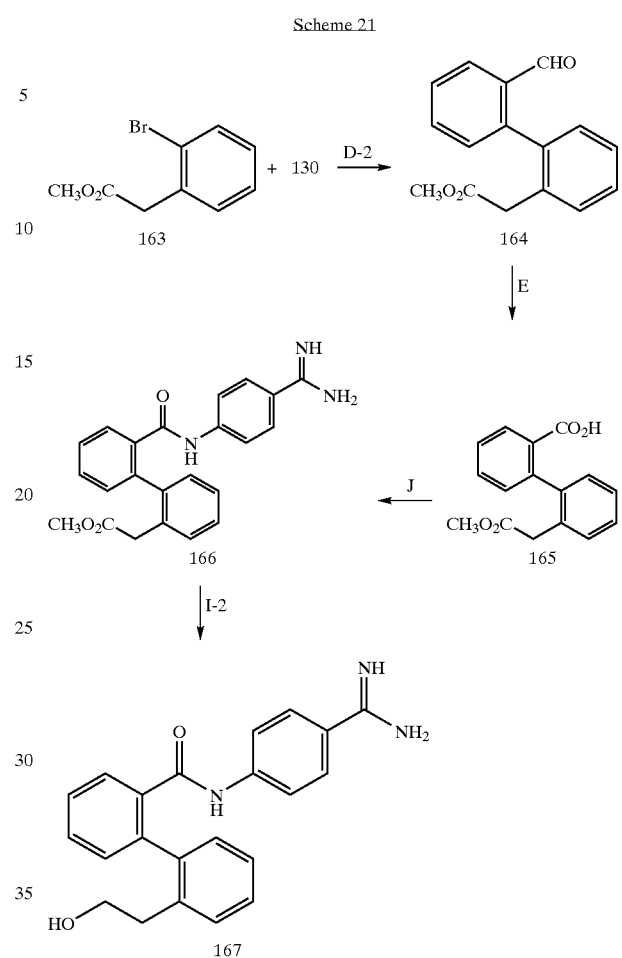
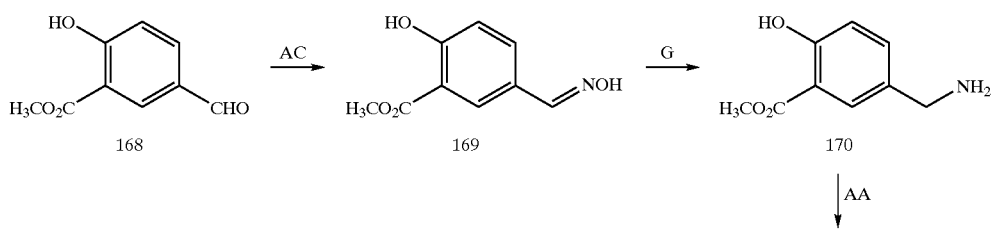
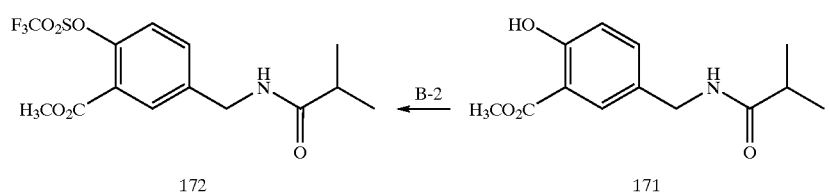

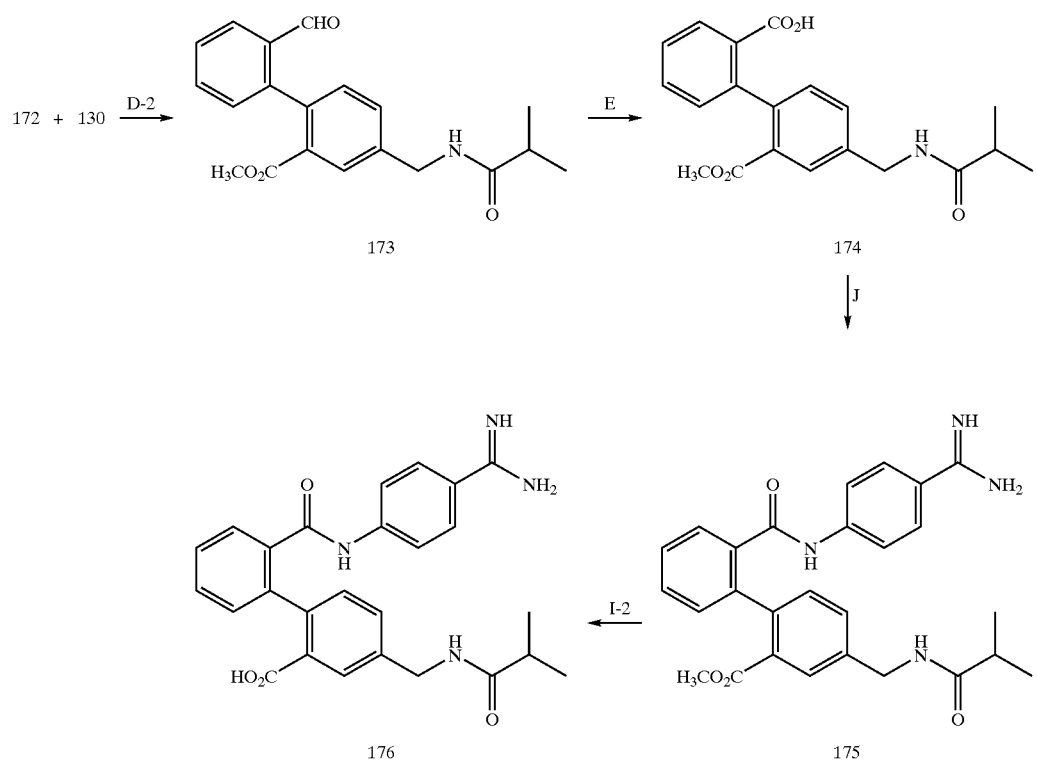
Scheme 23
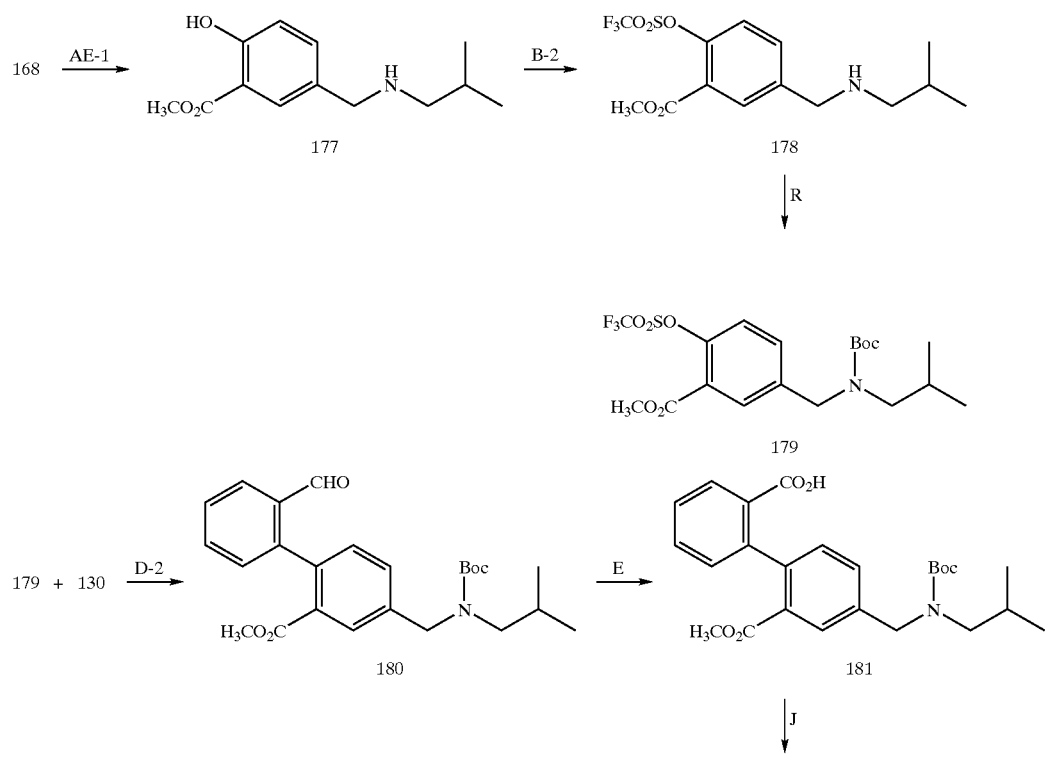

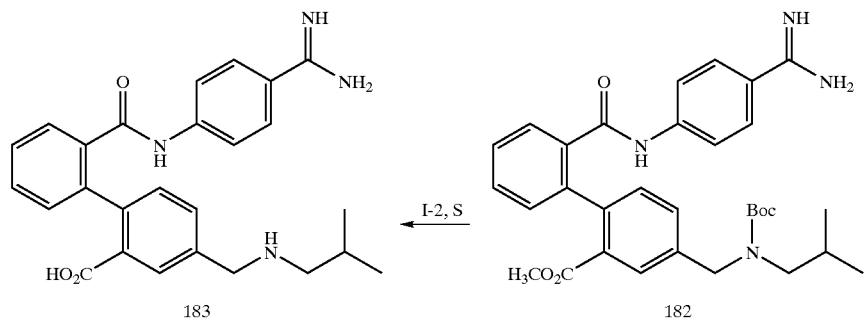
Scheme 24
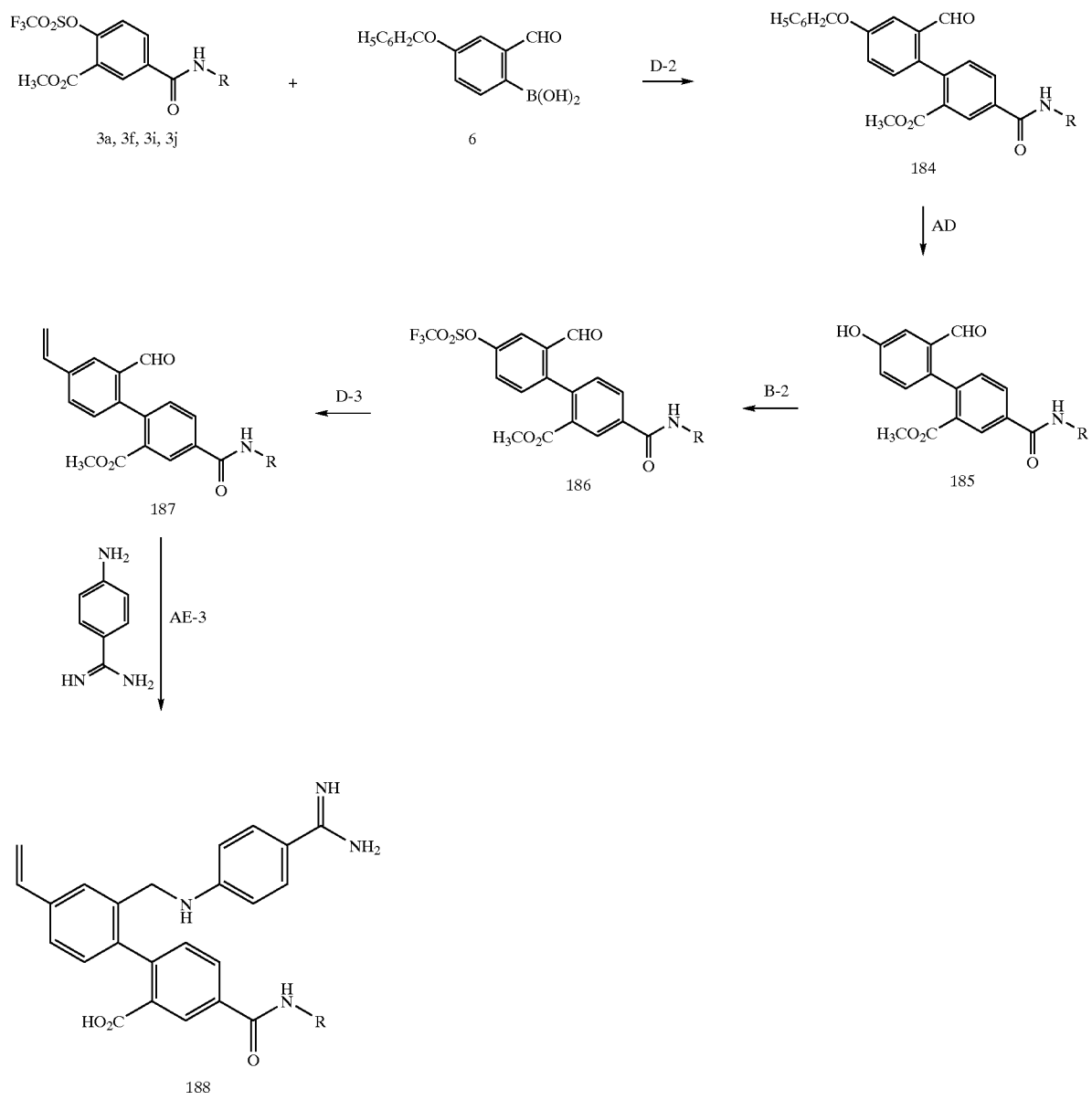

3a, 184a, 185a, 186a, 187a, 188a, R = 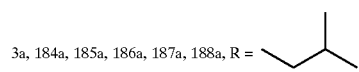
3f, 184b, 185b, 186b, 187b, 188b, R = CH₂CF₃
3i, 184c, 185c, 186c, 187c, 188c, R = CH₂CH₃
3j, 184d, 185d, 186d, 187d, 188d, R = 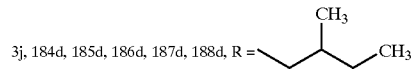
Scheme 25
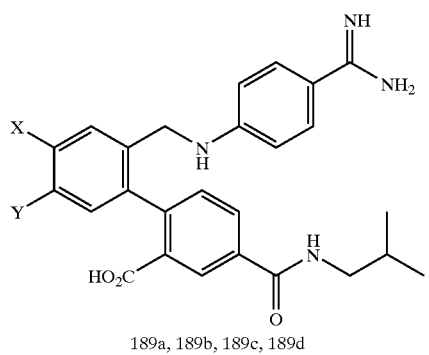
189a, 189b, 189c, 189d
74 —AE-4, I-2→ 189a
184a —AE-3→ 189b —G→ 189c
189a, X = H, Y = OCH₃
189b, X = OCH₂C₆H₅, Y = H
189c, X = OH, Y = H
131 —AE-3→ 189d
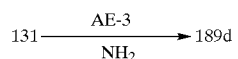
(Prepared by method AJ-1, AJ-2, or AJ-3)
189d, X = Y = H
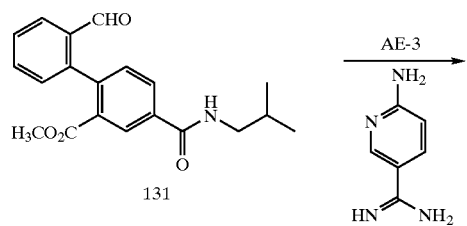
-continued
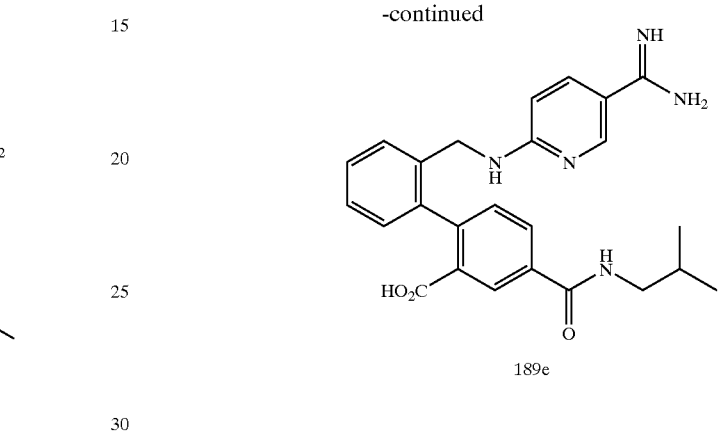
189e
Scheme 25a
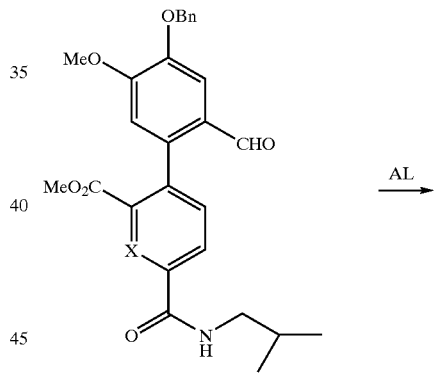
117a, X = CH
117n, X = N
—AL→
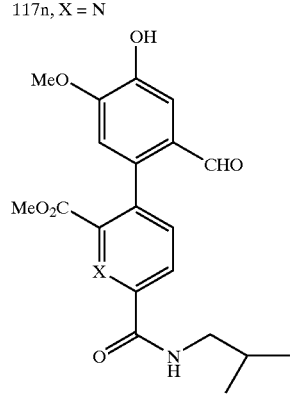
189f, X = CH
189g, X = N
—B-2→

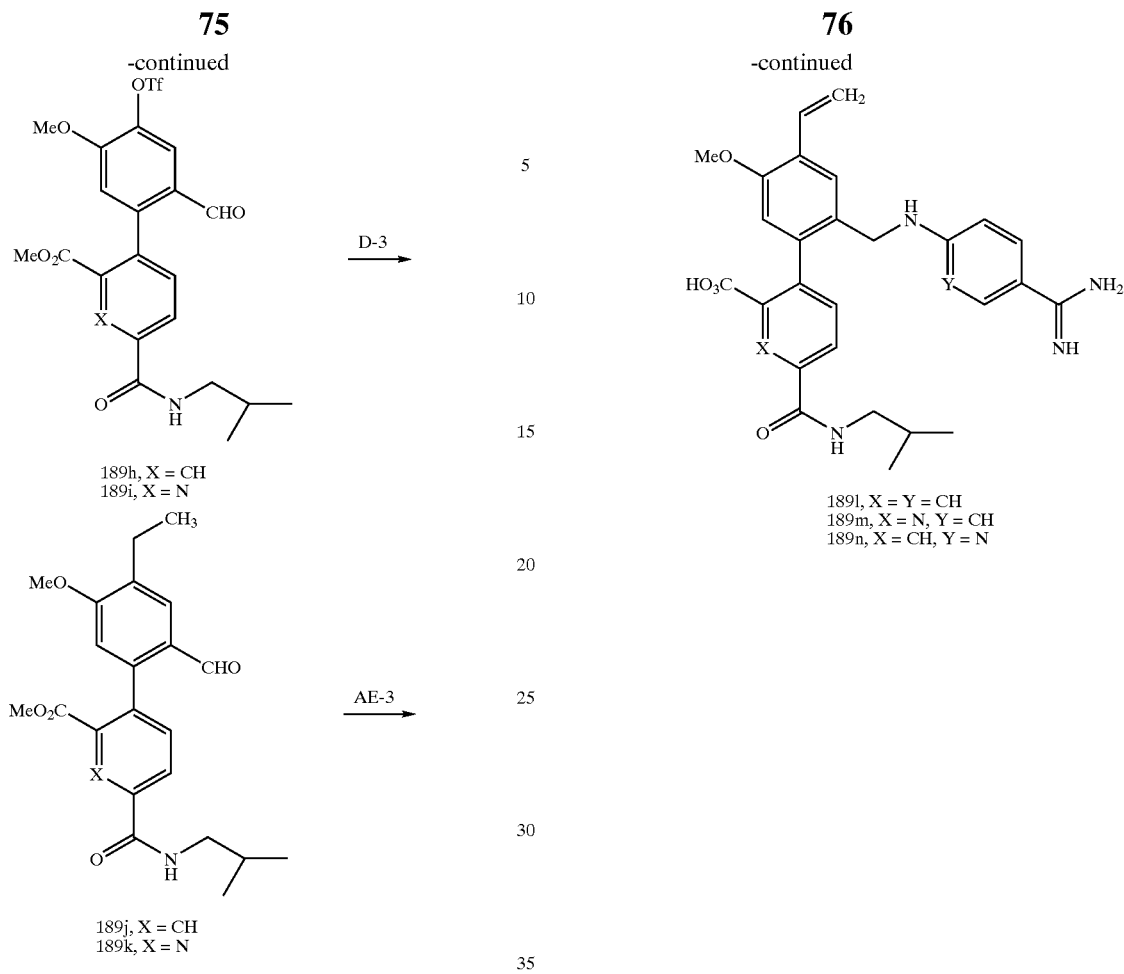
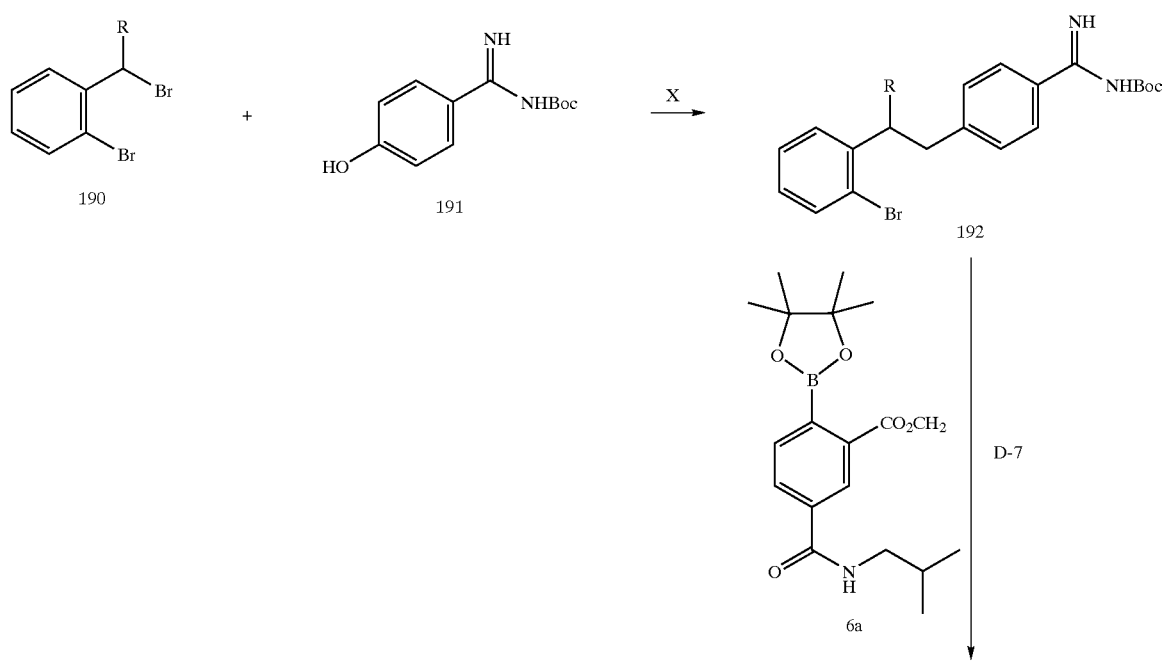
Scheme 26

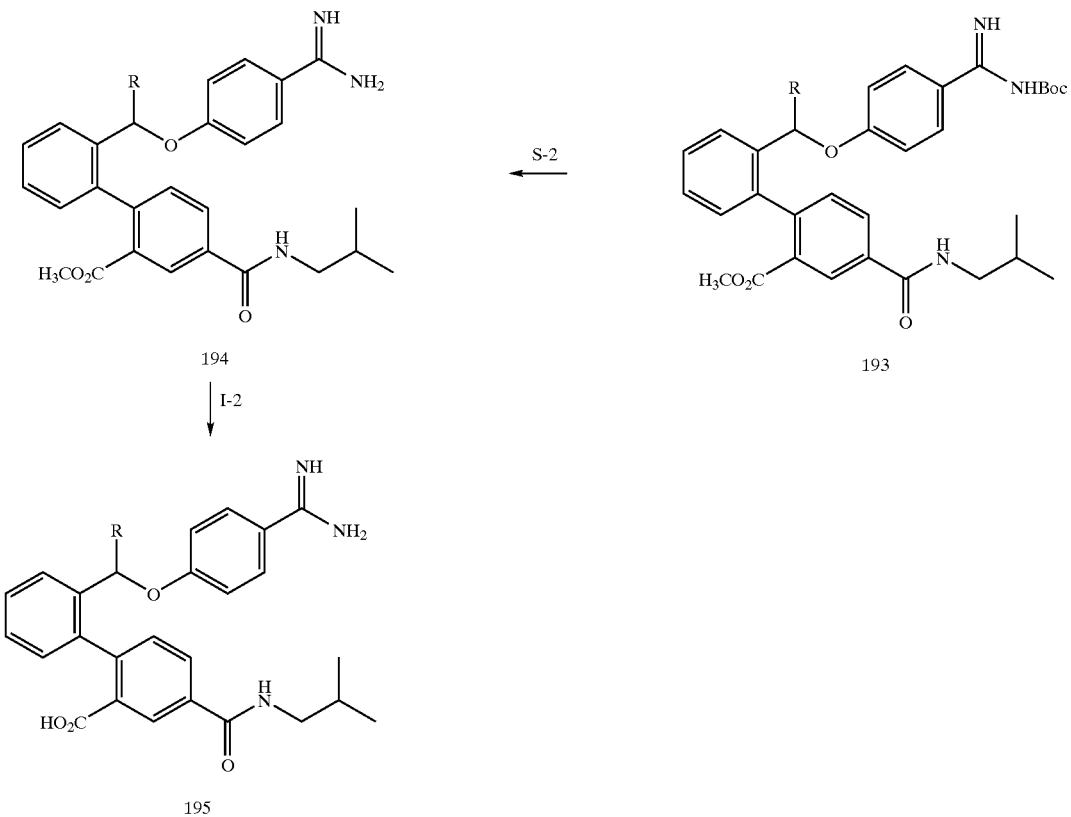
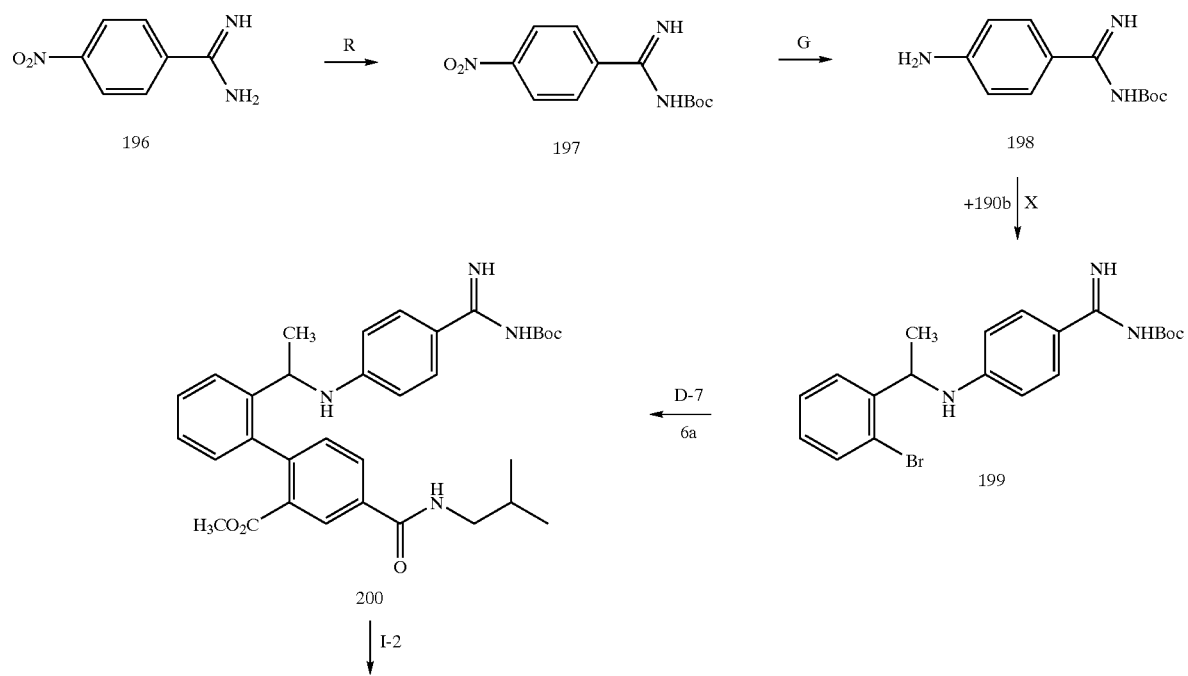
Scheme 27
190a, 192a-195a, R = H
190b, 192b-195b, R = CH₃

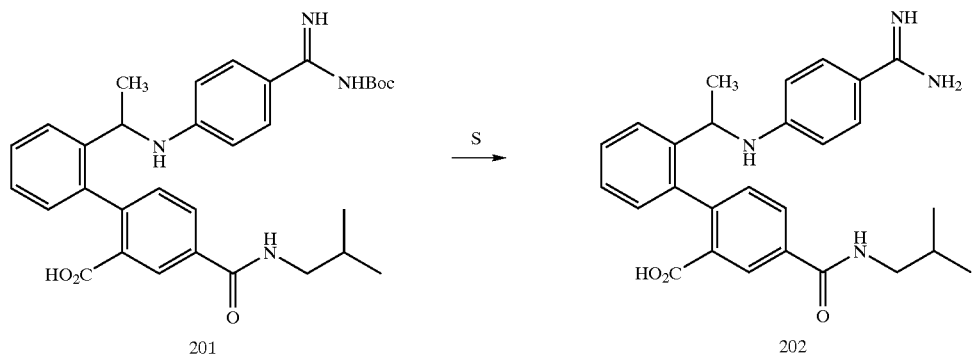
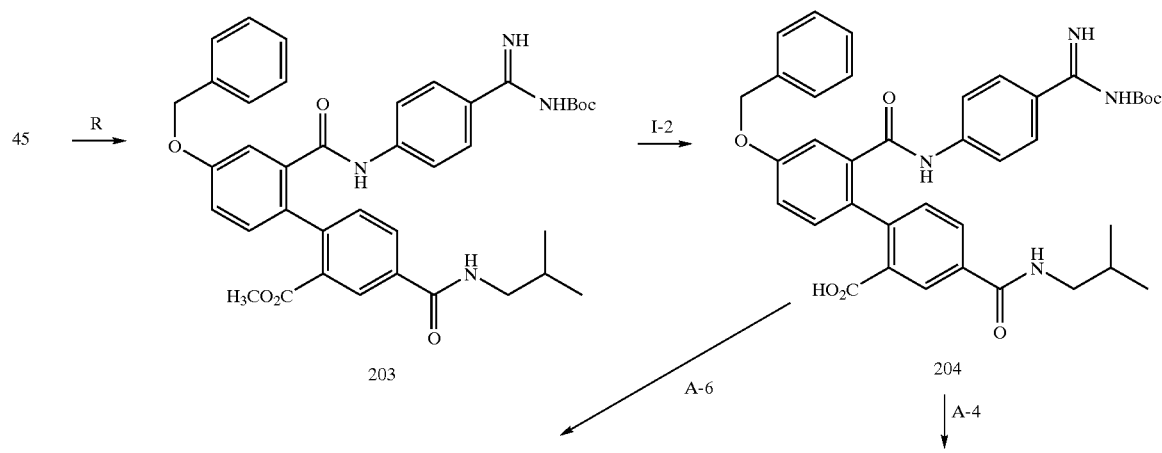
Scheme 28
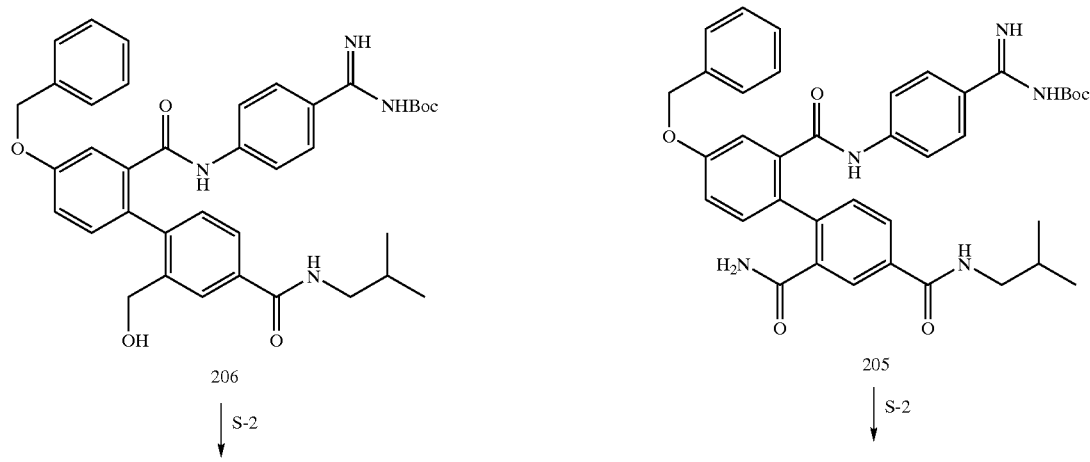

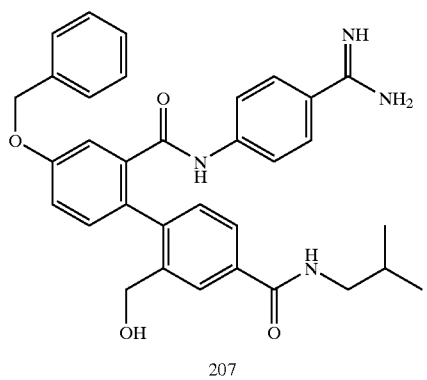
207
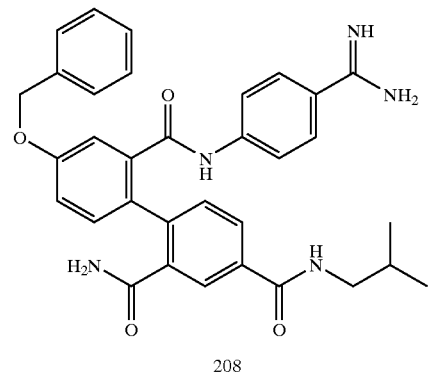
208
Scheme 29
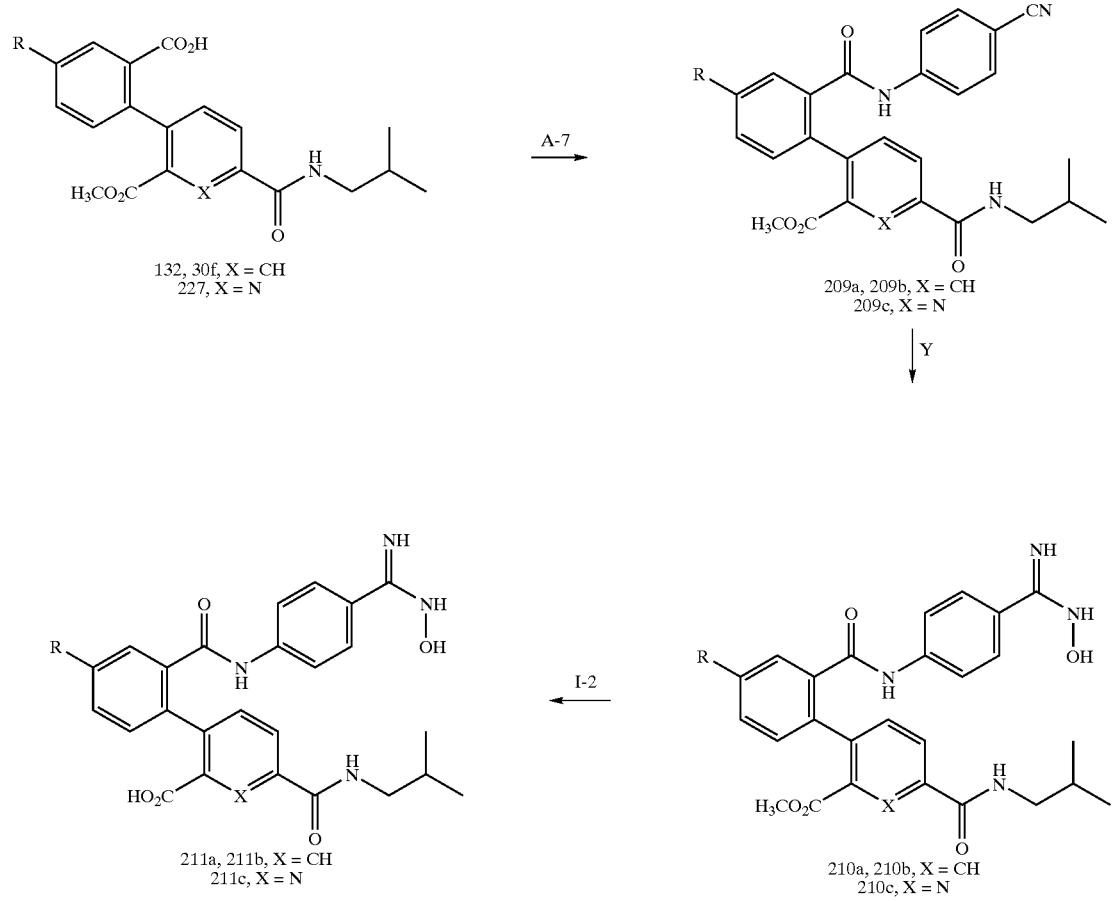

Scheme 30
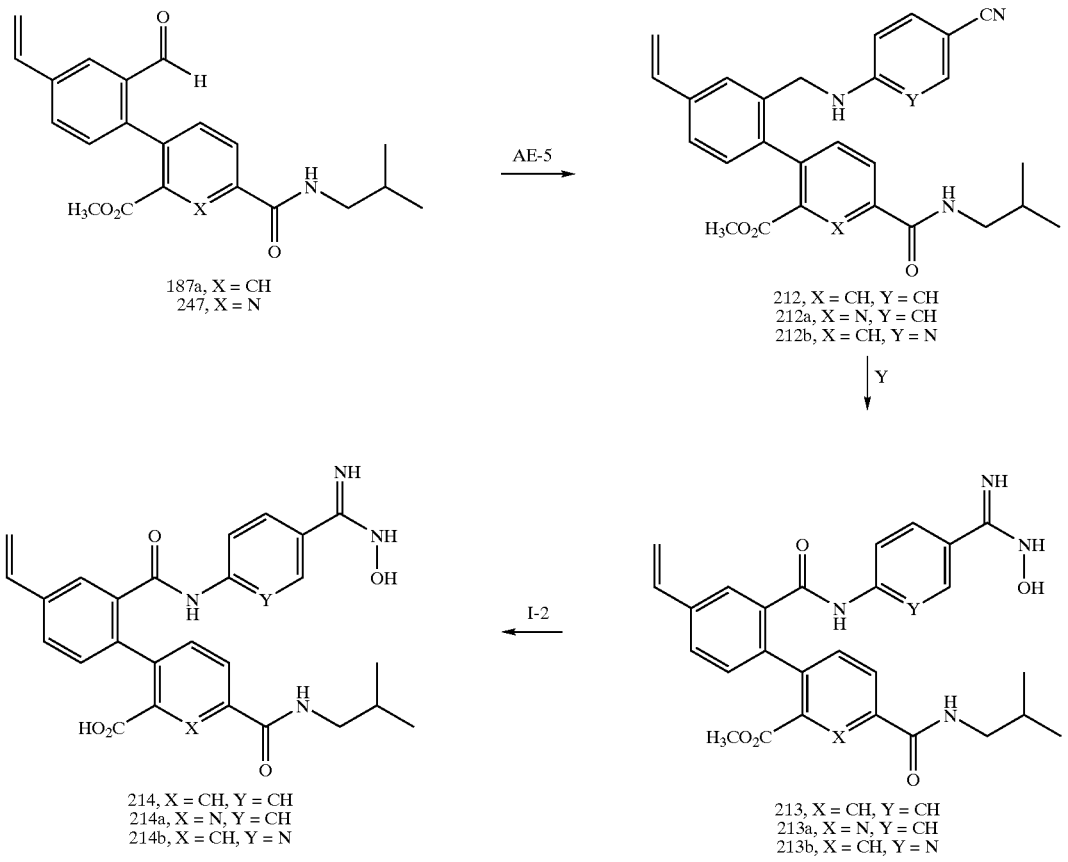
Scheme 31
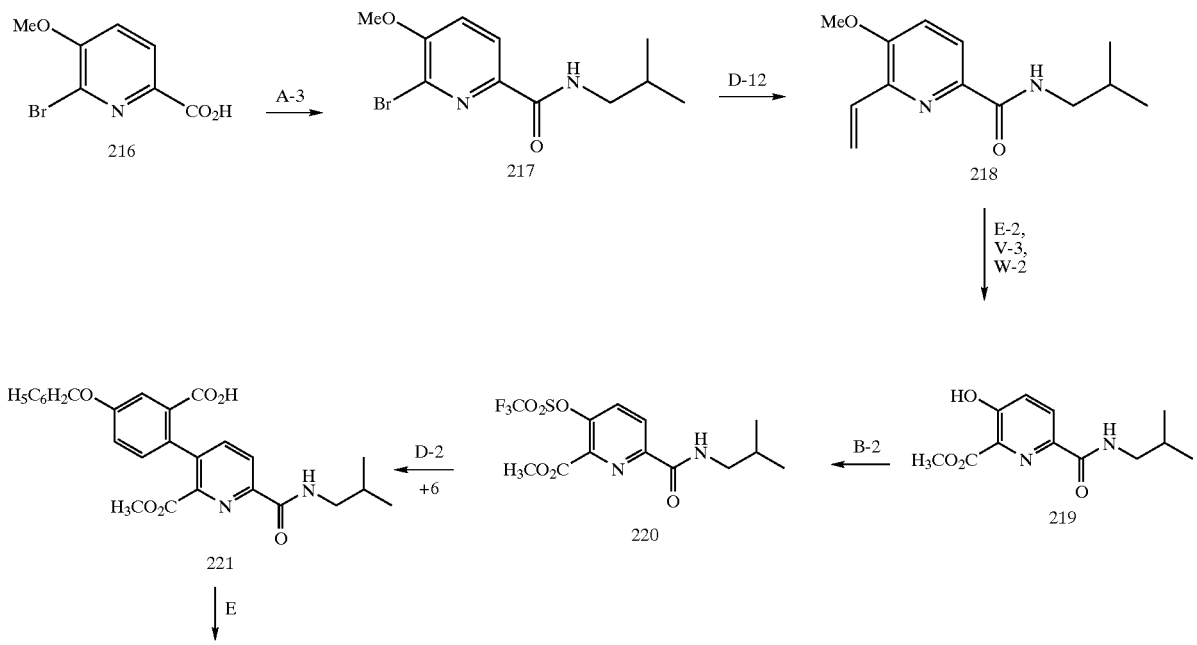

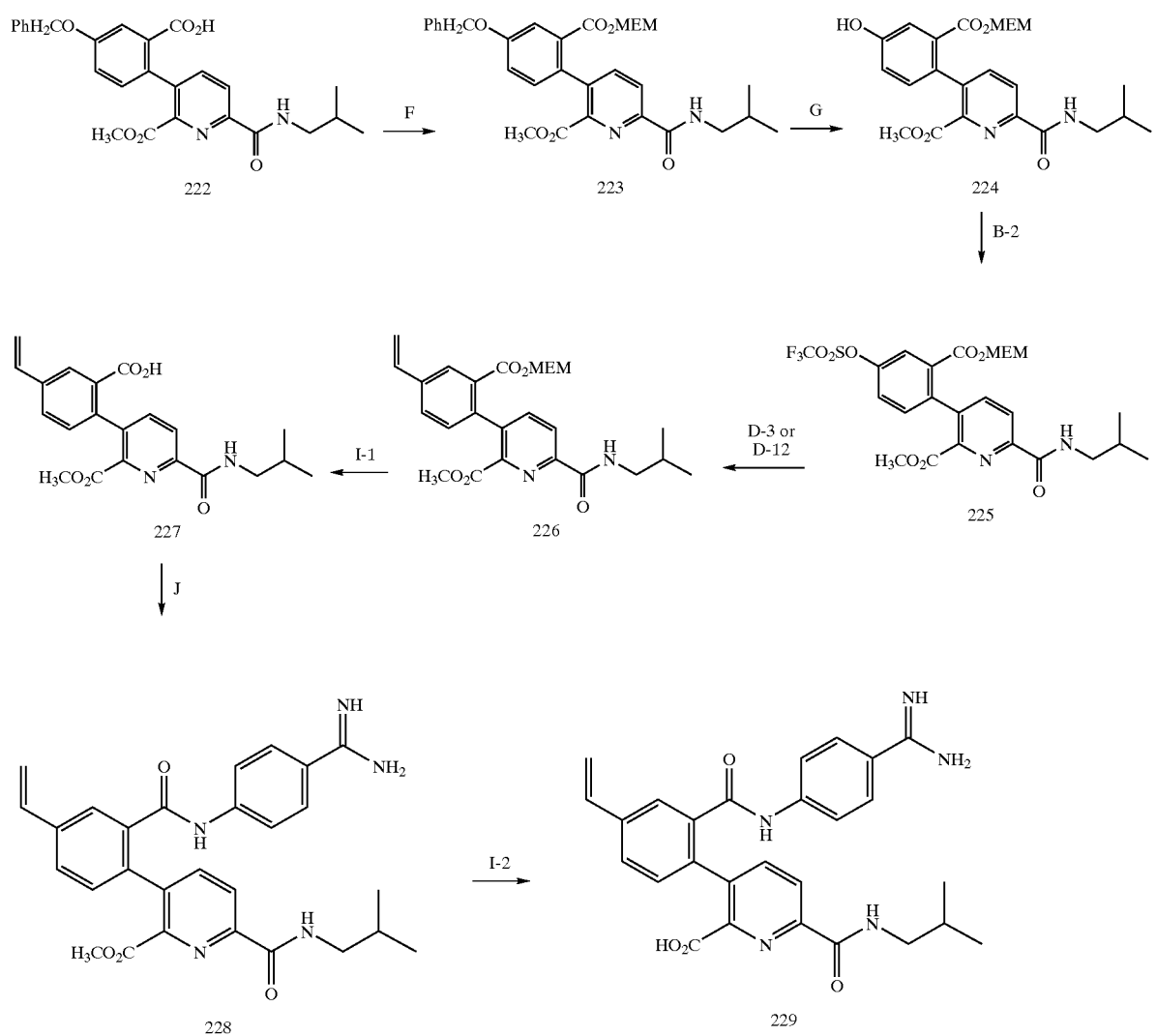
Scheme 31a
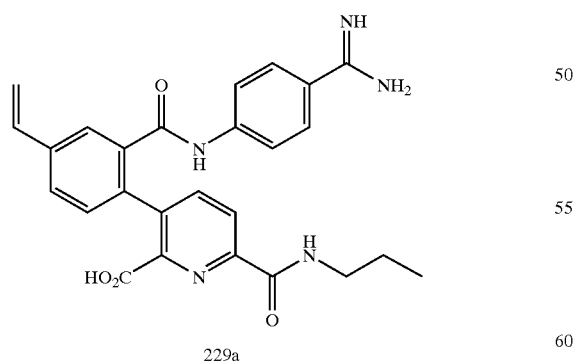
229a

It was prepared the same way as 229 using propylamine in method A-3
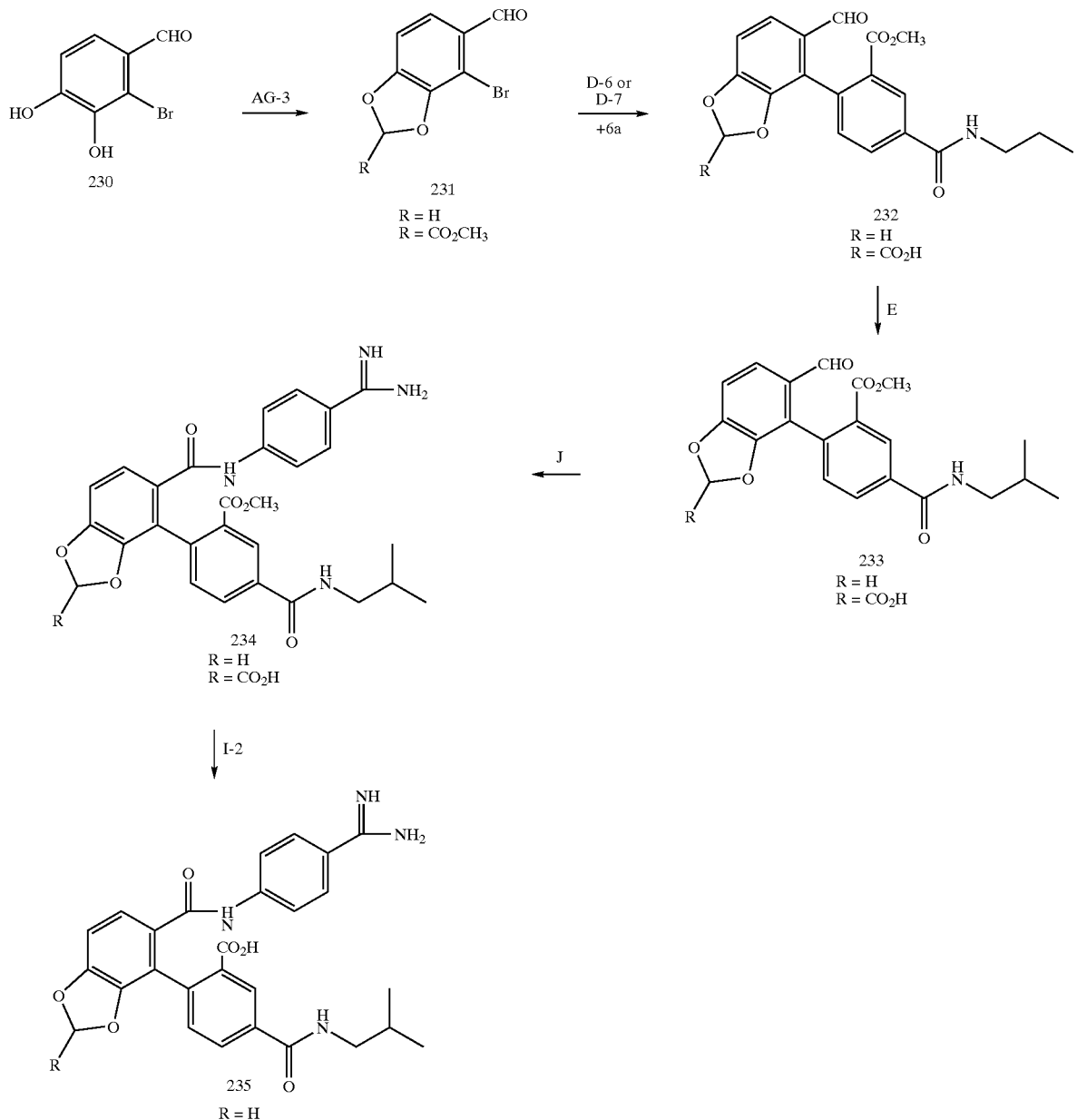
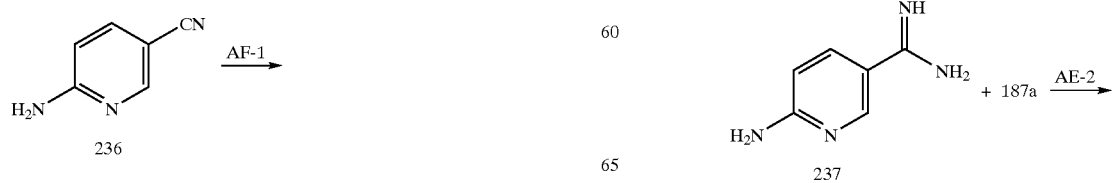

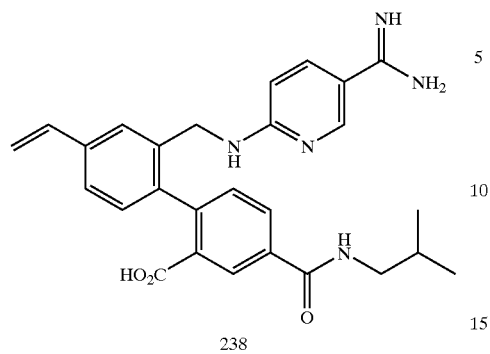
238
Scheme 34
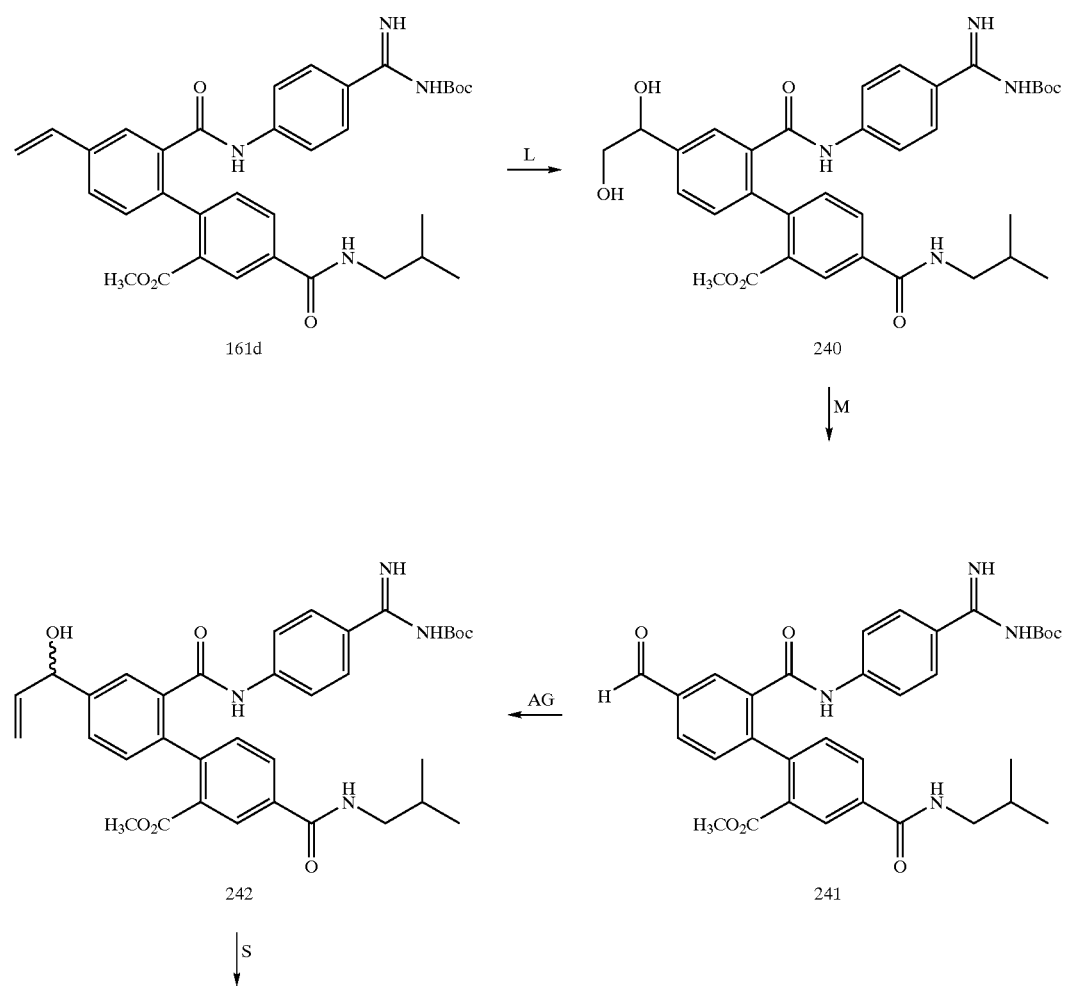

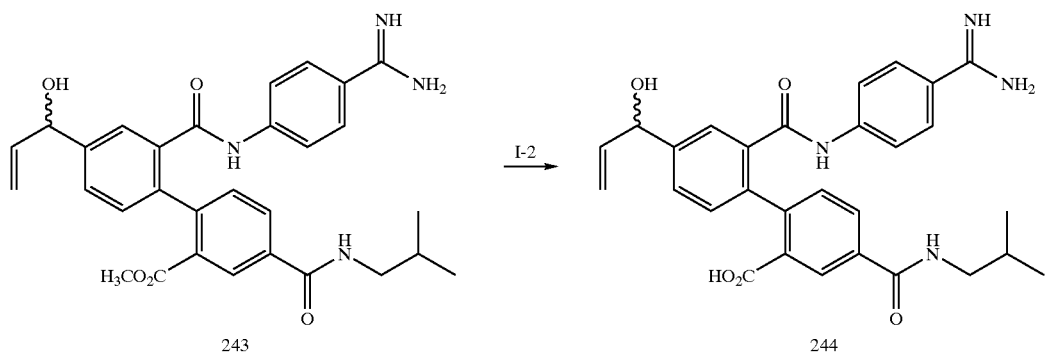
Scheme 35
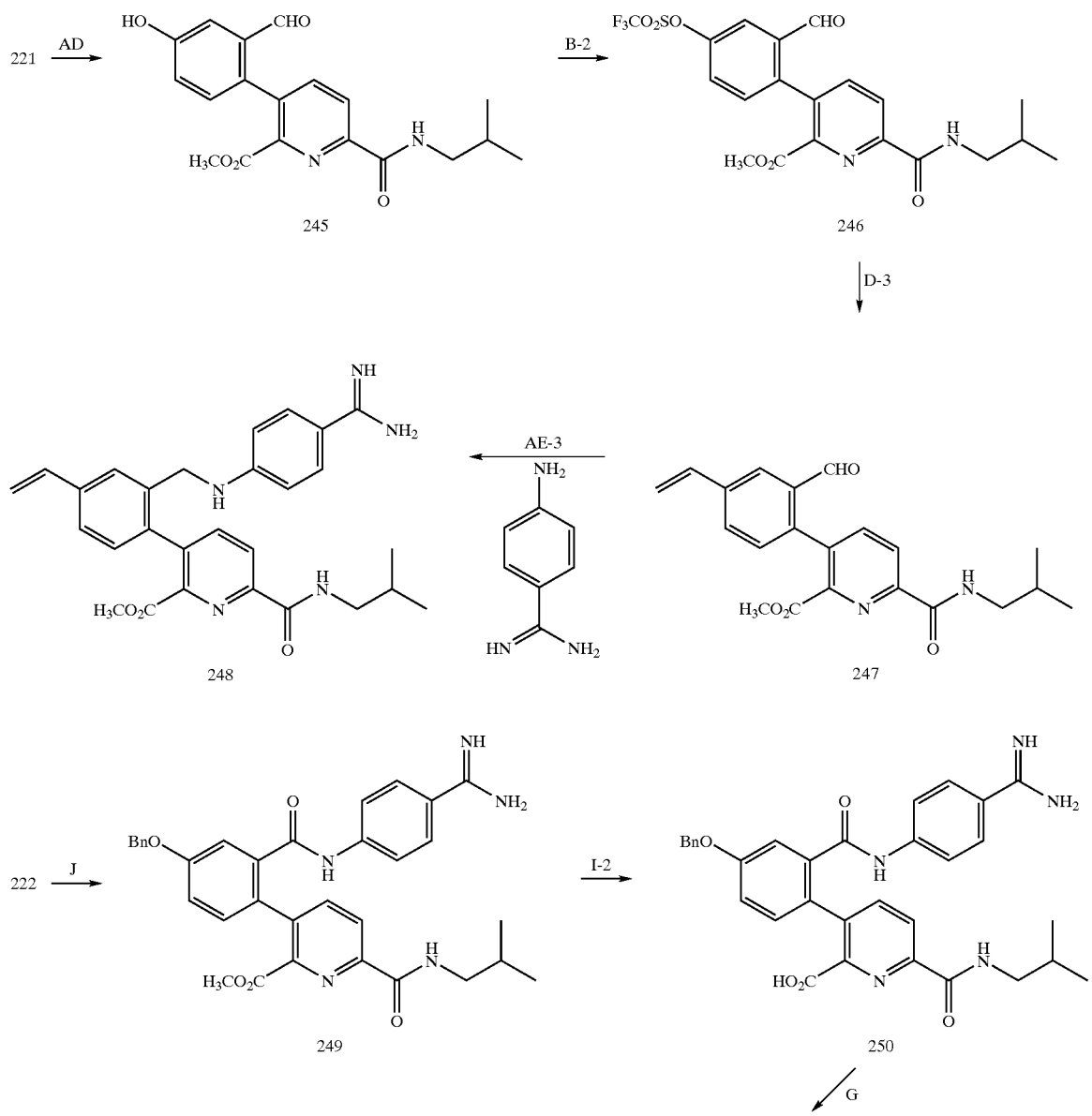

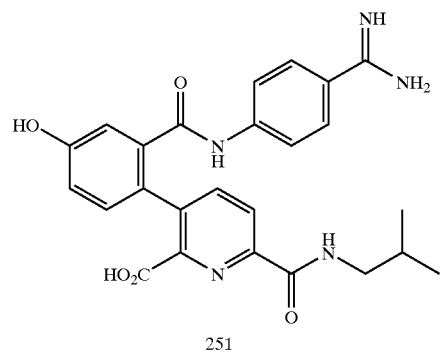
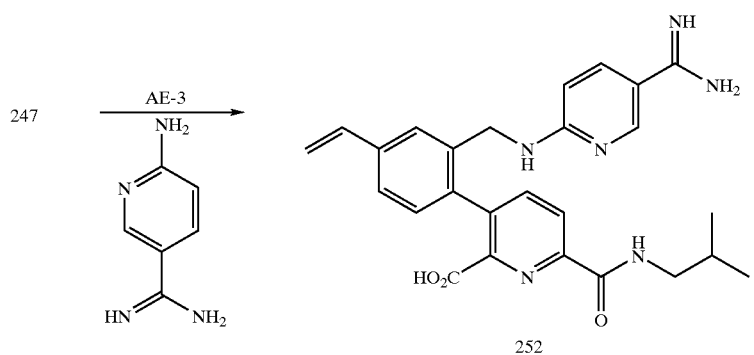
Scheme 36
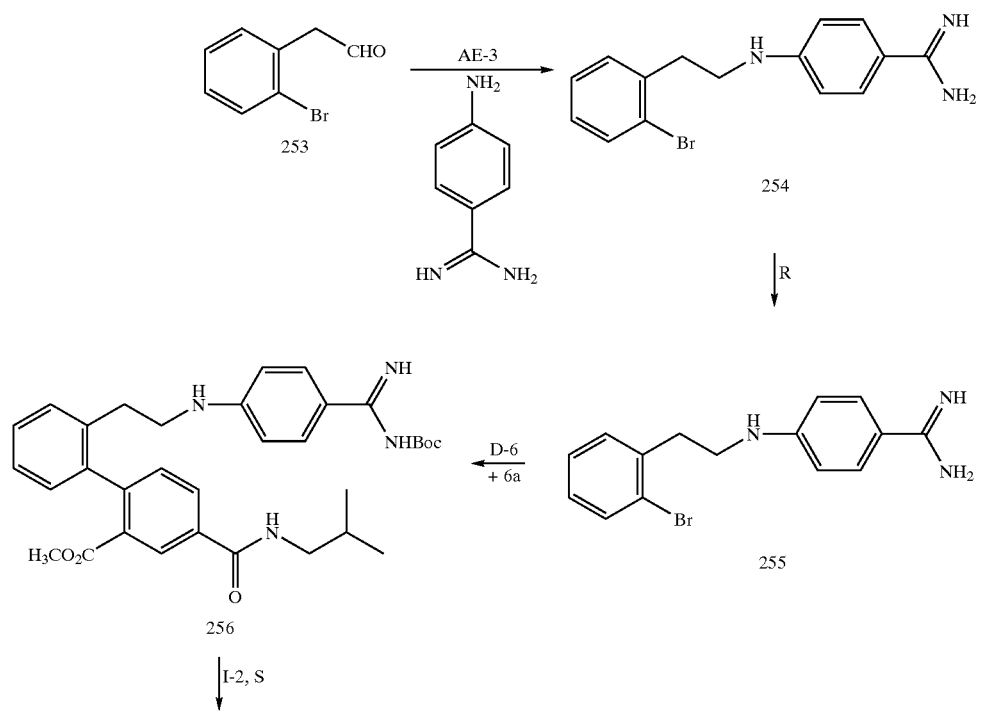

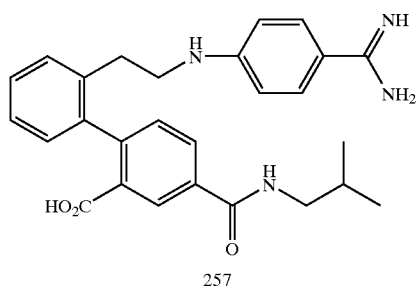
257
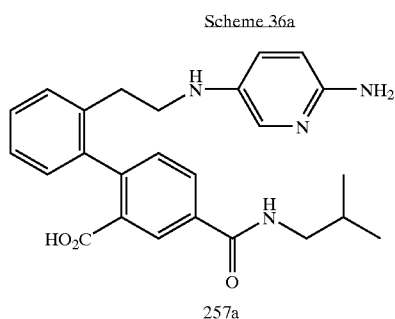
Scheme 36a
257a
It was prepared the same way as 257 starting from 253 and
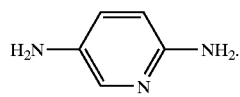
Scheme 37
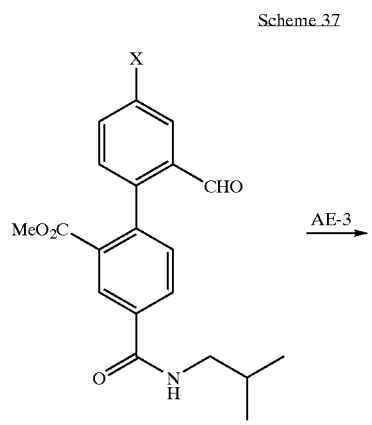
133, X = H
187a, X = —CH=CH$_2$
AE-3 →
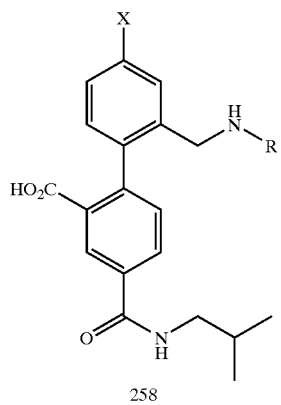
258
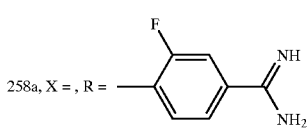
258a, X = , R =
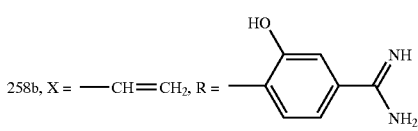
258b, X = —CH=CH$_2$, R =
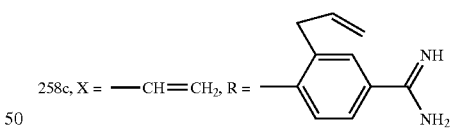
258c, X = —CH=CH$_2$, R =
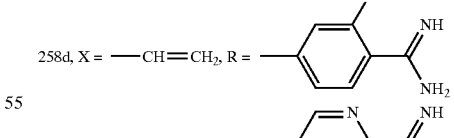
258d, X = —CH=CH$_2$, R =
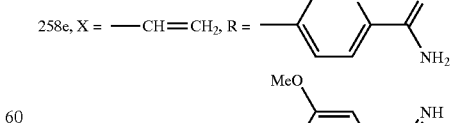
258e, X = —CH=CH$_2$, R =
258f, X = —CH=CH$_2$, R =
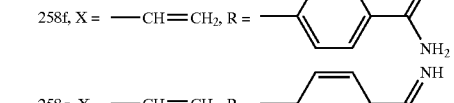
258g, X = —CH=CH$_2$, R =

Scheme 38
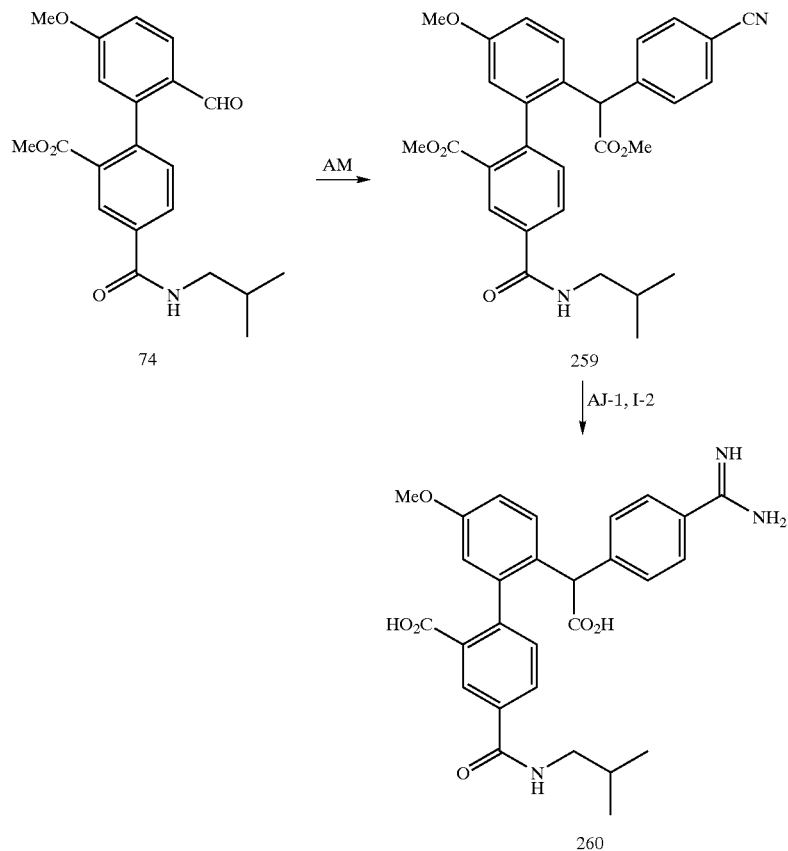
Scheme 39
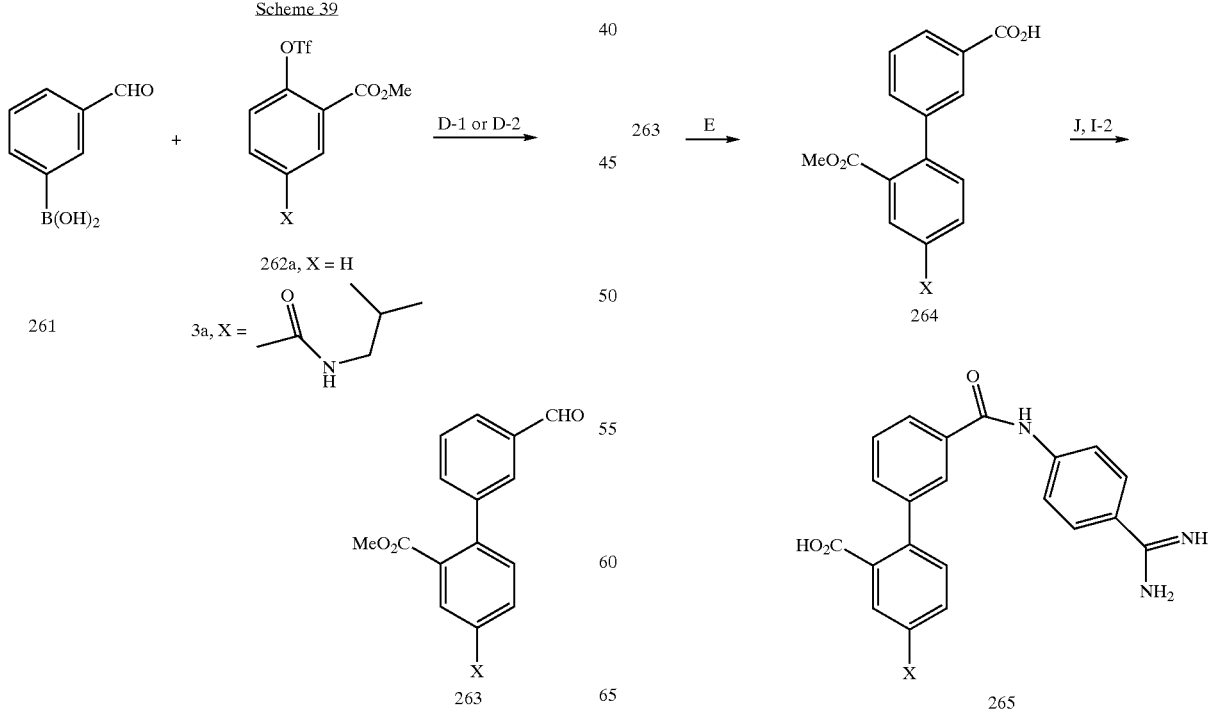

263 →AE-3→

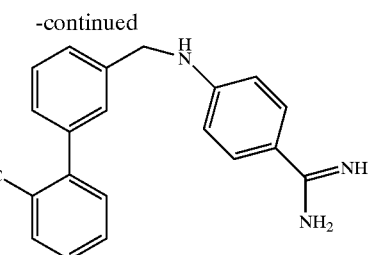

266

263a, 264a, 265a, 266a, X = H 263b, 264b, 265b, 266b, X = 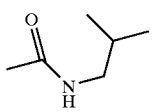

General Methods of Preparation

The following abbreviations have been used:
THF: Tetrahydrofuran; DMF: Dimethylformamide
DME: 1,2-Dimethoxyethane; DMAP: 4-(Dimethylamino)pyridine
Boc anhydride: Di-tert-butyl dicarbonate; TIPS: Triisopropylsilyl
MEM: Methoxyethoxymethyl; Bn: Phenylmethyl or Benzyl The organic extracts were dried over sodium sulfate or magnesium sulfate.

The general methods for the preparation of the compounds of formula (I) are given below:

A-1: Conversion of Acid to Amide

To derivative (1 mmol), was added thionyl chloride (12.6 mmol) and a few drops of DMF. The reaction mixture was refluxed for 2 h and concentrated in vacuo to obtain an oily residue. The residue was dissolved in dichloromethane (3 mL); cooled with ice water and amine (5 mmol) was added. The reaction mixture was stirred at room temperature overnight, washed with 1N HCl, saturated sodium hydrogen carbonate, water, brine, dried and concentrated in vacuo. The product obtained was purified by crystallization or flash column chromatography to furnish the desired amide.

A-2: Conversion of Acid to Amide

To a solution of acid derivative (1 mmol) in dichloromethane (10 mL) at 0° C. was added triethylamine (3 mmol) and ethyl chloroformate (3 mmol). The reaction mixture was stirred at the same temperature for 30 min and the corresponding amine (6 mmol) was added. The reaction mixture was stirred at room temperature overnight and quenched with 1N HCl. The organic layer was separated washed with water, brine, dried and concentrated in vacuo. The product obtained was purified by crystallization or flash column chromatography to furnish the desired amide.

A-3: Conversion of Acid to Amide

To a solution of acid (1 mmol) in dichloromethane (5 mL) was added 2M oxalyl chloride in dichloromethane (2.5 mmol), followed by a drop of DMF. The reaction mixture was stirred for 2h at room temperature and concentrated in vacuo. The residue was co-evaporated once with dichloromethane (5 mL) and then dried in vacuo. To the residue in dichloromethane (10 mL) were further added triethylamine (3 mmol) and the corresponding amine (1.2 mmol). The reaction mixture was stirred for 16 h and washed with water, brine, dried and concentrated in vacuo. The product obtained was purified by crystallization or flash column chromatography to furnish the desired amide.

A-4: Conversion of Acid to Amide

To a solution of acid (1 mmol) in dichloromethane or THF (10 mL) cooled with an ice bath was added triethylamine (1.2 mmol) and ethyl chloroformate or isobutyl chloroformate (1.2 mmol). The reaction mixture was stirred at 0° C. for 30 min and the corresponding amine (2.5 mmol) was added. The reaction mixture was stirred at room temperature overnight and quenched with 1N HCl. The organic layer was separated,washed with water, brine, dried and concentrated in vacuo. The product obtained was purified by crystallization or flash column chromatography to furnish the desired amide.

A-5: Conversion of Acid to Amide

A mixture of carboxylic acid (1 mmol), amine (1.1 mmol), 1-hydroxybenzotriazole (1 mmol) and 1-(3-dimethylaminopropyl)-3-ethylcarbodiimide methiodide (1.1 mmol) in pyridine (10 mL) was stirred overnight at room temperature and was concentrated in vacuo to dryness. The residue obtained was purified by column chromatography or used as such for the next step.

A-6: Reduction of Acid to Alcohol

To a solution of acid (1 mmol) in dichloromethane or THF (10 mL) at 0° C. was added triethylamine (1.2 mmol) and ethyl chloroformate or isobutyl chloroformate (1.2 mmol). The reaction mixture was stirred at 0° C. for 30 min and sodium borohydride (1.25 mmol) was added. The reaction mixture was stirred at room temperature overnight and quenched with 1N HCl. The reaction mixture was extracted with ethyl acetate. The organic layers were combined, washed with water, brine, dried and concentrated in vacuo to furnish the desired alcohol. This can be purified further, if needed, by crystallization or column chromatography.

A-7: Conversion of Acid to Amide

A mixture of carboxylic acid (1 mmol), amine (1 mmol), and 4-dimethylaminopyridie (0.12 mmol) in xylene (10 mL) was stirred at 80° C. for 10 min. Phosphorus trichloride (1 mmol) was added and the reaction mixture was heated with stirring at 150° C. for 2 hr. After cooling, the product was extracted with EtOAc. The organic layers were combined, washed with water, brine, dried and concentrated in vacuo. The product obtained was purified by flash column chromatography to furnish the desired amide.

B-1: Conversion of Phenolic Hydroxyl to Triflate

To a phenol (1 mmol) in dichloromethane (2.5 mL) was added pyridine (5 mmol) under a nitrogen atmosphere and cooled to −10 C. To the cold reaction mixture was added dropwise triflic anhydride (2 mmol) in dichloromethane (2.5 mL) over a period of 10 mins and allowed to warm to room temperature and stirred for 16 h. The reaction mixture was quenched with saturated aqueous sodium hydrogen carbonate solution and the organic layer was separated. The organic layer was washed with 1N HCl, saturated sodium hydrogen carbonate, water, brine, dried and concentrated in vacuo. The product obtained was purified by crystallization or flash column chromatography to furnish the desired triflate.

B-2: Conversion of Phenolic Hydroxyl to Triflate

To a solution of substituted phenol (1 mmol) in DMF (10 mL) was added N-phenylbis(trifluoromethanesulphonimide) (1.1 mmol), and triethylamine (2 mmol) and stirred at room temperature overnight. The reaction mixture was quenched with ice water and extracted twice with ether. The organic layers were combined, washed with brine, dried and concentrated in vacuo to furnish the desired triflate.

C: Conversion of Acid to MEM Ester

To a solution of acid derivative (1 mmol) in DMF (10 mL) was added sodium bicarbonate (1.05 mmol), and MEM-Cl (1.05 mmol) and was stirred at room temperature for 24 h.

The reaction mixture was quenched with ice water and extracted twice with ether. The organic layers were combined, washed with brine, dried and concentrated in vacuo to furnish crude product. Purification by flash column chromatography or crystallization gave the desired MEM ester.

D-1: Coupling of Boronic Acid with Triflate

A mixture of triflate (1 mmol), aryl boronic acid (1.5 mmol), potassium phosphate (3 mmol), potassium bromide (2.4 mmol) and tetrakis(triphenylphosphine)palladium (0.05 mmol) in dioxane (10 mL) was heated at reflux overnight under an argon atmosphere. The reaction mixture was cooled, quenched with water and was extracted with ethyl acetate. The organic layers were combined, dried and concentrated in vacuo. Purification by flash column chromatography or crystallization gave the coupled product.

D-2: Coupling of Boronic Acid with Triflate

A mixture of triflate (1 mmol), aryl boronic acid (2 mmol), sodium hydrogen carbonate (3 mmol) and tetrakis(triphenylphosphine)palladium (0.05 mmol) or bis(triphenylphosphine)palladium(II)chloride (0.05 mmol) in DME/water (9:1, 10 mL) was heated at reflux overnight. The reaction mixture was cooled, quenched with water and extracted with ethyl acetate. The organic layer was dried and concentrated in vacuo. Purification by flash column chromatography or crystallization gave the coupled product.

D-3: Coupling of Tributyltin Derivative with Triflate

A mixture of triflate (1 mmol), tributyltin derivative (3 mmol), tetraethylammonium chloride (6 mmol), and bis(triphenylphosphine)palladium(II)-chloride (0.05 mmol) in DMF (10 mL) was heated at 70° C. overnight under an argon atmosphere. The reaction mixture was cooled, quenched with water (20 mL) and extracted with ethyl acetate (2×10 mL). The organic layers were combined, dried and concentrated in vacuo. Purification by flash column chromatography or crystallization gave the coupled product.

D-4: Coupling of Trimethyltin Derivative with Triflate

A mixture of triflate (1 mmol), trimethyltin derivative (3 mmol), and bis(triphenylphosphine)palladium(II)chloride (0.05 mmol) in THF (10 mL) was heated at 70° C. overnight under an argon atmosphere. The reaction mixture was cooled, quenched with water and extracted with ethyl acetate (2×10 mL). The organic layers were combined, dried and concentrated in vacuo. Purification by flash column chromatography or crystallization gave the coupled product.

D-5: Coupling of Alkyne with Triflate

A mixture of triflate (1 mmol), triethylamine (4.5 mmol), substituted alkyne (3.5 mmol), and bis(triphenylphosphine)palladium(II)chloride (0.05 mmol) in DMF (10 mL) was heated at 70° C. overnight under an argon atmosphere. The reaction mixture was cooled, quenched with water (20 mL) and extracted with ethyl acetate (2×10 mL). The organic layers were combined, dried and concentrated in vacuo. Purification by flash column chromatography or crystallization gave the coupled product.

D-6: Coupling of Boronate Ester with Aryl Bromides

A mixture of boronate ester (2 mmol), aryl bromide (1 mmol), potassium phosphate (3 mmol) and bis(diphenylphosphinoferrocene)palladium(II)chloride (0.05 mmol) in DMF (10 mL) was heated at 100° C. for overnight under an argon atmosphere. The reaction mixture was cooled, quenched with water (20 mL) and extracted with ethyl acetate (2×10 mL). The organic layers were combined, dried and concentrated in vacuo. Purification by flash column chromatography or crystallization gave the desired product.

D-7: Coupling of Boronate Ester with Aryl Bromides

A mixture of boronate ester (2 mmol), aryl bromide (1 mmol), sodium hydrogen carbonate (3 mmol) and bis(diphenylphosphinoferrocene)palladium(II)chloride (0.05 mmol) in DME/water (9:1, 10 mL) was heated at 50–70° C. for overnight under an argon atmosphere. The reaction mixture was cooled, quenched with water (20 mL) and was extracted with ethyl acetate (2×10 mL). The organic layers were combined, dried and concentrated in vacuo. Purification by flash column chromatography or crystallization gave the coupled product.

D-8: Coupling of Phenol with Boronic Acid

A mixture of phenol (1 mmol), aryl boronic acid (3 mmol), molecular sieves (4A°), pyridine (5 mmol), copper (II)acetate (1 mmol) and bis(triphenylphosphine)-palladium (II)chloride (0.05 mmol) in dichloromethane (10 mL) was stirred at room temperature overnight under an argon atmosphere. The reaction mixture was cooled, filtered through a pad of Celite and concentrated in vacuo. Purification of the crude by flash column chromatography gave the coupled aryl ether.

D-9: Coupling of Trimethyltin Derivative with Triflate

To a solution of triflate (1 mmol), LiCl (4 mmol), $PPh_3$ (0.15 mmol), CuBr (0.2 mmol), and bis(triphenylphosphine) palladium(II)chloride (0.07 g) in DMF (10 mL) under an atmosphere of argon was added trimethylstannyl compound (0.8 mmol) and a crystal of 2,6-di-t-butyl-4-methylphenol. After the mixture was stirred at 90° C. for 3 h, a second portion of aryl-trimethylstannyl compound (0.5 mmol) was added. The reaction mixture was stirred at 90° C. overnight. Water was added and extracted with ethyl acetate. The organic layer was dried ($MgSO_4$), concentrated and purified by flash column chromatography or crystallization to furnish the desired coupled product.

D-10: Coupling of Amine with Triflate

A mixture of triflate (0.75 mmol), amine (0.9 mmol), potassium phosphate (1.1 mmol), 2-(di-t-butylphosphino) biphenyl (0.015 mmol) and tris(dibenzylideneacetone) dipalladium(0) (10 mg) in DME (10 mL) was heated at reflux overnight under an argon atmosphere. The reaction mixture was concentrated in vacuo and the residue was purified by flash column chromatography to furnish the desired coupled product.

D-11: Conversion of Triflate to Cyano Compound

To a solution of triflate (0.84 mmol), zinc cyanide (0.54 mmol), Palladium acetate (0.016 mmol), 2-(di-tert-butylphosphine)biphenyl (0.016 mmol) and N-methyl pyrrolidine (10 mL) was heated under argon at 160° C. for 48 h. The reaction mixture was cooled to room temperature and quenched with water (50 mL). The reaction mixture was extracted with ethyl acetate (2×25 mL). The organic layers were combined, dried, filtered and concentrated in vacuo. The residue obtained was purified by flash column chromatography to furnish the desired cyano compound.

D-12: Coupling of Tetravinyltin with Triflate or Halide

To a solution of aryl triflate or bromide (1 mmol) in DMF (5 mL) were added LiCl (5 mmol), tetravinyltin (2 mol), and dichlorbis(triphenylphosphine)palladium (II) (0.01 mmol). The reaction mixture was stirred at 70° C. under nitrogen for 5 h and then diluted with ethyl acetate and filtered. The organic layer was washed with water and brine and dried ($MgSO_4$). After evaporating the solvent in vacuo, the compound was purified by flash-column chromatography to give the desired product.

E: Oxidation of Aryl Aldehyde to Acid

A mixture of aldehyde (1 mmol), tert-butanol (5 mL), water (2 mL) and acetonitrile (1 mL, additional amount may be added until the reaction mixture was homogenous) was stirred at room temperature. The solution was cooled in ice-bath and 2-methyl-2-butene (1 mL), sodium chlorite (6 mmol) and sodium dihydrogenphosphate (1.6 mmol) were added. The reaction mixture was stirred at room temperature for 2 h. If the solid separated out, the mixture was filtered to collect the solid, the desired product. If no solid separated out, then the reaction mixture was concentrated in vacuo to remove acetonitrile, diluted with water (10 mL) and extracted with ethyl acetate (2×10 mL). The organic layers were combined, washed with water, brine, dried and concentrated in vacuo to furnish crude acid. Purification was achieved, if needed, by crystallization or using flash column chromatography to obtain pure acid.

E-2: Oxidation of Vinyl Compound to Acid

To a solution of vinyl compound (1 mmol) in acetone (5 mL) was added $KMnO_4$ (4 mmol). The reaction mixture was stirred for 3 h (the reaction is exothermic, and refluxed on its own during the addition of $KMnO_4$). The reaction mixture was diluted with methanol and water and filtered. The organic solvents were evaporated in vacuo and the aqueous layer was acidified to pH 1 and extracted several times with ethyl acetate/DME. The combined organic layers were dried ($MgSO_4$) to furnish the desired acid.

F: Conversion of Aromatic Acid to MEM Ester

To a solution of aromatic acid (1 mmol) in THF (10 mL) was added diisopropylethylamine (2 mmol) and 2-methoxyethoxymethylchloride (1.1 mmol). The reaction mixture was stirred a room temperature for 3 h and diluted with ether (25 mL). The reaction mixture was washed with water (10 mL), brine (10 mL), dried and concentrated in vacuo to obtain product as colorless oil. The product was purified by flash column chromatography to furnish desired product.

G: Conversion of Aromatic Benzyl Ether to Aromatic Phenol, Benzyl Ester to Acid, Benzyl Carbamate to Amine, Alkene to Alkane, Azide to Amine, Nitro to Amine, and Oxime to Amine To a solution of appropriate substrate (1 mmol) in ethanol (10 mL) was added 10% palladium on carbon (10-wt %). The reaction mixture was hydrogenated at 50 psi for 2 to 24 h (until all starting material disappeared as confirmed by MS and TLC analysis). The catalyst was removed by filtration through a pad of Celite under nitrogen. The filtrate was concentrated in vacuo to furnish the product, which was purified by flash column chromatography or crystallization.

H: Conversion of Aromatic Acid to Benzyl Ester

To a solution of aromatic acid (1 mmol) in DMF (10 mL) was added sodium bicarbonate (1.05 mmol), and benzyl bromide (1.05 mmol) and stirred at room temperature for 24 h. The reaction mixture was quenched with ice water and extracted twice with ethyl acetate. The organic layers were combined, washed with water and brine, dried and concentrated in vacuo to furnish crude product. Purification by crystallization or flash column chromatography gave the desired ester.

I-1: Hydrolysis of MEM Ester to Acid

To a solution of MEM ester (1 mmol) in DME (8 mL) was added 6 N HCl (2 mL) and stirred at room temperature overnight. The reaction mixture was neutralized with solid sodium hydrogen carbonate (18 mmol) and concentrated in vacuo. The reaction mixture was acidified with 0.5 N HCl (20 mL) and extracted with ethyl acetate (2×20 mL). The organic layers were combined, washed with brine (20 mL), dried and concentrated in vacuo to furnish crude product. Purification of the crude by flash column chromatography gave the product. Alternatively the crude reaction mixture was diluted with water (10 mL) and concentrated in vacuo to remove DME. The solid obtained was collected by filtration and dried in vacuo to furnish pure acid.

I-2: Hydrolysis of Ester to Acid

To a solution of ester (1 mmol) in MeOH (10 mL) was added 1 N NaOH (10 mmol). The reaction mixture was stirred at room temperature for 2–3 h, filtered through a plug of cotton, and concentrated in vacuo to remove MeOH. The pH of the aqueous layer was adjusted to below 7. The solid that separated, was collected by filtration, washed with water and dried in vacuo to furnish the desired acid.

J: Coupling of Acid with Amino Compounds

To a solution of acid (1 mmol) in DMF (5 mL) was added corresponding amine (1.1 mmol) and stirred at room temperature until homogenous. Pyridine (5 mL) was added to the reaction mixture followed by 1,3-dicyclohexylcarbodiimide (1.2 mmol) and stirred overnight at room temperature. The mixture was quenched with 6 N HCl (10 mL), diluted with ice cold water (10 mL) and extracted with chloroform (2×10 mL). The organic layers were combined washed with brine (10 mL), dried and filtered. Purification of the crude by flash column chromatography gave the product as a solid. If the product was soluble in water, then the reaction mixture was concentrated in vacuo to remove pyridine and DMF and purified by flash column chromatography.

K: Reduction of Aldehyde to Alcohol

To a solution of aldehyde (1 mmol) in THF (10 mL) was added sodium borohydride (0.4 mmol). The reaction mixture was stirred for 30 mins and quenched with glacial acetic acid (0.3 mL). The reaction mixture was diluted with water (10 mL) and extracted with ethyl acetate (2×10 mL). The organic layers were combined and washed with brine (10 mL), dried, filtered and concentrated in vacuo to obtain crude product which was purified by flash column chromatography.

L: Conversion of Vinyl Group to Diol

To a solution of vinyl compound (1 mmol) in THF/tert-butanol (1:1, 10 mL) and water (2 mL) was added 4-methylmorpholine N-oxide (2.5 mmol) and osmium tetraoxide (1 mL, 2.5 wt % in tert-butanol, 0.1 mmol). The reaction mixture was stirred at room temperature for 2 h and quenched with saturated aqueous solution of sodium sulfite (5 mL). The reaction was stirred at room temperature for 30 mins and diluted with brine (10 mL) and ethyl acetate (10 mL). The organic layer was separated and the aqueous layer was extracted with ethyl acetate (10 mL). The organic layers were combined and washed with brine (10 mL), dried, filtered and concentrated in vacuo. The crude product was purified by flash column chromatography to furnish the desired diol.

M: Conversion of Diol to Aldehyde

To a solution of diol (1 mmol) in DME/water (9:1, 10 mL) was added sodium metaperiodate (3 mmol) and stirred at room temperature for 30 min. The reaction mixture was quenched with water (10 mL) and extracted with ethyl acetate (2×10 mL). The organic layers were combined and washed with brine (10 mL), dried, filtered and concentrated in vacuo. The crude product was purified by flash column chromatography to furnish the desired aldehyde.

N: Conversion of Alcohol to Mesylate

To a solution of alcohol (1 mmol) in DME (10 mL) was added dimethylaminopyridine (0.1 mmol), methane sulfonyl chloride (3 mmol) and diisopropylethylamine or triethylamine (5 mmol). The reaction mixture was stirred at room temperature overnight. The reaction mixture was diluted with water (10 mL) and extracted with ethyl acetate (2×10 mL). The combined organic layers were washed with brine, dried, filtered and concentrated in vacuo. The residue obtained, was purified by column chromatography to furnish the desired mesylate.

O: Conversion of Mesylate to Azide

To a solution of mesylate (1 mmol) in DMSO (10 mL) was added sodium azide (25 mmol) and heated at 100° C. overnight. The reaction mixture was cooled and diluted with cold water (25 mL). The reaction mixture was extracted with ethyl acetate (2×15 mL). The combined organic layers were washed with water (10 mL), brine (10 mL), dried, filtered and concentrated in vacuo The residue obtained was purified by column chromatography to furnish the desired azido compound.

P: Protection of Amine as Benzyl Carbamate

A mixture of amino compound (1 mmol), benzyl chloroformate (2 mmol) and triethylamine (10 mL) in pyridine (10 mL) was stirred at room temperature overnight. The reaction mixture was concentrated in vacuo to remove organic solvents and diluted with 0.1 N HCl (10 mL). The product was extracted with chloroform (2×10 mL), dried, filtered and concentrated in vacuo. The residue obtained was purified by column chromatography to furnish the desired carbamate.

Q: Conversion of Silyl Protected Amine to Amine

A mixture of silyl protected amine (1 mmol), tetrabutylammonium fluoride (1.0 M in THF, 2 mmol) in THF (10 mL) was stirred at room temperature for 1.5 h. The reaction mixture was concentrated in vacuo and purified by column chromatography to obtain the desired product.

R: Protection of Amine as tert-Butyl Carbamate

To a solution of amino compound (1 mmol) in acetonitrile (5 mL) was added triethylamine (2 mmol) and BOC anhydride (1.2 mmol). The reaction mixture was stirred for 2 h and concentrated in vacuo. Water was added to the residue and extracted with ethyl acetate. The organic layer was washed with brine, dried (MgSO$_4$), and the solvent was evaporated in vacuo to furnish tert-butyl carbamate. If needed, the product was purified by crystallization or column chromatography.

S: Conversion of tert-Butyl Carbamate to Amine

To a solution of tert-butyl carbamate (1 mmol) in dichloromethane (10 mL) was added trifluoroacetic acid (2 mL). The solution was stirred at room temperature for 4 h and concentrated in vacuo. The residue was purified by column chromatography or crystallization to give the desired amine.

S-2: Conversion of tert-Butyl Carbamate to Amine

To a solution of tert-butyl carbamate (1 mmol) in methanol (13 mL) was added 6 N HCl (8.75 mL, 52 mmol) and water (4.25 mL). The reaction mixture was stirred at room temperature for 2 days. The pH was adjusted to 7 using conc. ammonium hydroxide and the solid that separated out, was collected by filtration, washed with ether, dried in vacuo to furnish the desired product. If no solid separated out, the product was isolated by extraction with chloroform and evaporating the organic layer.

T: Protection of Aldehyde as Acetal

To a solution of aldehyde (1 mmol) in ethanol (5 mL) was added triethyl orthoformate (1.4 mmol), ammonium nitrate (0.2 mmol) and stirred at room temperature overnight (if reaction was not complete by TLC and NMR analysis of an aliquot, the reaction mixture was heated at 50° C. until complete). After completion of the reaction, the mixture was quenched with triethylamine (0.2 mmol) and concentrated in vacuo to remove ethanol. The residue was dissolved in ether, filtered to remove any insoluble inorganic impurities, and evaporated to dryness. The product obtained was used as such without further purification.

U-1: Conversion of Bromide to Boronic Acid

To a mixture of bromo compound (1 mmol) in ether (10 mL), cooled to −78° C., n-butyl lithium (1.2 mmol) was added dropwise and the reaction mixture was stirred for 30 mins after the addition was completed. Tributyl borate (1.3 mmol) in ether (10 mL) was added to the reaction and stirred at −78° C. for 2 h. The reaction mixture was allowed to warm to 0° C. and quenched with 2 M HCl (10 mL). The reaction mixture was stirred at room temperature for 1 h and cooled with ice. The aqueous layer was separated and the organic layer was extracted twice with 1N NaOH (2×10 mL). The basic extracts were combined and washed with ether (10 mL). The basic layer was acidified to pH 4 using 6 N HCl and the solid that separated out was collected by filtration, washed with water and hexane and dried in vacuo to furnish boronic acid as a solid. If no solid product is obtained then the basic layer was extracted with ether (2×10 mL). The organic layers were combined, dried and concentrated in vacuo to furnish boronic acid.

U-2: Synthesis of Boronic Acid by Ortho Lithiation of Aryl Aldehyde

To a solution of N,N,N'-trimethylethylenediamine (1 mmol) in THF/ether (10 mL, 1:1) cooled to −20° C. was added dropwise, over a period of 15 mins, n-butyl lithium (1 mmol) and stirred at −20° C. for 15 mins. Aldehyde (1 mmol) at −20° C. was added dropwise over a period of 10 mins to this mixture. The reaction mixture was further stirred for 15 mins at −20° C. followed by the addition of n-butyl lithium (2.8 mmol) dropwise over a period of 15 mins and stirred at 4° C. overnight. The reaction mixture was cooled to −40° C. and tributyl borate (5.6 mmol) in ether (20 mL) was added to the reaction and stirred at 4° C. for 12 h. The reaction mixture was allowed to warm to 0° C. and quenched with 2 M HCl (3 mmol) and heated at reflux for 2 h and added to ice water (25 mL). The aqueous layer was separated and the organic layer extracted twice with 1N NaOH (2×10 mL). The basic extracts were combined and washed with ether (10 mL). The basic layer was acidified to pH 3 using 6 N HCl and the solid that separated out was collected by filtration, washed with water and hexane and dried in vacuo to furnish boronic acid as a solid. If no solid product was obtained, then the basic layer was extracted with ether (2×10 mL). The organic layers were combined, dried and concentrated in vacuo to furnish boronic acid.

U-3: Synthesis of Boronic Acid by Ortho Lithiation of Aryl Acetal

To a solution of aryl acetal compound (1 mmol) in ether (10 mL) at −78° C., tert-butyl lithium (1.1 mmol) was added dropwise and the reaction mixture was stirred for 3 h at −20° C. after the addition was completed. Tributyl borate (1.2 mmol) in ether (10 mL) was added to the reaction and stirred at −20° C. for 1 h. The reaction mixture was allowed to warm to 0° C. and quenched with 2 M HCl (10 mL). The reaction mixture was stirred at room temperature for 1 h. The aqueous layer was separated and the organic layer was extracted twice with 1N NaOH (2×10 mL). The basic extracts were combined and washed with ether (10 mL). The basic layer was acidified to pH 4 using 6 N HCl and the solid that separated out was collected by filtration, washed with water and hexane and dried in vacuo to furnish boronic acid as a solid. If no solid product was obtained then the mixture was extracted with ether (2×10 mL). The organic layers were combined, dried and concentrated in vacuo to furnish boronic acid.

V-1: Demethylation of Aryl Methyl Ether to Phenol

In a round bottom flask (50 mL), pyridine hydrochloride (10 g) was heated in an oil bath at 180° C. After the entire solid had melted, the corresponding aryl methyl ether (1 mmol) was added in small portions over a period of 20 min. The reaction mixture was heated at 180° C. for 4 h, cooled and quenched with water (100 mL). The reaction mixture was extracted with ethyl acetate (3×10 mL). The combined organic layers were washed with brine, dried over $MgSO_4$, concentrated to give phenol. This can be further purified if needed by crystallization or column chromatography.

V-2: Demethylation of Aryl Methyl Ether to Phenol

To a solution of aryl ether (1 mmol) in dichloromethane (10 mL) cooled to −78° C. was added boron tribromide (3 mmol). The reaction mixture was allowed to warm to room temperature overnight and quenched with water (10 mL). The solid obtained was collected by filtration to give the desired product. More product was obtained after evaporation of the organic layer and washing the residue with water. Alternatively, if a homogenous biphasic mixture was obtained on addition of water, the organic layer was separated, washed with brine, dried over $MgSO_4$, and concentrated to give the desired phenol. This can be further purified if needed by crystallization or column chromatography.

V-3: Demethylation of Aryl Methyl Ether to Phenol

To a solution of aryl methyl ether (1 mmol) in dichloromethane (5 mL) was added $AlCl_3$ (8.5 mmol). The reaction mixture was heated to reflux for 12 h under nitrogen. To this mixture was added 12 mL of 1 N HCl slowly and the organic layer was separated. The aqueous layer was re-extracted several times with ethyl acetate/DME. The combined organic layers were washed with brine, dried ($MgSO_4$), and evaporated in vacuo to furnish the desired phenol, which was purified by column chromatography.

V-4: Demethylation of Aryl Methyl Ether to Phenol

To a stirred slurry of NaH (2 mmol) in anhydrous toluene (5 mL) under nitrogen atmosphere was added para-thiocresol (2 mmol) dissolved in toluene (40 mL). The mixture was stirred at room temperature for 30 min and hexamethylphosphoric triamide (2 mmol) in toluene (5 mL) was added dropwise over a period of 30 min. A solution of aryl ether (1 mmol) in toluene (5 mL) was added in one portion. The reaction mixture was stirred at reflux for 9.5 h, cooled to room temperature and diluted with ethyl acetate (40 mL). The organic layer was extracted with 1 N aqueous NaOH solution (2×20 mL). The basic layer was acidified to pH 5 and extracted with ethyl acetate (2×20 mL). The organic layers were combined, washed with water, dried ($MgSO_4$) and concentrated in vacuo. The residue obtained was purified by flash column chromatography to afford the desired phenol compound.

W: Conversion of Acid to Methyl Ester

A mixture of acid (1 mmol), conc. $H_2SO_4$ or conc HCl (0.5 mL) and methanol (10 mL) was heated at reflux for 16 h. The mixture was concentrated to half of its volume and the residue poured into a saturated sodium bicarbonate solution. The precipitate was collected by filtration, washed with water and dried to give the desired ester. If the ester did not come as solid, it was extracted with ethyl acetate. The organic layer was dried, filtered and concentrated to give the desired ester.

W-2: Conversion of Acid to Ester

A solution of methanolic HCl or ethanolic HCl was prepared by the addition of acetyl chloride (1 mL) to methanol/ethanol (9 mL) at 0° C. and stirred for 30 mins. To the solution of anhydrous methanolic HCl was added acid (1 mmol) and stirred at room temperature (or reflux if needed) overnight. The reaction mixture was concentrated to dryness in vacuo and the residue was purified by column chromatography or crystallization to furnish the desired ester.

X: Conversion of Phenol to Alkyl Aryl Ethers or Alkylation of Amines

To a solution phenol or amine (1 mmol) in DMF (10 mL) was added cesium carbonate (1.25 mmol) and corresponding bromide (1.1 mmol). The reaction mixture was stirred at room temperature overnight and quenched with water (25 mL). The product was extracted with ether (2×25 mL), the organic layers were combined and washed with water (25 mL), brine (25 mL), dried and concentrated in vacuo to furnish crude product. The crude was purified by crystallization or flash column chromatography.

Y: Conversion of Nitrile to Hydroxycarbamimidoyl

To a solution of nitrile compound (1 mmol) in ethyl alcohol (10 mL) was added hydroxylamine (50% aqueous solution, 5 mmol). The mixture was stirred at reflux for 2–5 h. The reaction mixture was concentrated in vacuo to furnish the desired hydroxycarbamimidoyl compound.

Z: Opening of Aromatic Methylene Dioxy Compound with Alcohol

A solution of potassium tert-butoxide (2.25 mmol) in DMSO (1.25 mL) was heated at 50° C. for 30 min. Methanol (1.25 mL) was added to it and continued heating at 50° C. for 30 min. To the reaction mixture was added 1,2-methylenedioxy aromatic compound (1 mmol) and continued heating at 50° C. for 30 min. The reaction mixture was cooled to room temperature and quenched with water (10 mL) and 1 N sodium hydroxide (16 mL). The reaction m mixture was washed with ether (2×10 mL) and acidified to pH 4 using conc HCl. The solid obtained was collected by filtration to furnish the desired product.

Z-1: Opening of Aromatic Methylene Dioxy Compound with Alcohol

To a mixture of methylene dioxy compound (1 mmol) in HMPA (2.5 mL) were added sodium methoxide (2.5 mmol) and heated with stirring at 150° C. for 12 min. The mixture was cooled and poured into ice water (20 mL), NaOH (30 mg) and stirred for 10 min. It was then extracted with ether and the aqueous layer was acidified to pH 4 with HCl and extracted with ether. The later ethereal extracts were combined, dried and concentrated. The residue was purified by crystallization or column chromatography.

AA: Conversion of Amine to Amide in the Presence of a Phenol

To a solution of amino compound (1 mmol) in pyridine (5 mL) was added, dropwise, acid chloride (2 mmol) at 0° C. under $N_2$. The mixture was stirred for 45 min and was then poured into ice water and acidified with 1 N HCl. The precipitated solid was collected by filtration, washed with 1N HCl, hexane, and then dried in vacuo to give crude product. The crude product was added to freshly prepared sodium methoxide solution (0.1 M, 10 mL) and stirred for 30 min at room temperature. The reaction mixture was quenched with acetic acid (1 mmol) and concentrated in vacuo. The residue was dissolved in ethyl acetate and washed with water. The water layer was extracted with ethyl acetate, and the combined organic layers were washed with brine, dried ($MgSO_4$) and evaporated to yield a solid. The solid was washed with hexane and dried in vacuo to furnish the desired amide.

AB-1: Conversion of Amino of Amidine to Amino Carbamate

To amidine compound (1 mmol) was added 0.1N NaOH (10 mL) and stirred at room temperature for 5 min. The reaction mixture was concentrated in vacuo and to the residue was added alkyl or aryl 4-nitrophenyl carbonate (2 mmol) in 20 mL of hexamethylphosphoramide and stirred at 45° C. for 24 h. The reaction was quenched with water (100 mL) and extracted with ethyl acetate (2×100 mL). The combined extracts were washed with water (100 mL) and brine (100 mL), dried over anhydrous magnesium sulfate, filtered and concentrated in vacuo. The residue obtained was purified by flash column chromatography to furnish the desired product.

AB-2: Conversion of Amino of Amidine to Amino Carbamate

To a solution of amidine compound (1 mmol) in acetonitrile (25 mL) was added triethylamine (5 mL) and aryl/alkyl chloroformate (2 mmol) or dialkyl/aryl carbonate. The reaction mixture was stirred at room temperature for 16 h and quenched with water (100 mL). The reaction mixture was extracted with ethyl acetate (2×100 mL). The combined extracts were washed with brine (100 mL), dried over anhydrous magnesium sulfate, filtered and concentrated in vacuo. The residue obtained was purified by flash column chromatography to furnish the desired product.

AC: Conversion of Aldehyde to Oxime

To a stirred solution of aldehyde (1 mmol) in ethanol (10 mL) was added pyridine (10 mL) and hydroxylamine hydrochloride (1.25 mmol). The reaction mixture was stirred overnight at room temperature under nitrogen and then concentrated in vacuo to one third of its original volume. Water (10 mL) was added and the precipitated solid was collected by filtration and dried in vacuo. The product was used as such for next step without further purification.

AD: Debenzylation in the Presence of Aldehyde

To a solution of phenyl methoxyaryl aldehyde (1 mmol) in dichloromethane (10 mL) cooled to −78° C. was added dropwise under a nitrogen atmosphere boron tribromide (1M solution in dichloromethane, 1.2 mmol). The reaction mixture was allowed to warm to room temperature and stirred at room temperature overnight. The reaction mixture was quenched with water (10 mL) and the layers were separated. The aqueous layer was extracted with chloroform (10 mL). The organic layers were combined, washed with brine (10 mL), dried, filtered and concentrated in vacuo to furnish crude product. Purification of the crude by flash column chromatography furnished the desired phenolic aldehyde AE-1: Reductive Amination of Aldehyde To a stirred solution of aldehyde (1 mmol) in methanol (40 mL) was added amine (3.3 mmol) followed by the addition of glacial acetic acid (0.3 mL). The reaction mixture was stirred for 30 min under nitrogen at room temperature, and then sodium cyanoborohydride (1.5 mmol) was added. After stirring for 20 min, the solvent was evaporated in vacuo, and the residue was taken in ethyl acetate. The organic layer was washed with water, and the insoluble material was removed from the organic layer by filtration. The pH of the aqueous phase was adjusted to 7 with 1N NaOH and was extracted twice with ethyl acetate. The combined organic layers were washed with brine and dried (MgSO$_4$). The solvent was evaporated in vacuo to furnish crude product. The crude product was purified by crystallization or flash column chromatography.

AE-2: Reductive Amination of Aldehyde

To a mixture of aminoarylamidine (1.2 mmol), 4A° molecular sieves, and sodium hydroxide (1 N solution in anhydrous methanol, 1.2 mL, 1.2 mmol) in methanol (10 mL) was added a solution of aldehyde (1 mmol) in THF (10 mL). The reaction mixture was heated for 15 mins at reflux temperature and was cooled to room temperature. Acetic acid (1%) and sodium cyanoborohydride (1 M solution in THF, 5 mmol) was added to the reaction mixture and stirred at room temperature overnight. The reaction mixture was quenched with 1 N NaOH (30 mmol) and stirred for additional 2 h and concentrated in vacuo to remove methanol. The mixture was diluted with water (15 mL) and washed with ether (2×10 mL). The aqueous layer was acidified to pH 2 using 6 N HCl and the solid that separated out was collected by filtration, washed with ether, dried in vacuo to furnish product, which was purified by flash column chromatography, if needed.

AE-3: Reductive Amination of Aldehyde

A mixture of aminoarylamidine (2 mmol), 4A° molecular sieves, pyridine (6 mL) in methanol (9 mL) was heated at 50° C. for one hour. A solution of aldehyde (1 mmol) in methanol (7.5 mL) containing acetic acid (1%) was added and continued heating for 4 h to 12 h. The reaction mixture was cooled and sodium cyanoborohydride (1 M solution in THF, 5 mmol) was added to the reaction mixture and stirred at room temperature overnight. The reaction mixture was quenched with 5 N NaOH (30 mmol) and stirred for additional 2 h. The reaction mixture was filtered through Celite (to remove molecular sieves) and concentrated to remove methanol. The mixture was diluted with water (15 mL) and washed with ether (2×10 mL). The aqueous layer was filtered and solid obtained was kept aside (mainly product). The aqueous layer was acidified to pH 2 using 6 N HCl and the solid that separated out was collected by filtration. The combined solid materials were purified, if needed, by flash column chromatography.

AE-4: Reductive Amination of Aldehyde

To a mixture of aldehyde (1 mmol) and aminoarylamidine (1.1 mmol) in MeOH at room temperature was added triethyl amine (2.75 mmol), sodium cyanoborohydride (0.83 mmol) and zinc chloride (0.9 mmol). The reaction mixture was stirred at room temperature overnight and concentrated to remove methanol. The reaction mixture was quenched with 1 N NaOH (10 mL), diluted with water (10 mL), and extracted with EtOAc (5×20 mL). The combined organic extracts were washed with brine (15 mL), dried (MgSO4), filtered through Celite and concentrated to give the product. Purification of the crude by flash column chromatography gave the desired product.

AE-5: Reductive Amination of Aldehyde

To a solution of amine (1.2 mmol) in MeOH (10 mL) was added aldehyde (1 mmol) in THF (10 mL) containing acetic acid (0.1 mL) drop-wise. The mixture was stirred at 50° C. for 4–12 h and then cooled to room temperature. Sodium cyanoborohydride (1.5 mmol) was added to the reaction mixture and stirred at room temperature overnight. Water was added and pH of the solution was adjusted to 7. The solution was extracted with ethyl acetate. The organic layer was dried (MgSO$_4$) and evaporated in vacuo. The residue was purified by flash column chromatography to furnish the desired amine.

AF-1: Synthesis of Amidine from Nitrile

Acetyl chloride (5 mL) was added to methanol (5 mL) at 0° C. drop-wise and stirred at room temperature for 15 mins. To this solution of methanolic HCl was added nitrile compound (1 mmol) and stirred at room temperature overnight. The reaction mixture was concentrated in vacuo and dried. The residue obtained of the resulting methyl imidate was dissolved in methanol (10 mL). Dry ammonia gas was bubbled into the reaction mixture at reflux temperature for 5 h. The reaction mixture was concentrated to furnish the required amidine.

AG: Addition of Grignard Reagent to Aryl Aldehyde

To a solution of aryl aldehyde (1 mmol) in THF (15 mL) cooled to −78° C. was added drop wise under a nitrogen atmosphere, vinyl magnesium bromide (1 M solution in THF, 5 mmol). The reaction mixture was allowed to warm to room temperature and stirred for 48 h. The reaction was quenched carefully with saturated aqueous ammonium chloride solution (10 mL) and extracted with ethyl acetate (2×10 mL). The organic layers were combined, washed with brine (10 mL), dried and concentrated in vacuo. The residue obtained was purified by flash column chromatography to obtain the desired addition product.

AG-1: Synthesis of Tributylvinyltin Compounds from Vinyl Bromide Containing Hydroxyl To a solution of vinyl bromide with hydroxyl (1 mmol) in dichloromethane (20 mL) was added tert-butyldimethylsilyl chloride (1.5 mmol) and DMAP (1.5 mmol) and stirred at room temperature overnight. The reaction mixture was quenched with water (20 mL) and the aqueous layer separated. The organic layer was washed with 0.1 N aqueous HCl (10 mL), brine (20 mL), dried and concentrated in vacuo to furnish corresponding tert-butyldimethylsilyloxy compound as an oil which was used as such for the next step.

To a solution of the above oily residue (1 mmol) in diethyl ether (20 mL) cooled to −78° C. was added dropwise tert-butyllithium (1.7 M in pentane, 2 mmol) over a period of 15 mins. The reaction mixture was stirred at −78° C. for 3 h and quenched at −78° C. with 2 N aqueous sulfuric acid (2 mL) and water (18 mL). The reaction mixture was neutralized using 2 N NaOH and the organic layer was separated. The organic layer was washed with water (20 mL), brine (20 mL), dried and concentrated in vacuo. Purification of the crude residue obtained by flash column chromatography furnished the desired tributyltin compound.

AG-2: Synthesis of Tributylmethyltin Compounds from Arylmethyl Bromides or Allyl Bromides To lithium clippings (10 mmol) in THF (10 mL) cooled to −40° C. was added dropwise tributyltin chloride (0.27 mL, 1 mmol) in THF (5 mL) over a period of 15 min. The reaction mixture was allowed to warm to room temperature and stirred for 16 h. The reaction mixture was filtered through glass wool to remove insoluble impurities and cooled to −40° C. A freshly prepared solution of arylmethyl bromide or allyl bromide (1 mmol) was added dropwise over a period of 10 mins and stirred at room temperature overnight. The reaction mixture was quenched with saturated aqueous ammonium chloride solution (10 mL) and extracted with ether (2×10 mL). The organic layers were combined, washed with brine (10 mL), dried, filtered and concentrated in vacuo to furnish desired tributyltinalkyl and was used as such without further purification.

AG-3: 4-Bromo-5-formyl-benzo[1,3]dioxole-2-carboxylic acid methyl ester

To a mixture of 2-bromo-3,4-dihydroxy-benzaldehyde (2.17 g, 10.0 mmol) and $K_2CO_3$ (5.56 g, 40.2 mmol) in n-propanol (25 mL) was added dibromoacetic acid (2.18, 10.0 mmol) and the mixture was heated at reflux temperature for 24 h. After cooling to room temperature, another portion of dibromoacetic acid (1.75 g, 8.0 mmol) was added. The mixture was stirred at reflux for 46 h. n-Propanol was evaporated and water (30 mL) was added. The resulting aqueous solution was acidified to pH 2 by adding 1 N HCl and extracted with ethyl acetate (3×100 mL). The combined organic layers were dried ($MgSO_4$) and evaporated in vacuo to afford crude 4-bromo-5-formyl-benzo[1,3]dioxole-2-carboxylic acid (1.34 g) as a brownish solid. This crude product was dissolved in anhydrous methanol (50 mL) and conc. $H_2SO_4$ (5 mL) was added drop by drop. The resulting mixture was refluxed overnight and cooled to room temperature. Water (50 mL) was added and the resulting aqueous solution was extracted with ethyl acetate (100 mL×3). The combined organic layers were dried ($MgSO_4$) and evaporated in vacuo. The residue was purified by flash column chromatography (ethyl acetate:hexane=5:95) to furnish 4-bromo-5-formyl-benzo[1,3]dioxole-2-carboxylic acid methyl ester as a white solid.

AH: Synthesis of tert-Butyl Ester of Phenol

To a solution of phenol (1 mmol) in pyridine (10 mL) was added 2,2-dimethyl-propionyl chloride (1.2 mmol) dropwise. The mixture was stirred at room temperature for overnight and diluted with water (100 mL). The reaction mixture was extracted with ethyl acetate (3×50 mL). The organic layers were combined and washed with aqueous 0.5 N HCl (100 mL), water, brine, dried ($MgSO_4$) and concentrated in vacuo. The crude residue was purified by flash column chromatography to furnish the desired ester.

AI: Preparation of 2-bromo-5-hydroxy benzaldehyde

To a solution 3-hydroxybenzaldehyde (Aldrich, 101.39 g, 805 mmol) in chloroform (1000 mL), was added bromine (45 mL, 845 mmol) in chloroform (200 mL) drop wise over a period of 2 h at room temperature. The reaction mixture was stirred at room temperature overnight and filtered to collect crude 2-bromo-5-hydroxy benzaldehyde (32 g) as a dark brown solid. The filtrate was concentrated to 200 mL, filtered through a pad of Celite and silica gel (40 g) and washed with ether (1000 mL). The filtrate was concentrated in vacuo to give a second crop of the crude desired aldehyde (60 g) as a dark brown solid. The above solids were combined and dissolved in glacial acetic acid (360 mL) by heating. Water (840 mL) was added and the solution was filtered hot. The solution was allowed to attain room temperature and kept in a refrigerator overnight. The crystals obtained were collected by filtration and washed with water, dried overnight in vacuo to furnish (60 g, 37%) of the desired product as a purplish brown crystalline solid, mp: 135° C.

AJ-1: Amidine from Nitrile

A mixture of nitrile (1 mmol) and hydroxylamine (aqueous 50%, 1.8 mL) in EtOH (15 mL) was refluxed for 3 h and concentrated in vacuo. To the residue obtained was added EtOH (20 mL), acetic acid (2 mL) and a small amount of Raney nickel. The reaction mixture was hydrogenated (50 psi) for 14–24 h, filtered and concentrated in vacuo. The residue obtained, was purified by flash column chromatography to obtain the corresponding amidine.

AJ-2: Amidine from Nitrile

A mixture of nitrile (1 mmol) and saturated methanolic HCl solution (freshly prepared by bubbling HCl gas or prepared in-situ by premixing methanol and acetyl chloride at ice cold temperature) was stirred at room temperature overnight. The reaction mixture was concentrated in vacuo to furnish methyl imidate. To the residue of methyl imidate was added MeOH (40 mL) and ammonia gas was bubbled at reflux temperature for 16 h or till the reaction was complete. The reaction mixture was concentrated in vacuo and dried to furnish the desired amidine. Alternatively, the methyl imidate was dissolved in methanol and ammonium acetate (10 mmol) was added. The reaction mixture was concentrated in vacuo and purified by flash column chromatography to obtain the corresponding amidine.

AJ-3: Amidine from Nitrile

To a solution of nitrile (1 mmol) dissolved in methanol (5 mL) was added N-acetyl cystein (0.1 or 1 mmol) and ammonium acetate (5 mmol) and heated at reflux till the reaction was complete. The reaction mixture was concentrated in vacuo and purified by flash column chromatography to obtain the corresponding amidine.

AK: Conversion of Aryl Triflates or Halides to Boronate Ester

To dichloro[1,1'-bis(diphenylphosphino)ferrocene] palladium (II) dichloro-methane adduct (0.75 mmol) under argon in dioxane (100 mL) was added aryl triflate (25 mmol), pinacolborane (31.5 mmol) and triethylamine (75 mmol). The reaction mixture was heated under argon at 100° C. for 3 h or until complete as evidenced from TLC analysis. The reaction mixture was concentrated in vacuo. The residue obtained was purified by flash column chromatography to furnish the desired boronate ester. Alternatively, the following method can be used.

To dichloro[1,1'-bis(diphenylphosphino)ferrocene] palladium (II) dichloro-methane adduct (0.03 mmol), 1,1'-bis(diphenylphosphino)ferrocene (0.03 mmol) under argon in dioxane (100 mL) was added aryl triflate (1 mmol), bis(pinacolata)diboron (1.1 mmol) and potassium acetate (3 mmol). The reaction mixture was heated under argon at 100° C. for 3 h or until complete as evidenced from TLC analysis. The reaction mixture was concentrated in vacuo. The residue obtained was purified by flash column chromatography to furnish the desired boronate ester.

The examples of the compounds prepared are given in the following tables. The tables describe the compounds, their method of preparation, the starting material, and the analytical data. In some cases, where analytical data have not been given, those compounds were characterized at the later step in the synthesis.

AL: Deprotection of the Benzyl Ester

The aldehyde (1 mmol) was mixed with ammonium nitrate (0.2 mmol) in 10 mL of EtOH. The mixture was treated with HC(OEt)$_3$ (1.5 mmol) and stirred at 70° C. for 2 h. The reaction mixture was diluted with 30 mL of EtOH and dried with molecular sieves followed by filtration.

The above filtrate (40 mL) was treated with 1 drop of concentrated HCl and 10% Pd/C (0.1 g) followed by hydrogenation for 5 h. The reaction mixture was filtered and concentrated. The residue was treated with 10 mL of DME and 1 mL of 1N HCl followed by stirring at room temperature for 0.5 h. Water (5 mL) was added and the mixture was extracted with EtOAc (2×10 mL). The combined extracts were washed with water (2×10 mL) and brine (10 mL), dried over MgSO$_4$, filtered, and concentrated. The residue was purified by flash column chromatography (EtOAc/Hex/MeOH, 1:1:0 to 1:1:0.2) to afford the desired product.

AM: Preparation of α-Amino Esters:

A mixture of methyl 2'-formyl-4-[(isobutylamino)carbonyl]-5'-methoxy-1,1'-biphenyl-2-carboxylate (1 mmol) and 4-aminobenzonitrile (1 mmol) in toluene (5 mL) was heated at reflux for 16 h. The reaction mixture was concentrated and the residue taken in dry methanol (5 mL), cooled in an ice bath and tosylmethyl isocyanide (1.1 mmol) added to it followed by BF$_3$.ethereate (3.0 mmol) over a period of 5 min. The reaction mixture was stirred for 0.5 h in ice-bath and then at room temperature for 1.5 h. Water (90 μL) was added to the reaction and further stirred for 16 h. The reaction mixture was taken in ethyl acetate (50 mL), washed with water and brine, and dried over MgSO$_4$. After filtration, the filtrate was concentrated and the residue was purified on silica gel using ethyl acetate: hexane as an eluent to give 0.37 g (67%) of the desired product, 2'-{1-[4-cyanophenyl)amino]-2-methoxy-2-oxoethyl}-4-[(isobutylamino)carbonyl]-5'-methoxy-1,1'-biphenyl-2-carboxylate.

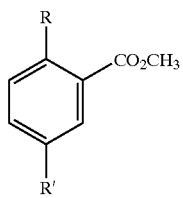

| Cpd. No. | —R | —R' | Starting From | Method Used | Analytical Data |
|---|---|---|---|---|---|
| 2a | —OH | ![isobutylamino carbonyl] | 1 | A-1 or A-2 | $^1$H NMR (DMSO-d$_6$): δ 10.26 (s, 1H), 9.84 (s, 1H), 8.15 (d, J=3.0Hz, 1H), 7.64 (dd, J=2.0Hz and 8.9Hz, 1H), 6.94 (d, J=8.9Hz, 1H), 3.90 (s, 3H), 2.15 (d, J=6.9Hz, 2H), 2.06 (m, J=6.9Hz, 1H), 0.93 (d, J=6.9Hz, 1H), 0.93 (d, J=6Hz, 6H); MS (ES$^+$): 252.12 |
| 2b | —OH | ![isopropylamino carbonyl] | 1 | A-1 or A-2 | Characterized in the next step |
| 2c | —OH | ![sec-pentylamino carbonyl] | 1 | A-1 or A-2 | MS (ES$^+$): 294.54 |
| 2d | —OH | ![propylamino carbonyl] | 1 | A-1 or A-2 | MS (ES$^+$): 288.49 (M + Na)$^+$ |

-continued

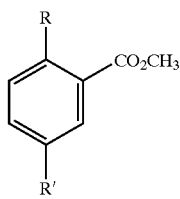

| Cpd. No. | —R | —R' | Starting From | Method Used | Analytical Data |
|---|---|---|---|---|---|
| 2e | —OH | -C(O)NH-CH2CH2CH2CH3 | 1 | A-1 or A-2 | Characterized in the next step |
| 2f | —OH | -C(O)NH-CH2CF3 | 1 | A-1 or A-2 | MS (ES+): 300.40 (M + Na)+ |
| 2g | —OH | -C(O)NH-CH2-cyclopropyl | 1 | A-1 or A-2 | MS (ES+): 272.48 (M + Na)+; MS (ES−): 248.66 |
| 2h | —OH | -C(O)NH-cyclopentyl | 1 | A-1 or A-2 | MS (ES+): 286.48 (M + Na)+ |
| 2i | —OH | -C(O)NH-CH2CH3 | 1 | A-1 or A-2 | MS (ES+): 224.54 |
| 2j | —OH | -C(O)NH-CH2CH(CH3)CH2CH3 | 1 | A-1 or A-2 | Characterized in the next step |
| 3a | —OSO2CF3 | -C(O)NH-CH2CH(CH3)2 | 2a | B-1 or B-2 | MS (ES+): 384.37 |
| 3b | —OSO2CF3 | -C(O)NH-CH(CH3)2 | 2b | B-1 or B-2 | MS (ES+): 370.36 |
| 3c | —OSO2CF3 | -C(O)NH-CH(CH2CH3)(CH2CH2CH2CH3) | 2c | B-1 or B-2 | MS (ES+): 426.37 |
| 3d | —OSO2CF3 | -C(O)NH-CH2CH2CH2CH3 | 2d | B-1 or B-2 | Characterized in the next step |

-continued

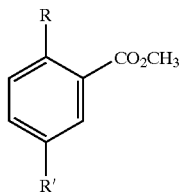

| Cpd. No. | —R | —R' | Starting From | Method Used | Analytical Data |
|---|---|---|---|---|---|
| 3e | —OSO₂CF₃ | CH₃CH₂CH₂CH₂NHC(O)CH₂– | 2e | B-1 or B-2 | ¹HNMR (CDCl₃): δ 8.41 (d, J=2.3Hz, 1H), 8.10 (dd, J=8.5, 2.4Hz, 1H), 7.37 (d, J=8.5Hz, 1H), 6.48 (broad, 1H), 3.98 (s, 3H), 3.46 (q, J=7.2Hz, 2H), 1.62 (m, 2H), 1.42 (m, 2H), 0.96 (t, J=7.2 Hz, 3H); MS (ES⁺): 384.1 |
| 3f | —OSO₂CF₃ | CF₃CH₂NHC(O)CH₂– | 2f | B-1 or B-2 | ¹HNMR (CDCl₃): δ 8.45 (d, J=2.4Hz, 1H), 8.14 (dd, J=8.7, 2.4Hz, 1H), 7.42 (d, J=8.7Hz, 1H), 6.52 (broad, 1H), 4.14 (m, 2H), 4.00 (s, 3H); MS (ES⁺): 410.2 |
| 3g | —OSO₂CF₃ | cyclopropyl-CH₂NHC(O)CH₂– | 2g | B-1 or B-2 | ¹HNMR (CDCl₃): δ 8.42 (d, J=2.3Hz, 1H), 8.12 (dd, J=8.5, 2.3Hz, 1H), 7.39 (d, J=8.7Hz, 1H), 6.31 (broad, 1H), 4.00 (s, 3H), 3.34 (dd, J=7.2, 5.5Hz, 2H), 1.07 (m, 1H), 0.59 (m, 2H), 0.30 (m, 2H); MS (ES⁺): 382.2 |
| 3h | —OSO₂CF₃ | cyclopentyl-NHC(O)CH₂– | 2h | B-1 or B-2 | MS (ES⁺): 396.36 |
| 3i | —OSO₂CF₃ | CH₃CH₂NHC(O)CH₂– | 2i | B-1 or B-2 | ¹HNMR (DMSO-d₆): δ 8.85 (t, J=5.5Hz, 1H), 8.49 (d, J=2.3Hz, 1H), 8.23 (dd, J=8.7, 2.3Hz, 1H), 7.70 (d, J=8.7Hz, 1H), 3.92 (s, 3H), 3.31 (m, 2H), 1.14 (t, J=7.2Hz, 3H); MS (ES⁺): 356.1 |
| 3j | —OSO₂CF₃ | CH₃CH₂CH(CH₃)CH₂NHC(O)CH₂– | 2j | B-1 or B-2 | ¹HNMR (DMSO-d₆): δ 8.81 (t, J=6.0Hz, 1H), 8.49 (d, J=2.3Hz, 1H), 8.24 (dd, J=8.7, 2.4Hz, 1H), 7.71 (d, J=8.7Hz, 1H), 3.92 (s, 3H), 3.15 (m, 2H), 1.64 (m, 1H), 1.41 (m, 1H), 1.12 (m, 1H), 0.88 (m, 6H); MS (ES⁺): 398.2 |
| 5 | —OSO₂CF₃ | —CO₂MEM | 4 | B-2 | ¹HNMR (DMSO-d₆): δ 8.52 (d, J=2.0Hz, 1H), 8.32 (dd, J=2.0 and 8.9Hz, 1H), 7.72 (d, J=7.9 Hz, 1H), 5.50 (s, 2H), 3.88 (s, 3H), 3.78 (t, J=4.9 Hz, 2H), 3.44 (d, J=4.9Hz, 2H), 3.17 (s, 3H); MS (ES⁺): 439.1 (M + Na)⁺ |
| 6a | pinacol boronate | (CH₃)₂CHCH₂NHC(O)CH₂– | 3a | AK | ¹HNMR (CDCl₃): δ 8.29 (d, J=1.6Hz, 1H), 7.96 (dd, J=7.5 & 1.6Hz, 1H), 7.58 (d, J=7.5Hz, 1H), 6.24 (bs, 1H), 3.94 (s, 3H), 3.30 (t, J=6.5Hz, 2H), 1.92 (m, 1H), 1.43 (s, 12H), 0.99 (d, J=6.5 Hz, 6H); MS (ES+) 362.2 |
| 139 | —OH | CH₃NHC(O)CH₂CH(CH₃)₂ | 138 | AA | ¹HNMR (DMSO-d₆): δ 10.26 (s, 1H), 9.84 (s, 1H), 8.15 (d, J=3.0Hz, 1H), 7.64 (dd, J=2.0Hz and 8.9Hz, 1H), 6.94 (d, J=8.9Hz, 1H), 3.90 (s, 3H), 2.15 (d, J=6.9Hz, 2H), 2.06 (m, J=6.9Hz, 1H), 0.93 (d, J=6.9Hz, 6H); MS (ES⁺): 252.12 |
| 140 | —OSO₂CF₃ | CH₃NHC(O)CH₂CH(CH₃)₂ | 139 | B-2 | ¹HNMR (DMSO-d₆): δ 10.38 (s, 1H), 8.36 (d, J=2.8Hz, 1H), 7.99 (dd, J=2.6 and 8.9Hz, 1H), 7.52 (d, J=9.0Hz, 1H), 3.89 (s, 3H), 2.23 (d, J=7.0Hz, 2H), 2.09 (m, J=6.6Hz, 1H), 0.94 (d, J=6.6Hz, 6H); MS (ES⁺): 384.0 |

-continued

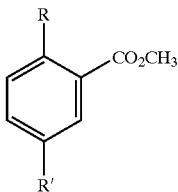

| Cpd. No. | —R | —R' | Starting From | Method Used | Analytical Data |
|---|---|---|---|---|---|
| 169 | —OH | =NOH (oxime CH=NOH) | 168 | AC | $^1$HNMR (CDCl$_3$): δ 8.08 (s, 1H), 8.00 (d, J=2.3 Hz, 1H), 7.75 (dd, J=2.3 and 8.7Hz, 1H), 7.01 (d, J=8.7Hz, 1H), 3.97 (s, 3H), 3.50 (s, 1H); MS (ES$^+$): 196.1 |
| 170 | —OH | —CH$_2$NH$_2$ | 169 | G | $^1$HNMR (DMSO-d$_6$): δ 7.79 (d, J=2.0Hz, 1H), 7.51 (dd, J=2.3 and 8.5Hz, 1H), 6.95 (d, J=8.5 Hz, 1H), 7.01 (d, J=8.7Hz, 1H), 3.90 (s, 3H), 3.72 (s, 2H), 3.50 (bs, 2H); MS (ES$^+$): 182.12 |
| 171 | —OH | —CH$_2$NHC(O)CH(CH$_3$)$_2$ | 170 | AA | MS (ES$^-$): 250.50; MS (ES$^+$): 274.50 (M + Na)$^+$ |
| 172 | —OSO$_2$CF$_3$ | —CH$_2$NHC(O)CH(CH$_3$)$_2$ | 171 | B-2 | $^1$HNMR (CDCl$_3$): δ 7.96 (d, J=2.3Hz, 1H), 7.55 (d, J=2.3 and 8.3Hz, 1H), 7.26 (d, J=8.3Hz, 1H), 5.90 (br s, 1H), 4.50 (d, J=4.1Hz, 2H), 3.97 (s, 3H), 2.44 (sep, J=7.0Hz, 1H), 1.20 (d, J=7.0 Hz, 6H); MS (ES$^+$): 384.1 |
| 177 | —OH | —CH$_2$NHCH$_2$CH(CH$_3$)$_2$ | 168 | AE-1 | $^1$HNMR (DMSO-d$_6$): δ 10.62 (s, 1H), 8.88 (m, 2H), 7.99 (d, J=2.3Hz, 1H), 7.70 (dd, J=2.3 and 8.5Hz, 1H), 7.06 (d, J=8.7Hz, 1H), 4.09 (m, 2H), 3.91 (s, 3H), 2.70 (m, 2H), 1.98 (m, 1H, J=6.8Hz), 0.93 (d, J=6.8Hz, 6H); MS (ES$^+$): 238.1 |
| 178 | —OSO$_2$CF$_3$ | —CH$_2$NHCH$_2$CH(CH$_3$)$_2$ | 177 | B-2 | $^1$HNMR (CDCl$_3$): δ 8.05 (d, J=2.3Hz, 1H), 7.63 (dd, J=2.3 and 8.3Hz, 1H), 7.25 (d, J=8.3Hz, 1H), 3.96 (s, 3H), 3.85 (s, 2H), 2.43 (d, J=6.8Hz, 2H), 1.77 (m, J=6.6Hz, 1H), 0.93 (d, J=6.6Hz, 1H); MS (ES$^+$): 370.2 |
| 179 | —OSO$_2$CF$_3$ | —CH$_2$N(Boc)CH$_2$CH(CH$_3$)$_2$ | 178 | R | $^1$HNMR (DMSO-d$_6$): δ 7.93 (m, 1H), 7.47 (m, 1H), 7.26 (m, 1H), 4.48 (m, 2H), 3.96 (s, 3H), 3.03 (m, 2H), 1.91 (m, 1H), 1.52 (m, 9H), 0.89 (d, J=6.6Hz, 6H); MS (ES$^+$): 492.2 (M + Na)$^+$ |

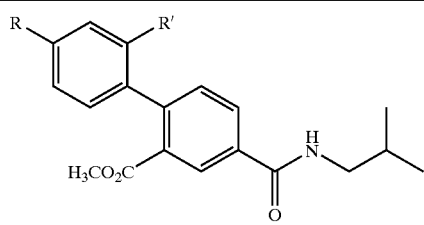

| Cpd. No. | —R | —R' | Starting From | Method Used | Analytical Data |
|---|---|---|---|---|---|
| 7 | —OBn | —CHO | 6 + 3a | D-2 | $^1$HNMR (DMSO-d6): δ 9.78 (s, 1H), 8.85 (t, J=5.7Hz, 1H), 8.50 (d, J=2.0Hz, 1H), 8.20 (dd, J=8.2, 1.9Hz, 1H), 7.55 (m, 9H), 5.35 (s, 2H), 3.69 (s, 3H), 3.23 (t, J=6.5Hz, 2H), 1.98 (m, 1H), 1.02 (d, J=6.8Hz, 6H); MS (ES+): 446.3 |
| 8 | —OBn | —CO$_2$H | 7 | E | MS (ES$^+$): 484.33 (M + Na)$^+$ |
| 9 | —OBn | —CO$_2$MEM | 8 | F | MS (ES$^+$): 572.2 (M + Na)$^+$ |

-continued

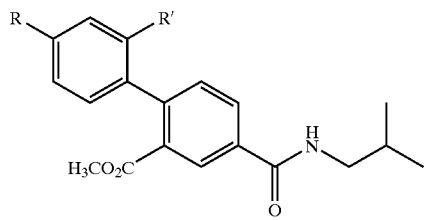

| Cpd. No. | —R | —R' | Starting From | Method Used | Analytical Data |
|---|---|---|---|---|---|
| 10 | —OH | —CO$_2$MEM | 9 | G | MS (ES$^+$): 482.33 [(M-MBM) + Na]$^+$ |
| 11 | —OSO$_2$CF$_3$ | —CO$_2$MEM | 10 | B-2 | $^1$HNMR (DMSO-d6): δ 8.75 (t, J=5.6Hz, 1H), 8.44 (d, J=1.6 Hz, 1H), 8.11 (dd, J=8.0, 1.9Hz, 1H), 8.01 (d, J=2.9Hz, 1H), 7.84 (dd, J=8.4, 2.6Hz, 1H), 7.47 (d, J=8.5Hz, 1H), 7.41 (d, J=8.0Hz, 1H), 5.23 (q, AB system, 2H), 3.59 (s, 3H), 3.44 (m, 2H), 3.30 (m, 2H), 3.18 (s, 3H), 3.13 (t, J=6.6Hz, 2H), 1.88 (m, 1H), 0.91 (d, J=6.7Hz, 6H); MS (ES+): 614.3 (M + Na)$^+$ |
| 29a | acetyl (C(=O)CH$_3$) | —CO$_2$MEM | 11 | D-3 | Characterized in the next step |
| 29b | CH=CH-CH$_3$ (propenyl) | —CO$_2$MEM | 11 | D-3 | MS (ES$^+$): 520.2 (M + Na)$^+$ |
| 29c | CH=CH-CH$_2$ (allyl/propenyl) | —CO$_2$MEM | 11 | D-3 | MS (ES$^+$): 482.3 |
| 29d | 2-thienylethyl | —CO$_2$MEM | 11 | D-3 | MS (ES$^+$): 562.3 (M + Na)$^+$ |
| 29e | benzyl/phenylethyl | —CO$_2$MEM | 11 | D-3 | MS (ES$^+$): 556.4 (M + Na)$^+$ |
| 29f | CH=CH$_2$ (vinyl) | —CO$_2$MEM | 11 | D-3 | $^1$HNMR (DMSO-d6): δ 8.50 (t, J=5.6Hz, 1H), 8.18 (d, J=1.9 Hz, 1H), 7.86 (dd, J=7.9, 1.9Hz, 1H), 7.78 (d, J=1.7Hz, 1H), 7.56 (dd, J=8.0, 1.8Hz, 1H), 7.13 (d, J=8.0Hz, 1H), 7.00 (d, J=7.9Hz, 1H), 6.67 (dd, J=17.6, 11.1Hz, 1H), 5.76 (d, J=17.6Hz, 1H), 5.19 (d, J=11.1Hz, 1H), 4.99 (q, AB system, 2H), 3.37 (s, 3H), 3.20 (m, 2H), 3.11 (m, 2H), 2.97 (s, 3H), 2.91 (t, J=6.7Hz, 2H), 1.67 (m, 1H), 0.70 (d, J=6.6Hz, 6H); MS (ES+): 492.3 (M + Na)$^+$ |
| 29g | 4-methyl-3-formylthienyl | —CO$_2$MEM | 11 | D-2 | MS (ES$^+$): 576.2 (M + Na)$^+$; MS (ES$^-$): 552.2 |
| 29h | 2-methyl-3-formylfuryl | —CO$_2$MEM | 11 | D-2 | MS (ES$^+$): 538.2 |
| 29i | 4-methyl-3-formylfuryl | —CO$_2$MEM | 11 | D-2 | MS (ES$^+$): 560.4 (M + Na)$^+$ |

-continued

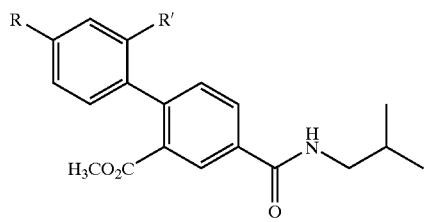

| Cpd. No. | —R | —R' | Starting From | Method Used | Analytical Data |
|---|---|---|---|---|---|
| 30a | acetyl (COCH₃) | —CO₂H | 29a | I-1 | MS (ES⁺): 398.3; MS (ES⁻): 396.3 |
| 30b | CH₃CH=CHCH₂— | —CO₂H | 29b | I-1 | Characterized in the next step |
| 30c | CH₂=CHCH₂— | —CO₂H | 29c | I-1 | MS (ES⁻): 392.1 |
| 30d | 2-thienylmethyl | —CO₂H | 29d | I-1 | MS (ES⁺): 452.1 |
| 30e | benzyl | —CO₂H | 29e | I-1 | MS (ES⁺): 446.2 |
| 30f | CH₂=CHCH₂ (allyl) | —CO₂H | 29f | I-1 | MS (ES⁻): 380.1 |
| 30g | (4-methyl-3-azidomethyl-thienyl) | —CO₂H | 29g | K, N, O, I-1 | MS (ES⁺): 515.3 (M + Na)⁺; MS (ES⁻): 491.2 |
| 30h | (2-methyl-3-hydroxymethyl-furyl) | —CO₂H | 29h | K, I-1 | MS (ES⁻): 450.1 |
| 30i | (4-methyl-3-hydroxymethyl-furyl) | —CO₂H | 29i | K, I-1 | MS (ES⁻): 450.3 |
| 33 | —OSO₂CF₃ | —CO₂H | 11 | I-1 | Characterized in the next step |
| 41 | —O—phenyl | —CO₂MEM | 10 | D-8 | MS (ES⁻): 534.30 |
| 42 | —O—phenyl | —CO₂H | 41 | I-1 | MS (ES⁻): 446.30 |
| 48 | —OCH₃ | —CHO | 47 + 3a | D-2 | MS (ES⁺): 392.2 (M + Na)⁺ |
| 49 | —OCH₃ | —CO₂H | 48 | E | MS (ES⁺): 386.1; 408.1 (M + Na)⁺ |

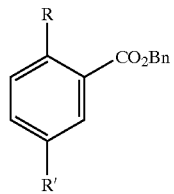

| Cpd. No. | —R | —R' | Starting From | Method Used | Analytical Data |
|---|---|---|---|---|---|
| 14 | —OSO₂CF₃ | —CHO | 13 | B-2 | Characterized in the next step |
| 15 | —OSO₂CF₃ | —CO₂H | 14 | E | MS (ES⁻): 403.58 |
| 16 | —OSO₂CF₃ | -NHC(O)CH₂CH(CH₃)₂ (acetamido isobutyl) | 15 | A-3 or A-4 | $^1$HNMR (DMSO-d$_6$): δ 8.83 (t, J=6Hz, 1H), 8.49 (d, J=2.6Hz, 1H), 8.23 (dd, J=8.6Hz, 1H), 7.72 (d, J=8.6Hz, 1H), 7.49 (m, 2H), 7.41 (m, 3H), 5.43 (s, 2H), 3.1 (t, J=6.9 Hz, 2H), 2.29 (m, 1H), 0.89 (d, J=6.9Hz, 6H). |

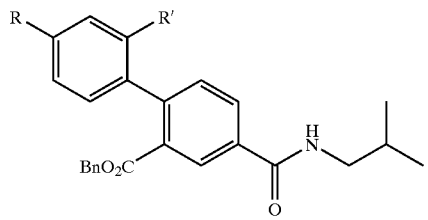

| Cpd. No. | —R | —R' | Starting From | Method Used | Analytical Data |
|---|---|---|---|---|---|
| 17 | —OBn | —CHO | 16 + 6 | D-2 | $^1$HNMR (DMSO-d$_6$): δ 0.88 (d, J=6.0Hz, 6H), 1.85 (m, 1H), 3.1 (t, J=6.0Hz, 2H), 5.02 (q, J=13 and 2.5Hz, 2H), 5.18 (s, 2H), 6.88 (m, 2H), 7.17 (d, J=8.6Hz, 1H), 7.26 (m, 4H), 7.35 (m, 1H), 7.40 (m, 4H), 7.49 (d, J=7.7Hz, 2H), 8.07 (dd, J=7.7 and 1.7Hz, 1H), 8.38 (d, J=1.7Hz, 1H), 8.72 (t, J=6Hz, 1H), 9.63 (s, 1H); MS (ES+): 522.89 |
| 18 | —OBn | —CO₂H | 17 | E | $^1$HNMR (DMSO-d$_6$): δ 0.86 (d, J=6.9Hz, 6H), 1.85 (m, 1H), 3.09 (t, J=6.9Hz, 2H), 5.01 (d, J=5.01Hz, 2H), 5.14 (s, 2H), 7.08 (m, 3H), 7.14 (dd, J=8.6 and 2.6Hz, 1H), 7.27 (m, 4H), 7.34 (m, 1H), 7.41 (m, 3H), 7.48 (m, 2H), 7.99 (dd, J=6.9 and 1.8Hz, 1H), 8.32 (s, 1H), 8.64 (t, J=6Hz, 1H), 12.57 (s, 1H); MS (ES+): 538.86 |
| 19 | —OBn | —CO₂MEM | 18 | F | $^1$HNMR (DMSO-d$_6$): δ 0.90 (d, J=6.8Hz, 6H), 1.86 (m, 1H), 3.10 (t, J=6.5Hz, 2H), 3.16 (s, 3H), 3.28 (dd, J=3 and 6Hz, 2H), 3.36 (dd, J=3 and 6Hz, 2H), 5.02 (d, J=3.8Hz, 2H), 5.12 (d, J=15Hz, 2H), 5.64 (s, 2H), 7.11 (m, 3H), 7.24 (dd, J=8.25 and 2.75Hz, 1H), 7.29 (m, 4H), 7.35 (m, 1H), 7.42 (m, 3H), 7.49 (m, 2H), 8.02 (dd, J=1.7 and 8.2Hz, 1H), 8.36 (d, 1.7Hz, 1H), 8.68 (t, J=6Hz, 1H); MS (ES+): 626.44 |
| 21 | —OH | —CO₂MEM | 19 | G, H | $^1$HNMR (DMSO-d$_6$): δ 0.88 (d, J=6Hz, 6H), 1.85 (m, 1H) 3.10 (t, J=6Hz, 2H) 3.16 (s, 3H), 3.28 (m 2H), 3.35 (m, 2H), 5.04 (d, J=3.5Hz, 2H) 5.11 (d, J=14Hz, 2H), 6.98 (m, 2H), 7.11 m, 2H), 7.29 (m, 5H), 8.03 (dd, J=8 and 2Hz, 1H), 8.32 (d, J=2Hz, 1H), 8.67 (t, J=6Hz, 1H), 9.9 (s, 1H); MS (ES+) 536.30 (100%: M$^{+1}$) |
| 22 | —OSO₂CF₃ | —CO₂MEM | 21 | B-2 | $^1$HNMR (DMSO-d$_6$): δ 0.89 (d, J=6.8Hz, 6H), 1.86 (m, 1H), 3.12 (t, J=6.5Hz, 2H), 3.16 (s, 3H), 3.29 (m, 2H), 3.40 (m, 2H), 5.04 (s, 2H), 5.16 (dd, J=18 and 6Hz, 2H), 7.15 (m, 2H), 7.31 (m, 3H), 7.36 (d, J=8.5Hz, 1H), 7.41 (d, J=8.5Hz, 1H), 7.73 (dd, J=8.6 and 2.6Hz, 1H), 7.85 (d, J=2.6Hz, 1H), 8.07 (dd, J=7.7 and 1.7Hz, 1H), 8.45 (d, J=1.7Hz, 1H), 8.73 (t, J=6Hz, 1H); MS (ES+) 668.15 |

-continued

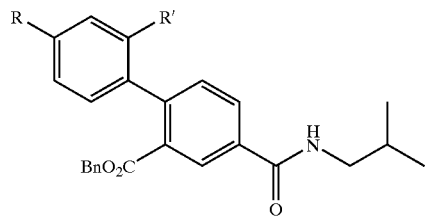

| Cpd. No. | —R | —R' | Starting From | Method Used | Analytical Data |
|---|---|---|---|---|---|
| 24a | 2-methylthiophene | —CO$_2$MEM | 22 + 23 | D-1 | $^1$HNMR (DMSO-d$_6$): δ 0.89 (d, J=6.8Hz, 6H), 1.87 (m, 1H), 3.12 (t, J=6Hz, 2H), 3.16 (s, 3H), 3.29 (m, 2H), 3.39 (m, 2H), 5.05 (d, J=2.6Hz, 2H), 5.16 (d, J=17Hz, 2H), 7.08 (m, 2H), 7.21 (m, 4H), 7.24 (d, J=7.7Hz, 1H), 7.35 (d, J=7.7Hz, 1H), 7.62 (d, J=3.5Hz, 1H), 7.64 (d, J=5Hz, 1H), 7.86 (d, J=8.6 Hz, 1H), 8.06 (m, 2H), 8.42 (s, 1H), 8.73 (t, J=6Hz, 1H); MS (ES+) 602.52 |
| 24b | 3-thienyl | —CO$_2$MEM | 22 + 23 | D-1 | $^1$HNMR (DMSO-d$_6$): δ 0.89 (d, J=6.8Hz, 6H), 1.87 (m, 1H), 3.12 (t, J=6 and 6.8Hz, 2H), 3.16 (s, 3H), 3.30 (m, 2H), 3.39 (dd, J=5.2 and 3.4Hz, 2H), 5.04 (d, J=4.3Hz, 2H), 5.16 (d, J=16Hz, 2H), 7.08 (m, 2H), 7.20 (m, 3H), 7.24 (d, J=8.6Hz, 1H), 7.35 (d, J=8.6Hz, 1H), 7.61 (d, J=5Hz, 1H), 7.71 (dd, J=4.8 and 3Hz, 1H), 7.91 (dd, J=1.7 and 7.7Hz, 1H), 8.00 (m, 1H), 8.06 (dd, J=2 and 8Hz, 1H), 8.14 (d, J=1.7Hz, 1H), 8.41 (d, J=1.7Hz, 1H), 8.68 (t, J=6Hz, 1H); MS (ES+) 602.27 |
| 24c | phenyl | —CO$_2$MEM | 22 + 23 | D-1 | $^1$HNMR (DMSO-d$_6$): δ 0.89 (d, J=6.8Hz, 6H), 1.87 (m, 1H), 3.12 (t, J=6 and 6.8Hz, 2H), 3.16 (s, 3H), 3.30 (m, 2H), 3.40 (m, 2H), 5.05 (d, J=5Hz, 2H), 5.17 (d, J=17Hz, 2H), 7.09 (m, 2H), 7.21 (m, 3H), 7.30 (d, J=7.7Hz, 1H), 7.37 (d, J=7.7Hz, 1H), 7.44 (m, 1H), 7.54 (t, J=7.7Hz, 2H), 7.73 (d, J=6.8Hz, 2H), 7.88 (dd, J=1.7 and 7.7Hz, 1H), 8.07 (dd, J=7.7 and 1.7 Hz, 1H), 8.11 (d, J=1.7Hz, 1H), 8.42 (d, J=1.7Hz, 1H), 8.72 (t, J=6Hz, 1H); MS (ES+) 596.45 |
| 24d | 2,5-dimethylthiophene | —CO$_2$MEM | 22 + 23 | D-1 | MS (ES+) 616 |
| 24e | 3-furyl | —CO$_2$MEM | 22 + 23 | D-1 | MS (ES+) 586.4 |
| 24f | 2-furyl | —CO$_2$MEM | 22 + 23 | D-1 | MS (ES$^+$): 586.39 |
| 24g | 4-methyl-2-thienyl | —CO$_2$MEM | 22 + 23 | D-1 | MS (ES$^+$): 616.63 |
| 24h | 2-pyridyl | —CO$_2$MEM | 22 + 23 | D-1 | MS (ES$^+$): 597.25 |
| 24i | 3-pyridyl | —CO$_2$MEM | 22 + 23 | D-1 | MS (ES$^+$): 597.4 |

-continued

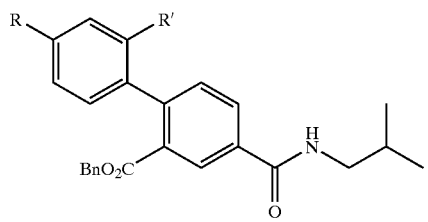

| Cpd. No. | —R | —R' | Starting From | Method Used | Analytical Data |
|---|---|---|---|---|---|
| 24j | 4-pyridyl | —CO₂MEM | 22 + 23 | D-1 | MS (ES⁺): 597.4 |
| 24k | 5-methyl-2-acetylthiophene | —CO₂MEM | 22 + 23 | D-1 | MS (ES⁺): 644.3 |
| 24l | 1,2-dimethylpyrrol-N-yl | —CO₂MEM | 22 + 23 | D-3 | Characterized at the next step |
| 24m | N-methylpyrrolidinyl | —CO₂MEM | 22 + 23 | D-10 | Characterized at the next step |
| 24n | CH₂=CH-CH₂-CH₂- (but-3-enyl) | —CO₂MEM | 22 + 23 | D-3 | MS (ES⁺): 560.74 |
| 24o | 2-methylthiazolyl | —CO₂MEM | 22 + 23 | D-4 | MS (ES⁺): 603.72 |
| 24p | CH₃-C≡C-CH₂- | —CO₂MEM | 22 + 23 | D-5 | MS (ES⁺): 558.3 |
| 24q | (CH₃)₂C(OH)-C≡C-CH₂- | —CO₂MEM | 22 + 23 | D-5 | Characterized in the next step |
| 24r | HO-CH₂-CH₂-C≡C-CH₂- | —CO₂MEM | 22 + 23 | D-5 | MS (ES⁺): 610.4 (M + Na)⁺ |
| 24s | CH₃-CH=CH-C(CH₃)=CH₂ | —CO₂MEM | 22 + 23 | D-3 | Characterized in the next step |
| 24t | CH₂=C(CH₃)-CH₂- | —CO₂MEM | 22 + 23 | D-3 | Characterized in the next step |
| 24u | HO-CH₂-CH=CH-CH₂- | —CO₂MEM | 22 + 23 | D-3 | MS (ES⁺): 598.4 (M + Na)⁺ |

-continued

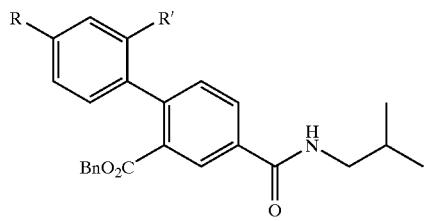

| Cpd. No. | —R | —R' | Starting From | Method Used | Analytical Data |
|---|---|---|---|---|---|
| 24v | 3-methylbut-3-en-1-ol (CH₂=C(CH₃)CH₂CH₂OH) | —CO₂MEM | 22 + 23 | D-3 | MS (ES⁻): 500.4 [(M − MEM) − 1]⁻ |
| 24w | propynyl (CH₃C≡CH) | —CO₂MEM | 22 + 23 | D-3 | Characterized in the next step |
| 24x | 2-methylbut-2-enyl | —CO₂MEM | 22 + 23 | D-3 | MS (ES⁺): 610.5 (M + Na)⁺ |
| 24y | but-2-yn-1,4-diol derivative (CH₃C≡CCH₂OH) | —CO₂MEM | 22 + 23 | D-3 | MS (ES⁺): 596.4 (M + Na)⁺ |
| 24z | 2-methylallyl alcohol (CH₂=C(CH₂OH)—) | —CO₂MEM | 22 + 23 | D-3 | MS (ES⁺): 576.3 (M + Na)⁺ |
| 24aa | cyanomethyl (—C≡N with CH₂) | —CO₂MEM | 22 + 23 | D-11 | Characterized in the next step |
| 24ab | 2-methylthiophene-3-carbaldehyde | —CO₂MEM | 22 + 23 | D-2 | MS (ES⁺): 630.55 |
| 24ac | 3-methylthiophene-2-carbaldehyde | —CO₂MEM | 22 + 23 | D-2 | MS (ES⁺): 630.74 |
| 24ad | 4-methylthiophene-3-carbaldehyde | —CO₂MEM | 22 + 23 | D-2 | MS (ES⁺): 652.3 |
| 24ae | 5-methylthiophene-2-carbaldehyde | —CO₂MEM | 22 + 23 | D-2 | Characterized in the next step |
| 24ag | N-Boc-2-methylpyrrole | —CO₂MEM | 22 + 23 | D-1 | MS (ES⁺): 685.01 |
| 24ah | allyl (CH₂=CH—) | —CO₂MEM | 22 + 23 | D-3 | MS (ES⁺): 546.49 |

-continued

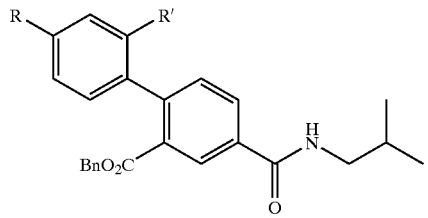

| Cpd. No. | —R | —R' | Starting From | Method Used | Analytical Data |
|---|---|---|---|---|---|
| 25a | 2-methylthiophene | CO₂H | 24a | I-1 | ¹HNMR (DMSO-d₆): δ 0.91 (d, J=6.9Hz, 6H), 1.88 (m, 1H), 3.13 (t, J=6.9 and 6Hz, 2H), 5.07 (d, J=11.2Hz, 2H), 7.09 (m, 2H), 7.22 (m, 5H), 7.35 (d, J=7.7Hz, 1H), 7.63 (d, 2.6Hz, 1H), 7.65 (d, J=5.2Hz, 1H), 7.82 (dd, J=7.7 and 1.7Hz, 1H), 8.05 (d, J=1.7Hz, 1H), 8.07 (s, 1H), 8.40 (s, 1H), 8.72 (t, J=6Hz, 1H), 12.77 (brs, 1H); MS (ES+) 514.19 |
| 25b | 3-methylthiophene | CO₂H | 24b | I-1 | ¹HNMR (DMSO-d₆): δ 0.92 (d, J=6.9Hz, 6H), 1.88 (m, 1H), 3.12 (t, J=6.9 and 6Hz, 2H), 5.07 (d, J=13Hz, 2H), 7.09 (m, 2H), 7.22 (m, 4H), 7.35 (d, J=8.6Hz, 1H), 7.63 (d, J=5.2Hz, 1H), 7.70 (dd, J=2.6 and 4.3Hz, 1H), 7.88 (dd, J=7.2 and 1.7 Hz, 1H), 8.02 (d, J=1.7Hz, 1H), 8.07 (dd, J=1.7 and 7.7Hz, 1H), 8.15 (m, 1H), 8.39 (d, J=1.7Hz, 1H), 8.72 (t, J=6Hz, 1H), 12.70 (brs, 1H); MS (ES+) 514.06 |
| 25c | phenyl | CO₂H | 24c | I-1 | ¹HNMR (DMSO-d₆): δ 12.73 (bs, 1H), 8.73 (t, J=6Hz, 1H), 8.41 (d, J=1.7Hz, 1H), 8.12 (d, J=1.7Hz, 1H), 8.07 (dd, J=7.7 & 1.7Hz, 1H), 7.83 (dd, J=7.7 & 1.7Hz, 1H), 7.72 (d, J=6.9Hz, 2H), 7.54 (t, J=7.7, 2H), 7.44 (t, J=7.7Hz, 1H), 7.37 (d, J=7.7Hz, 1H), 7.28 (d, J=7.7Hz, 1H), 7.21 (m, 3H), 7.09 (m, 2H), 5.08 (d, J=14Hz, 2H), 3.13 (t, J=6.5Hz, 2H), 1.88 (m, 1H), 0.91 (d, 6.8Hz, 6H); MS (ES+) 507.93 |
| 25d | 2,5-dimethylthiophene | CO₂H | 24d | I-1 | ¹HNMR (DMSO-d₆): δ 12.75 (bs, 1H), 8.71 (t, J=6Hz, 1H), 8.39 (d, J=1.7Hz, 1H), 8.05 (dd, J=1.7 & 7.7Hz, 1H), 8.01 (d, J=2.5Hz, 1H), 7.75 (dd, J=2.5 & 7.7Hz, 1H), 7.42 (d, 3.4Hz, 1H), 7.34 (d, J=7.7Hz, 1H), 7.22 (m, 3H), 7.19 (d, J=8.6Hz, 1H), 7.09 (m, 2H), 6.95 (d, J=3.4Hz, 1H), 5.06 (d, J=11Hz, 2H), 3.12 (t, J=6.5Hz, 2H), 2.52 (s, 3H), 1.89 (m, 1H), 0.81 (d, 6.8Hz, 6H); MS (ES+) 528.51 |
| 25e | 3-methylfuran | CO₂H | 24e | I-1 | ¹HNMR (DMSO-d₆): δ 0.89 (d, J=6Hz, 6H), 1.86 (m, 1H), 3.12 (t, J=6.8 and 6.0Hz, 2H), 5.03 (d, J=10Hz, 2H), 7.02 (s, 1H), 7.06 (m, 2H), 7.16 (d, J=8.6Hz, 1H), 7.21 (m, 3H), 7.31 (d, J=7.7Hz, 1H), 7.75 (dd, J=8.5 and 1.7Hz, 1H), 7.78 (t, J=1.7 Hz, 1H), 8.04 (m, 2H), 8.29 (s, 1H), 8.36 (d, J=1.7Hz, 1H), 8.66 (t, J=6 and 5.2Hz, 1H), 12.58 (bs, 1H); MS (ES+) 498.49 |
| 25f | 2-methylfuran | CO₂H | 24f | I-1 | MS (ES⁺): 498.36 |
| 25g | 2,4-dimethylthiophene | CO₂H | 24g | I-1 | ¹HNMR (DMSO-d₆): δ 12.72 (bs, 1H), 8.69 (t, J=6Hz, 1H), 8.39 (d, J=1.7Hz, 1H), 8.06 (m, 2H), 7.79 (dd, J=1.7 & 7.7 Hz, 1H), 7.45 (s, 1H), 7.35 (d, J=7.7Hz, 1H), 7.21 (m, 5H), 7.1 (m, H), 5.07 (d, J=8.6Hz, 2H), 3.12 (t, J=6.5Hz, 2H), 2.29 (s, 3H), 1.89 (m, 1H), 0.91 (d, 6.8Hz, 6H); MS (ES+) 528.38 |
| 25h | 2-methylpyridine | CO₂H | 24h | I-1 | ¹HNMR (DMSO-d₆): δ 12.74 (bs, 1H), 8.73 (m, 2H), 8.63 (d, J=1.7Hz, 1H), 8.41 (d, J=1.7Hz, 1H), 8.23 (dd, J=1.7 and 7.7 Hz, 1H), 8.08 (dd, J=1.7 & 7.7Hz, 1H), 8.05 (d, J=7.7Hz, 1H), 7.96 (dt, J=7.7 & 1.7Hz, 1H), 7.43 (dd, J=6 & 7Hz, 1H), 7.37 (d, J=7.7Hz, 1H), 7.29 (d, J=8.6Hz, 1H), 7.18 (m, 3H), 7.08 (m, 2H), 5.01 (q, J=10 & 25Hz, 2H), 3.13 (t, J=6.9 and 6 Hz, 2H), 1.89 (m, 1H), 0.92 (d, J=6.9Hz, 6H); MS (ES+) 509.58 |
| 25i | 3-methylpyridine | CO₂H | 24i | I-1 | ¹HNMR (DMSO-d₆): δ 12.70 (bs, 1H), 8.91 (d, J=2.6Hz, 1H), 8.68 (t, J=6 &Hz, 1H), 8.62 (d, J=2Hz, 1H), 8.4 (d, J=1.7 Hz, 1H), 8.12 (m, 2H), 8.05 (dd, J=8.6 & 1.7Hz, 1H), 7.88 (d, 8.5 & 1.7Hz, 1H), 7.53 (dd, J=8.6 & 5.2Hz, 1H), 7.34 (d, J=7.7Hz, 1H), 7.28 (d, J=8.6Hz, 1H), 7.18 (m, 3H), 7.08 (m, 2H), 5.04 (d, J=12Hz, 2H), 3.11 (t, J=6.5Hz, 2H), 1.87 (m, 1H), 0.9 (d, 6.8Hz, 6H); MS (ES+) 509.11 |

-continued

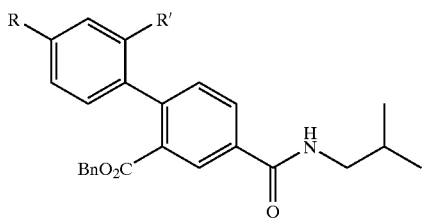

| Cpd. No. | —R | —R' | Starting From | Method Used | Analytical Data |
|---|---|---|---|---|---|
| 25j | 4-pyridyl | CO$_2$H | 24j | I-1 | $^1$HNMR (DMSO-d$_6$): δ 0.90 (d, J=6.9Hz, 6H), 1.88 (m, 1H), 3.11 (t, J=6.9 and 6Hz, 2H), 5.03 (s, 2H), 7.06 (m, 2H), 7.18 (m, 3H), 7.33 (d, 8.4Hz, 1H), 7.30 (d, J=8.4Hz, 1H), 7.75 (d, J=6.2Hz, 2H), 7.85 (m, 1H), 8.05 (dd, J=7.6 and 1.7Hz, 1H), 8.18 (s, 1H), 8.40 (d, J=2Hz, 1H), 8.71 (m, 4H); MS (ES+) 509.49 |
| 25k | 1-(5-methylthien-2-yl)ethanone | CO$_2$H | 24K | I-1 | Characterized in the next step |
| 25l | 1,2-dimethylpyrrol-2-yl | CO$_2$H | 24l | I-1 | MS (ES$^+$): 511.54 |
| 25m | 1-methylpyrrolidin-2-yl | CO$_2$H | 24m | I-1 | MS (ES$^+$): 501.66 |
| 25n | CH$_2$=CHCH$_2$CH$_2$— | CO$_2$H | 24n | I-1 | MS (ES$^+$): 472.4 |
| 25o | 2-methylthiazol-2-yl | CO$_2$H | 24o | I-1 | MS (ES$^+$): 515.65 |
| 25p | —C≡C—CH$_3$ (propynyl) | CO$_2$H | 24p | I-1 | Characterized in the next step |
| 25q | —C≡C—C(CH$_3$)$_2$OH | CO$_2$H | 24q | I-1 | MS (ES$^+$): 536.3 (M + Na)$^+$ |
| 25r | —C≡C—CH$_2$CH$_2$OH | CO$_2$H | 24r | I-1 | MS (ES$^-$): 500.4 |
| 25s | CH$_2$=C(CH$_3$)CH=CHCH$_3$ | CO$_2$H | 24s | I-1 | Characterized in the next step |
| 25t | CH$_2$=C(CH$_3$)— | CO$_2$H | 24t | I-1 | Characterized in the next step |
| 25u | —CH=CH—CH$_2$OH | CO$_2$H | 24u | I-1 | MS (ES$^-$): 486.4 |

-continued

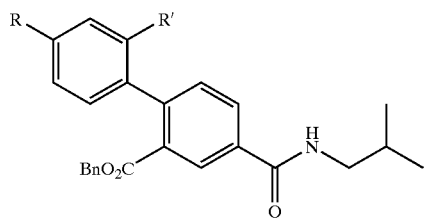

| Cpd. No. | —R | —R' | Starting From | Method Used | Analytical Data |
|---|---|---|---|---|---|
| 25v | CH2=C(CH3)CH2CH2OH | CO2H | 24v | I-1 | MS (ES+): 524.3 (M + Na)+ |
| 25w | —C≡CH (with CH3) | CO2H | 24w | I-1, Q | Characterized in the next step |
| 25x | CH3-C=C(CH3)-CH2CH3 | CO2H | 24x | I-1 | MS (ES−): 498.3 |
| 25y | CH3-C≡C-CH2OH | CO2H | 24y | I-1 | MS (ES−): 484.3 |
| 25z | CH2=C(CH3)CH2OH | CO2H | 24z | I-1 | MS (ES+): 488.3 |
| 25aa | —C≡N (with CH3) | CO2H | 24aa | I-1 | Characterized in the next step |
| 25ab | 2-methyl-3-(hydroxymethyl)thiophene | CO2H | 24ab | K, I-1 | MS (ES+): 544.27 |
| 25ac | 3-methyl-2-(hydroxymethyl)thiophene | CO2H | 24ac | K, I-1 | MS (ES+): 544.2 |
| 25ad | 4-methyl-3-(BnO2C)thiophene | CO2H | 24ad | E, H, I-1 | MS (ES+): 670.3 (M + Na)+ |
| 25ae | 5-methyl-2-(hydroxymethyl)thiophene | CO2H | 24ae | K, I-1 | 1HNMR (DMSO-d6): δ 9.1 (bs, 2H), 8.8 (bs, 2H), 8.5 (t, J=6 Hz, 1H), 8.02 (s, 1H), 7.68 (s, 1H), 7.62 (m, 6H), 7.53 (d, J=5.8Hz, 1H), 7.15 (d, J=6Hz, 1H),), 7.13 (m, 1H), 7.01 (s, 1H), 5.5 (t, J=5Hz, 1H), 4.7 (d, J=5Hz, 2H), 3.01 (m, 2H), 1.8 (m, 1H), 0.85 (d, J=6.8Hz, 6H) |
| 25af | 4-methyl-3-(hydroxymethyl)thiophene | CO2H | 24ad | K, I-1 | MS (ES+): 566.2 (M + Na)+ |

-continued

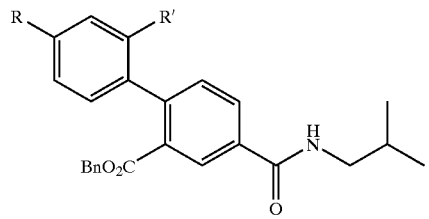

| Cpd. No. | —R | —R' | Starting From | Method Used | Analytical Data |
|---|---|---|---|---|---|
| 25ag | 2-methyl-1-Boc-pyrrole | CO$_2$H | 24ag | I-1 | MS (ES$^+$): 597.7 |
| 25ah | propane-1,2-diol (OH, OH) | CO$_2$H | 24ah | L, I-1 | MS (ES$^+$): 492.54 |
| 25ai | ethyl azide (N$_3$) | CO$_2$H | 24ai | L, M, K, N, O, I-1 | Characterized in the next step |

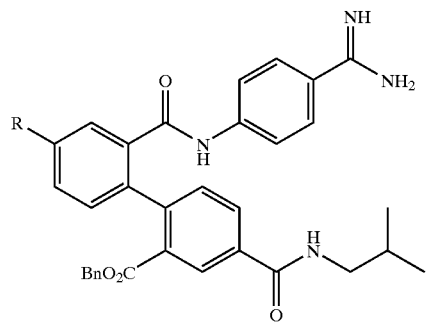

| Cpd. No. | —R | Starting From | Method Used | Analytical Data |
|---|---|---|---|---|
| 26a | 2-methylthiophene | 25a | J | $^1$HNMR(DMSO-d$_6$): δ 0.88 (d, J=6.9 Hz, 6H), 1.84 (m, 1H), 3.07 (t, J=6.9 and 6.0 Hz, 2H), 5.05 (s, 2H), 7.04 (d, J=6.9 Hz, 2H), 7.20 (m, 4H), 7.35 (d, J=7.7 Hz, 1H), 7.43 (d, J=7.7 Hz, 1H), 7.66 (d, J=5.2 Hz, 1H), 7.70 (d, J=4.3 Hz, 1H), 7.75 (m, 4H), 7.82 (dd, J=7.7 and 1.7 Hz, 1H), 7.94 (d, J=1.7 Hz, 1H), 8.03 (dd, J=7.7 and 1.7 Hz, 1H), 8.26 (dd, J=7.7, and 1.7 Hz, 1H), 8.69 (t, J=6 Hz, 1H), 8.80 (s, 2H), 9.17 (s, 2H), 10.76 (s, 1H); MS (ES+) 631.05 |
| 26b | 3-methylthiophene | 25b | J | $^1$HNMR (DMSO-d$_6$): δ 0.88 (d, J=6.9 Hz, 6H), 1.84 (m, 1H), 3.07 (t, J=6.8 and 6.0 Hz, 2H), 5.04 (s, 2H), 7.02 (d, J=6.8 Hz, 2H), 7.20 (m, 3H), 7.34 (d, J=7.7 Hz, 1H), 7.43 (d, J=8.6 Hz, 1H), 7.72 (m, 6H), 7.90 (dd, J=1.7 and 7.7 Hz, 1H), 8.05 (m, 3H), 8.23 (d, J=1.7 Hz, 1H), 8.68 (t, J=6 and 5.2 Hz, 1H), 8.82 (s, 2H), 9.17 (s, 2H), 10.73 (s, 1H); MS (ES+) 631.82 |
| 26c | toluene | 25c | J | $^1$HNMR (DMSO-d$_6$): δ 10.75 (s, 1H), 9.19 (s, 2H), 8.89 (s, 2H), 8.69 (t, J=6 Hz, 1H), 8.29 (d, J=1.7 Hz, 1H), 8.07 (dd, J=7.7 & 1.7 Hz, 1H), 7.99 (d, J=1.7 Hz, 1H), 7.87 (dd, J=7.7 & 1.7 Hz, 1H), 7.83 (d, J=7.7 Hz, 2H), 7.77 (m 5H), 7.54 (t, J=7.7 Hz, 2H), 7.43 (m, 3H), 7.19 (m, 3H), 7.03 (d, J=6.9 Hz, 2H), 5.04 (bs, 2H), 3.09 (t, J=6.5 Hz, 2H), 1.84 (m, 1H), 0.89 (d, 6.8 Hz, 6H); MS (ES+) 625.81 |

-continued

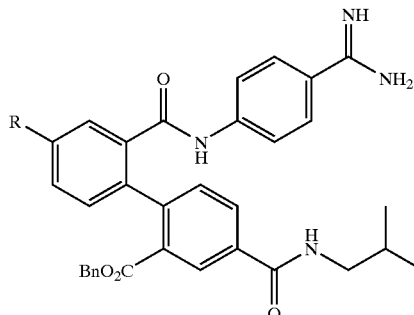

| Cpd. No. | —R | Starting From | Method Used | Analytical Data |
|---|---|---|---|---|
| 26d | H₃C-(2,5-dimethylthiophene) | 25d | J | ¹HNMR (DMSO-d₆): δ 10.7 (s, 1H), 9.14 (s, 2H), 8.82 (s, 2H), 8.64 (t, J=6 Hz, 1H), 8.21 (s, 1H), 7.98 (dd, J=7.8 & 2 Hz, 1H), 7.8 (d, J=2 Hz, 1H), 7.7 (m, 4H), 7.68 (dd, J=2 & 7.8 Hz, 1H), 7.44 (d, J=3 Hz, 1H), 7.37 (d, Hz, 1H), 7.27 (d, J=7.7 Hz, 1H), 7.16 (m, 3H), 7.0 (s, 1H), 6.99 (s, 1 H), 6.86 (d, J=3 Hz, 1H), 5.0 (s, 2H), 3.03 (t, J=6.5 Hz, 2H), 2.46 (s, 3H), 1.78 (m, 1H), 0.83 (d, J=6.8 Hz, 6H); MS (ES+) 645.77 |
| 26e | 3-methylfuran | 25e | J | ¹HNMR (DMSO-d₆): δ 0.87 (d, J=6.2 Hz, 6H), 1.73 (m, 1H), 3.07 (t, J=6.7 and 6.2 Hz, 2H), 5.05 (s, 2H), 7.03 (dd, J=1.7 and 8 Hz, 2H), 7.11 (d, J=1.7 Hz, 1H), 7.21 (m, 3H), 7.31 (d, J=8 Hz, 1H), 7.42 (d, J=8 Hz,1H), 7.78 (m, 5H), 7.92 (d, J=1.7 Hz, 1H), 8.02 (dd, J=8 and 1.7 Hz, 1H), 8.25 (d, J= 1.9 Hz, 1H), 8.33 (s, 1H), 8.63 (t, J=6 and 5 Hz, 1H), 8.80 (bs, 2H), 9.14 (bs, 2H), 10.67 (s, 1H); MS (ES+) 615.75 |
| 26f | 2-methylfuran | 25f | J | ¹HNMR (DMSO-d⁶): δ 0.87 (d, J=6.7 Hz, 6H), 1.83 (m, 1H), 3.06 (t, J=6.7 and 6.2 Hz, 2H), 5.04 (s, 2H), 6.67 (m, 1H), 7.03 (m, 2H), 7.16 (m, 3H), 7.35 (d, J=8.6 Hz, 1H), 7.42 (d, J=8 Hz, 1H), 7.74 (m, 4H), 7.85 (m, 2H), 7.98 (d, J=1.2 Hz, 1H), 8.03 (dd, J =1.7 and 8 Hz, 1H), 8.25 (d, J=1.8 Hz, 1 H), 8.67 (t, J=6.2 and 5.5 Hz, 1H), 8.88 (bs, 2H), 9.12 (bs, 2H), 10.772 (bs, 1H); MS (ES+) 615.75 |
| 26g | H₃C-(3,5-dimethylthiophene) | 25g | J | ¹HNMR (DMSO-d₆): δ 10.67 (s, 1H), 9.12 (s, 2H), 8.78 (s, 2H), 8.61 (t, J=6 Hz, 1H), 8.21 (s, 1H), 7.98 (dd, J=7.8 & 2 Hz, 1H), 7.84 (d, J=2 Hz, 1H), 7.7 (m, 5H), 7.46 (s, 1H), 7.39 (d, J=7.8 Hz, 1H), 7.29(d, J=7.7 Hz, 1H), 7.16 (m, 4H), 7.01(s, 1H), 6.99 (s, 1H), 5.0 (s, 2H), 3.03 (t, J=6.5 Hz, 2H), 2.23 (s, 3H), 1.79 (m, 1H), 0.83 (d, J=6.8 Hz, 6H); MS (ES+) 645.77 |
| 26h | 2-pyridyl | 25h | J | ¹HNMR (DMSO-d₆): δ 10.77 (bs, 1H), 8.95 (bs, 4H), 8.76 (d, J=4.3 Hz, 1 H), 8.69 (t, J=6Hz, 1H), 8.4 (s, 1H), 8.29 (m, 2H), 8.15 (d, J=7.7 Hz, 1H), 8.07 (dd, J=1.7 and 7.7 Hz, 1H), 7.99 (dt, J=1.7 & 7.7 Hz, 1H), 7.76 (m, 4 H), 7.46 (m, 2H), 7.18 (m, 3H), 7.05 (s, 1H), 7.03 (s, 1H), 5.06 (s, 2H), 3.10 (t, J=6.9 and 6 Hz, 2H), 1,86 (m, 1H), 0.89 (d, J=6.9 Hz, 6H); MS (ES+) 626.69 |
| 26i | 3-pyridyl | 25i | J | ¹HNMR (DMSO-d₆): δ 10.73 (bs, 1H), 9.16 (bs, 2H), 9.05 (d, J=1.9 Hz, 1 H), 8.79 (s, 2H), 8.69 (t,J=6 & Hz, 1H), 8.64 (dd, J=1.2 & 5 Hz, 1H), 8.29 (d, J=1.7 Hz,1H), 8.24 (d, J=8 Hz, 1H), 8.05 (m, 2H), 7.93 (dd, 8 & 1.8 Hz, 1H), 7.76 (m, 5H), 7.56 (dd, J=8 & 4.3 Hz, 1H), 7.44 (d, J=7.4 Hz, 2H), 7.18 (m, 3H), 7.0 (m, 2H), 5.0 (s, 2H), 3.08 (t, J=6.5 Hz, 2H), 1.82 (m, 1H), 0.88 (d, J=6.8 Hz, 6H);; MS (ES+) 626.44 |
| 26j | 4-methylpyridyl | 25j | J | ¹HNMR (DMSO-d₆): δ 0.87 (d, J=6.9 Hz, 6H), 1.75 (m, 1H), 3.08 (t, J=6.9 and 6.0 Hz, 2H), 5.03 (s, 2H), 7.03 (m, 1H), 7.18 (m, 3H), 7.45 (f, J=7.8 and 7 Hz, 2H), 7.76 (s, 4H), 7.87 (d, J=6 Hz, 2H), 7.94 (dd, J=8 and 2 Hz, 1H), 8.05 (dd, J=8 and 2 Hz, 1H), 8.08 (d, J=2 Hz,1H), 8.29 (d, J=2 Hz, 1H), 8.70 (m, 3H), 8.84 (s, 2H), 9.11 (s, 2H), 10.76 (s, 1H); MS (ES+) 626.76 |
| 26k | H₃C-CO-(5-methylthiophene) | 25k | J | ¹HNMR (DMSO-d₆): δ 10.72 (bs, 1H), 9.15 (bs, 2H), 8.81 (bs, 2H), 8.86 (t, J 6 Hz, 1H), 8.28 (s, 1H), 8.03 (m,3H), 7.91 (d, J=7.9 Hz, 1H),7.81 (d, J= 4 Hz, 1H), 7.74 (s, 4H), 7.42 (d, J=7.9 Hz, 1H), 7.38 (d, J=7.9 Hz, 1H), 7.18 (m, 3H), 7.04 (m, 2H), 5.04 (bs, 2H), 3.07 (t, J=6 Hz, 2H), 2.57 (s, 3 H), 1.83 (m, 1H), 0.87 (d, J=6.8 Hz, 6H); MS (ES+) 673.7 |

-continued

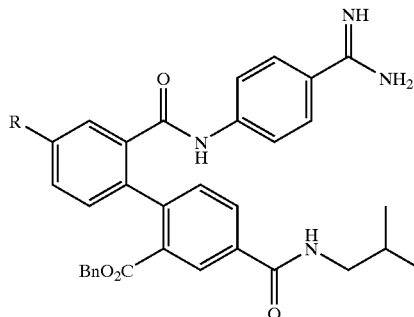

| Cpd. No. | —R | Starting From | Method Used | Analytical Data |
|---|---|---|---|---|
| 26l | (1-methyl-pyrrol-2-yl) | 25l | J | $^1$HNMR (DMSO-$d_6$): δ 10.66 (s, 1H), 9.20 (s, 2H), 8.86 (s, 2H), 8.66 (t, J=6 Hz, 1H), 8.24 (d, J=2 Hz, 1H), 8.15 (dd, J=7.8 & 2Hz, 1H), 7.69 (m, 4H), 7.68 (d, J=Hz, 1H), 7.63 (d, J=7.9 Hz, 1H), 7.43 (d, J=7.9 Hz, 1H), 7.37 (d, J=7.9 Hz, 1H), 7.24 (m, 3H), 7.09 (m, 2H), 6.92 (s, 1H), 6.40 (s, 1H), 6.17 (t, J=4 Hz, 1H), 5.10 (bs, 2H), 3.74 (s, 3H), 3.09 (t, J=6 Hz, 2H), 1.83 (m, 1H), 0.88 (d, J=6.8 Hz, 6H); MS (ES+) 628.65 |
| 26m | (1-pyrrolidinyl) | 25m | J | MS (ES+); 618.91 |
| 26n | (but-1-en-4-yl / CH₂=CHCH₂CH₂–) | 25n | J | $^1$HNMR (DMSO-$d_6$): δ 10.56 (s, 1H), 9.15 (bs, 2H), 8.84 (bs, 2H), 8.64 (t, J = 6 Hz, 1H), 8.19 (d, J=2 Hz, 1H), 7.99 (d, J=7 Hz, 1H), 7.70 (m, 4H), 7.46 (s, 1H), 7.36 (m, 2H), 7.24 (m, 3H), 7.05 (s, 1H), 7.00 (s, 1H), 6.0 (m, 1H), 5.18 (d, J=16 Hz, 1H), 5.10 (d, J=11 Hz, 1H), 5.0 (s, 2H), 3.47 (d, J = 6 Hz, 1H), 3.03 (t, J=6 Hz, 2H), 1.79 (m, 1H), 0.83 (d, J=6.8 Hz, 6H); MS (ES+) 589.5 |
| 26o | (2-methyl-thiazol-4-yl) | 25o | J | $^1$HNMR (DMSO-$d_6$): δ 10.84 (s, 1H), 9.16 (s, 2H), 8.78 (s, 2H), 8.69 (t, J=6 Hz, 1H), 8.27 (d, J=2Hz, 1H), 8.19 (s, 1H), 8.09 (dd, J=2 & 7.7 Hz, 1H), 8.04 (dd, J=2 & 7.7 Hz, 1H), 8.01 (d, J=4 Hz, 1H), 7.89 (d, J=3 Hz, 1H), 7.73 (m, 4H), 7.44 (dd, J=3 & 7.8 Hz, 2H), 7.16 (m, 3H), 7.30 (s, 1H), 7.05 (s, 1H), 5.03 (bs, 2H), 3.06 (t, J=6.5 Hz, 2H), 1.82 (m, 1H), 0.86 (d, 6.8 Hz, 6H); MS (ES+) 632.4 |
| 26p | (prop-1-ynyl / CH₃C≡C–) | 25p | J | MS (ES⁺): 609.3 (M + Na)⁺ |
| 26q | (3-hydroxy-3-methyl-but-1-ynyl) | 25q | J | MS (ES+) 631.5 |
| 26r | (5-hydroxy-pent-2-ynyl) | 25r | J | $^1$HNMR (DMSO-$d_6$): δ 10.71 (s, 1H), 9.16 (s, 2H), 8.81 (s, 2H), 8.68 (t, J=6 Hz, 1H), 8.25 (s, 1H), 8.03 (d, J=7.8 Hz, 1H), 7.73 (m, 5H), 7.69 (s, 1H), 7.55 (d, J=7.8 Hz, 1H), 7.39 (d, J=8.9 Hz, 1H), 7.26 (m, 3H), 7.03 (m, 2 H), 5.02 (bs, 2H), 4.95 (t, J=5 Hz, 1H), 3.62 (q, J=6 & 12.8 Hz, 2H), 3.07 (t, J=6 Hz, 2H), 2.62 (t, J=6 Hz, 2H), 1.83 (m, 1H), 0.88 (d, J=6.8 Hz, 6 H); MS (ES+) 617.4 |
| 26s | (2-methyl-penta-1,3-dienyl) | 25s | J | $^1$HNMR (DMSO-$d_6$): δ 0.89 (d, J=6.8 Hz, 6H), 1.84 (m, 1H), 1.99 (s, 3H), 3.09 (t, J=6 Hz, 2H), 5.04 (s, 2H), 5.18 (s, 1H), 5.28 (s, 1H), 6.73 (d, J=16 Hz, 1H), 7.04 (d, J=6 Hz, 2H), 7.23 (m, 5H), 7.42 (d, J=9 Hz, 1H), 7.73 (m, 5H), 7.85 (s, 1H), 8.03 (dd, J=9 and 2 Hz, 1H), 8.26 (d, J=2 Hz, 1H), 8.69(t,J=6 Hz, 1H), 8.87 (bs, 4H), 10.91 (s, 1H); MS (ES+) 615.4 |
| 26t | (isopropenyl / CH₂=C(CH₃)–) | 25t | J | $^1$HNMR (DMSO-$d_6$): δ 10.8 (br s, 1H), 9.1 and 8.9 (2 br s, 4H), 8.6 (m, 1H), 8.2 (s, 1H), 8.0 (m, 1H), 7.8–7.6 (m, 6H), 7.40 (,J=6.9 Hz, 1H), 7.3 (m, 4 H), 7.0 (d, 1H), 5.6 (m, 1H), 5.2 (m, 1H), 5.0 (br s, 1H), 3.1 (t, J=6.8 Hz, 2 H), 2.2 (s, 3H), 1.8 (m, 1H), 0.95 (d, 6H); MS (ES+) 589.4, MS (ES−) 587.5 |

-continued

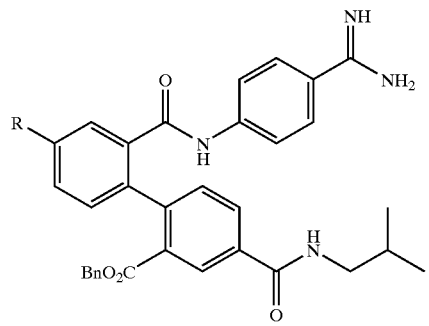

| Cpd. No. | —R | Starting From | Method Used | Analytical Data |
|---|---|---|---|---|
| 26u | (Z)-CH₃-CH=CH-CH₂-OH (but-2-enyl attached via methyl) | 25u | J | ¹HNMR (DMSO-d₆): δ 0.88 (d, J=6.8 Hz, 6H), 1.84 (m, 1H), 3.09 (t, J=6 Hz, 2H), 4.33 (t, J=5.5 Hz, 2H), 5.02 (s, 2H), 5.01 (t, J=5.5 Hz, 1H), 5.95 (m, 1H), 6.57 (d, J=11.5 Hz, 1H), 7.04 (d, J=6.7 Hz, 2H), 7.25 (m, 3H), 7.31 (d, J=7.8 Hz, 1H), 7.43 (m, 2H), 7.54 (s, 1H), 7.74 (s, 4H), 8.05 (dd, J = 7.8 and 2 Hz, 1H), 8.23 (d, J=2 Hz, 1H), 8.69 (t, J=6 Hz, 1H), 8.83 (bs, 2 H), 9.18 (bs, 2H), 10.66 (s, 1H); MS (ES+) 605.3 |
| 26v | CH₂=C(CH₂CH₂OH)– (3-methylenebutyl with OH) | 25v | J | ¹HNMR (DMSO-d₆): δ 0.88 (d, J=6.8 Hz, 6H), 1.84 (m, 1H), 2.75 (t, J=7 Hz, 2H), 3.09 (t, J=6 Hz, 2H), 3.60 (m, 2H), 4.65 (t, J=5 Hz, 1H), 5.05 (s, H), 7.05 (d, J=7 Hz, 2H), 7.29 (m, 5H), 7.42 (d, J=7.8 Hz, 1H), 7.66 (dd, J=7.8 and 2 Hz, 1H), 7.75 (m, 6H), 8.03 (dd, J=7.8 and 2 Hz, 1H), 8.25 (s, 1H), 8.68 (t, J=6 Hz, 1H), 8,82 (bs, 2H), 9.18 (bs, 2H), 10.68 (s, 1H); MS (ES+) 619.4 |
| 26w | HC≡C–CH₂– (propargyl) | 25w | J | ¹HNMR (DMSO-d₆): δ 0.88 (d, J=6.8 Hz, 6H), 1.84 (m, 1H), 3.09 (t, J=6 Hz, 2H), 4.41 (s, 1H), 5.04 (d, J=11 Hz, 2H), 7.05 (d, J=5.5 Hz, 2H), 7.29 (m, 3H), 7.34 (d, J=8 Hz, 1H), 7.40 (d,J=8 Hz, 1H), 7.65 (dd, J=8 and 2 Hz, 1H), 7.75 (s, 4H), 7.79 (s, 1H), 8.05 (dd, J=8 and 2 Hz, 1H), 8.28 (d, J = 2 Hz, 1H), 8.71 (t, J=6 Hz, 1H), 8,82 (bs, 2H), 9.17 (bs, 2H), 10.73 (s, 1 H); MS (ES+) 573.3 |
| 26x | CH₃CH₂–C(CH₃)=C(CH₃)–CH₂– (trisubstituted alkene) | 25x | J | ¹HNMR (DMSO-d₆): δ 0.86 (d, J=6.8 Hz, 6H), 1.47 (s, 3H), 1.74 (s, 3H), 1.85 (m, 1H), 3.06 (t, J=6 Hz, 2H), 3.43 (d, J=8 Hz, 1H), 5.04 (s, 2H), 5.11 (m, 1H), 7.03 (m, 2H), 7.23 (m, 5H), 7.52 (m, 2H), 7.72 (m, 5H), 8.02 (m, 1H), 8.21 (s, 1H), 8.66 (t, J=6 Hz, 1H), 8.81 (bs, 2H), 9.23 (bs, 2H), 10.52 (s, 1H); MS (ES+) 617.6 |
| 26y | HOCH₂–C≡C–CH₂– (but-2-ynyl alcohol) | 25y | J | ¹HNMR (DMSO-d₆): δ 0.87 (d, J=6.8 Hz, 6H), 1.72 (m, 1H), 3.07 (t, J=6 Hz, 2H), 4.36 (d, J=6 Hz, 2H), 5.0 (m, 2H), 5.42 (t, J=6 Hz, 1H), 7.03 (d, J=7 Hz, 2H), 7.25 (m, 3H), 7.31 (d, J=8 Hz, 1H), 7.39 (d, J=8 Hz, 1H), 7.58 (d, J=8 Hz, 1H), 7.73 (m, 5H), 8.02 (dd, J=10 and 2 Hz, 1H), 8.23 (s, 1H), 8.68 (t, J=6 Hz, 1H), 8,76 (bs, 1H), 9.15 (bs, 2H), 10.71 (s, 1H); MS (ES+) 603.4 |
| 26z | CH₂=C(–)CH₂OH (2-methylene-3-hydroxypropyl) | 25z | J | ¹HNMR (DMSO-d₆): δ 10.6 (s, 1H), 9.17 (s, 1H), 8.85 (s, 1H), 8.68 (d, J = 5.9 Hz, 2H), 8.25 (d, 1.98 Hz, 1H), 8.05 (d, J=1.96 Hz, 1H), 8.03 (d, J=1.9 1H), 7.75 (m, 4H), 7.65 (m, 4H), 7.41 (d, J=7.87 Hz, 4H), 7.25 (m, 1 H) 5.4 (s, 1H), 5.2 (d, J=5.9 Hz, 2H), 4.44 (d, J=5.9 Hz, 1H), 3.09 (d, J = 6.89 Hz, 2H), 1.89 (d, J=6.89 Hz, 2H), 0.88 (d, J=5.9 Hz, 6H); MS (ES +) 605.69 |
| 26aa | –C≡N | 25aa | J | Characterized in the next step |
| 26ab | 2-methyl-3-(hydroxymethyl)thiophen-yl | 25ab | J | ¹HNMR (DMSO-d₆): δ 10.70 (s, 1H) 9.15 (bs, 2H), 8.77 (bs, 2H), 8.67 (t, J = Hz, 1H), 8,25 (s, 1H), 8.04 (d, J=7 Hz, 1H), 7.77 (d, J=2 Hz, 1H), 7.71 (m 4H), 7.70 (d, J=2 Hz, 1H), 7.59 (d, J= 6 Hz, 1H), 7.46 (d, J=8 Hz, 1 H), 7.41 (d, J=8 Hz, 1H), 7.22 (m, 3H), 7.05 (s, 1H), 7.03 (d, J=2 Hz, 1 H), 5.31 (t, J=6 Hz, 1H), 5.04 (bs, 2H), 4.51 (d, J=6 Hz, 2H), 3.07 (t, J = 6 Hz, 2H), 1.82 (m, 1H), 0.86 (d, J=6.8 Hz, 6H); MS (ES+) 661.74 |
| 26ac | 3-methyl-2-(hydroxymethyl)thiophen-yl | 25ac | J | ¹HNMR (DMSO-d₆): δ 0.87 (d, J=6.8 Hz, 6H), 1.83 (m, 1H), 3.07 (t, J=6 Hz, 2H), 4.71 (d, J=5 Hz, 2H), 5.04 (bs, 2H), 5.69 (t, J=5 Hz, 1H), 7.03 (d, J=5.8 Hz, 2H), 7.21 (m, 3H), 7.35 (d, J=5 Hz, 1H), 7.38 (d, J=8 Hz, 1 H), 7.44 (m, d, J=8 Hz, 1H), 7.58 (d, J=5 Hz, 1H), 7.74 (m, 6H), 8.03 (d, J = 8 Hz, 1H), 8.24 (s, 1H), 8.67 (t, J=6 Hz, 2H), 8.79 (bs, 2H), 9.14 (bs, 2 H), 10.64 (s, 1H); MS (ES+) 661.74 |

-continued

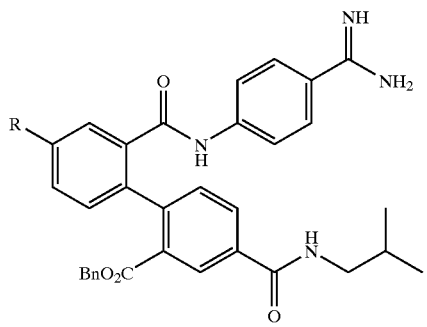

| Cpd. No. | —R | Starting From | Method Used | Analytical Data |
|---|---|---|---|---|
| 26ad | BnCO₂-(4-methyl-thiophen-3-yl) | 25ad | J | ¹HNMR (DMSO-d₆): δ 9.65 (s, 1H), 8.71 (t, J=5.15 Hz, 1H) 8.39 (d, J = 2.57 Hz, 4H), 8.09 (d, J=1.79 Hz, 4H), 8.05 (d, J=1.79 Hz, 4H), 7.43 (d, J = 7.77 Hz, 2H), 7.29 (s, 2H), 7.19 (m, 2H), 7.08 (m, 2H), 5.03 (d, J=2.58 Hz, 2H) 3.29 (m, 2H), 3.12 (s, 4H), 2.49 (m, 2H), 1.87 (m, 2H), 0.90 (d, J = 6.87 Hz, 6H); MS (ES+) 765.4 |
| 26ae | HOH₂C-(5-methyl-thiophen-2-yl) | 25ae | J | ¹HNMR (DMSO-d₆): δ 9.1 (bs, 2H), 8.8 (bs, 2H), 8.5 (t, J=6 Hz, 1H), 8.02 (s; 1H), 7.68 (s, 1H), 7.62 (m, 6H), 7.53 (d, J=5.8 Hz, 1H), 7.15 (d, J=6 Hz, 1H), ), 7.13 (m, 1H), 7.01 (s, 1H), 5.5 (t, J=5 Hz, 1H), 4.7 (d, J=5 Hz, 2H), 3.01 (m, 2H), 1.8 (m, 1H), 0.85 (d, J=6.8 Hz, 6H); MS (ES+) 571.2 |
| 26af | HOH₂C-(4-methyl-thiophen-3-yl) | 25af | J | ¹HNMR (DMSO-d₆): δ 10.6 (s, 1H), 9.17 (s, 1H), 8.85 (s, 1H), 8.68 (d, J = 5.9 Hz, 2H), 8.25 (d, 1.98 Hz, 1H), 7.75 (m, 4H), 7.65 (m, 4H), 7.41 (d, J = 7.87 Hz, 4H), 7.25 (m, 4H), 5.4 (s, 1H), 5.2 (a, J=5.9 Hz, 2H), 4.44 (d, J = 5.9 Hz, 1H), 3.09 (d, J=6.89 Hz, 2H), 1.89 (d, J=6.89 Hz, 2H), 0.88 (d, J = 5.9 Hz, 6H). |
| 26ag | N-Boc-2-methyl-pyrrole | 25ag | J | ¹HNMR (DMSO-d₆): δ 0.90 (d, J=6.9 Hz, 6H), 1.41 (s, 9H), 1.87 (m, 1H), 3.11 (t, J=6.9 and 6Hz, 2H), 5.07 (s, 2H), 6.37 (t, J=3.4 Hz, 1H), 6.51 (s, 1 H), 7.11 (m, 2H), 7.26 (m, 3H), 7.33 (d, 7.7 Hz, 2H), 7.41 (d, J=8.6 Hz, 1 H), 7.45 (d, J=1.7 Hz, 1H), 7.61 (dd, J=1.7 and 7.7, 1H), 7.74 (m, 5H), 8.05 (dd, J=8.6 and 1.7 Hz, 1H), 8.26 (d, J=1.7 Hz, 1H), 8.66 (t, J=5 and 6 Hz, 1H), 8.77 (bs, 2H), 9.15 (bs, 2H), 10.58 (s, 1H); MS (ES+) 714.78 |
| 26ah | propane-1,2-diol | 25ah | J | MS (ES+): 609.6 |
| 26ai | ethyl-N₃ | 25ai | J | ¹HNMR (DMSO-d₆): δ 10.8 (s, 1H), 6.2 and 8.9 (2 br s, 2 H each, 4H), 8.7 (t, 1H), 8.2 (s, 1H), 8.0 (d, J=6 Hz, 1H), 7.7 (m, 5H), 7.6 (d, J=5 Hz, 1H), 7.4 (d, J=5.8 Hz, 1H), 7.35 (d, J=6.9 Hz, 1H), 7.29 (m, 3H), 7.0 (m, 2H), 5.0 (m, 2H), 4.6 (s, 2H), 3.01 (t, J=6.8 Hz, 2H), 1.81 (m, 1H), 0.95 (d, J = 6.8 Hz, 6H); MS (ES+)604.3 |

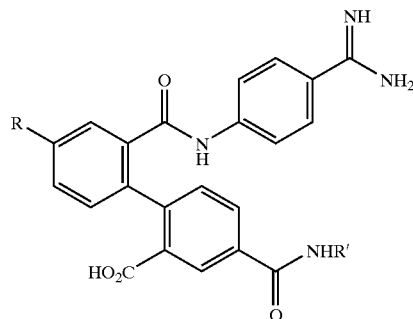

| Cpd. No. | —R | —R' | Starting From | Method Used | Analytical Data |
|---|---|---|---|---|---|
| 27a | 2-methylthiophene | sec-butyl | 26a | I-2 | ¹HNMR (DMSO-$d_6$): δ 14.95 (s, 1H), 8.97 (s, 4H), 8.5 (t, J=6 Hz, 1H), 7.97 (d, J=2 Hz, 1H), 7.80 (d, J=2 Hz, 1H), 7.73 (dd, J=7.9 and 2 Hz, 1H), 7.61 (m, 7H), 7.18 (t, J=3.9 Hz, 1H), 7.05 (d, J=7.9 Hz, 1H), 6.93 (d, J=7.9 Hz, 1H), 3.01 (t, J=6.9 and 6.0 Hz, 2H), 1.81 (m, 1H), 0.84 (d, J=6.9 Hz, 6H); MS (ES⁺): 541.17 |
| 27b | 3-methylthiophene | sec-butyl | 26b | I-2 | ¹HNMR (DMSO-$d_6$): δ 13.24 (s, 1H), 9.05 (s, 2H), 8.9 (s, 2H), 8.49 (t, J=6 and 5.2 Hz, 1H), 7.97 (s, 1H), 7.99 (s, 1H), 7.87 (s, 1H), 7.75 (d, J=7.7 Hz, 1H), 7.65 (m, 1 H), 7.62 (m,6H), 7.05 (d, J=7.7 Hz, 1H), 6.93 (d, J = 7.7 Hz, 1H), 3.01 (t, J=6.9 and 6.0 Hz, 2H), 1.81 (m, 1 H), 0.85 (d, J=6.9 Hz, 6H); MS (ES⁺): 541.42 |
| 27c | phenyl | sec-butyl | 26c | I-2 | ¹HNMR (DMSO-$d_6$): δ 13.28 (s, 1H), 9.04 (s, 4H), 8.5 (t, J=6 Hz, 1H), 7.97 (s, 1H), 7.82 (s, 1H), 7.74 (m, 3 H), 7.62 (m, 5H), 7.5 (t, J=7.7 Hz, 2H), 7.4 (t, J=7.7, 1H),7.1 (d, J=7.7 Hz,2H), 6.97 (d, J=7.7. Hz, 1H), 3.01 (t, J=6.5 Hz, 2H), 1.8 (m, 1H), 0.85 (d, 6.8 Hz, 6 H); MS (ES⁺): 535.48 |
| 27d | 2,5-dimethylthiophene | sec-butyl | 26d | I-2 | ¹HNMR (DMSO-$d_6$): δ 9.03 (s, 2H), 8.89 (s, 2H), 8.49 (t, J=6 Hz, 1H), 7.99 (s, 1H), 7.65 (m, 8H), 7.37 (d, J = 3 Hz, 1H), 7.04 (d, J=7.7 Hz, 1H), 6.98 (s, 1H), 6.82 (d, J=3 Hz, 1H), 2.98 (t, J=6.5 Hz, 2H), 2.46 (s, 3H), 1.76 (m, 1H), 0.81 (d, 6.8 Hz, 6H); MS (ES⁺): 555.61 |
| 27e | 3-methylfuran | sec-butyl | 26e | I-2 | ¹HNMR (DMSO-$d_6$): δ 14.10 (s, 1H), 9.05 (bs, 2H), 8.79 (bs, 2H), 8.47 (t, J=5.6 Hz, 1H), 8.3 (s, 1H), 7.96 (d, J=2 Hz, 1H), 7.78 (m, 1H), 7.63 (m, 7H), 7.05 (m, 1H),7.01 (d, J=7.7 Hz, 1H), 6.92 (d, J=7.7 Hz, 1H), 3.02 (t, J=4.9 Hz, 2H), 1.81 (m, 1H), 0.85 (d, J=6.3 Hz, 6H); MS (ES⁺): 525.36 |
| 27f | 2-methylfuran | sec-butyl | 26f | I-2 | ¹HNMR (DMSO-$d_6$): δ 9.07 (s, 2H), 8.86 (s, 2H), 8.53 (t, J=5 Hz, 1H), 8.03 (s, 1H),7.89 (d, J=1.4 Hz, 1H), 7.78 (m, 2H), 7.65 (m, 6H), 7.1 (m, 2H), 7.08 (d, J=7 Hz, 1H), 6.64 (dd, J=3.5 and 2 Hz, 1H), 3.03 (t, J=6.9 and 6.0 Hz, 2H), 1.81 (m, 1H), 0.86 (d, J=6.9 Hz, 6H); MS (ES⁺); 525.43 |
| 27g | 4-methyl-2-thienyl | sec-butyl | 26g | I-1 | ¹HNMR (DMSO-$d_6$): δ 13.81 (s, 1H), 8.74 (bs, 4H), 8.43 (t, J=6 Hz, 1H), 7.92 (d, J=2 Hz, 1H), 7.69 (d, J = Hz, 1H), 7.62 (dd, J=7.7 & 2 Hz, 1H), 7.54 (m, 5H), 7.38 (s, 1H), 7.15 (s, 1H), 6.99 (d, J=7.8 Hz, 1H), 6.89 (d, J=6.8 Hz, 1H), 2.97 (t, J=6.5 Hz, 2H), 2.20 (s, 3 H), 1.76 (m, 1H), 0.8 (d, 6.8 Hz, 6H); MS (ES⁺): 555.67 |
| 27h | 2-methylpyridine | sec-butyl | 26h | I-2 | ¹HNMR (DMSO-$d_6$): δ 13.95 (bs, 1H), 8.99 (bs, 2H), 8.79 (bs, 2H), 8.65 (d, J=5 Hz, 1H), 8.43 (t, J=6 Hz, 1 H), 8.25 (s, 1H), 8.09 (d, J=7.8 Hz, 1H), 8.00 (d, J = 7.8 Hz, 1H), 7.94 (s, 1H), 7.87 (t, J=7.8 Hz, 1H), 7.58 (m, 5H), 7.34 (dd, J=7.8 & 5Hz, 1H), 7.09 (dd, J=7.7 Hz, 1H), 6.90 (d, J=7.8 Hz, 1H), 2.97 (t, J=5 Hz, 2H), 1.76 (m, 1H), 0.81 (d, 6.8 Hz, 6H); MS (ES⁺): 268.64 (m/2) |

-continued

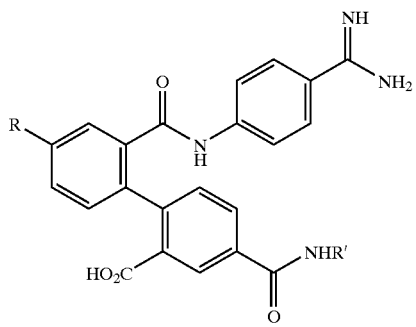

| Cpd. No. | —R | —R' | Starting From | Method Used | Analytical Data |
|---|---|---|---|---|---|
| 27i | 3-methylpyridine | sec-butyl | 26i | I-2 | $^1$HNMR (DMSO-$d_6$): δ 9.05 (bs, 2H), 8.95 (d, J=2.1 Hz, 1H), 8.75 (s, 2H), 8.65 (dd, J=5 & 1.4 Hz, 1H), 8.5 (t, J=5.6 Hz, 1H), 8.2 (dt, J=1.8 & 7.7 Hz, 1H), 7.99 (d, J=2.1 Hz, 1H), 7.9 (d, J=2.1 Hz, 1H), 7.85 (dd, J = 7.7 & 2.2 Hz, 2H), 7.65 (m, 5H), 7.55 (dd, J=7.7 & 4.5 Hz, 1H), 7.15 (d, J =7.7 Hz, 1H), 6.95 (d, J=7.7 Hz, 1 H), 3.08 (t, J=5 Hz, 2H), 1.82 (m, 1H), 0.9 (d, 6.8 Hz, 6 H); MS (ES$^+$): 268.85 (m/2) |
| 27j | 4-methylpyridine | sec-butyl | 26j | I-2 | $^1$HNMR(DMSO-$d_6$): δ 14.19 (s, 1H), 9.06 (bs, 2H), 8.67 (bs, 2H), 8.67 (d, J=6 Hz, 2H), 8.50 (t, J=6 Hz, 1 H), 7.97 (m, 2H), 7.91 (dd, J=7.7 and 2 Hz, 1H), 7.80 (d, J=6 Hz, 2H), 7.64 (m, 6H), 7.18 (d, J=7.7 Hz, 1 H), 6.95 (d, J=7.7 Hz, 1H), 3.02 (t, J=5.0 Hz, 2H), 1.82 (m, 1H), 0.80 (d, J=6.9 Hz, 6H); MS (ES$^+$): 536.43 |
| 27k | 2-acetyl-5-methylthiophene | sec-butyl | 26k | I-2 | $^1$HNMR (DMSO-$d_6$): δ 9.04 (bs, 2H), 8.78 (bs, 2H), 8.55 (t, J=6 Hz, 1H), 8.1 (s, 1H), 7.98 (d, J=4 Hz, 1 H), 7.95 (s, 1H), 7.87 (d, J=7.9 Hz, 1H), 7.75 (d, J = 6.9 Hz, 1H), 7.66 (m, 4H), 7.2 (m, 2H), 7.09 (s, 1H), 3.03 (t, J=6 Hz, 2H), 2.55 (s, 3H), 1.81 (m, 1H), 0.85 (d, J=6.8 Hz, 6H); MS (ES$^+$): 583.59 |
| 27l | 1-methyl-2-methylpyrrole | sec-butyl | 26l | I-2 | $^1$HNMR (DMSO-$d_6$): δ 9.1 (s, 2H), 8.84 (s, 2H), 8.56 (t, J=6 Hz, 1H), 8.08 (bs, 1H), 7.67 (m, J=7H), 7.58 (d, J = 7.9 Hz, 1H),7.11 (m, 2H), 6.91 (bs, 1H),6.31 (bs, 1 H), 6.11 (t, J=3 Hz, 1H), 3.74(s, 3H), 3.05 (t, J=6 Hz, 2H), 1.83 (m, 1H), 0.88 (d, J=6.8 Hz, 6H); MS (ES$^+$): 538.64 |
| 27m | 1-methylpyrrolidin-2-yl | sec-butyl | 26m | I-2 | $^1$HNMR (DMSO-$d_6$): δ 9.04 (s, 2H), 8.94 (s, 2H), 8.46 (t, J=6 Hz, 1H), 7.96 (s, 1H), 7.63 (m, 6H), 6.94 (s, 1 H), 6.83 (d, J=7.7 Hz, 1H), 6.7 (d, J=2, 1H), 6.62 (dd, J=7.7 and 2 Hz, 1H), 3.28 (m, 4H), 3.02 (t, J=6.5 Hz, 2H), 1.98 (m, 4H), 1.82 (m,1H), 0.82 (d, 6.8 Hz, 6H); MS (ES$^+$): 528.76 |
| 27n | but-3-enyl | sec-butyl | 26n | I-2 | $^1$HNMR (DMSO-$d_6$): δ 13.96 (s, 1H), 9.02 (s, 2H), 8.85 (s, 2H), 8.46 (t, J=6 Hz, IH), 7.91 (s, 1H), 7.58 (m, 4 H), 7.39 (s, 1H), 7.25 (d, J=7.8 Hz, 1H), 6.92 (d, J = 7.7, 1H), 6.87 (d, J=7.7 Hz, 1H), 6.01 (m, 1H), 5.17 (d, J=16.7 Hz, 1H), 5.08 (d, J=10 Hz, 1H), 3.45 (d, J=6 Hz, 2H), 2.99 (t, J=6 Hz, 2H), 1.78 (m, 1H), 0.83 (d, J = 6.8 Hz, 6H); MS (ES$^+$): 499.3 |
| 27o | 2-methylthiazole | sec-butyl | 26o | I-2 | $^1$HNMR (DMSO-$d_6$): δ 14.08 (bs, 1H), 9.06 (s, 2H), 8.79 (s, 2H), 8.51 (t, J=6 Hz, 1H), 8.11 (d, J=2 Hz, 1 H), 8.01 (m, 3H), 7.85 (d, J=3 Hz, 1H), 7.63 (m, 6H), 7.17 (d, J=7.8 Hz, 1H), 6.97 (d, J=7.8 Hz, 1H), 3.02 (t, J=6.5 Hz, 2H), 1.81 (m, 1H), 0.86 (d, 6.8 Hz, 6H); MS (ES$^+$): 542.2 |
| 27p | prop-1-enyl | sec-butyl | 26p | I-2 | $^1$HNMR (DMSO-$d_6$): δ 9.1 and 9.2 (2 br s, 4 H, NH proton), 8.6 (m, 1H), 8.3 (m, 1H), 8.0–7.6 (m, 8 H, aromatic proton), 7.3 (m, 2H), 3.1 (t, 2H), 2.2 (s, 3H), 1.8 (m, 1H), 0.9 (2s, 6H); JR (KBr Pellets) 2957, 1676, 1480, 1324, 844 cm$^{-1}$. MS (ES+): 497 |

-continued

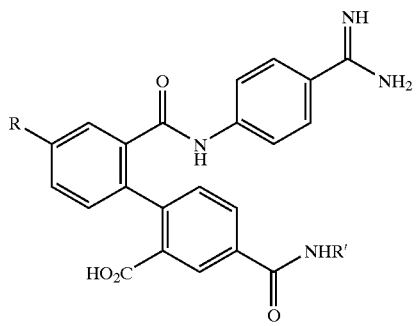

| Cpd. No. | —R | —R' | Starting From | Method Used | Analytical Data |
|---|---|---|---|---|---|
| 27q | H₃C-C≡C-C(CH₃)(OH)- | sec-butyl (CH(CH₃)CH₂CH₃) | 26q | I-2 | ¹HNMR (DMSO-d₆): δ 9.06 (s, 2H), 8.77 (s, 2H), 8.53 (t, J=6 Hz, 1H), 8.03 (m, 1H), 7.64 (m, 6H), 7.46 (d, J = 6.9 Hz, 1H), 7.05 (s, 2H), 6.96 (s, 1H), 5.52 (s, 1H), 3.02 (t, J=6.8 Hz, 2H), 1.81 (m, 1H), 1.48 (s, 6H), 0.85 (d, J=6.8 Hz, 6H); MS (ES⁻): 539.4 |
| 27r | CH₃-C≡C-CH₂CH₂OH | sec-butyl | 26r | I-2 | ¹HNMR (DMSO-d₆): δ 9.06 (s, 2H), 8.78 (s, 2H), 8.52 (t, J=6 Hz, 1H), 8.01 (d, J=6.8 Hz, 1H), 7.62 (m, 7H), 7.46 (d, J=6.8 Hz, 1H), 7.0 (m, 2H), 4.94 (t, J=6 Hz, 1 H), 3.60 (q, J=6 & 12.8 Hz, 2H), 3.01 (t, J=6 Hz, 2H), 2.58 (t, J=6 Hz, 2H), 1.82 (m, 1H), 0.85 (d, J=6.8 Hz, 6H); MS (ES⁻): 525.4 |
| 27s | CH₃-CH=C(CH₃)-CH=CH₂ | sec-butyl | 26s | I-2 | ¹HNMR (DMSO-d₆): δ 9.01 (s, 2H), 8.88 (s, 2H), 8.5 (t, J=6 Hz, 1H), 8.07 (m, 1H), 7.73 (m, 1H), 7.63 (m, 7 H), 7.11 (d, J=17 Hz, 1H), 7.01 (d, J=17 Hz, 1H), 6.97 (m, 1H), 6.69 (d, J=17 Hz, 1H), 5.24 (s, 1H), 5.14 (s, 1H), 3.03 (t, J=6.9 and 6.0 Hz, 2H), 1.92 (s, 3H), 1.81 (m, 1H), 0.84 (d, J=6.9 Hz, 6H); MS (ES⁺): 525.4 |
| 27t | CH₂=C(CH₃)- | sec-butyl | 26t | I-2 | ¹HNMR (DMSO-d₆): δ 9.08 (s, 2H), 8.82 (s, 2H), 8.53 (t, J=6 Hz, 1H), 8.04 (m, 1H), 7.67 (m, 7H), 7.04 (m, 2 H), 5.55 (s, 1H), 5.20 (s, 1H), 3.04 (t, J=6.9 and 6.0 Hz, 2H), 2.19 (s, 3H), 1.81 (m, 1H), 0.87 (d, J=6.9 Hz, 6 H); MS (ES⁺): 499.4 |
| 27u | CH₃-CH=CH-CH₂OH (cis) | sec-butyl | 26u | I-2 | ¹HNMR (DMSO-d₆): δ 9.11 (s, 2H), 8.86 (s, 2H), 8.57 (t, J=6 Hz, 1H), 8.13 (m, 1H), 7.53 (m, 2H), 7.74 (m, 6 H), 7.37 (d, J=7 Hz, 1H), 7.17 (m, 2H), 6.54 (d, J=12 Hz, 1H), 5.91 (m, 1H), 4.99 (m, 1H), 4.31 (m, 2H), 3.06 (t, J=6.9 and 6.0 Hz, 2H), 1.83 (m, 1H), 0.87 (d, J = 6.9 Hz, 6H); MS (ES⁺): 515.4 |
| 27v | CH₂=C(CH₃)CH₂CH₂OH | sec-butyl | 26v | I-2 | ¹HNMR (DMSO-d₆): δ 9.08 (s, 2H), 8.82 (s, 2H), 8.54 (t, J=6 Hz, 1H), 8.05 (m, 1H), 7.63 (m, 8H), 7.06 (m, 2 H), 5.52 (s, 1H), 5.2 (s, 1H), 4.63 (t, J=5 Hz, 1H), 3.56 (m, 2H), 3.05 (t, J=6.9 and 6.0 Hz, 2H), 2.71 (t, J=7 Hz, 2H), 1.82 (m, 1H), 0.87 (d, J=6.9 Hz, 6H); MS (ES⁺): 529.4 |
| 27w | HC≡C-CH₃ | sec-butyl | 26w | I-2 | ¹HNMR (DMSO-d₆): δ 9.08 (s, 2H), 8.86 (s, 2H), 8.54 (t, J=6 Hz, 1H), 8.03 (m, 1H), 7.62 (m, 7H), 7.08 (d, J = 7.5 Hz, 1H), 6.99 (m, 1H), 4.32 (s, 1H), 3.03 (t, J = 6.9 and 6.0 Hz, 2H), 2.71 (t, J=7 Hz, 2H), 1.82 (m, 1 H), 0.87 (d, J=6.9 Hz, 6H); MS (ES⁺): 483.3 |
| 27x | (CH₃)(CH₂CH₃)C=CH-CH=CH₂ | sec-butyl | 26x | I-2 | ¹HNMR (DMSO-d₆): δ 13.8 (s, 1H), 9.04 (s, 2H), 8.96 (s, 2H), 8.47 (t, J=6 Hz, 1H), 7.93 (s, 1H), 7.61 (m, 6 H), 7.42 (m, 1H), 6.91 (m, 2H), 6.07 (dd, J=17 and 9 Hz, 1H), 5.35 (m, 1H), 5.09 (dd, J=17 and 11 Hz, 1H), 3.38 (d, J=6.5 Hz, 1H), 3.0 (t, J=7 Hz, 2H), 1.78 (m, 1 H), 1.72 (s, 3H), 1.41 (s, 3H), 0.84 (d, J=6.9 Hz, 6H); MS (ES⁺): 527.5 |
| 27y | CH₃-C≡C-CH₂OH | sec-butyl | 26y | I-2 | ¹HNMR (DMSO-d₆): δ 8.99 (s, 2H), 8.86 (s, 2H), 8.52 (t, J=6 Hz, 1H), 8.03 (m, 1H), 7.63 (m, 6H), 7.50 (d, J = 7 Hz, 1H), 7.07 (d, J=7 Hz, 1H), 7.12 (m, 1H), 5.40 (t, J=6 Hz, 1H), 4.33 (d, J=6.0 Hz, 2H), 3.01 (t, J=7 Hz, 2H), 1.80 (m, 1H), 0.84 (d, J=6.9 Hz, 6H); MS (ES⁺): 513.4 |

-continued

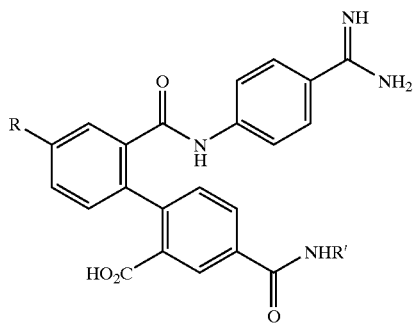

| Cpd. No. | —R | —R' | Starting From | Method Used | Analytical Data |
|---|---|---|---|---|---|
| 27z | CH₂=C(CH₃)CH₂OH (2-methylallyl alcohol group) | sec-butyl | 26z | I-2 | ¹HNMR (DMSO-d₆): δ 9.50 (bs, 1H), 8.77 (bs, 2H), 8.49 (t, J=6 Hz, 1H), 7.98 (m, 1H), 7.63 (m, 6H), 7.55 (d, J=6.9 Hz, 1H), 7.01 (d, J=7.9 Hz, 1H), 6.99 (m, 1H), 5.55 (s, 1H), 5.38 (s, 1H), 5.13 (t, J=5 Hz, 1H), 4.39 (d, J=5 Hz, 2H), 3.02 (t, J=6.9 and 6.0 Hz, 2H), 1.81 (m, 1H), 0.86 (d, J =6.9 Hz, 6H); MS (ES⁺): 515.4 |
| 27aa | CH₂CN | sec-butyl | 26aa | I-2 | ¹HNMR (DMSO-d₆): δ 9.08 (s, 2H), 8.73 (s, 2H), 8.53 (t, J=6 Hz, 1H), 8.06 (s, 1H), 8.02 (bs, 1H), 7.94 (d, J = 7.8 Hz, 1H), 7.62 (m, 6H), 7.24 (d, J=7.8 Hz, 1H), 6.95 (d, J=7.8 Hz, 1H), 3.03 (t, J=6 Hz, 2H), 1.82 (m, 1H), 0.87 (d, J=6.8 Hz, 6H); MS (ES⁺): 484.3 |
| 27ab | 2-methyl-3-(hydroxymethyl)thiophene | sec-butyl | 26ab | I-2 | ¹HNMR (DMSO-d₆): δ 9.05 (bs, 2H), 8.81 (bs, 2H), 8.49 (t, J =6 Hz, 1H), 8.02 (s, 1H), 7.68 (s, 1H), 7.62 (m, 6H), 7.53 (d, J=6 Hz, 1H), 7.21 (d, J=6 Hz, 1H), 7.13 (d, J=7 Hz, 1H), 7.01 (s, 1H), 5.25 (t, J=5 Hz, 1H), 4.51 (d, J=5 Hz, 2H), 3.01 (t, J=6 Hz, 2H), 1.81 (m, 1H), 0.85 (d, J=6.8 Hz, 6H); MS (ES⁺): 571.64 |
| 27ac | 3-methyl-2-(hydroxymethyl)thiophene | sec-butyl | 26ac | I-2 | ¹HNMR (DMSO-d₆): δ 9.05 (bs, 2H), 8.78 (s, 2H), 8.52 (t, J=6 Hz, 1H), 8.02 (bs, 1H), 7.65 (m, 6H), 7.53 (d, J = 1H), 7.54 (d, J=5 Hz, 1H), 7.26 (d, J=5 Hz, 1H), 7.10 (m, 1H), 6.99 (m, 1H), 5.64 (t, J=5 Hz, 1H), 4.71 (d, J=5 Hz, 2H), 3.07 (t, J=6.9 and 6.0 Hz, 2H), 1.73 (m, 1H), 0.84 (d, J=6.9 Hz, 6H); MS (ES⁺): 571.56 |
| 27ad | 3-methyl-2-carboxylic acid thiophene | sec-butyl | 26ad | I-2 | MS (ES⁺): 585.4 |
| 27ae | 5-(hydroxymethyl)thiophene substituent | sec-butyl | 26ae | I-2 | ¹HNMR(DMSO-d₆): δ 14.11 (bs, 1H), 9.05 (bs, 2H), 8.75 (bs, 2H), 8.5 (m, 1H), 8.0 (s, 1H), 7.8–7.6 (m, 8H), 7.49 (d, J=3 Hz, 1H),7.1 (d, J=6.9 Hz, 1H), 7.0 (m, 1H), 5.5 (m,1H), 4.7 (m, 2H), 3.09 (m, 2H), 1.74 (m, 1H) 0.86 (d, J=6.9 Hz, 6H); MS (ES+) 571.2 |
| 27af | 4-methyl-3-(hydroxymethyl)thiophene | sec-butyl | 26af | I-2 | ¹HNMR (DMSO-d₆): δ 14.11 (bs, 1H), 9.05 (bs, 2H), 8.75 (bs, 2H), 8.49 (t, J=6 Hz, 1H), 7.97 (s, 1H), 7.67 (d, J =3 Hz, 1H), 7.61 (m, 7H), 7.54 (d, J=3 Hz, 1H), 7.06 (d, J=6.9 Hz, 1H), 6.89 (d, J=6.9 Hz, 1H), 5.23 (t, J=5 Hz, 1H), 5.42 (d, J=5 Hz, 2H), 3.09 (t, J=26.9 and 6.0 Hz, 2H), 1.74 (m, 1H) 0.86 (d, J=6.9 Hz, 6H); MS (ES⁺): 571.3 |
| 27ag | 2-methylpyrrole | sec-butyl | 26ag | I-2 | ¹HNMR (DMSO-d₆): δ 11.45 (s, 1H), 9.08 (bs, 2H), 8.88 (bs, 2H), 8.75 (t, J=6 Hz, 1H), 8.04 (bs, 1H), 7.88 (m, 1H), 7.7 (m, 7H), 7.03 (m, 2H), 6.9 (m, 1H), 6.62 (m, 1H), 6.17 (m, 1H), 3.07 (t, J=6.9 and 6.0 Hz, 2H), 1.84 (m, 1H), 0.86 (d, J=6.9 Hz, 6H); MS (ES⁺): 524.65 |

-continued

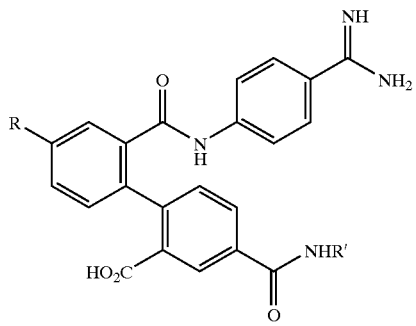

| Cpd. No. | —R | —R' | Starting From | Method Used | Analytical Data |
|---|---|---|---|---|---|
| 27ah | CH(OH)CH2OH (2-hydroxy, with CH3) | sec-butyl (CH(CH3)CH2CH3) | 26ah | I-2 | ¹HNMR (DMSO-d₆): δ 13.83 (s, 1H), 8.9 (bs, 4H), 8.47 (t, J=6 Hz, 1H), 7.95 (s, 1H), 5.3 (s, 1H), 7.61 (m, 6 H), 7.4 (m, 1H), 6.95 (d, J=7.7 Hz, 1H), 6.85 (d, J=7.7 Hz, 1H), 6.64 (d, J=9 Hz, 1H), 6.22 (s, 1H), 4.6 (t, J = 5.1 Hz, 1H), 3.51 (d, J=5.6 Hz, 2H), 3.01 (t, J=7 Hz, 2H), 1.8 (m, 1H), 0.85 (d, J=6.9 Hz, 6H); MS (ES⁺): 519.52 |
| 27ai | CH2N2 | sec-butyl | 26ai | I-2 | MS (ES+) 514.25 |
| 27aj | CH2CH2CH2CH3 | sec-butyl | 26n | G | ¹HNMR (DMSO-d₆): δ 9.05 (s, 2H), 8.67 (s, 2H), 8.47 (t, J=6 and 5 Hz, 1H), 7.95 (m, 1H), 7.95 (m, 1H), 7.63 (m, 5H), 7.40 (s, 1H), 7.38 (d, J=7.7 Hz, 1H), 6.92 (m, 2H), 3.02 (t, J=6.8 Hz, 2H), 2.64 (m, 2H), 1.80 (m, 1 H), 1.66 (m, 2H), 0.96 (t, J=8 and 6.5 Hz, 3H), 0.85 (d, J=6.8 Hz, 6H); MS (ES−) 499.31 |
| 27ak | CH2CH=CH2 (allyl/propenyl, CH3) | sec-butyl | 32f | G | ¹HNMR (DMSO-d₆): δ 14.3 (bs, 1H), 9.05 (bs, 2H), 8.75 (bs, 2H), 8.5 (m, 1H), 8.0 (s, 1H), 7.8–7.6 (m, 8H), 7.49 (d, J=3 Hz, 1H), 7.1 (d, J=6.9 Hz, 1H), 7.0 (m, 1 H), 5.5 (m,1H), 4.7 (m, 2H), 3.09 (m, 2H), 1.74 (m, 1 H), 0.86 (d, J=6.9 Hz, 6H); MS (ES+) 487.2 |
| 27al | CH2NH2 | sec-butyl | 26ai | G | MS (ES+) 488.3 (100%: M⁺¹) |
| 27am | (CH2)3OH | sec-butyl | 26u | G | ¹HNMR (DMSO-d₆): δ 13.9 (bs, 1H), 9.05 (2 bs, 4H), 8.5 (m, 1H), 7.9 (s, 1H), 7.7–7.5 (m, 8H), 7.3 (d, J=3 Hz, 1H), 6.9 (m, 2H), 4.6 (m, 1H), 3.5 (m, 2H), 3.09 (m, 2H), 2.6 (m, 2H), 1.8 (m, 1H) 0.85 (d, J=6.9 Hz, 6 H);□MS (ES+) 517.3 |
| 32a | C(O)CH3 | sec-butyl | 31a | I-2 | ¹HNMR (DMSO-d₆): δ 9.84 (bs, 1H), 9.07 (bs, 2H), 8.87 (bs, 2H), 8.51 (t, J=6 and 5 Hz, 1H), 8.13 (m, 1 H), 8.03 (m, 2H), 7.65 (m, 5H), 7.20 (d, J=7.7 Hz, 1 H), 6.94 (d, J=7.7.Hz, 1H), 3.04 (t, J=6.8 Hz, 2H), 2.66 (s, 3H), 1.83 (m, 1H), 0.86 (d, J=6.8 Hz, 6H); MS (ES−) 499.4, (ES+) 501.4 |
| 32b | CH=CHCH3 (propenyl) | sec-butyl | 31b | I-2 | Characterized in the next step |
| 32c | CH=CHCH2 | sec-butyl | 31c | I-2 | ¹HNMR (DMSO-d₆): δ 14.24 (s, 1H), 9.29 (bs, 2H), 9.01 (bs, 2H), 8.73 (t, J=6 Hz, 1H), 8.2 (d, J=2 Hz, 1 H), 7.85 (m, 5H), 7.74 (d, 2 Hz, 1H), 7.4 (d, J=8 Hz, 1 H), 7.22 (d, J=7.4 Hz, 1H), 7.13 (d, J=7.5, 1H), 6.73 (t, J=6.8 Hz, 1H), 5.59 (d, J=6.8 Hz, 2H), 3.25 (t, J = 6.8 Hz, 2H), 2.04 (m, 1H), 1.08 (d, J=6.8 Hz, 6H); MS (ES−) 495.1, (ES+) 497.2 |

-continued

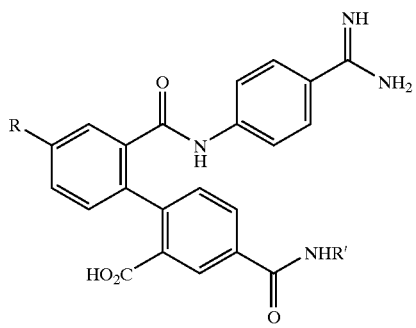

| Cpd. No. | —R | —R' | Starting From | Method Used | Analytical Data |
|---|---|---|---|---|---|
| 32d | 2-ethylthiophene | sec-butyl (CH(CH3)CH2CH3) | 31d | I-2 | MS (ES−) 553.3 |
| 32e | ethylphenyl | sec-butyl | 31e | I-2 | ¹HNMR (DMSO-d₆): δ 13.642 (bs, 1H), 9.06 (s, 2H), 8.89 (s, 2H), 8.50 (t, J=6 and 5 Hz, 1H), 7.98 (s, 1H), 7.62 (m, 7H), 7.43 (s, 1H), 7.33 (m, 4H), 6.95 (m, 2H), 4.04 (s, 2H), 3.02 (t, J=6.8 Hz, 2H), 1.80 (m, 1H), 0.86 (d, J=6.8 Hz, 6H); MS (ES−) 547.4 |
| 32f | CH2=CH–CH2– (allyl) | sec-butyl | 31f | I-2 | ¹HNMR (DMSO-d₆): δ 0.85 (d, J=6.9 Hz, 6H), 1.81 (m, 1H), 3.03 (t, J=7 Hz, 2H), 5.35 (d, J=11 Hz, 1H), 5.94 (d, J=17 Hz, 1H), 6.84 (dd, J=17 and 11 Hz, 2H), 7.0 (m, 2H), 7.64 (m, 8H), 8.01 (s, 1H), 8.54 (t, J=6 Hz, 1H), 8.77 (s, 2H), 9.06 (s, 2H); MS (ES+) :485.57 |
| 32g | N3H2C-(4-methylthiophene) | sec-butyl | 31g | I-2 | MS (ES+) 596..2 |
| 32h | (3-CH2OH, 2-methyl furan) | sec-butyl | 31h | I-2 | ¹HNMR (DMSO-d₆): δ 14.2 (bs, 1H), 9.1 (bs, 4H), 8.6 (m, 1H), 8.15 (s, 1H), 7.9–7.6 (m, 8H), 7.2 (m, 2H), 6.7 (s, 1H), 5.3 (br s, 1H), 4.6 (m, 2H), 3.1 (m, 2H), 1.9 (m, 1H), 0.9 (d, J=6.7 Hz, 6H); MS (ES+) 555.1 |
| 32i | HOH2C-(4-methyl furan) | sec-butyl | 31i | I-2 | ¹HNMR (DMSO-d₆): δ 13.84 (bs, IH), 9.01 (bs, 2H), 8.80 (bs, 2H), 8.46 (t, J=6 and 5 Hz, 1H), 8.03 (s, 1H), 7.95 (s, 1H), 7.77 (s, 1H), 7.67 (m, 2H), 7.61 (m, 5H), 7.02 (d, J=7.7 Hz, 1H), 6.94 (m, 1H), 5.13 (t, J=5 Hz, 1H), 4.47 (m, 2H), 2.97 (t, J=6.8 Hz, 2H), 1.78 (m, 1 H), 0.80 (d, J=6.8 Hz, 6H); MS (ES−) 553.3, (ES+) 555.3 |
| 40 | 3-methylpyrrole | sec-butyl | 39 | I-2 | MS (ES+) 524.3 |
| 44 | methoxyphenyl (–O–Ph) | sec-butyl | 43 | I-2 | ¹HNMR (DMSO-d₆): δ 13.82 (s, 1H), 9.20 (bs, 1H), 9.10 (bs, 1H), 8.51 (t, J=6 Hz, 1H), 7.97 (s, 1H), 7.73–7.45 (m, 5H), 7.43–7.39 (m, 2H), 7.20 (t, J=8 Hz, 1H), 7.10 (m, 6H), 6.96 (d, J=8 Hz, 1H), 3.0 (t, J=6 Hz, 2H), 1.80 (m, 1H), 0.68 (d, J=6.8 Hz, 6H); MS (ES+) 551.30 |
| 46 | –O–CH2–Ph (benzyloxy) | sec-butyl | 45 | I-2 | ¹HNMR (DMSO-d₆): δ 9.21 (2 bs, 2 H each, 4H), 8.61 (m, 1H), 8.1 (s, 1H), 7.8–7.4 (m, 10H), 7.3 (s, 1H), 7.2 (d, J=7 Hz, 1H), 7.1 (m, 2H), 5.2 (s, 2H), 3.1 (m, 2H), 1.8 (m, 1H), 0.91 (d, J=6.8 Hz, 6H); MS (ES+) 565.27 |

-continued

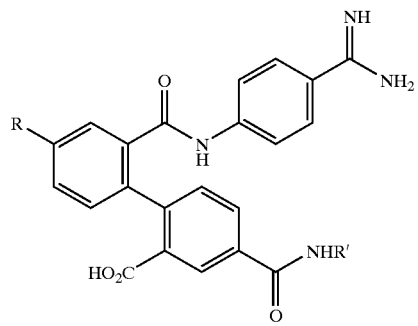

| Cpd. No. | —R | —R' | Starting From | Method Used | Analytical Data |
|---|---|---|---|---|---|
| 51 | —OCH₃ | CH(CH₃)CH₂CH₃ | 50 | I-2 | ¹HNMR (CF₃CO₂D): δ 8.43 (s, 1H), 8.01 (d, J=7.5 Hz, 1H), 7.67 (q, J=24 and 8.4 Hz, 4H), 7.56 (d, J=7.7 Hz, 1H), 7.38 (s, 1H), 7.23 (s, 2H), 3.98 (s, 3H), 3.43 (d, J = 7 Hz, 2H), 2.01 (m, 1H), 1.01 (d, J=6.8 Hz, 6H); MS (ES−) 487., (ES+) 489.3 |
| 53 | 4-methyl-3-(aminomethyl)thiophene | CH(CH₃)CH₂CH₃ | 52 | I-2 | ¹HNMR (DMSO-d₆): δ 14.00 (bs, 1H), 8.52 (t, J=6 and 5 Hz, 1H), 7.98 (s, 1H), 7.63 (m, 8H), 7.07 (d, J=7.7 Hz, 1H), 6.96 (d, J=7.7 Hz, 1H), 3.83 (s, 2H), 3.02 (t, J = 6.8 Hz, 2H), 1.81 (m, 1H), 0.86 (d, J=6.8 Hz, 6H); MS (ES−) 568.1 |
| 70a | CH₂=CH—CH< | n-pentyl (CH₂CH₂CH₂CH₂CH₃) | 68a | I-2, S | ¹HNMR (DMSO-d₆): δ 13.84 (br s, 1H), 9.05 (s, 2H), 8.94 (s, 2H), 8.48 (t, J=5.7 Hz, 1H), 7.97 (d, J=1.9 Hz, 1H), 7.70 (m, 7H), 7.00 (d, J=7.9 Hz, 1H), 6.92 (d, J=7.9 Hz, 1H), 6.84 (dd, J=10.9 and 17.7 Hz, 1H), 5.93 (d, J=17.7 Hz, 1H), 5.34 (d, J=10.9 Hz, 1H), 3.19 (m, 2H), 1.46 (qui, J=7.0 Hz, 2H), 1.29 (sex, J = 7.0 Hz, 2H), 0.87 (t, J=7.3 Hz, 3H); MS (ES⁺): 485.2 |
| 70b | CH₂=CH—CH< | 2-ethylhexyl | 68b | I-2, S | ¹HNMR (DMSO-d₆): δ 12.71 (br s, 1H), 9.12 (s, 2H), 8.93 (s, 2H), 8.20 (m, 2H), 7.86 (m, 1H), 7.70 (m, 6H), 7.20 (m, 2H), 6.87 (dd, J=10.9 and 17.7 Hz, 1H), 5.99 (d, J=17.7 Hz, 1H), 5.40 (d, J=10.9 Hz, 1H), 3.97 (m, 1H), 1.50–1.20 (m, 8H) 0.86 (t, J=7.2 Hz, 6H); MS (ES⁺): 527.3 |
| 70c | CH₂=CH—CH< | cyclohexyl | 68c | I-2, S | ¹HNMR (DMSO-d₆): δ 12.84 (br s, 1H), 9.08 (m, 3H), 8.36 (d, J=7.7 Hz, 1H), 8.18 (s, 1H), 7.83 (m, 1H), 7.67 (m, 6H), 7.15 (m, 3H), 6.86 (dd, J=10.9 and 17.7 Hz, 1H), 5.98 (d, J=17.7 Hz, 1H), 5.39 (d, J=10.9 Hz, 1H), 3.74 (m, 1H), 1.84–1.55 (m, 5H), 1.38–1.04 (m, 5 H); MS (ES⁺): 511.3 |
| 70d | CH₂=CH—CH< | CH₂CH₂CH=CH₂ | 68d | I-2, S | ¹HNMR (DMSO-d₆): δ 9.11 (s, 2H), 8.89 (s, 2H), 8.81 (t, J=5.7 Hz, 1H), 8.21 (s, 1H), 7.85 (m, 1H), 7.68 (m, 7H), 7.17 (m, 3H), 6.87 (dd, J=10.9 and 17.7 Hz, 1H), 5.99 (d, J=17.7 Hz, 1H), 5.88 (m, 1H), 5.39 (d, J=10.9 Hz, 1H), 5.12 (m, 2H), 3.88 (t, J=5.0 Hz, 1H); MS (ES⁺): 469.2 |
| 70e | CH₂=CH—CH< | isopropyl CH(CH₃)₂ | 68e | I-2, S | ¹HNMR (DMSO-d₆): δ 9.11 (s, 2H), 9.01 (s, 2H), 8.38 (d, J=7.5 Hz, 1H), 8.18 (s, 1H), 7.83 (m, 1H), 7.67 (m, 6H), 7.16 (m, 3H), 6.86 (dd, J=10.9 and 17.7 Hz, 1H), 5.98 (d, J 17.7 Hz, 1H), 5.39 (d, J 10.9 Hz, 1H), 4.09 (m, 1H), 1.15 (d, J=6.6 Hz, 6H); MS (ES⁺): 471.3 |
| 70f | CH₂=CH—CH< | sec-butyl CH(CH₃)CH₂CH₃ | 68f | I-2, S | ¹HNMR (DMSO-d₆): δ 9.11 (s, 2H), 9.05 (s, 2H), 8.31 (d, J=8.1 Hz, 1H), 8.20 (s, 1H), 7.85 (d, J=7.7 Hz, 1 H), 7.69 (m, 6H), 7.17 (m, 3H), 6.86 (dd, J=10.9 and 17.7 Hz, 1H), 5.98 (d, J=17.7 Hz, 1H), 5.39 (d, J = 10.9 Hz, 1H),3.91 (m, 1H), 1.50 (m,2H), 1.12 (d,J = 6.6 Hz, 3H). 0.85 (t, J=7.3 Hz, 3H); MS (ES⁺): 485.3 |

-continued

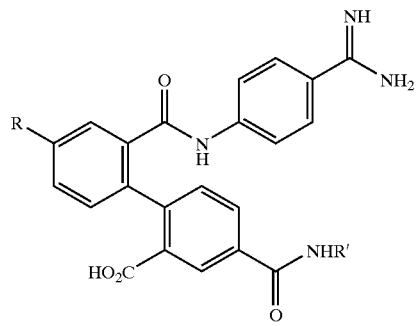

| Cpd. No. | —R | —R' | Starting From | Method Used | Analytical Data |
|---|---|---|---|---|---|
| 70g | CH₂=CH-CH₂- | -CH₂CH₂CF₃ | 68g | I-2, S | ¹HNMR (DMSO-d₆): δ 12.82 (br s, 1H), 9.25 (m, 1H), 9.12 (s, 2H), 8.91 (s, 2H), 8.23 (s, 1H), 7.87 (m, 1H), 7.68 (m, 7H), 7.18 (m, 3H), 6.87 (dd, J=10.9 and 17.7 Hz, 1H), 5.99 (d, J=17.7 Hz, 1H), 5.40 (d, J=10.9 Hz, 1H), 4.07 (m, 2H); MS (ES⁺): 511.2 |
| 70h | CH₂=CH-CH₂- | phenyl | 68h | I-2, S | ¹HNMR (DMSO-d₆): δ 10.34 (s, 1H), 9.05 (m, 4H) 8.18 (s, 1H), 7.71 (m, 11H), 7.34 (t, J=7.8 Hz, 2H), 7.09 (m, 3H), 6.86 (ad, J=10.9 and 17.7 Hz, 1H), 5.98 (d, J = 17.7 Hz, 1H), 5.39 (d, J=10.9 Hz, 1H); MS (ES⁺): 505.3 |
| 70i | CH₂=CH-CH₂- | -(CH₂)₄-OH | 68i | I-2, S | ¹HNMR (DMSO-d₆): δ 12.64 (br s, 1H), 9.09 (m, 4H), 8.56 (m, 1H), 8.09 (s, 1H), 7.66 (m, 9H), 7.08 (m, 3H), 6.86 (dd, J=10.9 and 17.7 Hz, 1H), 5.96 (d, J=17.7 Hz, 1H), 5.37 (d, J=10.9 Hz, 1H), 4.40 (m, 2H) 3.39 (m, 2 H), 3.22 (m, 2H), 1.48 (m, 4H); MS (ES⁺): 501.3 (100%: Me⁺¹) |
| 70j | CH₂=CH-CH₂- | -CH₂-cyclopropyl | 68j | I-2, S | ¹HNMR (DMSO-d₆): δ 9.08 (m, 4H), 8.69 (t, J=6.0 Hz, 1H), 8.16 (s, 1H), 7.69 (m, 5H), 7.13 (d, J=7.7 Hz, 2 H), 7.09 (m, 3H), 6.86 (dd, J=10.9 and 17.7 Hz, 1H), 5.97 (d, J=17.7 Hz, 1H), 5.38 (d, J=10.9 Hz, 1H), 3.11 (t, J=6.0 Hz, 2H), 1.01 (m, 1H), 0.41 (m, 2H), 0.21 (m, 2H); MS (ES⁺): 483.3 |
| 70k | CH₂=CH-CH₂- | -CH₃ | 68k | I-2, S | ¹HNMR (DMSO-d₆): δ 9.11 (s, 2H), 8.97 (s, 2H), 8.54 (m, 1H), 8.12 (s, 1H), 7.68 (m, 7H), 7.17 (m, 4H), 6.86 (dd, J=10.9 and 17.7 Hz, 1H), 5.97 (d, J=17.7 Hz, 1 H), 5.38 (d, J=10.9 Hz, 1H), 2.75 (d, J=4.3 Hz, 1H); MS (ES⁺): 443.26 |
| 70l | CH₂=CH-CH₂- | -CH₂CH₃ | 68l | I-2, S | ¹HNMR (DMSO-d₆): δ 9.07 (s, 2H), 8.92 (s, 2H), 8.53 (t, J=5.5 Hz, 1H), 8.02 (s, 1H), 7.62 (m, 7H), 7.01 (m, 2H), 6.85 (dd, J=10.9 and 17.7 Hz, 1H), 5.95 (d, J = 17.7 Hz, 1H), 5.36 (d, J=10.9 Hz, 1H), 3.24 (qui, J = 6.7 Hz, 2H), 1.08 (t, J=7.2 Hz, 3H); MS (ES⁺): 457.2 |
| 70m | CH₂=CH-CH₂- | cycloheptyl | 68m | I-2, S | ¹HNMR (DMSO-d₆): δ 12.53 (br s, 1H), 9.10 (m, 3H), 8.38 (d, J=7.9 Hz, 1H), 8.11 (s, 1H), 7.68 (m, 7H), 7.12 (m, 3H), 6.86 (dd, J=10.9 and 17.7 Hz, 1H), 5.96 (d, J=17.7 Hz, 1H), 5.37 (d, J=10.9 Hz, 1H), 3.94 (m, 1H), 1.88–1.33 (m, 12H); MS (ES⁺): 525.3 |
| 70n | CH₂=CH-CH₂- | -CH₂CH₂CH₂CH₃ | 68n | I-2, S | ¹HNMR (DMSO-d₆): δ 9.09 (m, 4H), 8.59 (t, J=5.2 Hz, 1H), 8.17 (s, 1H), 7.70 (m, 7H), 7.16 (m, 4H), 6.87 (dd, J=10.9 and 17.7 Hz, 1H), 5.98 (d, J=17.7 Hz, 1 H), 5.39 (d, J=10.9 Hz, 1H), 3.20 (q, J=6.7 Hz, 2H), 1.52 (sex, J=7.2 Hz, 2H), 0.87 (t, J=7.3 Hz, 3H); MS (ES⁺): 471.3 |
| 70o | CH₂=CH-CH₂- | -(CH₂)₄CH₃ | 68o | I-2, S | ¹HNMR (DMSO-d₆): δ 12.97 (br s, 1H), 9.08 (s, 2H), 8.99 (s, 2H), 8.53 (t, J=5.1 Hz, 1H), 8.06 (s, 1H), 7.64 (m, 7H), 7.06 (m, 2H), 6.85 (dd, J=10.9 and 17.7 Hz, 1 H), 5.96 (d, J=17.7 Hz, 1H), 5.36 (d, J=10.9 Hz, 1H), 3.20 (q, J=6.5 Hz, 2H), 1.49 (qui, J=6.6 Hz, 2H), 1.27 (m, 4H), 0.86 (t, J=6.6 Hz, 3H); MS (ES⁺): 499.3 |

-continued

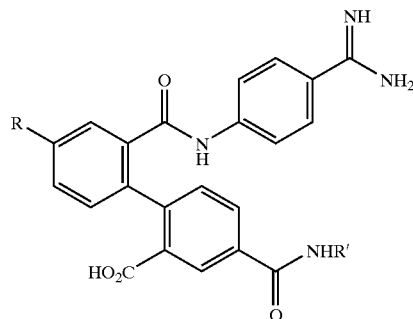

| Cpd. No. | —R | —R' | Starting From | Method Used | Analytical Data |
|---|---|---|---|---|---|
| 70p | CH₂=CH-CH₂- | -CH₂-CH(CH₃)-CH₂-CH₃ | 68p | I-2, S | ¹HNMR (DMSO-d₆): δ 9.10 (s, 2H), 8.91 (s, 2H), 8.55 (t, J=5.5 Hz, 1H), 8.13 (s, 1H), 7.68 (m, 7H), 7.12 (m, 2H), 6.86 (dd, J=10.9 and 17.7 Hz, 1H), 5.98 (d, J = 17.7 Hz, 1H), 5.38 (d, J=10.9 Hz, 1H), 3.10 (m, 2H), 1.62 (m, 1H), 1.39 (m, 1H), 1.10 (m, 1H), 0.86 (m, 6 H); MS (ES⁺): 499.3 |
| 70q | CH₂=CH-CH₂- | -CH(CH₃)-CH₂-CH₂-CH₂-CH₃ (branched) | 68q | I-2, S | ¹HNMR (DMSO-d₆): δ 9.06 (s, 2H), 8.82 (s, 2H), 8.11 (t, J=7.9 Hz, 1H), 8.00 (s, 1H), 7.62 (m, 7H), 6.99 (m, 2H), 6.85 (dd, J=10.9 and 17.7 Hz, 1H), 5.95 (d, J = 17.7 Hz, 1H), 5.35 (d, J=10.9 Hz, 1H), 3.81 (q, J=7.5 Hz, 1H), 1.45 (m, 4H), 1.24 (m, 4.H), 0.82 (m, 6H); MS (ES⁺): 527.3 |
| 70r | CH₂=CH-CH₂- | -(CH₂)₅-NH₂ | 68r | I-2, S | ¹HNMR (DMSO-d₆): δ 13.81 (s, 1H), 8.44 (m, 4H), 7.97 (s, 1H), 7.61 (m, 7H), 6.90 (m, 3H), 5.93 (d, J = 17.7 Hz, 1H), 5.34 (d, J=10.9 Hz, 1H), 3.22 (m, 5H), 2.73 (m, 2H), 1.52 (m, 4H); MS (ES⁺): 500.3 |
| 70s | CH₂=CH-CH₂- | cyclopentyl | 68s | I-2, S | ¹HNMR (DMSO-d₆): δ 9.09 (s, 2H), 8.86 (s, 2H), 8.42 (d, J=7.5 Hz, 1H), 8.11 (s, 1H), 7.68 (m, 8H), 7.10 (m, 4 2H), 6.86 (dd, J=10.9 and 17.7 Hz, 1H), 5.97 (d, J = 17.7 Hz, 1H), 5.38 (d, J=10.9 Hz, 1H), 4.20 (q, J=7.2 Hz, 1H), 1.93–1.44 (m, 8H); MS (ES⁺): 497.2 |
| 70t | CH₂=CH-CH₂- | trans-4-hydroxycyclohexyl | 68t | I-2, S | ¹HNMR (DMSO-d₆): δ 13.78 (br s, 1H), 9.07 (s, 2H), 8.87 (s, 2H), 8.25 (d, J=8.1 Hz, 1H), 8.00 (s, 1H), 7.62 (m, 7H), 6.98 (m, 2H), 6.85 (dd, J=10.9 and 17.7 Hz, 1 H), 5.94 (d, J=17.7 Hz, 1H), 5.35 (d, J=10.9 Hz, 1H), 4.55 (d, J=4.1 Hz, 1H), 3.68 (m, 1H), 3.39 (m, 1H), 1.79 (m, 4H), 1.28 (m, 4H); MS (ES⁺): 527.2 |
| 70u | CH₂=CH-CH₂- | cyclopropyl | 68u | I-2, S | ¹HNMR (DMSO-d₆): δ 13.36 (br s, 1H), 9.05 (m, 3H), 8.49 (s, 1H), 7.98 (s, 1H), 7.61 (m, 8H), 6.92 (m, 3H), 5.94 (d, J=17.7 Hz, 1H), 5.35 (d, J=10.9 Hz, 1H), 2.81 (m, 1H), 0.69–0.48 (m, 4H); MS (ES⁺): 469.3 |
| 70v | CH₂=CH-CH₂- | -CH₂-cyclobutyl | 68v | I-2, S | ¹HNMR (DMSO-d₆): δ 9.05 (m, 4H), 8.75 (d, J=7.5 Hz, 1H), 8.15 (s, 1H), 7.70 (m, 7H), 7.14 (d, J=7.9 Hz, 2H), 6.86 (dd, J=10.9 and 17.7 Hz, 1H), 5.97 (d, J = 17.7 Hz, 1H), 5.39 (d, J=10.9 Hz, 1H), 4.40 (q, J=8.2 Hz, 1H), 2.12 (m, 4H) 1.65 (m, 2H); MS (ES⁺): 483.3 |
| 70w | CH₂=CH-CH₂- | -CH₂-CH₂-OH | 68w | I-2, S | ¹HNMR (DMSO-d₆): δ 13.17 (hr s, 1H), 9.05 (m, 4H), 8.51 (t, J=5.8 Hz, 1H), 8.06 (s, 1H), 7.64 (m, 7H), 7.03 (m, 2H), 6.85 (dd, J=10.9 and 17.7 Hz, 1H), 5.95 (d, J = 17.7 Hz, 1H), 5.36 (d, J=10.9 Hz, 1H), 4.72 (t, J = 5.4 Hz, 1H) 3.47 (q, J=5.7 Hz, 2H), 3.28 (m, 2H); MS (ES⁺): 473.2 |
| 70x | CH₂=CH-CH₂- | -CH₂-CH₂-CH(CH₃)₂ | 68x | I-2, S | ¹HNMR (DMSO-d₆): δ 9.07 (s, 2H), 8.90 (s, 2H), 8.50 (t, J=5.5 Hz, 1H), 8.04 (s, 1H), 7.63 (m, 7H), 7.03 (m, 2H), 6.85 (dd, J=10.9 and 17.7 Hz, 1H), 5.96 (d, J = 17.7 Hz, 1H), 5.36 (d, J=10.9 Hz, 1H), 3.23 (q, J=6.5 Hz, 2H), 1.59 (m, J=7.0 Hz, 1H), 1.39 (q, J=6.8 Hz, 2 H), 0.88 (d, J=6.6 Hz, 6H). |

-continued

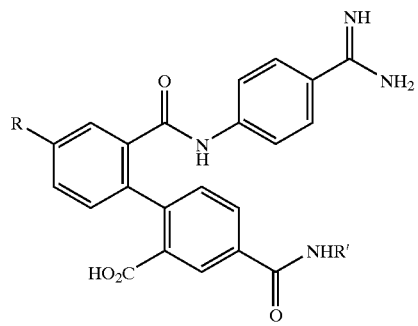

| Cpd. No. | —R | —R' | Starting From | Method Used | Analytical Data |
|---|---|---|---|---|---|
| 70y | CH₂=CH-CH₂- | pentanoic acid | 68y | I-2,S | ¹HNMR (DMSO-d₆): δ 13.77 (s, 1H), 9.48–8.58 (m, 5 H), 7.97 (s, 1H), 7.61 (m, 6H), 7.03 (m, 3H), 6.90 (m, 3 H), 5.93 (d, J=17.3 Hz, 1H), 5.34 (d, J=10.5 Hz, 1H), 3.22 (m, 2H), 2.22 (t, J=7.0 Hz, 2H), 1.71 (t, J=7.3 Hz, 2H); MS (ES⁻): 513.41. |
| 70z | CH₂=CH-CH₂- | butanoic acid | 68z | I-2,S | ¹HNMR (DMSO-d₆-DCl): δ 8.31 (s, 1H), 7.98 (m, 1H), 7.74 (m, 6H), 7.30 (m, 2H), 6.88 (dd, J=10.5 and 17.3 Hz, 1H), 6.02 (d, J=17.3 Hz, 1H), 5.41 (d, J=10.5 Hz, 1H), 3.46 (tJ=6.8 Hz, 2H), 2.54 (m, 2H); MS (ES⁻): 499.32. |
| 70aa | CH₂=CH-CH₂- | propylamine | 68aa | I-2,S | ¹HNMR (DMSO-d₆): δ 13.78 (s, 1H), 8.68 (m, 5H), 8.03 (s, 1H), 7.61 (m, 7H), 6.89 (m, 3H), 5.24 (d, J = 17.7 Hz, 1H), 5.34 (d, J=10.9 Hz, 1H), 3.42 (m, 2H), 2.93 (m, 2H); MS (ES⁺): 472.28. |
| 70ab | CH₂=CH-CH₂- | butane-1,2-diol | 68ab | I-2,S | ¹HNMR (DMSO-d₆): δ 13.41 (br s, 1H), 9.10 (m, 3H), 8.47 (m, 1H), 8.05 (s, 1H), 7.65 (m, 6H), 7.08–6.78 (m, 3H), 6.90 (m, 3H), 5.95 (d, J=17.3 Hz, 1H), 5.36 (d, J = 10.5 Hz, 1H), 4.82 (d, J=5.3 Hz, 1H), 4.58 (t, J=5.7 Hz, 1H), 3.61 (m, 1H), 3.33 (m, 2H), 3.18 (m, 1H); MS (ES⁺): 503.34. |
| 70ac | CH₂=CH-CH₂- | butanamide | 68ac | I-2,S | ¹HNMR (DMSO-d₆): δ 9.02 (m, 3H), 8.58 (m, 1H), 8.04 (s, 1H), 7.72-6.78 (m, 12 H, 6.90 (m, 3H), 5.95 (d, J=17.3 Hz, 1H), 5.36 (d, J=10.5 Hz, 1H), 3.40 (m, 2 H), 2.32 (t, J=7.0 Hz, 1H); MS (ES⁺): 500.30. |

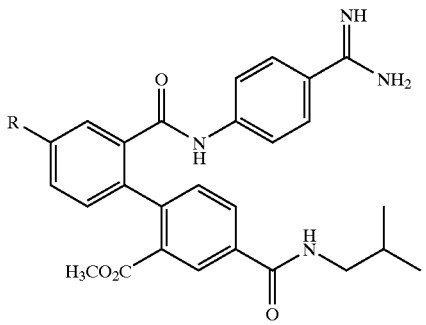

| Cpd. No. | -R | Starting From | Method Used | Analytical Data |
|---|---|---|---|---|
| 31a | acetone (CH₃-C(=O)-) | 30a | J | ¹HNMR (DMSO-d₆): δ 10.85 (s, 1H), 9.21 (s, 2H), 8.91 (s, 2H), 8.71 (t, J=5.9 Hz, 1H), 8.21 (d, J=1.96Hz, 1H), 8.23 (d, J=1.96Hz, 1H), 8.19 (d, J=2.19 Hz, 1H), 8.17 (d, J=1.97Hz, 1H), 8.09 (d, J=1.91Hz, 1H), 7.77 (s, 4H), 7.53 (d, J=7.53Hz, 1H), 3.57 (s, 3H), 3.11 (q, J=6.89Hz, 1H), 2.71 (s, 3H), 1.86 (m, 1H), 3.88 (d, 6.87Hz, 6H); MS (ES+) 515.3 |
| 31b | CH₃-CH=CH-CH₂- | 30b | J | MS (ES⁺): 527.2 |

-continued

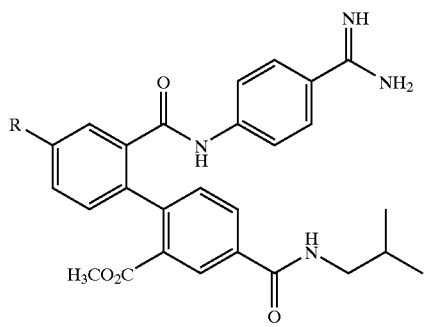

| Cpd. No. | -R | Starting From | Method Used | Analytical Data |
|---|---|---|---|---|
| 31c | (CH2-CH=CH-CH3 allyl) CH2 | 30c | J | Characterized in the next step |
| 31d | (2-ethylthiophene) | 30d | J | ¹HNMR (DMSO-d$_6$): δ 10.59 (bs, 1H), 9.16 (s, 2H), 8.85 (s, 2H), 8.69 (t, J=6 and 5Hz, 1H), 8.21 (s, 1H), 8.04 (d, J=1.5Hz, 1H), 7.73 (m, 4H), 7.58 (s, 1H), 7.50–7.38 (m, 3H), 7.32 (m, 1H), 7.03 (d, J=7.5Hz, 2H), 4.31 (s, 2H), 3.55 (s, 2H), 3.07 (t, J=6.8Hz, 2H), 1.85 (m, 1H), 0.87 (d, J=6.8Hz, 6H),; MS (ES-) 567.3, (ES+) 569.3 |
| 31e | (benzyl) | 30e | J | MS (ES$^-$): 561.4; MS (ES$^+$): 563.4 |
| 31f | CH2 (allyl) | 30f | J | ¹HNMR (DMSO-d$_6$): δ 10.73 (s, 1H), 9.24 (s, 2H), 9.00 (s, 2H), 8.71 (t, J=5.7 Hz, 1H), 8.24 (d, J=1.9Hz, 1H), 8.05 (dd, J=8.0, 1.9Hz, 1H), 7.77 (m, 5H), 7.71 (dd, J=7.9, 1.5Hz, 1H), 7.42 (d, J=7.9Hz, 1H), 7.31 (d, J=7.9Hz, 1H), 6.89 (dd, J=17.6, 11.0Hz, 1H), 6.04 (d, J=17.6Hz, 1H), 5.42 (d, J=11.0Hz, 1H), 3.56 (s, 3H), 3.10 (t, J=6.4Hz, 2H), 1.85 (m, 1H), 0.89 (d, J=6.7Hz, 6H): MS (ES+): 499.3 |
| 31g | N$_3$H$_2$C— (4-methylthiophene-3-yl) | 30g | J | ¹HNMR (DMSO-d$_6$): δ 10.73 (s, 1H), 9.19 (bs, 2H), 8.88 (bs, 2H), 8.71 (t, J=6Hz, 1H), 8.27 (d, J=2Hz, 1H), 8.07 (dd, J=7.7 and 2Hz, 1H), 7.88 (d, 2Hz, 1H), 7.8 (d, J=2Hz, 1H), 7.83 (m, 4H), 7.72 (dd, J=2 and 7.7Hz, 1H), 7.46 (d, J=7.7, 1H), 7.41 (d, J=7.7Hz, 1H), 4.56 (s, 2H), 3.56 (s, 3H), 3.11 (t, J=6.8Hz, 2H), 1.87 (m, 1H), 0.92 (d, J=6.8Hz, 6H); MS (ES-) 608.2, (ES+) 610.3 |
| 31h | CH$_2$OH (2-methylfuran-3-yl) | 30h | J | Characterized at the next step |
| 31i | HOH$_2$C— (4-methylfuran-3-yl) | 30i | J | ¹HNMR (DMSO-d$_6$): δ 10.68 (s, 1H), 9.17 (bs, 2H), 8.82 (bs, 2H), 8.68 (t, J=6Hz, 1H), 8.25 (d, J=2Hz, 1H), 8.16 (d, J=2Hz, 1H), 8.05 (dd, J=8 and 2 Hz, 1H), 7.87 (m, 1H), 7.89 (dd, J=8 and 2Hz, 1H), 7.75 (m, 5H), 7.44 (d, J=9Hz, 1H), 7.36 (d, J=8Hz, 1H), 5.22 (t, J=5Hz, 1H), 4.54 (d, J=5Hz, 2H), 3.57 (s, 3H), 3.10 (t, J= 6.8Hz, 2H), 1.84 (m, 1H), 0.88 (d, J=6.8Hz, 6 H; MS (ES-) 567.4, (ES+) 569.4 |
| 43 | —O—(phenyl) | 42 | J | MS (ES$^-$): 563.4 |
| 45 | —Obn | 8 | J | Characterized in the next step |
| 50 | —OCH$_3$ | 49 | J | MS (ES$^+$): 503.1 |
| 52 | (4-methylthiophen-3-yl)CH$_2$NH$_2$ | 31g | G | Characterized in the next step |

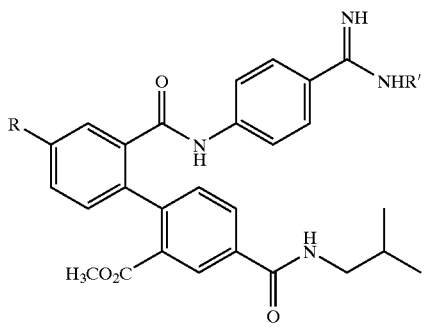

| Cpd. No. | -R | -R' | Starting From | Method Used | Analytical Data |
|---|---|---|---|---|---|
| 34 | —OSO₂CF₃ | ![OBn acetyl] | 33 | J | MS (ES⁺): 621.2 |
| 35 | —OSO₂CF₃ | ![OBn acetyl] | 34 | P | MS (ES⁺): 755.2; (ES⁻) 753.3 |
| 37 | N-TIPS methylpyrrole | ![OBn acetyl] | 35 + 36 | D-2 | MS (ES⁺): 828.5 |
| 38 | N-TIPS methylpyrrole | —H | 37 | G | MS (ES⁺): 694.4; (ES⁻) 692.4 |
| 39 | NH methylpyrrole | —H | 38 | Q | Characterized in the next step |

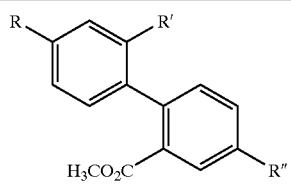

| Cpd. No. | -R | -R' | -R" | Starting From | Method Used | Analytical Data |
|---|---|---|---|---|---|---|
| 54 | —OBn | 13 CHO | —CO₂MEM | 5 + 6 | D-2 | ¹HNMR (DMSO-d₆): δ 9.69 (s, 1H), 8.49 (d, J=2.0Hz, 1H), 8.22 (d, J=6.9Hz, 1H), 7.53 (m, 4H), 7.43 (m, 2H), 7.37 (m, 2H), 7.24 (d, J=8.9Hz, 1H), 5.57 (s, 2H), 5.26 (s, 2H), 3.85 (t, J=4.9Hz, 2H), 3.60 (s, 3H), 3.51 (t, J=4.9Hz 2H), 3.32 (s, 3H); MS (ES⁺): 501.02 (M + Na)⁺ |
| 55 | —OBn | —CO₂H | —CO₂MEM | 54 | E | ¹HNMR (DMSO-d₆): δ 12.65 (s, 1H), 8.41 (d, J=2.0Hz 1H), 8.14 (dd, J=2.0 and 7.9Hz, 1H), 7.50 (m, 3H), 7.38 (m, 4H), 7.24 (dd, J= 3.0 and 8.9Hz, 1H), 7.11 (d, J=8.9Hz, 1H), 5.54 (s, 2H), 5.20 (s, 2H), 3.82 (t, J=4.9Hz, 2H), 3.57 (s, 3H), 3.49 (t, J=4.9Hz, 2H), 3.23 (s, 3H); MS (ES⁻): 493.2 |

-continued

| Cpd. No. | -R | -R' | -R'' | Starting From | Method Used | Analytical Data |
|---|---|---|---|---|---|---|
| 141 | —OBn | —CHO | N-methyl-3-methylbutanamide | 140 + 6 | D-2 | $^1$HNMR (DMSO-$d_6$): δ 10.2 (s, 1H), 9.65 (s, 1H), 8.25 (d, J=2.0Hz, 1H), 7.85 (dd, J=2.0 and 8.9Hz, 1H), 7.51 (d, J=7.9Hz, 2H), 7.45 (m, 2H), 7.35 (m, 3H), 7.29 (d, J=7.9 Hz, 1H) 7.2 (d, J=7.9Hz, 1H), 5.24 (s, 2H), 33.55 (s, 3H), 2.3 (d, J=6.9Hz, 2H) 2.1 (m, J==6.9Hz, 1H), 1.0 (d, J=6.9Hz, 6H); MS (ES$^+$): 446.31 |
| 142 | —OBn | —CO$_2$H | N-methyl-3-methylbutanamide | 141 | E | $^1$HNMR (DMSO-$d_6$): δ 12.38 (s, 1H), 10.01 (s, 1H), 8.05 (s, 1H), 7.68 (d, J=7.9Hz, 1H), 7.41 (d, J=7.9Hz, 2H), 7.35 (m, 5H), 7.27 (m, 1H), 7.11 (d, J=8.9Hz, 1H), 7.04 (d, J=8.9Hz, 1H), 6.99 (d, J=8.9Hz, 1H), 5.11 (s, 2H), 2.13 (d, J=6.9Hz, 2H), 2.02 (m, J=6.9 Hz, 1H), 0.852 (d, J=6.9Hz, 6H); MS (ES$^-$): 460.2 |
| 143 | —OBn | —CO$_2$MEM | N-methyl-3-methylbutanamide | 142 | F | $^1$HNMR (DMSO-$d_6$): δ 10.12 (s, 1H), 8.16 (d, J=1.9Hz, 1H), 7.80 (dd, J=1.9 and 8.3 Hz, 1H), 7.42 (m, 6H), 7.26 (dd, J=2.8 and 8.3Hz, 1H), 7.13 (m, 2H), 5.21 (s, 2H), 5.17 (s, 2H), 3.54 (s, 3H), 3.40 (m, 2H), 3.32 (m, 2H), 2.22 (d, J=7.0Hz, 2H), 2.10 (m, 4H), 0.95 (d, J=6.4Hz, 6H); MS (ES$^+$): 572.3 (M + Na)$^+$ |
| 144 | —OH | —CO$_2$MEM | N-methyl-3-methylbutanamide | 143 | G | $^1$HNMR (DMSO-$d_6$): δ 12.7 (brs, 1H), 9.09 (s, 2H), 8.91 (s, 2H), 8.57 (m, 1H), 8.11 (s, 1H), 7.92 (d, J=1.9Hz, 1H), 7.81 (m, 3H), 7.67 (m, 5H), 7.14 (m, 3H), 6.66 (m, 1H), 4.40 (t, J=5.3Hz, 1H), 3.39 (m, 2H), 3.22 (m, 2H), 1.48 (m, 4H); MS (ES$^-$): 592.2. |
| 145 | —OSO$_2$CF$_3$ | —CO$_2$MEM | N-methyl-3-methylbutanamide | 144 | B-2 | MS (ES$^+$): 592.2 |
| 146a | 5-methylfuran-2-yl | —CO$_2$MEM | N-methyl-3-methylbutanamide | 145 | D-2 | MS (ES$^+$): 532.5 (M + Na)$^+$ |
| 146b | 5-methylthiophen-2-yl | —CO$_2$MEM | N-methyl-3-methylbutanamide | 145 | D-2 | $^1$HNMR (DMSO-$d_6$): δ 10.1 (s, 1H), 8.21 (d, J=2.0Hz, 1H), 8.10 (d, J=2.0Hz, 1H), 7.89 (dd, J=2.0 and 7.9Hz, 1H), 7.84 (d, J=3.0 and 8.9Hz, 1H), 7.63 (m, 2H), 7.25 (d, J=7.9Hz, 1H), 7.19 (m, 2H), 5.22 (d, J=14.8 Hz, 2H), 3.57 (s, 3H), 3.43 (t, J=4.9Hz, 2H), 3.34 (t, J=4.9Hz, 2H), 3.20 (s, 3H), 2.23 (d, J=6.9Hz, 2H), 2.11 (m, J=6.9Hz, 1H), 0.96 (d, J=5.9Hz, 6H); MS (ES$^+$): 526.48 |
| 146c | —CH=CH$_2$ | —CO$_2$MEM | N-methyl-3-methylbutanamide | 145 | D-3 | MS (ES$^+$): 470.2 (M + Na)$^{30}$ |
| 147a | 5-methylfuran-2-yl | —CO$_2$H | N-methyl-3-methylbutanamide | 146a | I-1 | MS (ES$^-$): 420.29 |

-continued

| Cpd. No. | -R | -R' | -R" | Starting From | Method Used | Analytical Data |
|---|---|---|---|---|---|---|
| 147b | 2-methylthiophene | —CO₂H | N-methyl isovaleramide (CH₃NHC(O)CH₂CH(CH₃)₂) | 146b | I-1 | ¹HNMR (DMSO-d₆): δ 12.65 (s, 1H), 10.12 (s, 1H), 8.18 (d, J=1.9Hz, 1H), 8.07 (d, J=3.0Hz, 1H), 7.83 (m, 2H), 7.61 (m, 2H), 7.19 (m, 3H), 3.56 (s, 3H), 2.22 (d J=6.9Hz, 2 H), 2.11 (m, J=6.9Hz, 1H), 0.96 (d,J=6.9 Hz, 6H); MS (ES⁺): 438.52 |
| 147c | —CH=CH₂ | —CO₂H | N-methyl isovaleramide | 146c | I-1 | MS (ES⁻): 380.32 |
| 173 | —H | —CHO | N-ethyl isobutyramide | 172 + 130 | D-2 | ¹HNMR (DMSO-d₆): δ 9.70 (s, 1H), 8.42 (t, J=6.2Hz, 1H), 7.90 (dd, J=1.1 & 6.6Hz, 1H), H), 7.82 (d, J=1.9Hz, 1H), 7.72–7.50 (m, 3H), 7.34 (d, J=7.7Hz, 1H), 7.27 (dd, J=1.3 & 6.2Hz, 1H), 4.38 (d, J=6.0Hz, 2H), 3.53 (s, 3H), 2.47 (m, 1H),, 1.07 (d, J=7.0Hz, 6H); H); MS (ES⁺): 340.05 |
| 174 | —H | —CO₂H | N-ethyl isobutyramide | 173 | E | ¹HNMR (DMSO-d₆): δ 12.35 (brs, 1H), 8.31 (t, J=7.5Hz, 1H), 7.80–7.31 (m, 5H), 7.06 (m, 2H), 4.25 (d, J=6.0Hz, 2H), 3.41 (s, 3H), 2.37 (m, 1H), 0.97 (d, J=7.0Hz, 6H); MS (ES⁻): 353.83 |
| 180 | —H | —CHO | N-Boc-N-isobutyl ethylamine | 179 + 130 | D-2 | ¹HNMR (DMSO-d₆): δ 9.70 (s, 1H), 7.87 (m, 2H), 7.69 (m, 1H), 7.55 (m, 2H), 7.35 (d, J= 7.9Hz, 1H), 7.27 (d, J=7.5Hz, 1H), 4.51 (s, 2H), 3.52 (s, 3H), 3.05 (m, 2H), 1.92 (m, 1H), 1.40 (m, 9H), 0.85 (d, J=6.8Hz, 6H); MS (ES⁺): 448.3 (M + Na)⁺ |
| 181 | —H | —CO₂H | N-Boc-N-isobutyl ethylamine | 180 | E | ¹HNMR (DMSO-d₆): δ 7.81 (m, 2H), 7.56 (m, 1H), 7.44 (m, 2H), 7.16 (m, 2H), 4.47 (s, 2H), H), 3.51 (s, 3H), 3.02 (m, 2H), 1.92 (m, J= 7.0Hz, 1H), 1.41 (m, 9H), 0.85 (d, J=6Hz, 6H); MS (ES⁻): 440.2 |
| 184a | —OBn | —CHO | N-isobutyl acetamide | 3a + 6 | D-2 | ¹HNMR (DMSO-d₆): δ 9.78 (s, 1H), 8.85 (t, J=5.7Hz, 1H), 8.50 (d, J=2.0Hz, 1H), 8.20 (dd, J=8.2, 1.9Hz, 1H), 7.55 (m, 9H), 5.35 (s, 2H), 3.69 (s, 3H), 3.23 (t, J=6.5Hz, 2H), 1.98 (m, 1H), 1.02 (d, J=6.8Hz, 6H); MS (ES+): 446.3 |
| 184b | —OBn | —CHO | N-(2,2,2-trifluoroethyl) acetamide | 3f + 6 | D-2 | MS (ES³¹): 470.2 |
| 184c | —OBn | —CHO | N-ethyl acetamide | 3i + 6 | D-2 | MS (ES⁻): 418.3 |
| 184d | —OBn | —CHO | N-(2-methylbutyl) acetamide | 3j + 6 | D-2 | MS (ES⁺): 460.3 |

-continued

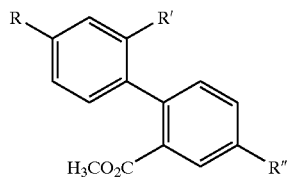

| Cpd. No. | -R | -R' | -R" | Starting From | Method Used | Analytical Data |
|---|---|---|---|---|---|---|
| 185a | —OH | —CHO | N-isobutyl acetamide | 184a | AD | ¹HNMR (DMSO-d$_6$): δ 10.06 (s, 1H), 9.63 (s, 1H), 8.73 (t, J=6.5Hz, 1H), 8.36 (d, J=2 Hz, 1H), 8.09 (dd J=2 and 8Hz, 1H), 7.45 (d, J=8Hz, 1H), 7.28 (s, 1H), 7.11 (s, 2H), 3.58 (s, 3H), 3.13 (d, J=7Hz, 2H), 1.87 (m, 1H), 0.91 (d, J=6.8Hz, 6H); MS (ES−): 354.2 and (ES+) 378.2 (M + Na)+) |
| 185b | —OH | —CHO | N-(2,2,2-trifluoroethyl) acetamide | 184b | AD | MS (ES−): 380.1 |
| 185c | —OH | —CHO | N-ethyl acetamide | 184c | AD | ¹HNMR (DMSO-d$_6$): δ 10.21 (s, 1H), 9.78 (s, 1H), 8.87 (t, J=5.80Hz, 1H), 8.51 (s, 1H), 8.23 (d, J=7.92Hz, 1H), 7.60 (d, J=7.9Hz, 1H), 7.43 (s, 1H), 7.25 (s, 2H), 3.74 (s, 3H), 3.46 (q, J=5.65, 2H), 1.32 (t, J=7.8Hz, 3H) |
| 185d | —OH | —CHO | N-(2-methylbutyl) acetamide | 184d | AD | ¹HNMR (DMSO-d$_6$): δ 10.06 (s, 1H), 9.62 (s, 1H), 8.69 (t, J=5.90Hz, 1H), 8.36 (s, 1H), 8.08 (d, J=7.92Hz, 1H), 7.45 (d, J=8.1Hz, 1H), 7.28 (s, 1H), 7.10 (s, 2H), 3.58 (s, 3H), 3.22 (m, 1H), 3.11 (m, 1H), 1.66 (m, 1H), 1.44 (m, 1H), 1.18 (m, 1H), 0.89 (t, J=6.4Hz, 6H). |
| 186a | —OSO$_2$CF$_3$ | —CHO | N-isobutyl acetamide | 185a | B-2 | MS (ES+): 488.24 |
| 186b | —OSO$_2$CF$_3$ | —CHO | N-(2,2,2-trifluoroethyl) acetamide | 185b | B-2 | ¹HNMR (DMSO-d$_6$): δ 9.74 (s, 1H), 9.44 (t, J=5.90Hz, 1H), 8.51 (s, 1H), 8.11 (d, J=7.91 Hz, 1H), 7.54 (m, 4H), 4.18 (m, 2H), 3.59 (s, 3H). |
| 186c | —OSO$_2$CF$_3$ | —CHO | N-ethyl acetamide | 185c | B-2 | ¹HNMR (DMSO-d$_6$): δ 9.45 (s, 1H), 8.59 (t, J=5.90Hz, 1H), 8.28 (s, 1H), 7.94 (d, J=8.10 Hz, 1H), 7.79 (d, J=2.8Hz, 1H), 7.67 (d, J=7.9Hz, 1H), 7.32 (d, J=7.9Hz, 2H), 3.40 (s, 3H), 3.12 (q, J=7.1Hz, 2H), 0.97 (t, J=7.16 Hz, 3H). |
| 186d | —OSO$_2$CF$_3$ | —CHO | N-(2-methylbutyl) acetamide | 185d | B-2 | ¹HNMR (DMSO-d$_6$): δ 9.71 (s, 1H), 8.78 (t, J=5.90Hz, 1H), 8.49 (s, 1H), 8.18 (d, J=7.92 Hz, 1H), 8.00 (s, 1H), 7.88 (d, J=8.51Hz, 1H), 7.52 (q, J=8.1Hz, 2H), 3.67 (s, 3H), 3.22 (m, 1H), 3.16 (m, 1H), 1.68 (m, 1H), 1.44 (m, 1H), 1.18 (m, 1H), 0.89 (t, J=6.4Hz, 6H). |
| 187a | —CH=CH$_2$ | —CHO | N-isobutyl acetamide | 186a | D-3 | ¹HNMR (DMSO-d$_6$): δ 9.74 (s, 1H), 8.76 (t, J=6.5Hz, 1H), 8.42 (d, J=2Hz, 1H), 8.11 (dd, J=2 and 8Hz, 1H), 8.00 (d, J=1.7Hz, 1H), 7.84 (dd, J=8 and 2Hz, 1H), 7.47 (d, J=8Hz, 1H), 7.27 (d, J=8Hz, 1H), 6.90 (dd, J=11 and 17.7Hz, 1H), 6.01 (d, J=17.7Hz, 1H), 5.42 (d, J=11Hz, 1H), 3.59 (s, 3H), 3.14 (d, J=7Hz, 2H), 1.88 (m, 1H), 0.92 (d, J=6.8Hz, 6H); MS (ES−): 364.2 and (ES+) 388.2 (M + Na)+ |

-continued

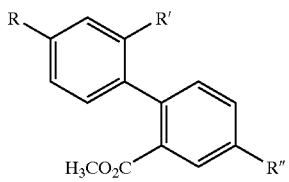

| Cpd. No. | -R | -R' | -R'' | Starting From | Method Used | Analytical Data |
|---|---|---|---|---|---|---|
| 187b | —CH=CH₂ | —CHO | acetamide-N-CH₂CF₃ | 186b | D-3 | MS (ES⁻): 390.1 |
| 187c | —CH=CH₂ | —CHO | acetamide-N-CH₂CH₃ | 186c | D-3 | MS (ES⁻): 336.2 |
| 187d | —CH=CH₂ | —CHO | acetamide-N-CH₂CH(CH₃)CH₂CH₃ | 186d | D-3 | MS (ES⁻): 378.2 |

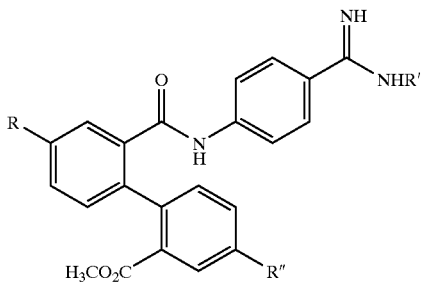

| Cpd. No. | -R | -R' | -R'' | Starting From | Method Used | Analytical Data |
|---|---|---|---|---|---|---|
| 56 | —OBn | —H | —CO₂MEM | 55 | J | ¹HNMR (DMSO-d₆): δ 10.67 (s, 1H), 9.2 (s, 2H), 8.87 (s, 2H), 8.33 (d, J=2.0Hz, 1H), 8.17 (dd, J=2.0 and 7.9Hz, 1H), 7.77 (s, 4H), 7.49 (m, 4H), 7.39 (m, 2H), 7.30 (s, 2H), 5.54 (s, 2H), 5.27 (s, 2H), 3.83 (t, J=4.9 Hz, 2H), 3.57 (s, 3H), 3.49 (t, J=4.9Hz, 2H), 3.23 (s, 3H); MS (ES⁺): 612.4 |
| 57 | —OBn | —Boc | —CO₂MEM | 56 | R | MS (ES⁺): 712.4 |
| 58 | —OH | —Boc | —CO₂MEM | 57 | G | ¹HNMR (DMSO-d₆): δ 10.4 (s, 1H), 10.0 (s, 1H), 8.9 (s, 1H), 8.28 (d, J=2.0Hz, 1H), 8.12 (dd, J=2.1 and 7.7Hz, 1H), 7.89 (d, J=8.4Hz, 2H), 7.61 (d, J=8.4 Hz, 2H), 7.45 (d, J=7.7Hz, 1H), 7.13 (d, J=8.4Hz, 1H) 7.06 (s, 1H), 6.98 (dd, J=2.8 and 8.4Hz, 1H), 5.52 (s, 2H), 3.81 (t, J=4.9Hz, 2H), 3.56 (s, 3H), 3.46 (t, J= 4.9Hz, 2H), 3.20 (s, 3H), 1.43 (s, 9H); MS (ES⁻): 620.5 |

-continued

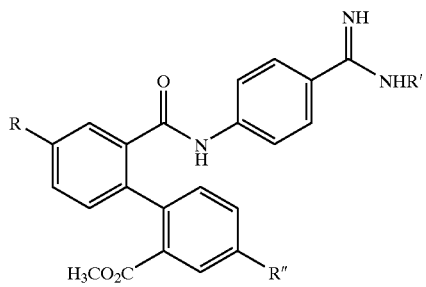

| Cpd. No. | -R | -R' | -R" | Starting From | Method Used | Analytical Data |
|---|---|---|---|---|---|---|
| 59 | —OSO₂CF₃ | —Boc | —CO₂MEM | 58 | B-2 | ¹HNMR (DMSO-d₆): δ 10.55 (s, 1H), 8.38 (d, J=2.0 Hz, 1H), 8.18 (dd, J= 2.0 and 7.9Hz, 1H), 7.86 (m, 4 H), 7.75 (dd, J=2.0 and 8.9Hz, 1H), 7.54 (m, 5H), 5.51 (s, 2H), 3.77 (t, J=4.9Hz, 2H), 3.55 (s, 3H), 3.46 (t, J=4.9Hz, 2H), 3.18 (s, 3H) 1.41 (s, 9H); MS (ES⁺): 754.3 |
| 60 | (5-methylfuran-2-yl) | —Boc | —CO₂MEM | 59 | D-2 | ¹HNMR (DMSO-d₆): δ 10.61 (s, 1H), 8.94 (s, 1H), 8.37 (s, 1H), 8.19 (dd, J=2.0 and 7.9Hz, 1H), 8.02 (s, 1H), 7.89 (m, 5H), 7.65 (d, J=8.9Hz, 2H), 7.54 (d, J= 7.9Hz, 1H), 7.39 (d, J=7.9Hz, 1H), 7.17 (d, J=3.9 Hz, 1H), 6.68 (m, 1H), 5.54 (s, 2H), 3.82 (t, J=4.9Hz, 2H), 3.58 (s, 3H), 3.49 (t, J=4.9Hz, 2H), 3.22 (s, 3H), 1.45 (s, 9H); MS (ES⁺): 672.5 |
| 61 | (5-methylfuran-2-yl) | —Boc | —CO₂H | 60 | I-1 | ¹HNMR (DMSO-d₆): δ 10.50 (s, 1H), 8.96 (s, 1H), 8.32 (s, 1H), 8.07 (d, J=7.9Hz, 1H), 7.98 (s, 1H), 7.87 (m, 5H), 7.63 (d, J=8.9Hz, 2H), 7.38 (m, 2H), 7.15 (d, J=3.0Hz, 1H), 6.67 (m, 1H), 3.57 (s, 3H), 1.45 (s, 9H); MS (ES¹): 582.4 |
| 66 | —CH=CH₂ | —Boc | —CO₂MEM | 59 | D-3 | ¹HNMR (DMSO-d₆): δ 10.56 (s, 1H), 9.02 (br s, 1H), 8.35 (d, J=1.7Hz, 1H), 8.18 (dd, J=1.9 and 6.0Hz, 1H), 7.88 (d, J=9.0Hz, 2H), 7.80 (d, J=1.3Hz, 1H), 7.71 (dd, J=1.7 and 6.2Hz, 1H), 7.63 (d, J=8.9Hz, 2 H), 7.50 (d, J=8.3Hz, 1H), 7.32 (d, J=8.1Hz, 1H), 6.89 (dd, J=10.7 and 17.7Hz, 1H), 6.04 (d, J=17.4 Hz, 1H), 5.54 (s, 2H), 5.43 (d, J=11.7Hz, 1H), 3.82 (t, J=4.5Hz, 2H), 3.57 (s, 3H), 3.48 (t, J=4.5Hz, 2H), 3.22 (s, 3H), 1.44 (s, 9H); MS (ES⁺): 632.1 |
| 67 | —CH=CH₂ | —Boc | —CO₂H | 66 | I-1 | HNMR (DMSO-d₆): δ 10.49 (s, 1H), 8.99 (br s, 1H), 8.31 (s, 1H), 8.07 (d, J=8.3Hz, 1H), 7.87 (d, J=9.0 Hz, 2H), 7.77 (m, 2H), 7.66 (m, 3H), 7.38 (d, J=7.7 Hz, 1H), 7.29 (d, J=7.7Hz, 1H), 6.88 (dd, J=10.7 and 17.7Hz, 1H), 6.03 (d, J=17.4Hz, 1H), 5.41 (d, J= 10.9Hz, 1H), 3.56 (s, 3H), 1.43 (s, 9H); MS (ES⁻): 542.1 |

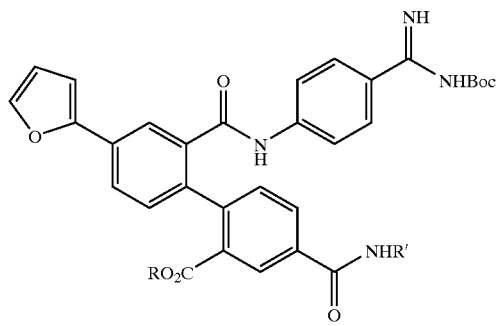

| Cpd. No. | -R | -R' | Starting From | Method Used | Analytical Data |
|---|---|---|---|---|---|
| 62a | —CH₃ | —(CH₂)₄CH₃ (n-pentyl) | 61 | A-4 | ¹HNMR (DMSO-d₆): δ 10.57 (s, 1H), 8.92 (s, 1H), 8.64 (t, J=5.4Hz, 1H), 8.24 (d, J=2.0Hz, 1H), 8.02 (dd, J=2.0 and 7.9 Hz, 1H), 7.98 (s, 1H), 7.88 (m, 3H) 7.84 (s, 1H), 7.64 (d, J=8.9Hz, 2H), 7.42 (d, J=7.9Hz, 1H), 7.36 (d, J=7.9Hz, 1H), 7.14 (d, J=3.0Hz, 1H), 6.67 (m, 1H), 3.55 (s, 3H), 3.26 (m, 2H) 1.50 (m, J=7.4Hz, 2H), 1.43 (s, 9H), 1.32 (m, J=7.4Hz, 2H), 0.89 (t, 3H); MS (ES⁻): 639.5 |
| 62b | —CH₃ | n-butyl | 61 | A-4 | MS (ES⁺): 625.5 |
| 62c | —CH₃ | allyl (CH₂=CHCH₂—) | 61 | A-4 | MS (ES⁺): 623.4 |
| 62d | —CH₃ | 3-methylbenzyl ethyl | 61 | A-4 | MS (ES⁺): 687.4 |
| 62e | —CH₃ | isobutyl | 61 | A-4 | MS (ES⁺): 625.4 |
| 62f | —CH₃ | 2-methylbutyl | 61 | A-4 | MS (ES⁺): 653.5 |
| 62g | —CH₃ | 3-methylbutyl-ethyl | 61 | A-4 | MS (ES⁺): 653.5 |
| 62h | —CH₃ | (tetrahydrofuran-2-yl)methyl | 61 | A-4 | MS (ES⁺): 667.3 |
| 62i | —CH₃ | 2-propylpentyl | 61 | A-4 | MS (ES⁺): 681.5 |
| 62j | —CH₃ | cyclopropylmethyl | 61 | A-4 | MS (ES⁺): 637.3 |
| 62k | —CH₃ | 2-hydroxypropyl | 61 | A-4 | MS (ES⁺): 640.3 |
| 62l | —CH₃ | cyclohexyl | 61 | A-4 | MS (ES⁺): 665.4 |

-continued

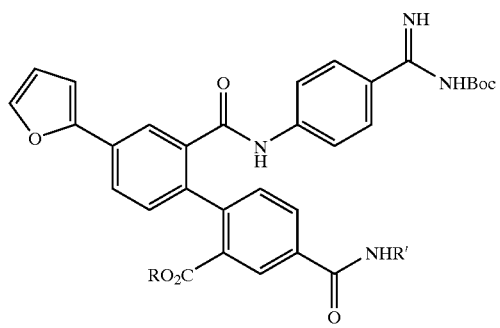

| Cpd. No. | -R | -R' | Starting From | Method Used | Analytical Data |
|---|---|---|---|---|---|
| 62m | —CH₃ | –CH₂CH₃ (ethyl) | 61 | A-4 | MS (ES⁺): 597.3 |
| 62n | —CH₃ | isobutyl | 61 | A-4 | MS (ES⁺): 639.4 |
| 62o | —CH₃ | benzyl (CH₂Ph) | 61 | A-4 | MS (ES⁺): 695.4 (M + Na)⁺ |
| 62p | —CH₃ | —CH₂CF₃ | 61 | A-4 | MS (ES⁻): 665.4 |
| 62q | —CH₃ | n-hexyl | 61 | A-4 | MS (ES⁺): 653.4 |
| 62r | —CH₃ | 2-ethylpentyl | 61 | A-4 | MS (ES⁺): 567.3 |
| 62s | —CH₃ | 3,3-dimethylbutyl | 61 | A-4 | MS (ES⁺): 667.5 |
| 62t | —CH₃ | —(CH₂)₃OH | 61 | A-4 | MS (ES⁺): 641.3 |
| 62u | —CH₃ | —(CH₂)₄OH | 61 | A-4 | MS (ES⁺): 655.3 |
| 62v | —CH₃ | furfuryl-CH₂ | 61 | A-4 | MS (ES⁺): 663.1 |
| 62w | —CH₃ | —(CH₂)₃-imidazolyl | 61 | A-4 | MS (ES⁻): 577.2 |
| 62x | —CH₃ | cyclohexylmethyl | 61 | A-4 | MS (ES⁺): 679.2 |
| 62y | —CH₃ | —CH₂CH₂C≡CH | 61 | A-4 | MS (ES⁺): 621.1 |
| 62z | —CH₃ | —CH₂CH₃ | 61 | A-4 | MS (ES⁺): 611.1 |
| 62aa | —CH₃ | 2-hydroxy-1-(hydroxymethyl)butyl | 61 | A-4 | MS (ES⁺): 657.1 |

-continued
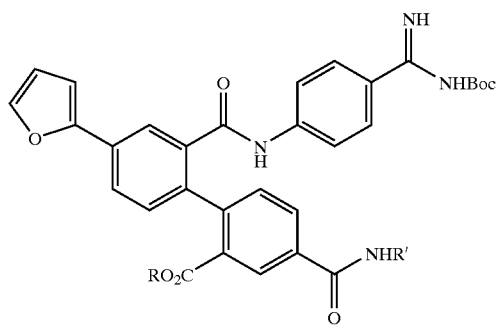
| Cpd. No. | -R | -R' | Starting From | Method Used | Analytical Data |
|---|---|---|---|---|---|
| 62ab | —CH₃ | 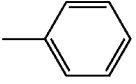 | 61 | A-4 | MS (ES⁺): 659.1 |
| 62ac | —CH₃ | 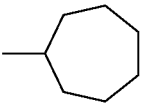 | 61 | A-4 | MS (ES⁺): 679.3 |
| 62ad | —CH₃ | 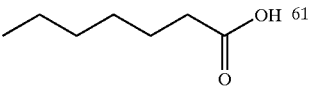 | 61 | A-4 | MS (ES⁻): 695.3 |
| 62ae | —CH₃ | NHR' = 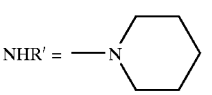 | 61 | A-4 | MS (ES⁺): 651.3 |
| 62af | —CH₃ | NHR' = 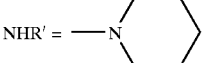 | 61 | A-4 | MS (ES⁺): 679.4 |
| 62ag | —CH₃ | 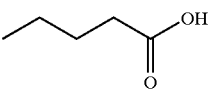 | 61 | A-4 | MS (ES⁻) 667.32 |

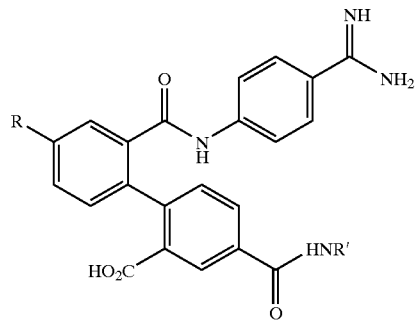

| Cpd. No. | -R | -R' | Starting From | Method Used | Analytical Data |
|---|---|---|---|---|---|
| 64a | 2-furyl | n-butyl (CH₂CH₂CH₂CH₃) | 62a | I-2, S | ¹HNMR (DMSO-d₆): δ 12.80 (s, 1H), 9.09 (s, 2H), 8.91 (s, 2H), 8.57 (m, 1H), 8.15 (s, 1H), 7.91 (s, 1H), 7.80 (m, 3H), 7.67 (m, 4H), 7.20 (m, 2H), 7.07 (s, 1H), 6.63 (s, 1H) 3.21 (t, J=5.9Hz, 2H), 1.46 (m, J=7.4Hz, 2H), 1.28 (m, J=7.4Hz, 2H) 0.86 (t, J=7.4 Hz, 3H); MS (ES⁺): 525.3 |
| 64b | 2-furyl | n-propyl | 62b | I-2, S | ¹HNMR (DMSO-d₆): δ 12.76 (s, 1H), 9.10 (s, 2H), 8.82 (s, 2H), 8.59 (m, 1H), 8.20 (s, 1H), 7.95 (s, 1H), 7.83 (m, 3H), 7.70 (s, 4H), 7.25 (m, 2H), 7.10 (s, 1H), 6.65 (s, 1H), 3.20 (q, J=6.0Hz, 2H), 1.51 (m, J=7.4 Hz, 2H), 0.87 (t, J=7.4Hz, 3H); MS (ES⁺): 511.2 |
| 64c | 2-furyl | allyl (CH₂CH=CH₂) | 62c | I-2, S | ¹HNMR (DMSO-d₆): δ 12.84 (s, 1H), 9.11 (s, 2H), 8.84 (m, 2H), 8.26 (m, 1H), 7.94 (m, 2H), 7.83 (m, 3H), 7.71 (s, 4H), 7.28 (m, 2H), 7.12 (s, 1H), 6.65 (s, 1H), 5.87 (m, 1H), 5.15 (d, J=17.2Hz, 1H), 5.07 (d, J=10.3Hz, 1H) 3.88 (t, J=5.2Hz, 2H); MS (ES⁺): 509.2 |
| 64d | 2-furyl | 3-methylbenzyl | 62d | I-2, S | ¹HNMR (DMSO-d₆): δ 12.78 (s, 1H), 9.11 (m, 2H), 8.85 (s, 2H), 8.22 (s, 1H), 7.93 (s, 1H), 7.83 (m, 3H), 7.68 (s, 4H), 7.19 (m, 3H), 7.10 (m, 5H), 6.65 (s, 1H), 4.41 (s, 2H), 2.27 (s, 3H); MS (ES⁺): 573.3 |
| 64e | 2-furyl | isopropyl | 62e | I-2, S | ¹HNMR (DMSO-d₆): δ 12.82 (s, 1H), 9.11 (s, 2H), 8.86 (s, 2H), 8.39 (d, J=7.7Hz, 1H), 8.24 (s, 1H), 7.95 (s, 1H), 7.90 (m, 1H), 7.84 (m, 2H), 7.71 (s, 4H), 7.28 (m, 2H), 7.11 (m, 1H), 6.65 (s, 1H), 4.08 (m, J=6.9Hz, 1H), 1.14 (d, J=6.9Hz, 6H); MS (ES⁺): 511.3 |
| 64f | 2-furyl | 2-methylbutyl | 62f | I-2, S | ¹HNMR (DMSO-d₆): δ 13.28 (br s, 1H), 9.05 (m, 2H), 8.84 (s, 2H), 8.46 (m, 1H), 7.99 (s, 1H), 7.88 (s, 1H), 7.77 (m, 2H), 7.63 (m, 5H), 7.07 (m, 2H), 6.96 (m, 1H), 6.63 (s, 1H), 3.16–2.96 (m, 2 H), 1.65–1.03 (m, 3H), H), 0.85 (m, 6H); MS (ES⁺): 539.3 |
| 64g | 2-furyl | 3-methylbutyl (isoamyl) | 62g | I-2, S | ¹HNMR (DMSO-d₆): δ 13.37 (s, 1H), 9.06 (s, 2H), 8.84 (s, 2H), 8.47 (m, 1H), 8.00 (s, 1 H), 7.88 (s, 1H), 7.78 (m, 2H), 7.70 (m, 5H), 7.08 (m, 2H), 6.97 (s, 1H), 6.63 (s, 1H), 3.22 (m, 2H), 1.58 (m, J=6.0Hz, 1H), 1.38 (m, J=6.9Hz, 2H), 0.87 (d, J=6.9Hz, 6H); MS (ES⁺): 539.3 |
| 64h | 2-furyl | (tetrahydrofuran-2-yl)methyl | 62h | I-2, S | ¹HNMR (DMSO-d₆): δ 12.71 (br s, 1H), 9.13 (s, 1H), 8.75 (m, 3H), 8.31 (m, 1H), 7.97 (m, 2H), 7.86 (m, 2H), 7.73 (m, 4H), 7.64 (m, 2H), 7.33 (m, 2H), 7.13 (m, 1H), 6.67 (m, 1H), 3.98 (m, 1H), 3.77 (q, J=6.9Hz, 1H), 3.62 (q, J=6.9Hz, 1H), 3.29 (m, 2H), 1.86 (m, 3H), 1.59 (m, 1H); MS (ES⁺): 553.3 |
| 64i | 2-furyl | 2-ethylpentyl | 62i | I-2, S | ¹HNMR (DMSO-d₆): δ 12.81 (br s, 1 H), 9.13 (s, 2 H), 8.85 (s, 2H), 8.26 (m, 2H), 7.96 (m, 2H), 7.86 (m, 2H), 7.74 (m, 5H), 7.32 (m, 1H), 7.13 (m, 1H), 6.67 (m, 1H), 3.99 (m, 1H), 1.5–0.85 (m, 14H); MS (ES⁺): 567.3 |

-continued

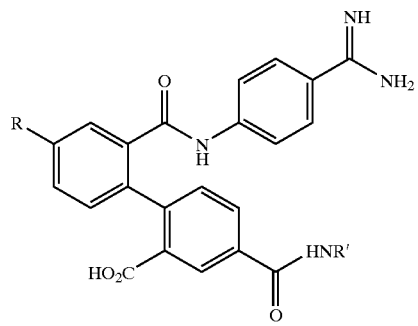

| Cpd. No. | -R | -R' | Starting From | Method Used | Analytical Data |
|---|---|---|---|---|---|
| 64j | 2-methylfuran | cyclopropylmethyl | 62j | I-2, S | ¹HNMR (DMSO-d$_6$): δ 13.74 (br s, 1H), 9.07 (s, 2H), 8.92 (s, 2H), 8.62 (t, J=5.6Hz, 1H), 8.03 (s, 1H), 7.89 (d, J=1.7Hz, 1H), 7.79 (m, 2H), 7.64 (m, 4H), 7.10 (m, 3H), 6.99 (d, J=8.5Hz, 1H), 6.64 (m, 1H), 3.08 (t, J=6.0Hz, 2H), 1.00 (m, 1H), 0.40 (m, 2H), 0.20 (m, 2H); MS (ES$^+$): 523.4 |
| 64k | 2-methylfuran | sec-butyl (OH) | 62k | I-2, S | ¹HNMR (DMSO-d$_6$): δ 9.12 (s, 2H), 8.88 (s, 2H), 8.52 (m, 1H), 8.12 (m, 1H), 7.92 (m, 2H), 7.81 (m, 3H), 7.67 (m, 4H), 7.14 (m, 3H), 6.66 (m, 1H), 4.75 (d, J=4.5Hz, 1H), 3.77 (m, 1H), 3.17 (m, 1H), 1.04 (d, J=6.0Hz, 3H); MS (ES$^+$): 527.2 |
| 64l | 2-methylfuran | cyclohexylmethyl | 62l | I-2, S | ¹HNMR (DMSO-d$_6$): δ 13.91 (br s, 1H), 9.07 (s, 2H), 8.90 (s, 2H), 8.29 (d, J=8.1Hz, 1H), 8.00 (s, 1H), 7.89 (m, 1H), 7.78 (m, 2H), 7.64 (m, 5H), 7.08 (m, 2H), 6.96 (d, J=7.7Hz 1H), 6.64 (m, 1H), 3.71 (m, 1H), 1.82–1.03 (m, 10H)p; MS (ES$^+$): 551.33 |
| 64m | 2-methylfuran | CH$_3$ | 62m | I-2, S | ¹HNMR (DMSO-d$_6$): δ 13.87 (br s, 1H), 9.07 (s, 2H), 8.90 (s, 2H), 8.48 (m, 1H), 7.99 (s, 1H), 7.89 (m, 1H), 7.79 (m, 2H), 7.62 (m, 5H), 7.10 (m, 2H), 6.97 (d, J=7.9Hz 1H), 6.64 (m, 1H), 2.73 (d, J=4.5Hz, 3H); MS (ES$^+$): 483.2 |
| 64n | 2-methylfuran | isobutyl | 62n | I-2, S | ¹HNMR (DMSO-d$_6$): δ 9.08 (s, 2H), 8.85 (s, 2H), 8.26 (d, J=8.7Hz, 1H), 8.07 (s, 1H), 7.91 (s, 1H), 7.80 (m, 2H), 7.67 (m, 5H), 7.09 (m, 3H), 6.65 (m, 1H), 3.89 (m, J=7.0Hz, 1H), 1.49 (m,J=6.9Hz, 2H), 1.10 (d, J=6.6Hz, 3H), 0.85 (t, J=7.2Hz, 3H); MS (ES$^+$): 525.2 |
| 64o | 2-methylfuran | benzyl | 62o | I-2, S | ¹HNMR (DMSO-d$_6$): δ 9.19 (m, 2H), 9.10 (s, 2H), 8.82 (s, 2H), 8.19 (m, 1H), 7.94 (s, 1H), 7.83 (m, 2H), 7.68 (m, 4H), 7.33–7.10 (m, 8H), 6.66 (m, 1H), 4.45 (d, J=5.7Hz, 2Hz); MS (ES$^+$): 559.2 |
| 64p | 2-methylfuran | CH$_2$CF$_3$ | 62p | I-2, S | ¹HNMR (DMSO-d$_6$): δ 9.22 (m, 2H), 9.09 (s, 2H), 8.81 (s, 2H), 8.17 (m, 1H), 7.95 (s, 1H), 7.82 (m, 2H), 7.68 (m, 4H), 7.16 (m, 4H), 6.66 (m, 1H), 4.06 (m, 2H); MS (ES$^+$): 551.22 |
| 64q | 2-methylfuran | n-hexyl | 62q | I-2, S | ¹HNMR (DMSO-d$_6$): δ 9.10 (s, 2H), 8.86 (s, 2H), 8.56 (m, 1H), 8.13 (m, 1H), 7.93 (s, 1H), 7.82 (m, 2H), 7.67 (m, 5H), 7.15 (m, 3H), 6.66 (m, 1H), 3.19 (m, 2H), 1.50 (m, 2H), 1.28 (m, 4H), 0.87 (t, J=7.0Hz, 3H); MS (ES$^+$): 539.3 |
| 64r | 2-methylfuran | 2-methylhexyl | 62r | I-2, S | ¹HNMR (DMSO-d$_6$): δ 9.09 (s, 2H), 8.90 (m, 2H), 8.15 (m, 2H), 7.93 (s, 1H), 7.81 (m, 3H), 7.68 (m, 4H), 7.13 (m, 3H), 6.66 (m, 1H), 3.83 (m, 1H), 1.47 (m, 4H), 1.25 (m, 4H), 0.83 (m, 6H); MS (ES$^+$): 567.3 |

-continued

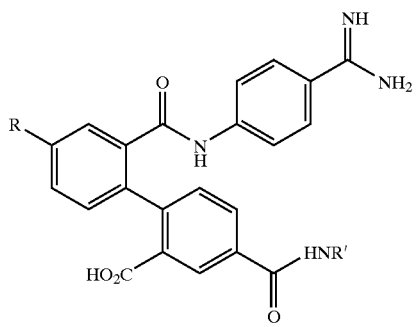

| Cpd. No. | -R | -R' | Starting From | Method Used | Analytical Data |
|---|---|---|---|---|---|
| 64s | 2-furyl | -CH₂CH₂C(CH₃)₃ (neopentyl-like: CH₂CH₂C(CH₃)₃) | 62s | I-2, S | ¹HNMR (DMSO-d₆): δ 9.08 (s, 2H), 8.86 (s, 2H), 8.48 (m, 1H), 8.03 (m, 1H), 7.90 (s, 1H), 7.79 (m, 2H), 7.65 (m, 5H), 7.12 (m, 2H), 7.02 (m, 1H), 6.65 (m, 1H), 3.22 (m, 2H), 1.42 (t, J= 8.2Hz, 2H), 0.91 (s, 9H); MS (ES⁺): 553.4 |
| 64t | 2-furyl | -(CH₂)₄OH | 62t | I-2, S | ¹HNMR (DMSO-d₆): δ 13.61 (br s, 1H), 9.07 (s, 2H), 9.00 (s, 2H), 8.52 (t, J=5.5Hz, 1H), 8.02 (s, 1H), 7.90 (d, J=1.9Hz, 1H), 7.79 (m, 2H), 7.64 (m, 5H), 7.10 (m, 2H), 7.00 (d, J= 7.7Hz, 1H), 6.64 (m, 1H), 4.47 (t, J=5.3Hz, 1H), 3.43 (m, 2H), 3.27 (m, 2H), 1.64 (qui, J=6.8Hz, 2H); MS (ES⁺): 527.23 |
| 64u | 2-furyl | -(CH₂)₅OH | 62u | I-2, S | ¹HNMR (DMSO-d₆): δ 12.7 (br s, 1H), 9.09 (s, 2H), 8.91 (s, 2H), 8.57 (m, 1H), 8.11 (s, 1H), 7.92 (d, J= 1.9Hz, 1H), 7.81 (m, 3H), 7.67 (m, 5H), 7.14 (m, 2H), 6.66 (m, 1H), 4.40 (t, J=5.3Hz, 1H), 3.39 (m, 2H), 3.22 (m, 2H), 1.48 (m, 4H); MS (ES⁺): 541.34 |
| 64v | 2-furyl | -CH₂-(2-furyl) | 62v | I-2, S | ¹HNMR (DMSO-d₆): δ 9.16–8.89 (m, 4H), 8.16 (m, 1H), 7.93 (s, 1H), 7.81 (m, 3H), 7.67 (m, 4H), 7.56 (s, 1H), 7.15 (m, 5H), 6.65 (m, 1H), 6.38 (m, 1H), 6.26 (m, 1H), 4.42 (d, J=4.9Hz, 2H); MS (ES⁺): 549.27 |
| 64w | 2-furyl | -(CH₂)₃-imidazol-1-yl | 62w | I-2, S | ¹HNMR (DMSO-d₆): δ 11.59 (br s, 1H), 9.14 (s, 2H), 8.98 (s, 2H), 8.70 (t, J=5.7Hz, 1H), 8.24 (s, 1H), 7.99 (m, 2H), 7.87 (m, 3H), 7.71 (m, 3H), 7.36 (s, 1H), 7.27 (m, 2H), 7.10 (m, 2H), 6.67 (m, 1H), 4.07 (t, J= 6.9Hz, 2H), 3.24 (q, J=6.5Hz, 2H), 1.98 (qui, J=6.7 Hz, 2H); MS (ES⁺): 577.17 |
| 64x | 2-furyl | -CH₂CH₂-cyclohexyl | 62x | I-2, S | ¹HNMR (DMSO-d₆): δ 13.72 (br s, 1H), 9.13 (s, 2H), 9.06 (s, 2H), 8.50 (t, J=5.7Hz, 1H), 8.00 (d, J=1.3 Hz, 1H), 7.89 (d, J=1.9Hz, 1H), 7.78 (m, 2H), 7.62 (m, 4H), 7.08 (m, 2H), 6.96 (d, J=7.9Hz, 1H), 6.64 (m, 1H), 3.04 (t, J=6.5Hz, 2H), 1.72–1.43 (m, 6H), 1.25–1.08 (m, 3H), 0.88 (m, 2H); MS (ES⁺): 565.25 |
| 64y | 2-furyl | -CH₂CH₂C≡CH | 62y | I-2, S | ¹HNMR (DMSO-d₆): δ 9.16–8.87 (m, 4H), 8.09 (s, 1H), 7.91 (s, 1H), 7.80 (m, 2H), 7.65 (m, 5H), 7.12 (m, 5H), 6.65 (m, 1H), 4.01 (m, 2H), 3.10 (m, 1H); MS (ES⁺): 507.2 |
| 64z | 2-furyl | -CH₂CH₂CH₃ | 62z | I-2, S | ¹HNMR (DMSO-d₆): δ 9.10 (s, 2H), 8.97 (s, 2H), 8.59 (t, J=5.7Hz, 1H), 8.13 (s, 1H), 7.93 (s, 1H), 7.80 (m, 3H), 7.68 (m, 4H), 7.16 (m, 4H), 6.65 (m, 1H), 3.26 (qui, J=6.0Hz, 2H), 1.10 (t, J=7.2Hz, 3H); MS (ES⁺): 497.2 |
| 64aa | 2-furyl | -CH₂CH(OH)CH₂OH | 62aa | I-2, S | ¹HNMR (DMSO-d₆): δ 14.1 (br s, 1H), 9.08 (s, 2H), 8.79 (s, 2H), 8.45 (m, 1H), 8.01 (s, 1H), 7.90 (s, 1H), 7.79 (m, 3H), 7.63 (m, 5H), 7.09 (m, 2H), 6.98 (m, 1H), 6.65 (m, 1H), 4.80 (d, J=4.7-Hz, 1H), 4.56 (t, J= 6.8Hz, 1H), 3.60 (m, 1H), 3.32–2.90 (m, 3H); MS (ES⁺): 543.2 |

-continued

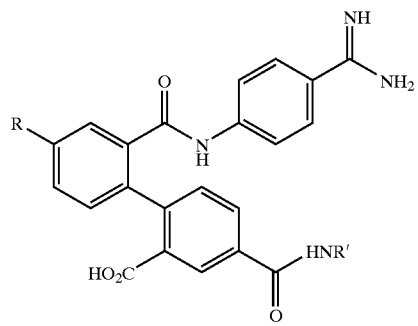

| Cpd. No. | -R | -R' | Starting From | Method Used | Analytical Data |
|---|---|---|---|---|---|
| 64ab | 2-methylfuran | phenyl | 62ab | I-2, S | ¹HNMR (DMSO-$d_6$): δ 10.34 (s, 1H), 9.07 (s, 2H), 8.85 (s, 2H), 8.18 (s, 1H), 7.93 (s, 1H), 7.80 (m, 6H), 7.66 (m, 4H), 7.34 (m, 2H), 7.11 (m, 4H), 6.65 (m, 1H); MS (ES⁺): 545.2 |
| 64ac | 2-methylfuran | cycloheptyl | 62ac | I-2, S | ¹HNMR (DMSO-$d_6$): δ 9.07 (m, 4H), 8.38 (d, J=8.5 Hz, 1H), 8.10 (s, 1H), 7.92 (s, 1H), 7.84–7.62 (m, 7H), 7.11 (m, 3H), 6.66 (m, 1H), 3.94 (m, 1H), 1.88–1.35 (m, 12H); MS (ES⁺): 565.3 |
| 64ad | 2-methylfuran | -(CH₂)₅COOH | 62ad | I-2, S | ¹HNMR (DMSO-$d_6$): δ 13.71 (m, 2H), 9.36–8.57 (m, 4H), 8.50 (m, 1H), 7.98 (s, 1H), 7.89 (s, 1H), 7.78 (2H), 7.61 (m, 5H), 7.08 (m, 2H), 6.95 (d, J=7.9Hz, 1H), 6.63 (m, 1H), 3.19 (m, 2H), 2.16 (t, J=7.2Hz, 2H), 1.48 (m, 4H), 1.28 (m, 2H); MS (ES⁻): 581.2 |
| 64ae | 2-methylfuran | NHR' = piperidinyl | 62ae | I-2, S | ¹HNMR (DMSO-$d_6$): δ 9.12 (s, 2H), 8.89 (s, 2H), 7.91 (m, 1H), 7.81 (m, 2H), 7.70 (d, J=8.7Hz, 2H), 7.62 (d, J=8.9Hz, 2H), 7.48 (m, 1H), 7.22 (m, 2H), 7.11 (d, J=3.4Hz, 1H), 7.05 (d, J=7.2Hz, 1H), 6.65 (m, 1H), 3.53 (m, 2H), 3.08 (m, 2H), 1.62–1.21 (m, 6H); MS (ES⁺): 537.20 |
| 64af | 2-methylfuran | NHR' = N(propyl)(cyclopropylmethyl) | 62af | I-2, S | ¹HNMR (DMSO-$d_6$): δ 12.81 (br s, 1H), 9.13 (s, 2H), 8.82 (s, 2H), 7.95 (s, 1H), 7.85 (m, 2H), 7.71 (m, 5H), 7.43 (m, 1H), 7.29 (m, 2H), 7.13 (m, 1H), 6.67 (m, 1H), 3.49–2.97 (m, 4H), 1.67–1.37 (m, 2H), 1.08 (m, 1H), 0.90 (m, 3H), 0.61–0.26 (m, 4H); MS (ES⁺): 565.3 |
| 64ag | 2-methylfuran | -(CH₂)₄COOH | 62ag | I-2, S | ¹HNMR (DMSO-$d_6$): δ 13.78 (s, 1H), 9.09–8.22 (m, 5H), 7.97 (s, 1H), 7.89 (s, 1H), 7.77 (m, 2H), 7.61 (m, 5H), 7.03 (m, 3H), 6.64 (m, 1H), 3.22 (m, 2H), 2.20 (t, J=7.0Hz, 2H), 1.71 (t, J=7.3Hz, 2H); MS (ES⁻): 553.24. |

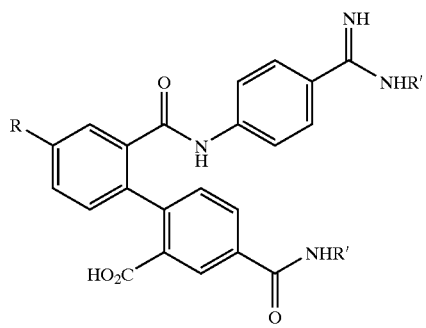

| Cpd. No. | -R | -R' | Starting From | Method Used | Analytical Data |
|---|---|---|---|---|---|
| 65 | 2-methylfuran | CH(CH₂CH₃)(CH₂CH₃)-like (sec-pentyl with two CH₃) | 61 | A-4, I-2, S | ¹H NMR (DMSO-d₆, D₂O): δ 13.87 (br s, 1 H), 9.56 (m, 2 H) 9.21 (s, 1 H), 8.74 (s, 1 H), 8.47 (m, 1 H), 7.97 (m, 1 H), 7.88 (s, 1 H), 7.78 (m, 3 H), 7.58 (m, 7 H), 7.09 (m, 3 H), 6.96 (m, 1 H), 6.65 (m, 1 H), 3.14 (m, 4 H), 1.77–0.80 (m, 18 H); MS (ES⁺): 609.4 |
| 71a | —CH=CH₂ | cyclobutyl | 67 | A-4, I-2, S | ¹H NMR (DMSO-d₆): δ 13.80 (br s, 1 H), 9.91 (s, 1 H), 9.41 (s, 1 H), 8.63 (m, 2 H), 8.07 (s, 1 H), 7.98 (s, 1 H), 7.60 (m, 8 H), 6.90 (m, 3 H), 5.94 (d, J=17.7 Hz, 1 H), 4.37 (m, 1 H), 4.16 (m, 1 H), 2.41–1.58 (m, 12 H); MS (ES⁺): 537.4 |
| 71b | —CH=CH₂ | cyclopropyl | 67 | A-4, I-2, S | ¹H NMR (DMSO-d₆): δ 9.76 (s, 1 H), 9.41 (s, 1 H), 8.95 (s, 1 H), 8.53 (m, 1 H), 8.07 (s, 1 H), 7.65 (m, 8 H), 7.08 (m, 2 H), 6.85 (dd, J 10.9 and 17.7 Hz, 1 H), 6.92 (m, 3 H), 5.97 (d, J=17.7 Hz, 1 H), 5.37 (d, J=10.9 Hz, 1 H), 2.84 (m, 1 H), 2.70 (m, 1 H), 0.98–0.51 (m, 8H); MS (ES⁺): 509.4 |
| 71c | —CH=CH₂ | CH₂CH₃ | 67 | A-4, I-2, S | ¹H NMR (DMSO-d₆): δ 12.51 (br s, 1 H), 9.59 (s, 1 H), 9.22 (s, 1 H), 8.79 (s, 1 H), 8.58 (t, J=5.5 Hz, 1 H), 8.17 (s, 1 H), 7.67 (m, 8 H), 7.12 (m, 2 H), 6.86 (dd, J=10.9 and 17.7 Hz, 1 H), 5.98 (d, J=17.7 Hz, 1 H), 5.38 (d, J=10.9 Hz, 1 H), 3.27 (m, 4 H), 1.20 (t, J=7.2 Hz, 1 H), 1.09 (t, J=7.2 Hz, 1 H); MS (ES⁺): 485.3 |

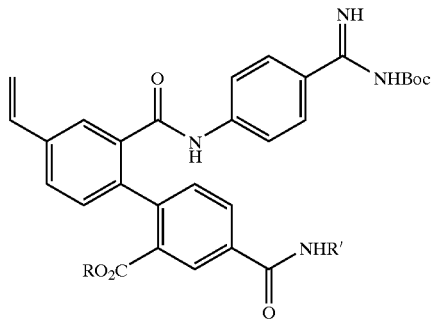

| Cpd. No. | -R | -R' | Starting From | Method Used | Analytical Data |
|---|---|---|---|---|---|
| 68a | —CH₃ | ~~~CH₃ (butyl) | 67 | A-4 | MS (ES⁺): 599.4 |
| 68b | —CH₃ | branched with CH₃ groups | 67 | A-4 | MS (ES⁺): 641.4 |
| 68c | —CH₃ | cyclohexylmethyl | 67 | A-4 | MS (ES⁺): 625.3 |
| 68d | —CH₃ | allyl CH₂ | 67 | A-4 | MS (ES⁺): 583.3 |
| 68e | —CH₃ | isobutyl (CH₃/CH₃) | 67 | A-4 | MS (ES⁺): 585.3 |
| 68f | —CH₃ | sec-butyl (CH₃/CH₃) | 67 | A-4 | MS (ES⁺): 599.4 |
| 68g | —CH₃ | CH₂CH₂CF₃ | 67 | A-4 | MS (ES⁺): 625.2 |
| 68h | —CH₃ | phenyl | 67 | A-4 | MS (ES⁺): 619.2 |
| 68i | —CH₃ | ~~~OH | 67 | A-4 | MS (ES⁺): 615.3 |
| 68j | —CH₃ | cyclopropylmethyl | 67 | A-4 | MS (ES⁺): 597.3 |
| 68k | —CH₃ | CH₃ (ethyl) | 67 | A-4 | MS (ES⁺): 557.3 |
| 68l | —CH₃ | CH₃ (propyl) | 67 | A-4 | MS (ES⁺): 571.4 |
| 68m | —CH₃ | cycloheptylmethyl | 67 | A-4 | MS (ES⁺): 639.4 |
| 68n | —CH₃ | ~~~CH₃ | 67 | A-4 | Characterized in the next step |
| 68o | —CH₃ | ~~~CH₃ (hexyl) | 67 | A-4 | MS (ES⁺): 613.5 |

-continued

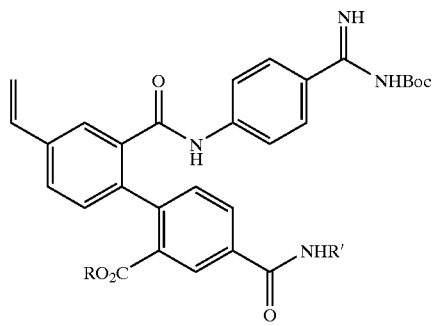

| Cpd. No. | -R | -R' | Starting From | Method Used | Analytical Data |
|---|---|---|---|---|---|
| 68p | —CH₃ | -CH(CH₂CH₃)CH₃ (sec-butyl-like, 2-methylbutyl) | 67 | A-4 | MS (ES⁺): 613.5 |
| 68q | —CH₃ | 2-methylhexyl | 67 | A-4 | MS (ES⁺): 641.5 |
| 68r | —CH₃ | —(CH₂)₄NHBoc | 67 | A-4 | MS (ES⁺): 714.5 |
| 68s | —CH₃ | cyclopentylmethyl | 67 | A-4 | MS (ES⁺): 611.4 |
| 68t | —CH₃ | trans-4-hydroxycyclohexyl (methyl) | 67 | A-4 | MS (ES⁺): 641.4 |
| 68u | —CH₃ | cyclopropylmethyl | 67 | A-4 | MS (ES⁺): 583.3 |
| 68v | —CH₃ | cyclobutylmethyl | 67 | A-4 | MS (ES⁺): 597.4 |
| 68w | —CH₃ | —CH₂CH₂CH₂OH | 67 | A-4 | MS (ES⁺): 587.4 |
| 68x | —CH₃ | —CH₂CH₂CH(CH₃)₂ (isopentyl) | 67 | A-4 | MS (ES⁺): 613.5 |
| 68y | —CH₃ | —(CH₂)₄COOH | 67 | A-4 | MS (ES⁻): 627.3 |
| 68z | —CH₃ | —(CH₂)₂COOH | 67 | A-4 | MS (ES⁻): 613.2 |
| 68aa | —CH₃ | —CH₂CH₂CH₂NH₂ | 67 | A-4 | MS (ES⁺): 686.2 |
| 68ab | —CH₃ | —CH₂CH(OH)CH₂OH (with ethyl) | 67 | A-4 | MS (ES⁺): 617.3 |

-continued

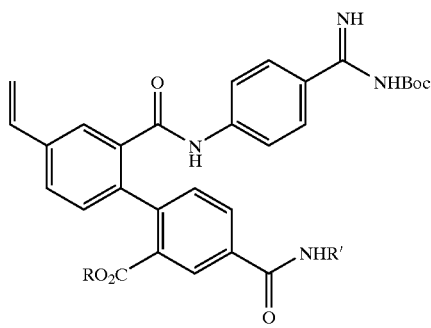

| Cpd. No. | -R | -R' | Starting From | Method Used | Analytical Data |
|---|---|---|---|---|---|
| 68ac | —CH$_3$ | ![butyramide group with C(=O)NH$_2$] | 67 | A-4 | MS (ES$^+$): 614.3 |

| Cpd. No. | -R (Position with Respect to Phenyl Ring) | -R' | -R" | X | Starting From | Method Used | Analytical Data |
|---|---|---|---|---|---|---|---|
| 74 | —OCH$_3$ (3) | —CHO | —CH$_3$ | CH | 73 + 3a | D-2 | MS (ES$^-$): 368.2 |
| 75a | —OH (3) | —CHO | —CH$_3$ | CH | 74 | V-2, W | MS (ES$^-$): 354.1 |
| 75b | —OH (3) | —CHO | —Bn | CH | 74 | V-1, H | MS (ES$^-$): 430.2 |
| 76a | —OSO$_2$CF$_3$ (3) | —CHO | —CH$_3$ | CH | 75a | B-2 | MS (ES$^+$): 488.1 |
| 76b | —OSO$_2$CF$_3$ (3) | —CHO | —Bn | CH | 75b | B-2 | MS (ES$^-$): 562.3 ; MS (ES$^+$): 586.3 (M + Na)$^+$ |
| 77a | —CH=CH$_2$ (3) | —CHO | —CH3 | CH | 76a | D-3 | MS (ES$^+$): 366.38 |
| 77b | —OCH$_2$CO$_2$C$_2$H$_5$ (3) | —CHO | —Bn | CH | 75b | X | Characterized in the next step |
| 77c | —OCH$_2$CONH$_2$ (3) | —CHO | —Bn | CH | 75b | X | MS (ES$^+$): 487.3; MS (ES$^-$): 511.35 (M + Na)$^+$ |
| 77d | 2-methylthiophene (3) | —CHO | —Bn | CH | 76b | D-2 | Characterized in the next step |
| 77e | —O-phenyl (3) | —CHO | —Bn | CH | 75b | D-8 | MS (ES$^+$): 530.3 (M + Na)$^+$); MS (ES$^-$):506.3 |
| 77f | —OCH$_2$CH$_2$CH$_3$ (3) | —CHO | —Bn | CH | 75b | X | MS (ES$^+$): 496.3 (M + Na)$^+$ |
| 77g | —OCH$_2$CH$_3$ (3) | —CHO | —Bn | CH | 75b | X | MS (ES+): 482.4 (M + Na)$^+$ |
| 77h | —OCH$_2$CH(CH$_3$)$_2$ (3) | —CHO | —Bn | CH | 75b | X | MS (ES$^+$): 510.4 (M + Na)$^+$ |

-continued

| Cpd. No. | -R (Position with Respect to Phenyl Ring) | -R' | -R" | X | Starting From | Method Used | Analytical Data |
|---|---|---|---|---|---|---|---|
| 77i | ~O~~OAc (3) | —CHO | —Bn | CH | 75b | X | $^1$HNMR (CDCl$_3$): δ 9.59 (s, 1 H), 8.39 (d, J=2 Hz, 1 H), 8.03 (m, 2 H), 7.84 (d, J=8.9 Hz, 1 H), 7.35 (d, J=8 Hz, 1 H), 7.28 (m, 2 H), 7.12 (m, 2 H), 6.93 (dd, J=2.5 and 8.8 Hz, 1 H), 6.64 (d, J=2.5 Hz, 1 H), 6.31 (t, J=6 and 5 Hz, 1 H), 5.06 (m, 2 H), 4.42 (t, J=4.5 Hz, 2 H), 4.13 (m, 2 H), 3.34 (t, J=6.8 Hz, 2 H), 2.11 (s, 3 H), 1.94 (m, 1H), 1.01 (d, J=6.8 Hz, 6 H) |
| 78a | —CH=CH$_2$ (3) | —CO$_2$H | —CH$_3$ | CH | 77a | E | MS (ES$^-$): 380.1 |
| 78b | —OSO$_2$CF$_3$ (3) | —CO$_2$H | —Bn | CH | 76b | E | Characterized in the next step |
| 78c | —OCH$_2$CO$_2$C$_2$H$_5$ (3) | —CO$_2$H | —Bn | CH | 77b | E | Characterized in the next step |
| 78d | —OCH$_2$CONH$_2$ (3) | —CO$_2$H | —Bn | CH | 77c | E | MS (ES$^+$): 527.35 (M + Na)$^+$ |
| 78e | 2-thienyl (3) | —CO$_2$H | —Bn | CH | 77d | E | MS (ES$^+$): 536.4 (M + Na)$^+$ |
| 78f | —O-phenyl (3) | —CO$_2$H | —Bn | CH | 77e | E | MS (ES$^-$): 522.3 |
| 78g | —OCH$_3$ (3) | —CO$_2$H | —CH3 | CH | 74 | E | MS (ES$^-$): 384.1 |
| 78h | —OCH$_2$CH$_2$CH$_3$ (3) | —CO$_2$H | —Bn | CH | 77f | E | MS (ES$^-$): 488.3 |
| 78i | —OCH$_2$CH$_3$ (3) | —CO$_2$H | —Bn | CH | 77g | E | MS (ES$^-$): 474.4 |
| 78j | —OCH$_2$CH(CH$_3$)$_2$ (3) | —CO$_2$H | —Bn | CH | 77h | E | MS (ES$^-$): 502.4 |
| 78k | —OCH$_2$CH(OAc)— (3) | —CO$_2$H | —Bn | CH | 77i | E | Characterized in the next step |
| 90 | —OBn (5) | —CHO | —CH$_3$ | CH | 89 + 3a | D-2 | $^1$HNMR (CDCl$_3$): δ 10.47 (s, 1 H), 8.36 (d, J=2 Hz, 1 H), 7.96 (dd, J=2.2 and 7.7 Hz, 1 H), 7.68 (m, 2 H), 7.46 (m, 5 H), 7.23 (d, J=8 Hz, 1 H), 7.12 (d, J=8.7 Hz, 1 H), 6.73 (d, J=7.2 Hz, 1 H), 5.23 (q, J=11 and 15 Hz, 2 H), 3.67 (s, 3 H), 3.31 (t, J=6.8 Hz, 2 H), 1.94 (m, 1 H), 1.01 (d, J=6.8 Hz, 6 H), MS (E+) 468.2 (M +Na)$^+$ (ES−) 444.2 |
| 91 | —OBn (5) | —CO$_2$H | —CH$_3$ | CH | 90 | E | $^1$HNMR (CDCl$_3$): δ 8.22 (s, 1 H), 7.83 (d, J=7.2 Hz, 1 H), 7.34 (m, 8 H), 7.02 (d, J=8.1 Hz, 1 H), 6.75 (d, J=7.4 Hz, 1 H), 5.16 (s, 2 H), 3.66 (s, 3 H), 3.21 (t, J=6.8 Hz, 2 H), 1.85 (m, 1 H), 0.94 (d, J=6.8 Hz, 6 H), MS (ES+) 484.1 (M + Na)$^+$ |

-continued

| Cpd. No. | -R (Position with Respect to Phenyl Ring) | -R' | -R" | X | Starting From | Method Used | Analytical Data |
|---|---|---|---|---|---|---|---|
| 92 | —OBn (5) | —CO$_2$MEM | —CH3 | CH | 91 | F | MS (ES$^+$): 572.2 (M + Na)$^+$ |
| 93 | —OH (5) | —CO$_2$MEM | —CH3 | CH | 92 | G | MS (ES$^+$): 482. (M + Na)$^+$ |
| 94 | —OSO$_2$CF$_3$ (5) | —CO$_2$MEM | —CH3 | CH | 93 | B-2 | MS (ES$^+$): 614.3 (M + Na)$^+$ |
| 95a | 2-ethylthiophene (5) | —CO$_2$MEM | —CH$_3$ | CH | 94 | D-3 | MS (ES+) 562.3 (M + Na)$^+$ |
| 96a | 2-ethylthiophene (5) | —CO$_2$H | —CH3 | CH | 95a | I-1 | MS (ES+) 452.1 (M + Na)$^+$ |
| 101 | —OCH$_3$ (2) | —CHO | —CH3 | CH | 100 + 3a | D-2 | MS (ES+) 370.1 |
| 102 | —OCH$_3$ (2) | —CO$_2$H | —CH$_3$ | CH | 101 | E | MS (ES$^-$) 384.2; MS (ES$^+$) 386.2 |
| 108 | —OBn (2) | —CHO | —CH3 | CH | 107 + 3a | D-2 | MS (ES$^+$): 446.2 |
| 109 | —OBn (2) | —CO$_2$H | —CH3 | CH | 108 | E | MS (ES$^-$): 460.1 |
| 131 | —H | —CHO | —CH$_3$ | CH | 130 + 3a | D-2 | $^1$HNMR (CDCl$_3$-d$_1$): δ 9.79 (s, 1 H), 8.39 (d, J=1.88 Hz, 1 H), 8.02 (t, J=6.0 Hz, 2 H), 7.59 (m, 2 H), 7.38 (d, J=7.9 Hz, 1 H), 7.22 (d, J=8.1 Hz, 1 H), 6.30 (b, 1 H), 3.72 (s, 3 H), 3.36 (t, J=6.6 Hz, 2 H), 1.96 (m, 1 H), 1.02 (d, J=6.8 Hz, 6 H), MS (ES+): 340.1 |
| 132 | —H | —CO$_2$H | —CH$_3$ | CH | 131 | E | $^1$HNMR (DMSO-d$_6$): δ 12.28 (b, 1 H), 8.52 (d, J=6.03 Hz, 1 H), 8.12 (s, 1 H), 7.86 (d, J=8.1 Hz, 1 H), 7.74 (d, J=7.74 Hz, 1 H), 7.41 (t, J=8.67 Hz, 1 H), 7.31 (t, J=7.9 Hz, 1 H), 7.12 (d, J=8.1 Hz, 1 H), 6.97 (d, J=7.5 Hz, 1 H), 3.39 (s, 3 H), 2.92 (t, J=6.0 Hz, 2 H), 1.66 (m, 1 H), 0.78 (d, J=7.4 Hz, 6 H), MS (ES-): 354.1 |
| 193a | —H | 4-ethoxy-N'-Boc-benzamidine | —CH$_3$ | CH | 192a + 6a | D-7 | MS (ES$^+$): 560.5 |
| 193b | —H | 4-isopropoxy-N'-Boc-benzamidine | —CH$_3$ | CH | 192b + 6a | D-7 | MS (ES$^+$): 574.5) |
| 194a | —H | 4-ethoxybenzamidine | —CH$_3$ | CH | 193a | S-2 | MS (ES$^+$): 460.3 |

-continued

| Cpd. No. | -R (Position with Respect to Phenyl Ring) | -R' | -R" | X | Starting From | Method Used | Analytical Data |
|---|---|---|---|---|---|---|---|
| 194b | —H | 4-isopropoxy-benzamidine | —CH₃ | CH | 193b | S-2 | MS (ES⁺): 474.3 |
| 195a | —H | 4-ethoxy-benzamidine | —H | CH | 194a | I-2 | ¹HNMR (DMSO-d₆): δ 8.79 (bs, 4 H), 8.63 (t, J=6.5 Hz, 1 H), 8.35 (s, 1 H), 7.85 (d, J=6 Hz, 1 H), 7.62 (d, J=8.2 Hz, 2 H), 7.26 (m, 5 H), 7.06 (m, 1 H), 5.0 (m, 2 H), 3.09 (t, J=6.2 Hz, 2 H), 1.86 (m, 1 H), 0.89 (d, J=6.6 Hz, 6 H); MS (ES−): 444.3 and (ES⁺) 446.3 |
| 195b | —H | 4-isopropoxy-benzamidine | —H | CH | 194b | I-2 | ¹HNMR (DMSO-d₆/DCl): δ 8.24 (d, J=1.6 Hz, 1 H), 7.91 (dd, J=7.7 and 1.6 Hz, 1 H), 7.56 (d, J=8.7 Hz, 1 H), 7.48 (d, J=8.7 Hz, 1 H), 7.32 (t, J=8 Hz, 1 H), 7.16 (m, 3 H), 6.91 (t, J=7.5 Hz, 1 H), 6.76 (d, J=8.5 Hz, 1 H), 6.66 (d, J=8.5 Hz, 1 H), 4.99 (m, 1 H), 2.92 (d, J=6.9 Hz, 2 H), 1.68 (m, 1 H), 1.33 (d, J=6 Hz, 1.2H), 1.27 (d, J=6 Hz, 1.8 H), 0.71 (d, J=6.5 Hz, 6 H); MS (ES−): 458.2 and (ES⁺) 460.3 |
| 200 | —H | 4-(isopropylamino)-N-Boc-benzamidine | —CH₃ | CH | 199 + 6a | D-7 | MS (ES⁺): 573.5 |
| 201 | —H | 4-(isopropylamino)-N-Boc-benzamidine | —H | CH | 200 | I-2 | ¹HNMR (DMSO-d₆/DCl): δ 8.49 (t, J=5.6 Hz, 1 H), 8.18 (d, J=6.9 Hz, 1 H), 7.84 (t, J=7.8 Hz, 1 H), 7.23 (m, 4 H), 7.01 (m, 2 H), 6.82 (d, J=7 Hz, 1 H), 6.22 (d, J=8.5 Hz, 1 H), 6.15 (d, J=8.5 Hz, 1 H), 3.95 (m, 1 H), 2.85 (t, J=5.8 Hz, 1 H), 1.62 (m, 1 H), 1.23 (s, 9H), 1.1 (d, J=6.7 Hz, 1.2 H), 1.05 (d, J=6.7 Hz, 1.8 H), 0.67 (d, J=6.6 Hz, 6 H); MS (ES+): 559.4 |
| 202 | —H | 4-(isopropylamino)-benzamidine | —H | CH | 201 | S | MS (ES⁺): 459.3 |

-continued

| Cpd. No. | -R (Position with Respect to Phenyl Ring) | -R' | -R" | X | Starting From | Method Used | Analytical Data |
|---|---|---|---|---|---|---|---|
| 203 | —OBn (4) | (acetamidophenyl C(=NH)NHBoc) | —CH₃ | CH | 45 | R | MS (ES⁺): 679.4 |
| 204 | —OBn (4) | (acetamidophenyl C(=NH)NHBoc) | —H | CH | 203 | I-2 | MS (ES⁻): 663.4 |
| 209a | —H | (acetamidophenyl C≡N) | —CH₃ | CH | 132 | A-7 | MS (ES⁻): 454.3 |
| 209b | —CH=CH₂ (4) | (acetamidophenyl C≡N) | —CH₃ | CH | 30f | A-7 | ¹HNMR (DMSO-d₆): δ 10.72 (s, 1 H), 8.65 (d, J=6.03 Hz, 1 H), 8.24 (s, 1 H), 8.03 (d, J=8.1 Hz, 1 H), 7.75 (m, 6 H), 7.40 (d, J=7.90 Hz, 1 H), 7.34 (d, J=8.1 Hz, 1 H), 6.88 (q, J=11.2 Hz, 1 H), 6.04 (d, J=7.5 Hz, 1 H), 5.41 (d, J=11.1 Hz, 1 H), 3.55 (s, 3 H), 3.10 (t, J=6.6 Hz, 2 H), 1.86 (m, 1 H), 0.88 (d, J=6.6 Hz, 6 H); MS (ES⁻): 480.3 |
| 209c | —CH=CH₂ (4) | (acetamidophenyl C≡N) | —CH₃ | N | 227 | A-7 | MS (ES⁻) 481.4 |
| 210b | —CH=CH₂ (4) | (acetamidophenyl C(=NH)NH—OH) | —CH₃ | CH | 209b | Y | ¹HNMR (DMSO-d₆): δ 10.12 (s, 1 H), 9.37 (b, 1 H), 8.48 (t, J=6.1 Hz, 1 H), 8.05 (d, J=1.9 Hz, 1 H), 7.85 (d, J=7.9 Hz, 1 H), 7.56 (d, J=7.8 Hz, 1 H), 7.49 (d, J=7.9 Hz, 1 H), 7.36 (s, 4 H), 7.21 (d, J=7.9 Hz, 1 H), 7.10 (d, J=2.8 Hz, 1 H), 6.69 (m, 1 H), 5.84 (d, J=15.5 Hz, 1 H), 5.60 (b, 1 H), 5.22 (d, J=11.4 Hz, 1 H), 3.38 (s, 3 H), 2.91 (t, J=6 Hz, 2 H), 1.66 (m, 1 H), 0.71 (d, J=6.8 Hz, 6 H); MS (ES+) 515.40 |

-continued

| Cpd. No. | -R (Position with Respect to Phenyl Ring) | -R' | -R" | X | Starting From | Method Used | Analytical Data |
|---|---|---|---|---|---|---|---|
| 210c | —CHCH₂ (4) | 4-(acetamido)phenyl-C(=NH)NHOH | —CH₃ | N | 209c | Y | ¹H NMR (DMSO-d₆): δ 10.50 (s, 1 H), 9.54 (s, 1 H), 8.58 (t, J=6.4 Hz, 1 H), 8.21–7.34 (m, 9H), 6.90 (dd, J=11.1 and 17.3 Hz, 1 H), 6.07 (d, J=17.3 Hz, 1 H), 5.74 (s, 2 H), 5.45 (d, J=11.1 Hz, 1 H), 3.60 (s, 3 H), 3.16 (t, J=6.2 Hz, 2 H), 1.88 (m, 1 H), 0.88 (d, J=6.4 Hz, 6 H); MS (ES⁺): 516.40 |
| 211b | —CH=CH₂ (4) | 4-(acetamido)phenyl-C(=NH)NHOH | —H | CH | 210b | I-2 | ¹HNMR (DMSO-d₆): δ 12.62 (bs, 1H), 10.24 (s, 1 H), 8.48 (t, J=5.65 Hz, 1 H), 8.15 (s, 1 H), 7.81 (d, J=10.9 Hz, 1 H), 7.61 (s, 1 H), 7.50 (d, J=7.9 Hz, 1 H), 7.49 (s, 6 H), 7.16 (d, J=8.1 Hz, 1 H), 7.08 (d, J=8.1 Hz, 1 H), 6.72 (m, 1 H), 5.85 (d, J=13.7 Hz, 1 H), 5.24 (d, J=11.5 Hz, 1 H), 2.93 (t, J=6 Hz, 2 H), 1.68 (m, 1 H), 0.72 (d, J=6.8 Hz, 6 H); MS (ES+) 501.40, (ES−) 499.2 |
| 211c | —CH=CH₂ (4) | 4-(acetamido)phenyl-C(=NH)NHOH | —H | N | 210c | I-2 | ¹H NMR (DMSO-d₆): δ 9.50 (s, 1 H), 8.68 (m, 1 H), 7.93–7.40 (m, 10 H), 7.13 (m, 2 H), 6.86 (dd, J=11.1 and 17.3 Hz, 1 H), 5.99 (d, J=17.3 Hz, 1 H), 5.69 (s, 1 H), 5.38 (d, J=11.1 Hz, 1 H), 3.14 (t, J=6.2 Hz, 2 H), 1.86 (m, 1 H), 0.88 (d, J=6.4 Hz, 6 H); MS (ES⁻): 500.36. |
| 212 | —CH=CH₂ (4) | 4-(ethylamino)phenyl-C≡N | —CH3 | CH | 187a | AE-5 | ¹HNMR (DMSO): δ 8.70 (t, J=5.6 Hz, 1 H), 8.36 (d, J=1.7 Hz, 1 H), 8.07 (dd, J=8.1, 1.9 Hz, 1 H), 7.42 (m, 4H), 7.09 (d, J=5.5 Hz, 1 H), 7.04 (d, J=7.7 Hz, 1 H), 6.74 (dd, J=17.5, 10.9 Hz, 1 H), 6.49 (d, J=8.8 Hz, 2 H), 5.79 (d, J=17.7 Hz, 1 H), 5.27 (d, J=10.9 Hz, 1 H), 4.0 (t, J=6.0 Hz, 2 H), 3.62 (s, 3 H), 3.11 (t, J=6.2, 2H), 1.86 (m, 1 H), 0.90 (d, J=6.6 Hz, 6 H) |
| 212a | —CH=CH₂ (4) | 4-(ethylamino)phenyl-C≡N | —CH₃ | N | 247 | AE-5 | MS (ES⁺) 469.3 |
| 212b | —CHαCH₂ (4) | 6-(ethylamino)pyridyl-C≡N | —CH₃ | CH | 187a | AE-5 | characterized in the next step |

| Cpd. No. | -R (Position with Respect to Phenyl Ring) | -R' | -R" | X | Starting From | Method Used | Analytical Data |
|---|---|---|---|---|---|---|---|
| 213 | —CH=CH₂ (4) | 4-(ethylamino)-N-hydroxybenzamidine | —CH₃ | CH | 212 | Y | ¹HNMR (DMSO): δ 9.23 (s, 1 H), 8.71 (t, J=6.2 Hz, 1 H), 8.36 (d, J=1.9 Hz, 1 H), 8.09 (dd, J=7.9, 1.7 Hz, 1 H), 7.49 (d, J=7.9 Hz, 2 H), 7.40 (d, J=8.3 Hz, 1 H), 7.32 (d, J=8.8 Hz, 2 H), 7.04 (d, J=7.9 Hz, 1 H), 6.73 (dd, J=17.7, 11.1 Hz, 1 H), 6.40 (d, J=8.5 Hz, 2 H), 6.33 (t, J=7.0 Hz, 1 H), 5.78 (d, J=17.7 Hz, 1 H), 5.58 (b, 1 H), 5.26 (d, J=11.1 Hz, 1 H), 3.96 (m. 2 H), 3.64 (s, 3 H), 3.11 (t, J=6.4 Hz, 2 H), 1.86 (m,, 1 H), 0.90 (d, J=6.8 Hz, 6 H); MS (ES⁺): 501.3 |
| 213a | —CH=CH₂ (4) | 4-(ethylamino)-N-hydroxybenzamidine | —CH₃ | N | 212a | Y | ¹H NMR (DMSO-d₆): δ 8.98 (s, 1 H), 8.46 (t, J=6.4 Hz, 1 H), 7.96 (d, J=8.0 Hz, 1 H), 7.87 (d, J=8.0 Hz, 1 H), 7.31 (s, 1 H), 7.21 (d, J=8.1 Hz, 2 H), 7.09 (d, J=8.5 Hz, 1 H), 6.88 (d, J=7.9 Hz, 1 H), 6.51 (dd, J=11.1 and 17.3 Hz, 1H), 6.15 (m, 3 H), 5.58 (d, J=17.3 Hz, 1 H), 5.30 (s, 1 H), 5.06 (d, J=11.1 Hz, 1 H), 3.77 (m, 2 H), 3.42 (s, 3 H), 2.93 (t, J=7.0 Hz, 2 H), 1.67 (m, 1 H), 0.66 (d, J=6.4 Hz, 6 H); MS (ES⁺): 502.35 |
| 213b | —CH=CH₂ (4) | 6-(ethylamino)-N-hydroxynicotinamidine | —CH₃ | CH | 212b | Y | ¹HNMR (DMSO-d₆): δ 9.4 (bs, 1 H), 8.70 (k, J=5.5 Hz, 1 H), 8.35 (d, J=1.7 Hz, 1 H), 8.17 (d, J=2.5 Hz, 1 H), 8.47 (dd, J=8.1, 2 Hz, 1 H), 7.58 (dd, J=8.8, 2.5 Hz, 1 H), 7.47 (m, 1H, 2 H), 7.38 (d, J=7.2 Hz, 1 H), 7.07 (t, J=5 Hz, 1 H), 7.03 (d, J=7.7 Hz, 1 H), 6.73 (dd, J=11.17 Hz, 1 H), 6.41 (d, J=8.8 Hz, 1 H), 5.80 (d, J=17 Hz, 1 H), 5.78 (bs, 2 H), 5.21 (d, J=11 Hz, 1 H), 4.16 (d, J=5.3 Hz), 3.62 (s, 3 H), 3.15 (t, J=6.78 Hz, 2 H), 1.87 (m, 1 H), 0.91 (d, J=6.7 Hz, 6 H); MS (ES⁺) 502.46. |
| 214 | —CH=CH₂ (4) | 4-(ethylamino)-N-hydroxybenzamidine | —H | CH | 213 | I-2 | ¹HNMR (DMSO): δ 8.76 (t, J=5.8 Hz, 1 H), 8.37 (s, 1 H), 8.04 (d, J=8.7 Hz, 1 H), 7.39 (m, 5 H), 7.06 (d, J=8.3 Hz, 1 H), 6.72 (dd, J=17.9, 11.3 Hz, 1 H), 6.43 (d, J=8.5 Hz, 3 H), 5.76 (d, J=17.9 Hz, 1 H), 5.24 (d, J=11.1 Hz, 1 H), 3.98 (m. 2 H), 3.11 (t, J=6.6 Hz, 2 H), 1.86 (h, J=6.8 Hz, 1 H), 0.90 (d, J=6.8, 6 H); MS (ES⁺): 487.2 |

-continued

| Cpd. No. | -R (Position with Respect to Phenyl Ring) | -R' | -R" | X | Starting From | Method Used | Analytical Data |
|---|---|---|---|---|---|---|---|
| 214a | —CH=CH₂ (4) | 4-(ethylamino)-N-hydroxybenzamidine | —H | N | 213a | I-2 | ¹H NMR (DMSO-d₆): δ 9.33 (s, 1 H), 8.98 (t, J=6.4 Hz, 1 H), 8.16 (d, J=8.0 Hz, 1 H), 8.00 (d, J=8.0 Hz, 1 H), 7.51 (s, 1 H), 7.41 (d, J=8.1 Hz, 1 H), 7.31 (d, J=8.5Hz, 2 H), 7.11 (d, J=7.9 Hz, 1 H), 6.75 (dd, J=11.1 and 17.3 Hz, 1 H), 6.46 (m, 3 H), 5.80 (d, J=17.3 Hz, 1 H), 5.72 (s, 2 H), 5.27 (d, J=11.1 Hz, 1 H), 3.97 (s, 2 H), 2.93 (t, J=7.0 Hz, 2 H), 1.90 (m, 1 H), 0.90 (d, J=6.4 Hz, 6 H); MS (ES⁺): 488.36. |
| 214b | —CH=CH₂ (4) | 6-(ethylamino)-N-hydroxypyridine-3-carboxamidine | H | CH | 213b | I-2 | ¹HNMR (DMSO-d₆): δ 8.69 (t, J=6 Hz, 1 H), 8.35 (1,1 H), 8.63 (s, 1 H), 8.03 (d, J=8 Hz, 1 H), 7.60 (d, J=9 Hz, 1 H), 7.47 (s, 1 H), 7.41 (m, 3 H), 7.06 (d, J=7.7 Hz, 1 H), 6.75 (dd, J=10.5, 17.5 Hz, 1 H), 6.47 (d, J=7 Hz, 1 H), 5.80 (d, J=17 Hz, 1 H), 5.27 (d, J=10.5 Hz, 1 H), 4.21 (m, 2 H), 3.10 (t, J=6.7 Hz, 2 H), 2.07 (s, 3 H), 1.87 (m, 1 H), 0.90 (d, J=6.5 Hz, 6 H); MS (ES⁺) 488.39. |
| 238 | —CH=CH₂ (4) | 4-(ethylamino)benzamidine | —H | CH | 237+ 187a | AE-2 | ¹HNMR (DMSO-d₆): δ 8.68–8.60 (m, 1 H), 8.50 (d, J=2.4 Hz, 1 H), 7.90–7.80 (m, 1 H), 7.76–7.70 (m, 1 H), 7.56–7.50 (m, 1 H), 7.48–7.42 (d, J=7.7 Hz, 1 H), 7.30–7.22 (d, J=7.9 Hz, 1 H), 7.10–7.02 (d, J=7.7 Hz, 1 H), 6.90–6.75 (dd, J=17, 11 Hz, 1 H), 6.5 (bs, 1 H), 5.92–5.80 (d, J=17 Hz, 1 H), 5.40–5.30 (d, 11 Hz, 1 H), 4.50–4.20 (m, 2 H), 3.20–3.10 (t, J=6.6 Hz, 2 H), 2.10–1.88 (m, 1 H), 1.2–0.94 (d, J=6.6 Hz, 6 H); MS (ES⁺) 471.3 |
| 256 | —H | N-Boc-4-(propylamino)benzamidine | —CH₃ | CH | 255 + 6a | D-6 | MS (ES⁺): 573.3 |
| 257 | —H | 4-(propylamino)benzamidine | —H | CH | 256 | I-2, S | MS (ES⁺): 459.1 |

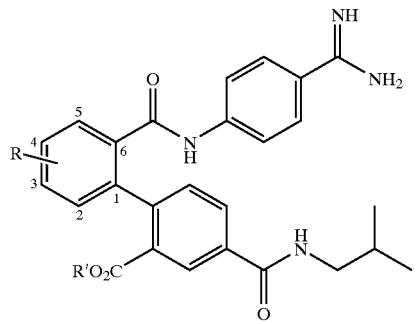

| Cpd. No. | —R | —R' | Starting From | Method Used | Analytical Data |
|---|---|---|---|---|---|
| 79a | —CH=CH₂ (3) | —CH₃ | 78a | J | MS (ES⁺): 499.2 |
| 79b | —OSO₂CF₃ (3) | —CH₂C₆H₅ | 78b | J | Characterized in the next step |
| 79c | —OCH₂CO₂C₂H₅ (3) | —CH₂C₆H₅ | 78c | J | Characterized in the next step |
| 79d | —OCH₂CONH₂ (3) | —CH₂C₆H₅ | 78d | J | MS (ES⁺): 622.4; (ES⁻) 620.4 |
| 79e | (2-methylthiophene) (3) | —CH₂C₆H₅ | 78e | J | Characterized in the next step |
| 79f | (methoxyphenyl) (3) | —CH₂C₆H₅ | 78f | J | Characterized in the next step |
| 79g | —OCH₃ (3) | —CH₃ | 78g | J | ¹HNMR (DMSO-d₆): δ 10.6 (bs, 1H), 9.29–9.32 (bs, 1H), 9.06 (bs, 1H), 8.82–8.75 (t, J=5.84 Hz, 1H), 8.32 (d, J=1.88 Hz, 1H), 8.13 (d, J=1.7 Hz, 1H), 7.83 (s, 4H), 7.78 (d, J=8.67 Hz, 1H), 7.50 (d, J=7.9 Hz, 1H), 7.20–7.15 (dd, J=8.67, 2.3 Hz, 1H), 6.92 (d, J=2.4Hz, 1H), 3.94 (s, 3H), 3.64 (s, 3H), 3.21–3.14 (t, J=6 Hz, 2H), 2.0–1.86 (m, 1H), 1.0–0.94 (d, J=6.5 Hz, 6H); MS (ES⁺) 503.3 |
| 79h | —OCH₂CH₂OCH₃ (3) | —Bn | 78h | J | MS (ES⁺): 607.3 |
| 79i | —OCH₂OCH₃ (3) | —Bn | 78i | J | MS (ES⁺): 593.4 |
| 79j | —OCH₂CH(CH₃)₂ (3) | —Bn | 78j | J | MS (ES⁺): 621.4 |
| 79k | —O—CH₂—CH₂—OAc (3) | —Bn | 78k | J | MS (ES⁺): 651.4 |
| 80a | —CH=CH₂ (3) | —H | 79a | I-2 | ¹HNMR (DMSO-d₆): δ 9.1 (s, 2H), 8.87 (s, 2H), 8.53 (t, J=6 Hz, 1H), 8.02 (s, 1H), 7.64 (m, 7H), 7.1 (s, 1H), 6.98 (d, 7.4 Hz, 1H), 6.80 (dd, J=11 Hz, J=17.6 Hz, 1H), 5.90 (d, J=17.6 Hz, 1H), 5.35 (d, J=12 Hz, 1H), 3.03 (t, 6 Hz, 2H), 1.83 (m, 1H), 0.86 (d, J=6.7 Hz, 6H); MS (ES⁺) 485.2 |
| 80b | —OH (3) | —H | 79b | I-2 | ¹HNMR (DMSO-d₆): δ 10.37 (s, 1H), 9.20 (m, 3H), 8.72 (t, J=6 Hz, 1H), 8.2 (s, 1H), 8.85 (m, 6H), 7.65 (d, J=8 Hz, 1H), 7.12 (d, 8 Hz, 1H), 7.02 (dd, J=2.5 Hz, J=8 Hz, 1H), 6.60 (d, J=2.5 Hz, 1H), 3.25 (t, J=6.5 Hz, 2H), 2.0 (m, 1H), 1.07 (d, J=6.8 Hz, 6H); MS (ES⁺) 475.2 |
| 80c | —OCH₂CO₂H (3) | —H | 79c | I-2 | ¹H NMR (DMSO-d₆): δ 12.7 (2H, bs, 1H), 9.01, 8.87 (2 bs, 4H), 8.36 (m, 1H), 7.83 (s, 1H), 7.44 (m, 6H), 6.75 (m, 2H), 6.31 (d, J=2.2 Hz, 1H), 4.42 (s, 2H), 2.84 (m, 2H), 1.63 (m, 1H), 0.67 (d, J=6.5 Hz, 6H); MS (ES+): 533.4 |
| 80d | —OCH₂CONH₂ (3) | —H | 79d | G | ¹H NMR (DMSO-d₆): δ 9.13 (bs, 5H), 8.59 (t, J=6.28 Hz, 1H), 8.14 (d, J=1.7 Hz, 1H), 7.63 (m, 9H), 7.42 (s, 1H), 7.09 (d, J=7.5 Hz, 1H), 7.03 (dd, J=2.5, 12.7 Hz, 1H), 6.70 (d, J=2.5 Hz, 1H), 4.48 (s, 2H), 3.05 (t, J=6.6 Hz, 2H), 1.83 (m, 1H), 0.87 (d, J=6.8 Hz, 6H); MS (ES+): 532.4 |
| 80e | (2-methylthiophene) (3) | —H | 79e | I-2 | ¹H NMR (DMSO-d₆): δ 12.6 (1H, bs, COOH), 8.98, 8.67 (2 bs, 4H), 8.46 (m, 1H), 8.08 (m, 1H), 7.76 (m, 1H), 7.53 (m, 6H), 7.39 (m, 2H), 7.06 (m, 1H), 7.04 (m, 1H), 2.89 (m, 2H), 1.66 (m, 1H), 0.69 (d, J=6.5 Hz, 6H); MS (ES+): 541.4 |

-continued

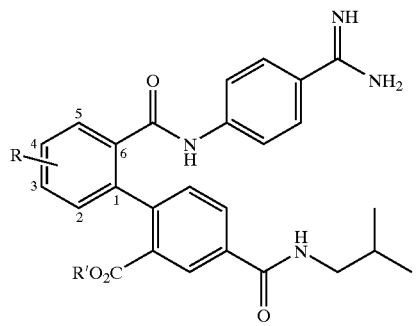

| Cpd. No. | —R | —R' | Starting From | Method Used | Analytical Data |
|---|---|---|---|---|---|
| 80f | ![methoxyphenyl] (3) | —H | 79f | I-2 | ¹HNMR (DMSO-d₆): δ 9.14 (d, J=10 Hz, 4H), 8.60 (t, J=6 Hz, 1H), 8.22 (bs, 1H), 7.87–7.62 (m, 7H), 7.47 (t, J=8 Hz, 2H), 7.26 (t, 7 Hz, 1H), 7.22 (m, 4H), 6.70 (bs, 1H), 3.09 (t, J=6 Hz, 2H), 1.83 (m, 1H), 0.91 (d, J=6.8 Hz, 6H); MS (ES⁺) 551.4 |
| 80g | —OCH₃ (3) | —H | 79g | I-2 | ¹HNMR (DMSO-d₆): δ 9.13 (bs, 2H), 8.78 (bs, 2H), 8.65 (t, J=6 Hz, 1H), 8.25 (bs, 1H), 7.78 (m, 1H), 7.76 (m, 5H), 7.25 (s, 1H), 7.17 (m, 1H), 6.73 (bs, 1H), 3.83 (s, 3H), 3.10 (t, J=6 Hz, 2H), 1.80 (m, 1H), 0.88 (d, J=6.8 Hz, 6H); MS (ES⁺) 489.3 |
| 80h | —O—CH₂CH₂—CH₃ (3) | —H | 79h | I-2 | MS (ES⁺): 517.7 |
| 80i | —O—CH₂—CH₃ (3) | —H | 79i | I-2 | MS (ES⁺): 503.4; MS (ES⁻): 501.4 |
| 80j | —O—CH₂—CH(CH₃)₂ (3) | —H | 79j | I-2 | MS (ES⁺): 531.4; MS (ES⁻): 529.4 |
| 80k | —O—CH₂—CH₂—OH (3) | —H | 79k | I-2 | ¹HNMR (DMSO-d₆): δ 13.52 (bs, 1H), 9.16 (bs, 2H), 9.03 (bs, 2H), 8.50 (t, J=6 Hz, 1H), 7.96 (d, J=1.7 Hz, 1H), 7.56 (m, 6H), 7.00 (dd, J=2.5 and 8.5 Hz, 1H), 6.90 (d, J=8 Hz, 1H), 6.48 (d, J=2.5 Hz, 1H), 4.91 (t, J=5.5 Hz, 1H), 4.00 (t, J=4.5 Hz, 2H), 3.69 (q, J=5.5 and 10 Hz, 2H), 3.05 (t, J=6.8 Hz, 2H), 1.80 (m, 1H), 0.84 (d, J=6.8 Hz, 6H); MS (ES⁺) 519.3, (ES−) 517.3 |
| 86a | —CH(OH)CH₂OH (3) | —H | 82 | S, I-2 | ¹HNMR (DMSO-d₆): δ 9.15 (bs, 3H), 8.65 (t, J=6 Hz, 1H), 8.12 (s, 2H), 7.82–7.56 (m, 7H), 7.55–6.96 (m, 4H), 5.5 (bs, 1H), 4.90 (bs, 1H), 4.65 (bs, 1H), 3.10 (t, J=6 Hz, 2H), 1.90 (m, 1H), 0.92 (d, J=6.8 Hz, 6H); MS (ES⁺) 519.3 |
| 86b | —CH₂OH (3) | —H | 84 | S, I-2 | ¹HNMR (DMSO-d₆): δ 8.82 (bs, 2H), 8.68 (bs, 2H), 8.40 (t, J=6 Hz, 1H), 7.88 (bs, 1H), 7.53 (m, 5H), 7.45 (d, 8 Hz, 1H), 7.25 (d, J=8 Hz, 1H), 6.81 (m, 2H), 5.22 (d, J=5.5 Hz, 1H), 4.41 (d, J=5.5 Hz, 2H), 2.88 (t, J=6 Hz, 2H), 1.65 (m, 1H), 0.71 (d, J=6.8 Hz, 6H); MS (ES⁺) 489.2 |
| 86c | —CO₂H (3) | —H | 85 | S, I-2 | ¹HNMR (DMSO-d₆.D₂O): δ 13.7 (bs, 1H), 8.32 (t, J=6 Hz, 1H), 7.63–7.17 (m, 7H), 6.72 (d, J=7.0 Hz, 1H), 2.81 (t, J=6 Hz, 2H), 1.53 (m, 1H), 0.64 (d, J=6.8 Hz, 6H); MS (ES⁺) 503.2 |
| 97a | ![ethylthiophene] (5) | —CH₃ | 96a | J | MS (ES⁺): 569.2 |

-continued

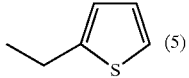

| Cpd. No. | —R | —R' | Starting From | Method Used | Analytical Data |
|---|---|---|---|---|---|
| 97b | —OBn (5) | —CH₃ | 91 | J | ¹HNMR (DMSO-d₆): δ 10.62 (s, 1H), 9.15 (bs, 2H), 8.82 (bs, 2H), 8.67 (t, J=6 Hz, 1H), 8.25 (d, J=2 Hz, 1H), 7.99 (dd, J=8.1 and 2 Hz, 1H), 7.69 (q, 8.8 and 16.2 Hz, 4H), 7.44 (m, 3H), 7.28 (m, 3H), 6.89 (d, J=7.7 Hz, 1H), 5.5 (s, 2H), 3.6 (s, 3H), 3.08 (t, J=5.8 and 6.8 Hz, 2H), 1.83 (m, 1H), 0.87 (d, J=6.8 Hz, 6H); MS (ES−) 577.2, (ES+) 579.3 |
| 98a | 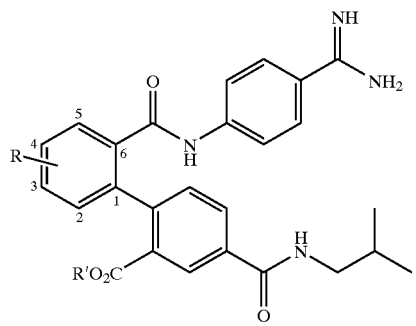 (5) | —H | 97a | I-2 | ¹HNMR (DMSO-d₆): δ 13.45 (bs, 1H), 9.06 (s, 2H), 8.99 (s, 2H), 8.51 (t, J=6 and 5 Hz, 1H), 7.99 (s, 1H), 7.62 (m, 5H), 7.47 (s, 1H), 7.36 (m, 2H), 6.99 (m, 4H), 4.26 (s, 2H), 3.02 (t, J=6.8 Hz, 2H), 1.80 (m, 1H), 0.86 (d, J=6.8 Hz, 6H); MS (ES−) 553.2, (ES+) 555.2 |
| 98b | —OBn (5) | —H | 97b | I-2 | ¹HNMR (DMSO-d₆): δ 13.52 (bs, 1H), 9.09 (bs, 2H), 9.04 (bs, 2H), 8.48 (t, J=6 Hz, 1H), 7.94 (s, 1H), 7.61 (m, 4H), 7.49 (s, 1H), 7.46 (s, 1H), 7.34 (m, 5H), 7.15 (d, J=8.2 Hz, 1H), 7.00 (d, J=8.2, 1H), 6.02 (d, J=7.4 Hz, 1H), 5.21 (s, 2H), 3.01 (t, J=6.8 Hz, 2H), 1.80 (m, 1H), 0.85 (d, J=6.8 Hz, 6H); MS (ES−) 563.2, (ES+) 565.2 |
| 98c | —OH (5) | —H | 98b | G | ¹HNMR (DMSO-d₆): δ 9.85 (s, 1H), 9.07 (s, 2H), 8.98 (s, 2H), 8.50 (t, J=6 and 5 Hz, 1H), 7.99 (d, J=1.7 Hz, 1H), 7.63 (m, 5H), 7.20 (t, J=8 Hz, 2H), 6.90 (d, J=7.9 Hz, 1H), 6.49 (d, J=7.2 Hz, 1H), 3.21 (t, J=6.8 Hz, 2H), 1.80 (m, 1H), 0.85 (d, J=6.8 Hz, 6H); MS (ES+) 475.2; (ES−) 473.2 |
| 103 | —OCH₃ (2) | —CH₃ | 102 | J | MS (ES+) 503.1 |
| 104 | —OCH₃ (2) | —H | 103 | I-2 | ¹HNMR (DMSO-d₆): δ 9.08 (bs, 2H), 8.80 (bs, 2H), 8.52 (t, J=6 Hz, 1H), 8.02 (s, 1H), 7.64 (m, 5H), 7.16 (m, 2H), 7.03 (m, 2H), 3.84 (s, 3H), 3.03 (t, J=6.8 Hz, 2H), 1.81 (m, 1H), 0.86 (d, J=6.8 Hz, 6H); MS (ES−) 487.3, (ES+) 489.3 |
| 110 | —OBn (2) | —CH₃ | 109 | J | MS (ES⁺): 579.3 |
| 111 | —OH (2) | —CH₃ | 110 | G | MS (ES⁺): 489.3 |
| 126 | —OC₂H₅ (3) —OBn (4) both | —CH₃ | 118b | J | Characterized in the next step |
| 127 | —OC₂H₅ (3) —OBn (4) both | —H | 126 | I-2 | ¹H NMR (DMSO-d₆): δ 9.06–9.09 (m, 3H), 8.56–8.50 (m, 1H), 8.05 (s, 1H), 7.71–7.58 (m, 6H), 7.55–7.28 (m, 6H), 7.10–7.01 (m, 1H), 6.63 (s, 1H), 5.19 (s, 2H), 4.05–3.97 (m, 2H), 3.05–3.01 (m, 2H), 1.86–1.77 (m, 1H), 1.29 (t, J=6.7 Hz, 3H), 0.87 (d, J=6.8 Hz, 6H) |
| 129 | —OCH₃ (3) —CH(OH)CH₃ (4) both | —H | 128 | I-2, S | ¹H NMR (DMSO-d₆): 13.64 (br s, 1H), 8.99 (br s, 2H), 8.49 (t, J=5.1 Hz, 1H), 7.99 (s, 1H), 7.73–7.56 (m, 5H), 7.32–6.83 (m, 5H), 6.50 (s, 1H), 5.17 (d, J=4.3 Hz, 1H), 5.01 (m, 1H), 3.75 (s, 3H), 3.03 (t, J=6.0 Hz, 1H), 1.81 (m, 1H), 1.32 (d, J=6.2 Hz, 3H), 0.86 (d, J=6.6 Hz, 6H); MS (ES⁺): 533.4 (100% M⁺¹) |

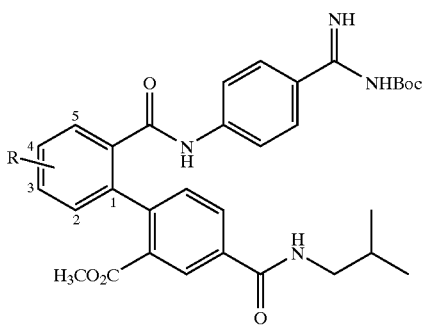

| Cpd. No. | —R (With Respect to Phenyl Ring) | Starting From | Method Used | Analytical Data |
|---|---|---|---|---|
| 81 | —CH=CH$_2$ (3) | 79a | R | MS (ES$^-$): 597.2 |
| 82 | —CH(OH)CH$_2$OH (3) | 81 | L | MS (ES$^{-1}$): 631.3 |
| 83 | —CH=O (3) | 82 | M | MS (ES$^+$): 601.3 |
| 84 | —CH$_2$OH (3) | 83 | K | MS (ES$^{-1}$): 601.4 |
| 85 | —CO$_2$H (3) | 83 | E | MS (ES$^{-1}$): 615.3 |
| 128 | —OCH$_3$ (3)<br>—CH=CH$_2$ (4) both | 124a | R | MS (ES$^+$): 629.4 |

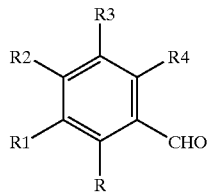

| Cpd. No. | —R | —R1 | —R2 | —R3 | —R4 | Starting From | Method Used | Analytical Data |
|---|---|---|---|---|---|---|---|---|
| 88 | —Br | —H | —H | —H | —OBn | 87 | X | $^1$HNMR (CDCl$_3$): δ 10.48 (s, 1 H), 7.42–7.25 (m, 7H), 7.00 (dd, J=2 and 7.4 Hz, 1H), 5.19 (s, 2H); IR (KBr) 1701, 1585, 1452, 1262, 1009 cm$^{-1}$; MS (ES+) 313.0, 315.0 (M + Na)$^+$ |
| 89 | —B(OH)$_2$ | —H | —H | —H | —OBn | 88 | T, U-1 | $^1$HNMR (CDCl$_3$): δ 10.61 (s, 1H), 7.65 (d, J=7.2 Hz, 1H), 7.60 (t, J=7.9 and 7.2 Hz, 1H), 7.41 (m, 5H), 7.19 (d, J=7.9 Hz, 1H), 6.81 bs, 2H), 5.20 (s, 2H) |
| 100 | —B(OH)$_2$ | —OCH$_3$ | —H | —H | —H | 99 | T, U-1 | $^1$HNMR (DMSO-d$_6$): δ 10.2 (s, 1H), 8.34 (s, 2H), 7.92 (d, J=9.4 Hz, 1H), 7.13 (m, 2H), 3.92 (s, 3H); MS (ES$^-$) 179.0 |
| 107 | —B(OH)$_2$ | —OBn | —H | —H | —H | 106 | T, U-1 | $^1$HNMR (DMSO-d6): δ 10.1 (s, 1H), 7.3–7.6 (m, 8H), 5.3 (m, 2H) |
| 114a | —Br | —H | —OCH$_3$ | —OH | —H | 113 | Z | MS (ES$^-$): 229.0 and 231.0 |
| 114b | —Br | —H | —OC$_2$H$_5$ | —OH | —H | 113 | Z-1 | MS (ES$^-$): 242.9 and 244.9 |
| 114c | —Br | —H | —OCH(CH$_3$)$_2$ | —OH | —H | 113 | Z-1 | MS (ES$^-$): 257.0 and 259.0 |
| 115a | —Br | —H | —OCH$_3$ | —OBn | —H | 114a | X | MS (ES$^+$): 321.0 and 323.0 |
| 115b | —Br | —H | —OC$_2$H$_5$ | —OBn | —H | 114b | X | MS (ES$^+$): 335.0 and 337.0 |
| 115c | —Br | —H | —OCH(CH$_3$)$_2$ | —OBn | —H | 114c | X | MS (ES$^+$): 349.0 and 351.0 |
| 115d | —Br | —H | ![structure: —O—C(=O)—O—C(CH$_3$)$_3$] | —OBn | —H | 115a | X, V-4, AH | Characterized in the next step |

-continued

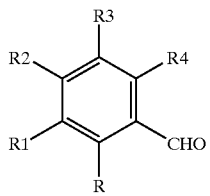

| Cpd. No. | —R | —R1 | —R2 | —R3 | —R4 | Starting From | Method Used | Analytical Data |
|---|---|---|---|---|---|---|---|---|
| 116a | —B(OH)$_2$ | —H | —OCH$_3$ | —OBn | —H | 115a | T, U-1 | Characterized in the next step |
| 116b | —B(OH)$_2$ | —H | —OC$_2$H$_5$ | —OBn | —H | 115b | T, U-1 | Characterized in the next step |
| 116c | —B(OH)$_2$ | —H | —OCH(CH$_3$)$_2$ | —OBn | —H | 115c | T, U-1 | Characterized in the next step |

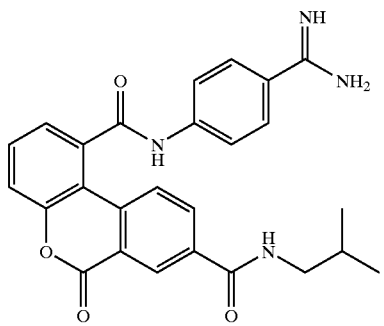

| Cpd. No. | Starting From | Method Used | Analytical Data |
|---|---|---|---|
| 112 | 111 | I-2 | $^1$HNMR (DMSO-d$_6$): δ 11.28 (s, 1H), 9.31 (s, 2H), 9.0 (s, 2H), 8.88 (d, J=11.30 Hz, 1H), 8.82 (d, J=1.88 Hz, 1H), 8.25 (d, J=1.88 Hz, 1H), 8.18 (d, J=1.88 Hz, 1H), 8.04 (d, J=8.47 Hz, 1H), 7.92 (m, J=24.48 Hz, 2H), 7.75 (m, J=15.82 Hz, 1H), 7.75 (m, J=8.28 Hz, 1H), 7.55 (m, J=8.66 Hz, 1H), 3.10 (m, J=12.6 Hz, 1H), 2.5 (m, J=3.5 Hz, 1H), 1.8 (m, J=19.9 Hz, 2H), 0.88 (m, J=6.6 Hz, 6H). |

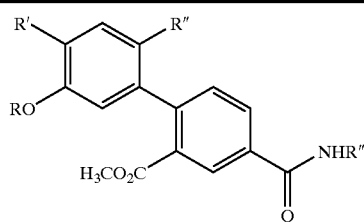

| Cpd. No. | —R | —R' | —R'' | —R''' | Starting From | Method Used | Analytical Data |
|---|---|---|---|---|---|---|---|
| 117a | —CH$_3$ | —OBn | —CHO | sec-butyl (CH$_3$CH$_2$CH(CH$_3$)—) | 3a + 116a | D-2 | MS (ES$^-$): 474.2 |

-continued

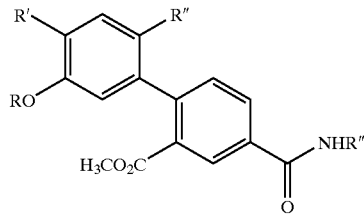

| Cpd. No. | —R | —R' | —R" | —R''' | Starting From | Method Used | Analytical Data |
|---|---|---|---|---|---|---|---|
| 117b | —C₂H₅ | —OBn | —CHO | CH(CH₃)CH₂CH₃ (sec-butyl) | 3a + 116b | D-2 | MS (ES⁻): 488.2 |
| 117c | —CH(CH₃)₂ | —OBn | —CHO | CH(CH₃)CH₂CH₃ | 3a + 116c | D-2 | MS (ES⁻): 502.3 |
| 117d | —CH₃ | —OBn | —CHO | CH₂CH(CH₃)₂ (isobutyl) | 3b + 116a | D-2 | ¹H NMR (CDCl₃): δ 9.56 (s, 1H), 8.34 (d, J=1.7 Hz, 1H), 8.5 (s, 1H), 8.01 (dd, J=7.9 and 1.9 Hz, 1H), 7.40 (m, 7H), 6.9 (s, 1H), 5.24 (m, 2H), 4.2 (m, 1H), 3.80 (s, 3H), 3.52 (s, 3H), 1.02 (d, J=7 Hz, 6H); MS (ES+): 484.3 (M + Na)⁺ |
| 117e | —CH₃ | —OBn | —CHO | CH₂CH(CH₃)CH₂CH₂CH₂CH₃ (2-methylhexyl) | 3c + 116a | D-2 | ¹HNMR (DMSO-d₆): δ 8.43 (d, J=1.65 Hz, 1H), 8.31 (d, J=8.66 Hz, 1), 8.12 (dd, J=1.69 Hz, 1H), 7.98 (s, 1H), 7.41 (d, J=8 and 10 Hz, 1H), 7.19 (d, J=8.1 Hz, 1H), 5.20 (dd, J=6.2 Hz, 1H), 3.98 (dd, J=7.75 Hz, 3H), 3.94 (s, 3H), 3.42 (m, 3H), 3.32 (m, 3H), 3.19 (s, 3H), 2.5 (m, 3H), 2.0 (s, 4H), 1.5 (m, 2H), 1.28 (m, 3H), 0.88 (d, J=6.59 Hz, 3H); MS (ES+): 664.3 |
| 117f | —CH₃ | —OBn | —CHO | CH₂CH₂CH₂CH₂CH₃ (pentyl) | 3d + 116a | D-2 | ¹H NMR (CDCl₃): δ 9.50 (s, 1H), 8.40 (d, J=2.1 Hz, 1H), 8.04 (dd, J=8.1, 2.1 Hz, 1H), 7.57 (s, 1H), 7.48 (m, 5H), 7.38 (m, 5H), 6.67 (s, 1H), 6.50 (broad, 1H), 5.27 (d, J=11.9 Hz, 1H), 5.22 (dd, J=11.7, 1H), 4.63, (m, 3H) 4.17 (m, 4H), 3.92 (s, 3H), 3.66 (s, 3H); MS (ES⁻): 488.3 |
| 117g | —CH₃ | —OBn | —CHO | CH₂CH₂CF₃ | 3f + 116a | D-2 | ¹H NMR (CDCl₃): δ 9.50 (s, 1H), 8.40 (d, J=2.1 Hz, 1H), 8.04 (dd, J=8.1, 2.1 Hz, 1H), 7.57 (s, 1H), 7.48 (m, 2H), 7.38 (m, 3H), 6.67 (s, 1H), 6.50 (broad, 1H), 5.27 (d, J=11.9 Hz, 1H), 5.22 (dd, J=11.7, 2H), 4.17 (m, 2H), 3.92 (s, 3H), 3.66 (s, 3H); MS (ES⁻): 500 |
| 117h | —CH₃ | —OBn | —CHO | CH₂CH₂CH₂CH₃ (butyl) | 3e + 116a | D-2 | ¹H NMR (CDCl₃): δ 9.56 (s, 1H), 8.34 (d, J=1.7 Hz, 1H), 8.01 (dd, J=7.9, 1.9 Hz, 1H), 7.57 (s, 1H), 7.50 (dd, J=7.2, 1.5, 2H), 7.40 (m, 4H), 6.67 (s, 1H), 6.21 (broad, 1H), 5.24 (d, J=2.8 Hz, 2H), 3.92 (s, 3H), 3.65 (s, 3H), 3.52 (m, 2H), 1.65 (m, 2H), 1.46 (m, 2H), 0.99 (t, J=7.3 Hz, 3H). |

-continued

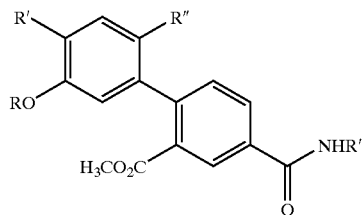

| Cpd. No. | —R | —R' | —R" | —R''' | Starting From | Method Used | Analytical Data |
|---|---|---|---|---|---|---|---|
| 117i | —CH$_3$ | —OBn | —CHO | CH$_2$-cyclopropyl | 3g + 116a | D-2 | $^1$H NMR (CDCl$_3$): δ 9.57 (s, 1H), 8.37 (d, J=1.9 Hz, 1H), 8.03 (dd, J=7.9, 1.9 Hz, 1H), 7.58 (s, 1H), 7.50 (d, J=7.2 Hz, 2H), 7.38 (m, 3H), 6.68 (s, 1H), 6.33 (broad, 1H), 5.26 (d, J=11.5 Hz, 1H), 5.21 (d, J=11.9 Hz, 1H), 3.92 (s, 3H), 3.65 (s, 3H), 3.37 (dd, J=7.2, 5.3 Hz, 2H), 1.09 (m, 1H), 0.60 (m, 2H), 0.32 (m, 2H); MS (ES$^+$): 474.2 |
| 117j | —CH$_3$ | —OBn | —CHO | cyclopentyl | 3h + 116a | D-2 | $^1$H NMR (CDCl$_3$): δ 9.55 (s, 1H), 8.32 (d, J=1.9 Hz, 1H), 8.00 (dd, J=1.9 and 7.9 Hz, 1H), 7.59–7.30 (m, 7H), 6.67 (s, 1H), 5.23 (m, 2H), 4.45 (q, J=7.0 Hz, 1H), 3.91 (s, 3H), 3.64 (s, 3H), 2.21–1.46 (m, 8 H); MS (ES$^+$): 510.3 (M + Na)$^+$ |
| 117k | —CH$_3$ | —OBn | —CHO | CH$_2$CH$_2$CH$_3$ (propyl) | 3i + 116a | D-2 | $^1$H NMR (CDCl$_3$): δ 9.56 (s, 1H), 8.35 (d, J=1.9 Hz, 1H), 8.02 (dd, J=1.9 and 7.9 Hz, 1H), 7.58–7.33 (m, 7H), 6.68 (s, 1H), 5.24 (m, 2H), 3.92 (s, 3H), 3.65 (s, 3H), 3.56 (m, 2H), 1.30 (t, J=7.2 Hz, 3H); MS (ES$^+$): 470.3 (M + Na)$^+$ |
| 117l | —CH$_3$ | —OBn | —CHO | CH$_2$CH(CH$_3$)CH$_2$CH$_3$ | 3j + 116a | D-2 | $^1$H NMR (CDCl$_3$): δ 9.56 (s, 1H), 8.35 (d, J=1.9 Hz, 1H), 8.02 (dd, J=1.9 and 7.9 Hz, 1H), 7.58–7.33 (m, 7H), 6.68 (s, 1H), 5.24 (m, 2H), 3.92 (s, 3H), 3.65 (s, 3H), 3.40 (m, 2H), 1.80–0.94 (m, 9H); MS (ES$^+$): 512.2 (M + Na)$^+$ |
| 117m | CH$_3$C(O)C(CH$_3$)$_3$ | —OBn | —CHO | CH$_2$CH(CH$_3$)CH$_2$CH$_3$ | 6a + 115d | D-6 | $^1$HNMR (DMSO-d$_6$): δ 9.73 (s, 1H), 8.86 (t, J=5.7 Hz, 1H), 8.52 (d, J=1.5 Hz, 1H), 8.22 (dd, J=8 and 2 Hz, 1H), 7.79 (s, 1H), 7.60 (d, J=8 Hz, 1H), 7.5(m, 5H), 7.22 (s, 1H), 5.35 (q, J=11 and 17 Hz, 1H), 3.70 (s, 3H), 3.23 (t, J=6.5 Hz, 2H), 1.98 (m, 1H), 1.3 (s, 9H), 1.01 (d, J=6.8 Hz, 6H); MS (ES$^+$): 546.4 |
| 118a | —CH$_3$ | —OBn | —CO$_2$H | CH$_2$CH(CH$_3$)CH$_2$CH$_3$ | 117a | E | MS (ES$^-$): 490.2 |
| 118b | —C$_2$H$_5$ | —OBn | —CO$_2$H | CH$_2$CH(CH$_3$)CH$_2$CH$_3$ | 117b | E | MS (ES$^-$): 504.2 |
| 118c | —CH(CH$_3$)$_2$ | —OBn | —CO$_2$H | CH$_2$CH(CH$_3$)CH$_2$CH$_3$ | 117c | E | MS (ES$^-$): 518.2 |

-continued

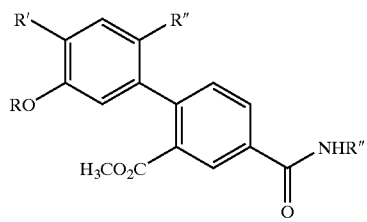

| Cpd. No. | —R | —R' | —R" | —R''' | Starting From | Method Used | Analytical Data |
|---|---|---|---|---|---|---|---|
| 118d | —CH$_3$ | —OBn | —CO$_2$H | isobutyl (—CH$_2$CH(CH$_3$)$_2$) | 117d | E | Characterized in the next step |
| 118e | —CH$_3$ | —OBn | —CO$_2$H | —CH$_2$CH(CH$_3$)CH$_2$CH$_2$CH$_3$ | 117e | E | MS (ES$^+$): 534.3 |
| 118f | —CH$_3$ | —OBn | —CO$_2$H | —(CH$_2$)$_5$CH$_3$ | 117f | E | MS (ES$^+$): 506.3 |
| 118g | —CH$_3$ | —OBn | —CO$_2$H | —CH$_2$CH$_2$CF$_3$ | 117g | E | Characterized in the next step |
| 118h | —CH$_3$ | —OBn | —CO$_2$H | —(CH$_2$)$_3$CH$_3$ | 117h | E | MS (ES$^{-1}$): 490.2 |
| 118i | —CH$_3$ | —OBn | —CO$_2$H | —CH$_2$-cyclopropyl | 117i | E | MS (ES$^{-1}$): 488.3 |
| 118j | —CH$_3$ | —OBn | —CO$_2$H | cyclopentyl | 117j | E | $^1$H NMR (DMSO-d$_6$): δ 12.19 (br s, 1H), 8.50 (d, J=7.4 Hz, 1H), 8.31 (d, J=1.9 Hz, 1H), 8.02 (dd, J=1.7 and 7.9 Hz, 1H), 7.58–7.29 (m, 7H), 6.71 (s, 1H), 5.17 (s, 2H), 4.27 (q, J=6.4 Hz, 1H), 3.80 (s, 3H), 3.57 (s, 3H), 1.97–1.51 (m, 8H) |
| 118k | —CH$_3$ | —OBn | —CO$_2$H | —CH$_2$CH$_2$CH$_3$ | 117k | E | MS (ES$^-$): 462.3 |
| 118l | —CH$_3$ | —OBn | —CO$_2$H | —CH$_2$CH(CH$_3$)CH$_2$CH$_3$ | 117l | E | $^1$H NMR (CDCl$_3$): δ 8.30 (d, J=1.9 Hz, 1H), 7.95 (dd, J=1.7 and 7.9 Hz, 1H), 7.66 (s, 1H), 7.52–7.27 (m, 6H), 6.62 (s, 1H), 6.49 (m, 1H), 5.21 (s, 2H), 3.88 (s, 3H), 3.61 (s, 3H), 3.38 (m, 2H), 1.79–0.94 (m, 9H); MS (ES$^-$): 504.4 |
| 118m | —C(O)C(CH$_3$)$_3$ | —OBn | —CO$_2$H | —CH$_2$CH(CH$_3$)CH$_2$CH$_3$ | 117m | E | Characterized in the next step |
| 119a | —CH$_3$ | —OBn | —CO$_2$MEM | —CH$_2$CH(CH$_3$)CH$_2$CH$_3$ | 118a | F | MS (ES$^-$): 578.3 |
| 119b | —C$_2$H$_5$ | —OBn | —CO$_2$MEM | —CH$_2$CH(CH$_3$)CH$_2$CH$_3$ | 118b | F | MS (ES$^-$): 592.3 |
| 119c | —CH(CH$_3$)$_2$ | —OBn | —CO$_2$MEM | —CH$_2$CH(CH$_3$)CH$_2$CH$_3$ | 118c | F | MS (ES$^-$): 606.3 |

-continued

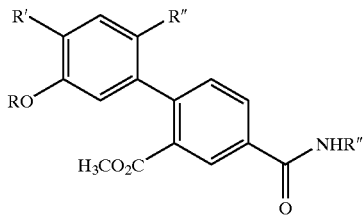

| Cpd. No. | —R | —R' | —R" | —R'" | Starting From | Method Used | Analytical Data |
|---|---|---|---|---|---|---|---|
| 119d | —CH₃ | —OBn | —CO₂MEM | isobutyl (CH(CH₃)CH₂–, with two CH₃) | 118d | F | MS (ES⁻): 564.2 |
| 119e | —CH₃ | —OBn | —CO₂MEM | 2-methylpentyl branched (CH₂CH(CH₃)CH₂CH₂CH₃ type) | 118e | F | MS (ES⁻): 620.1 |
| 119f | —CH₃ | —OBn | —CO₂MEM | n-hexyl (CH₂)₅CH₃ | 118f | F | MS (ES⁻): 592.3 |
| 119g | —CH₃ | —OBn | —CO₂MEM | —CH₂CH₂CF₃ | 118g | F | Characterized in the next step |
| 119h | —CH₃ | —OBn | —CO₂MEM | n-pentyl (CH₂)₄CH₃ | 118h | F | $^1$H NMR (CDCl₃): δ 8.32 (d, J=1.9 Hz, 1H), 7.96 (dd, J=7.9, 1.9 Hz, 1H), 7.68 (s, 1H), 7.50 (m, 2H), 7.35 (m, 4H), 6.62 (s, 1H), 6.33 (t, J=5.4 Hz, 1H), 5.24 (m, 4H), 3.88 (s, 3H), 3.63 (s, 3H), 3.46 (m, 6 H), 3.34 (s, 3H), 1.63 (m, 2H), 1.44 (m, 2H), 0.98 (t, J=7.3 Hz, 3H) |
| 119i | —CH₃ | —OBn | —CO₂MEM | —CH₂-cyclopropyl | 118i | F | $^1$H NMR (CDCl₃): δ 8.34 (d, J=1.9 Hz, 1H), 8.00 (dd, J=7.9, 2.1 Hz, 1H), 7.68 (s, 1H), 7.50 (m, 2H), 7.36 (m, 4H), 6.63 (s, 1H), 6.42 (broad, 1H), 5.24 (m, 4H), 3.89 (s, 3H), 3.64 (s, 3H), 3.45 (s, 3H), 3.35 (m, 5H), 1.07 (m, 1H), 0.58 (m, 2H), 0.30 (m, 2H) |
| 119j | —CH₃ | —OBn | —CO₂MEM | —CH₂-cyclopentyl | 118j | F | $^1$H NMR (DMSO-d₆): δ 8.55 (d, J=7.4 Hz, 1H), 8.39 (d, J=1.9 Hz, 1H), 8.10 (dd, J=1.7 and 7.9 Hz, 1H), 7.63–7.35 (m, 7H), 6.81 (s, 1H), 5.25–5.12 (m, 4H), 4.31 (q, J=6.4 Hz, 1H), 3.86 (s, 3H), 3.62 (s, 3H), 3.3 (s, 3H), 3.23 (s, 3H) 1.99–1.53 (m, 8H); MS (ES⁺): 614.3 (M + Na)⁺ |
| 119k | —CH₃ | —OBn | —CO₂MEM | —CH₂CH₃ | 118k | F | $^1$H NMR (DMSO-d₆): δ 8.70 (t, J=5.5 Hz, 1H), 8.35 (d, J=1.9 Hz, 1H), 8.05 (dd, J=1.7 and 7.9 Hz, 1H), 7.59–7.30 (m, 7H), 6.77 (s, 1H), 5.21–5.08 (m, 4H), 3.82 (s, 3H), 3.58 (s, 3H), 3.40–3.29 (m, 6H), 3.18 (s, 3H), 1.14 (t, J=7.2 Hz, 3H); MS (ES⁺): 574.3 (M + Na)⁺ |

-continued

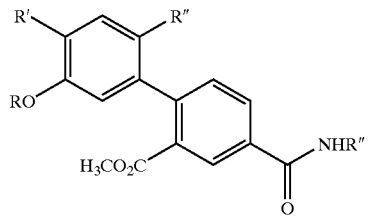

| Cpd. No. | —R | —R' | —R" | —R'" | Starting From | Method Used | Analytical Data |
|---|---|---|---|---|---|---|---|
| 119l | —CH$_3$ | —OBn | —CO$_2$MEM | CH$_3$CH(CH$_3$)CH$_2$CH$_3$ (2-methylbutyl) | 118l | F | $^1$H NMR (DMSO-d$_6$): δ 8.68 (t, J=5.8 Hz, 1H), 8.35 (d, J=1.9 Hz, 1H), 8.05 (dd, J=1.7 and 7.9 Hz, 1H), 7.63–7.33 (m, 7H), 6.77 (s, 1H), 5.22–5.08 (m, 4H), 3.82 (s, 3H), 3.58 (s, 3H), 3.39–3.22 (m, 6H), 3.18 (s, 3H), 1.56 (qui, J=7.0 Hz, 2H), 1.27 (m, 1H), 0.94–0.75 (m, 6H); MS (ES$^+$): 616.3 (M + Na)$^+$ |
| 119m | C(=O)C(CH$_3$)$_3$ | —OBn | —CO$_2$MEM | isobutyl (CH(CH$_3$)CH$_3$) | 118m | F | $^1$H NMR (DMSO-d$_6$): δ 8.72 (t, J=5.6 Hz, 1H), 8.38 (d, J=1.8 Hz, 1H), 8.70 (dd, J=1.8 and 8.1 Hz, 1H), 7.71 (s, 1H), 7.40 (m, 6H), 7.02 (s, 1H), 5.20 (m, 4H), 3.59 (s, 3H), 3.37 (m, 2H), 3.31 (m, 2H), 3.17 (s, 3H), 3.12 (t, J=6.5 Hz, 2H), 1.87 (m, 1H), 1.21 (s, 9H), 0.91 (d, J=6.8 Hz, 6H); MS (ES+): 650.4 and 672.3 (M + Na)$^+$ |
| 120a | —CH$_3$ | —OH | —CO$_2$MEM | 2-methylbutyl | 119a | G | MS (ES$^-$): 488.1 |
| 120b | —C$_2$H$_5$ | —OH | —CO$_2$MEM | 2-methylbutyl | 119b | G | MS (ES$^-$): 502.2 |
| 120c | —CH(CH$_3$)$_2$ | —OH | —CO$_2$MEM | 2-methylbutyl | 119c | G | MS (ES$^-$): 516.3 |
| 120d | —CH$_3$ | —OH | —CO$_2$MEM | isobutyl | 119d | G | MS (ES$^-$): 474.3 |
| 120e | —CH$_3$ | —OH | —CO$_2$MEM | 3-methylhexyl | 119e | G | MS (ES$^-$): 530.4 |
| 120f | —CH$_3$ | —OH | —CO$_2$MEM | n-hexyl | 119f | G | MS (ES$^-$): 502.3 |
| 120g | —CH$_3$ | —OH | —CO$_2$MEM | CH$_2$CH$_2$CF$_3$ | 119g | G | Characterized in the next step |
| 120h | —CH$_3$ | —OH | —CO$_2$MEM | n-pentyl | 119h | G | Characterized in the next step |
| 120i | —CH$_3$ | —OH | —CO$_2$MEM | cyclopropylmethyl | 119i | G | MS (ES$^-$): 486.3 |

-continued

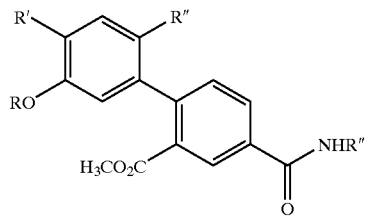

| Cpd. No. | —R | —R' | —R" | —R''' | Starting From | Method Used | Analytical Data |
|---|---|---|---|---|---|---|---|
| 120j | —CH₃ | —OH | —CO₂MEM | cyclopentylmethyl | 119j | G | MS (ES⁺): 524.3 (M + Na)⁺ |
| 120k | —CH₃ | —OH | —CO₂MEM | —CH₂CH₂CH₃ | 119k | G | MS (ES⁺): 484.2 (M + Na)⁺ |
| 120l | —CH₃ | —OH | —CO₂MEM | 2-ethylbutyl | 119l | G | MS (ES⁻): 502.3 |
| 120m | —OC(O)C(CH₃)₃ | —OH | —CO₂MEM | sec-butyl | 119m | G | ¹HNMR (DMSO-d₆): δ 10.83 (bs, 1H), 8.77 (t, J=5.6 Hz, 1H), 8.42 (d, J=1.8 Hz, 1H), 8.12 (dd, J=1.8 and 8.1 Hz, 1H), 7.68 (s, 1H), 7.41 (d, J=8.1 Hz, 1H), 6.73 (s, 1H), 5.21 (q, J=21 and 6 Hz, 2H), 3.65 (s, 3H), 3.48 (m, 2H), 3.37 (m, 2H), 3.24 (s, 3H), 3.18 (t, J=6.5 Hz, 2H), 1.94 (m, 1H), 1.39 (s, 9H), 0.97 (d, J=6.8 Hz, 6H); MS (ES+): 560.5 and 582.4 (M + Na)⁺, (ES⁻) 558.4 |
| 121a | —CH₃ | —OSO₂CF₃ | —CO₂MEM | sec-butyl | 120a | B-2 | MS (ES⁺): 644.1 (M + Na)⁺ |
| 121b | —C₂H₅ | —OSO₂CF₃ | —CO₂MEM | sec-butyl | 120b | B-2 | MS (ES⁺): 658.2 (M + Na)⁺ |
| 121c | —CH(CH₃)₂ | —OSO₂CF₃ | —CO₂MEM | sec-butyl | 120c | B-2 | MS (ES⁺): 672.2 (M + Na)⁺ |
| 121d | —CH₃ | —OSO₂CF₃ | —CO₂MEM | isobutyl | 120d | B-2 | ¹HNMR (DMSO-d₆): δ 8.43 (d, J=1.9 Hz, 1H), 8.31 (s, 1H), 8.12 (d, J=1.69 Hz, 1H), 7.98 (s, 1H), 7.41 (d, J=8.1 Hz, 1H), 7.19 (s, 1H), 5.20 (m, 2H), 3.98 (m, 1H), 3.94 (s, 3H), 3.42 (s, 3H), 3.19 (s, 3H), 2.50 (m, 2H), 1.08 (d, J=6.59, 6H); MS (ES+) 608.3 |
| 121e | —CH₃ | —OSO₂CF₃ | —CO₂MEM | 3-methylhexyl | 120e | B-2 | ¹HNMR (DMSO-d₆): δ 8.49 (s, 1H), 8.34 (d, J=1.8 Hz, 1H), 8.2 (d, J=1.8 Hz, 1H), 7.97 (s, 1H), 7.4 (d, J=7.8 Hz, 1H), 7.2 (s, 1H), 5.2 (q, J=6 and 10 Hz, 2H), 4.0 (m, 3H), 3.6 (s, 3H), 3.4 (m, 4H), 3.2 (s, 3H), 1.5 (m, 4H), 1.3 (m, 4H), 0.85 (m, 6H); MS (ES+): 664.3 |

-continued

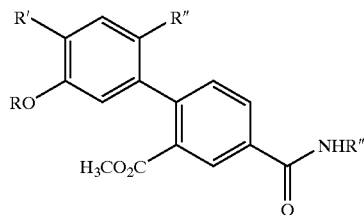

| Cpd. No. | —R | —R' | —R" | —R''' | Starting From | Method Used | Analytical Data |
|---|---|---|---|---|---|---|---|
| 121f | —CH₃ | —OSO₂CF₃ | —CO₂MEM | pentyl (CH₂)₄CH₃ | 120f | B-2 | ¹HNMR (DMSO-d₆): δ 8.83 (d, J=5.46, 1H), 8.55 (d, J=1.88 Hz, 1H), 8.23 (dd, J=1.88 Hz, 1H), 8.19 (s, 1H), 7.73 (d, J=7.93 Hz, 1H), 7.29 (s, 1H), 5.29 (dd, J=6.217 Hz, 2H), 4.06 (s, 3H), 3.71 (s, 2H), 3.54 (m, 5H), 2.62 (t, J=3.57 Hz, 3H), 1.66 (t, J=6.59 Hz, 2H), 1.42 (m, 6H), 0.99 (t, J=6.79 Hz, 3H); MS (ES+) 636.6 |
| 121g | —CH₃ | —OSO₂CF₃ | —CO₂MEM | CH₂CF₃ | 120g | B-2 | ¹H NMR (CDCl₃): δ 8.43 (d, J=1.9 Hz, 1H), 8.03 (dd, J=7.9 Hz, 2.1 Hz, 1H), 8.00 (s, 1H), 7.35 (d, J=7.9 Hz, 1H), 6.79 (m, 2H), 5.29 (d, J=6.2 Hz, 1H), 5.26 (d, J=6.2 Hz, 1H), 4.16 (m, 2H), 3.94 (s, 3H), 3.67 (s, 3H), 3.48 (m, 4H), 3.36 (s, 3H); MS (ES⁻): 646.3 |
| 121h | —CH₃ | —OSO₂CF₃ | —CO₂MEM | butyl (CH₂)₃CH₃ | 120h | B-2 | ¹H NMR (CDCl₃): δ 8.41 (s, 1H), 7.96 (d, J=8.3 Hz, 2H), 7.8 (m, 1H), 6.80 (s, 1H), 6.34 (m, 1H), 5.32 (m, 2H), 3.90 (s, 3H), 3.66 (s, 3H), 3.55 (m, 6H), 3.4 (s, 3H), 1.7 (m, 2H), 1.45 (m, 2H), 0.98 (t, J=7.3 Hz, 3H); MS (ES⁻): 620 |
| 121i | —CH₃ | —OSO₂CF₃ | —CO₂MEM | CH₂-cyclopropyl | 120i | B-2 | ¹H NMR (CDCl₃): δ 8.41 (d, J=2.1 Hz, 1H), 8.03 (dd, J=7.9, 1.9 Hz, 1H), 8.00 (s, 1H), 7.32 (d, J=7.9 Hz, 1H), 6.43 (t, J=4.9 Hz, 1H), 5.30 (q, J=6.0 Hz, 2H), 3.94 (s, 3H), 3.67 (s, 3H), 3.55 (m, 2H), 3.48 (m, 2H), 3.35 (m, 5H), 1.09 (m, 1H), 0.59 (m, 2H), 0.31 (m, 2H); MS (ES⁻): 618.4 |
| 121j | —CH₃ | —OSO₂CF₃ | —CO₂MEM | cyclopentyl | 120j | B-2 | ¹H NMR (CDCl₃): δ 8.35 (d, J=1.9 Hz, 1H), 8.00 (m, 2H), 7.31 (d, J=7.9 Hz, 1H), 6.77 (s, 1H), 6.27 (m, 1H), 5.28 (m, 2H), 4.44 (q, J=7.0 Hz, 1H), 3.94 (s, 3H), 3.66 (s, 3H), 3.57–3.45 (m, 4H), 3.35 (s, 3H), 2.19–1.45 (m, 8H); MS (ES⁺): 656.3 (M + Na)⁺ |
| 121k | —CH₃ | —OSO₂CF₃ | —CO₂MEM | CH₂CH₃ | 120k | B-2 | ¹H NMR (CDCl₃): δ 8.38 (s, 1H), 8.00 (m, 2H), 7.31 (d, J=7.9 Hz, 1H), 6.78 (s, 1H), 6.37 (m, 1H), 5.27 (m, 2H), 3.94 (s, 3H), 3.66 (s, 3H), 3.59–3.43 (m, 6H), 3.35 (s, 3H), 1.28 (t, J=7.2 Hz, 3H); MS (ES⁺): 616.3 (M + Na)⁺ |
| 121l | —CH₃ | —OSO₂CF₃ | —CO₂MEM | CH₂CH(CH₃)CH₃ (isobutyl) | 120l | B-2 | ¹H NMR (CDCl₃): δ 8.38 (s, 1H), 8.00 (m, 2H), 7.31 (d, J=7.9 Hz, 1H), 6.78 (s, 1H), 6.37 (m, 1H), 5.27 (m, 2H), 3.94 (s, 3H), 3.66 (s, 3H), 3.57–3.25 (m, 9H), 1.78–0.92 (m, 9H); MS (ES⁺): 658.4 (M + Na)⁺ |

-continued

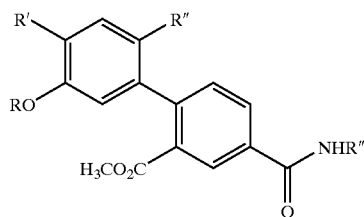

| Cpd. No. | —R | —R' | —R" | —R''' | Starting From | Method Used | Analytical Data |
|---|---|---|---|---|---|---|---|
| 121m | ![C(O)C(CH3)3] | —OSO$_2$CF$_3$ | —CO$_2$MEM | CH(CH$_3$)CH$_2$CH$_3$ (isobutyl-like) | 121m | B-2 | $^1$HNMR (DMSO-d$_6$): δ 8.75 (t, J=5.6 Hz, 1H), 8.45 (d, J=1.8 Hz, 1H), 8.11 (dd, J=1.8 and 8.1 Hz, 1H), 8.04 (s, 1H), 7.57 (s, 1H), 7.42 (d, J=8.1 Hz, 1H), 5.23 (q, J=21 and 6 Hz, 2H), 3.60 (s, 3H), 3.41 (m, 2H), 3.32 (m, 2H), 3.17 (s, 3H), 3.13 (t, J=6.5 Hz, 2H), 1.87 (m, 1H), 1.37 (s, 9H), 0.91 (d, J=6.8 Hz, 6H); MS (ES−): 690.4 |
| 122a | —CH$_3$ | —CH=CH$_2$ | —CO$_2$MEM | isopentyl | 121a | D-3 | Characterized in the next step |
| 122b | —C$_2$H$_5$ | —CH=CH$_2$ | —CO$_2$MEM | isopentyl | 121b | D-3 | MS (ES$^+$): 536.3 (M + Na)$^+$ |
| 122c | —CH(CH$_3$)$_2$ | —CH=CH$_2$ | —CO$_2$MEM | isopentyl | 121c | D-3 | MS (ES$^+$): 550.3 (M + Na)$^+$ |
| 122d | —CH$_3$ | —CH=CH$_2$ | —CO$_2$MEM | isobutyl | 121d | D-3 | MS (ES$^+$): 486.2 |
| 122e | —CH$_3$ | —CH=CH$_2$ | —CO$_2$MEM | 3-methylhexyl | 121e | D-3 | MS (ES$^+$): 564.5 (M + Na)$^+$ |
| 122f | —CH$_3$ | —CH=CH$_2$ | —CO$_2$MEM | n-pentyl | 121f | D-3 | MS (ES$^+$): 514.4 (M + Na)$^+$ |
| 122g | —CH$_3$ | —CH=CH$_2$ | —CO$_2$MEM | CH$_2$CH$_2$CF$_3$ | 121g | D-3 | Characterized in the next step |
| 122h | —CH$_3$ | —CH=CH$_2$ | —CO$_2$MEM | n-butyl | 121h | D-3 | Characterized in the next step |
| 122i | —CH$_3$ | —CH=CH$_2$ | —CO$_2$MEM | cyclopropylmethyl | 121i | D-3 | Characterized in the next step |
| 122j | —CH$_3$ | —CH=CH$_2$ | —CO$_2$MEM | cyclopentyl | 121j | D-3 | MS (ES−): 422.3 [(M-MeM)-1] |
| 122k | —CH$_3$ | —CH=CH$_2$ | —CO$_2$MEM | n-propyl(CH$_3$) | 121K | D-3 | MS (ES$^+$): 494.2 (M + Na)$^+$ |
| 122l | —CH$_3$ | —CH=CH$_2$ | —CO$_2$MEM | 3-pentyl | 121l | D-3 | MS (ES$^+$): 536.42 (M + Na)$^+$ |

-continued

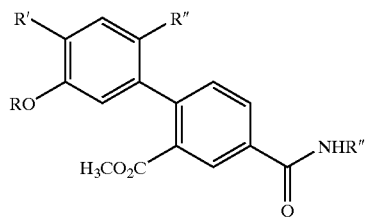

| Cpd. No. | —R | —R' | —R" | —R''' | Starting From | Method Used | Analytical Data |
|---|---|---|---|---|---|---|---|
| 122m | ![O=C-C(CH3)3 ketone group] | —CH=CH$_2$ | —CO$_2$MEM | isobutyl (CH(CH$_3$)CH$_2$CH$_3$) | 121m | D-3 | $^1$HNMR (DMSO-d$_6$): δ 8.73 (t, J=5.6 Hz, 1H), 8.43 (d, J=1.8 Hz, 1H), 8.11 (dd, J=1.8 and 8.1 Hz, 1H), 7.61 (s, 1H), 7.57 (s, 1H), 7.42 (d, J=8.1 Hz, 1H), 6.72 (dd, J=11 and 17.5 Hz, 1H), 6.03 (d, J=17.5 Hz, 1H), 5.52 (d, J=11 Hz, 1H), 5.19 (q, J=18 and 6 Hz, 2H), 3.60 (s, 3H), 3.41 (m, 2H), 3.32 (m, 2H), 3.18 (s, 3H), 3.13 (t, J=6.5 Hz, 2H), 1.89 (m, 1H), 1.38 (s, 9H), 0.91 (d, J=6.8 Hz, 6H); MS (ES−): 480.4 [(M-MEM)-1] |
| 123a | —CH$_3$ | —CH=CH$_2$ | CO$_2$H | sec-butyl | 122a | I-1 | MS (ES$^−$): 410.2 |
| 123b | —C$_2$H$_5$ | —CH=CH$_2$ | CO$_2$H | sec-butyl | 122b | I-1 | MS (ES$^−$): 424.2 |
| 123c | —CH(CH$_3$)$_2$ | —CH=CH$_2$ | CO$_2$H | sec-butyl | 122c | I-1 | MS (ES$^−$): 438.2 |
| 123d | —CH$_3$ | —CH=CH$_2$ | CO$_2$H | isobutyl (CH$_2$CH(CH$_3$)$_2$) | 122d | I-1 | MS (ES$^−$): 396.2 |
| 123e | —CH$_3$ | —CH=CH$_2$ | CO$_2$H | 3-methylhexyl branched | 122e | I-1 | MS (ES$^+$): 454.3 |
| 123f | —CH$_3$ | —CH=CH$_2$ | CO$_2$H | n-hexyl | 122f | I-1 | MS (ES$^+$): 426.3 |
| 123g | —CH$_3$ | —CH=CH$_2$ | CO$_2$H | CH$_2$CH$_2$CF$_3$ | 122g | I-1 | $^1$H NMR (DMSO): δ 12.37 (s, 1H), 9.35 (t, J=6.0 Hz, 1H), 8.42 (d, J=1.7 Hz, 1H), 8.10 (dd, J=8.1 Hz, 1.9 Hz, 1H), 8.06 (s, 1H), 7.40 (d, J=7.9 Hz, 1H), 6.98 (dd, J=17.9, 11.5 Hz, 1H), 6.77 (s, 1H), 5.89 (dd, J=17.7, 1.3 Hz, 1H), 5.37 (dd, J=11.1, 1.3 Hz, 1H), 4.14 (m, 2H), 3.84 (s, 3H), 3.61 (s, 3H); MS (ES$^−$): 436.3 |

US 6,936,719 B2

-continued

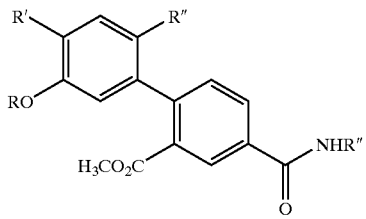

| Cpd. No. | —R | —R' | —R" | —R'" | Starting From | Method Used | Analytical Data |
|---|---|---|---|---|---|---|---|
| 123h | —CH$_3$ | —CH=CH$_2$ | CO$_2$H | (n-butyl) | 122h | I-1 | $^1$H NMR (DMSO): δ 8.66 (t, J=5.5 Hz, 1H), 8.35 (d, J=1.7 Hz, 1H), 8.05 (s, 1H), 8.03 (dd, J=8.1, 1.9 Hz, 1H), 7.34 (d, J=7.9 Hz, 1H), 6.98 (dd, J=17.9, 11.3 Hz, 1H), 6.75 (s, 1H), 5.88 (dd, J=17.7, 1.3, 1H), 5.36 (dd, J=11.3, 1.3 Hz, 1H), 3.84 (s, 3H), 3.60 (s, 3H), 3.30 (q, J=5.6 Hz, 2H), 1.52 (m, 2H), 1.33 (m, 2H), 0.96 (t, J=7.3 Hz, 3H); MS (ES$^-$): 410.4 |
| 123i | —CH$_3$ | —CH=CH$_2$ | CO$_2$H | (cyclopropylmethyl) | 122i | I-1 | $^1$H NMR (DMSO): δ 12.34 (s, 1H), 8.80 (t, J=6.1 Hz, 1H), 8.37 (d, J=1.9 Hz, 1H), 8.06 (dd, J=9.8, 7.9 Hz, 1H), 8.05 (s, 1H), 7.36 (d, J=7.9 Hz, 1H), 6.98 (dd, J=17.9, 11.3 Hz, 1H), 6.76 (s, 1H), 5.89 (dd, J=17.9, 1.5 Hz, 1H), 5.36 (dd, J=10.9, 1.5 Hz, 1H), 3.84 (s, 3H), 3.60 (s, 3H), 3.18 (t, 6.2, 2H), 1.06 (m, 1H), 0.45 (m, 2H), 0.25 (m, 2H); MS (ES$^-$): 408.4 |
| 123j | —CH$_3$ | —CH=CH$_2$ | CO$_2$H | (cyclopentyl) | 122j | I-1 | $^1$H NMR (DMSO): δ 12.31 (br s, 1H), 8.52 (d, J=7.3 Hz, 1H), 8.34 (d, J=1.7 Hz, 1H), 8.05 (m, 2H), 7.34 (d, J=7.9 Hz, 1H), 6.97 (dd, J=11.5 and 17.9 Hz, 1H), 6.74 (s, 1H), 5.89 (d, J=17.9 Hz, 1H), 5.37 (d, J=11.5 Hz, 1H), 4.27 (q, J=7.3 Hz, 1H), 3.84 (s, 3H), 3.60 (s, 3H), 1.98–1.50 (m, 8H); MS (ES$^-$): 422.3 |
| 123k | —CH$_3$ | —CH=CH$_2$ | CO$_2$H | (ethyl) | 122k | I-1 | $^1$H NMR (DMSO-d$_6$): δ 12.27 (br s, 1H), 8.58 (m, 1H), 8.23 (s, 1H), 7.92 (m, 2H), 7.47 (m, 1H), 7.22 (m, 1H), 6.84 (m, 1H), 6.63 (s, 1H), 5.76 (d, J=17.9 Hz, 1H), 5.24 (d, J=11.5 Hz, 1H), 3.71 (s, 3H), 3.47 (s, 3H), 1.02 (m, 3H); MS (ES$^-$): 382.2 |
| 123l | —CH$_3$ | —CH=CH$_2$ | CO$_2$H | (2-methylbutyl/isopentyl) | 122l | I-1 | $^1$H NMR (DMSO-d$_6$): δ 12.30 (br s, 1H), 8.52 (d, J=6.0 Hz, 1H), 8.33 (d, J=1.7 Hz, 1H), 8.02 (m, 2H), 7.31 (d, J=7.9 Hz, 1H), 6.95 (dd, J=11.5 and 17.9 Hz, 1H), 6.73 (s, 1H), 5.86 (d, J=17.9 Hz, 1H), 5.33 (d, J=11.5 Hz, 1H), 3.81 (s, 3H), 3.57 (s, 3H), 3.14 (m, 2H), 1.65 (m, 1H), 1.39 (m, 1H), 1.11 (m, 1H), 0.87 (m, 6H) |

-continued

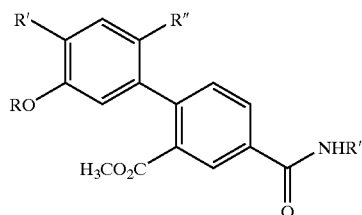

| Cpd. No. | —R | —R' | —R" | —R''' | Starting From | Method Used | Analytical Data |
|---|---|---|---|---|---|---|---|
| 123m | O=C(CH₃)-C(CH₃)₃ (ketone with tert-butyl) | —CH=CH₂ | —CO₂H | CH(CH₃)CH₂CH₃ (sec-butyl, via CH with two CH₃ branches shown) | 122m | I-1 | $^1$H NMR (DMSO-$d_6$): δ 12.81 (bs, 1H), 8.72 (t, J=5.6 Hz, 1H), 8.38 (d, J=1.8 Hz, 1H), 8.08 (dd, J=1.8 and 8.1 Hz, 1H), 7.61 (s, 1H), 7.57 (s, 1H), 7.39 (d, J=8 Hz, 1H), 6.72 (dd, J=11 and 17.5 Hz, 1H), 5.99 (d, J=17.5 Hz, 1H), 5.49 (d, J=11 Hz, 1H), 3.57 (s, 3H), 3.13 (t, J=6.5 Hz, 2H), 1.87 (m, 1H), 1.37 (s, 9H), 0.91 (d, J=6.8 Hz, 6H); MS (ES−): 480.3 |

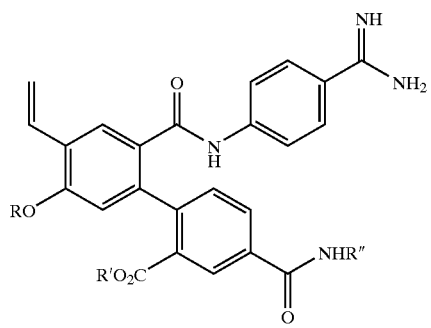

| Cpd. No. | —R | —R' | R" | Starting From | Method Used | Analytical Data |
|---|---|---|---|---|---|---|
| 124a | —CH₃ | —CH₃ | CH(CH₃)CH₂CH₃ | 123a | J | MS (ES⁺): 529.3 |
| 124b | —C₂H₅ | —CH₃ | CH(CH₃)CH₂CH₃ | 123b | J | MS (ES⁺): 543.3 |
| 124c | —CH(CH₃)₂ | —CH₃ | CH(CH₃)CH₂CH₃ | 123c | J | MS (ES⁺): 557.3 |
| 124d | —CH₃ | —CH₃ | CH₂CH(CH₃)₂ (isobutyl) | 123d | J | Characterized in the next step |
| 124e | —CH₃ | —CH₃ | CH₂CH(CH₃)CH₂CH₂CH₂CH₃ (2-methylhexyl-like branched chain) | 123e | J | MS (ES⁺): 571.6 |
| 124f | —CH₃ | —CH₃ | (CH₂)₅CH₃ (n-hexyl) | 123f | J | MS (ES⁺): 543.6 |

-continued

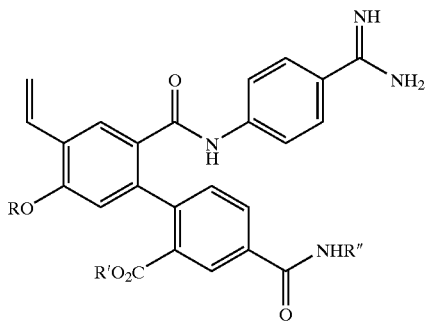

| Cpd. No. | —R | —R' | R" | Starting From | Method Used | Analytical Data |
|---|---|---|---|---|---|---|
| 124g | —CH$_3$ | —CH$_3$ | ~CF$_3$ | 123g | J | $^1$H NMR (DMSO): δ 10.62 (s, 1H), 9.35 (t, J=6.6 Hz, 1H), 9.20 (s, 2H), 8.90 (s, 2H), 8.30 (d, J= 1.9 Hz, 1H), 8.11 (dd, J=8.1, 1.9 Hz, 1H), 7.86 (s, 1H), 7.76 (m, 4H), 7.50 (d, J=8.1 Hz, 1H), 7.04 (dd, J=17.9, 11.5 Hz, 1H), 6.94 (s, 1H), 6.01 (dd, J=17.7, 1.3 Hz, 1H), 5.42 (dd, J=11.3, 1.3 Hz, 1H), 4.11 (m, 2H), 3.89 (s, 3H), 3.57 (s, 3H) |
| 124h | —CH$_3$ | —CH$_3$ | n-butyl CH$_3$ | 123h | J | $^1$H NMR (DMSO): δ 9.03 (broad, 3H), 8.49 (broad, 1H), 8.04 (s, 1H), 7.65 (m, 6 H), 6.99 (m, 2H), 6.61 (s, 1H), 5.90 (d, J=17.5 Hz, 1H), 5.35 (d, J=11.5 Hz, 1H), 3.78 (s, 3H), 3.20 (m, 2H), 1.46 (m, 2H), 1.28 (m, 2H), 0.87 (t, J=7.3 Hz, 3H) |
| 124i | —CH$_3$ | —CH$_3$ | cyclopropylmethyl | 123i | J | MS (ES$^+$): 527.4 |
| 124j | —CH$_3$ | —CH$_3$ | cyclopentyl | 123j | J | MS (ES$^+$): 541.4 |
| 124k | —CH$_3$ | —CH$_3$ | ethyl CH$_3$ | 123K | J | MS (ES$^+$): 501.3 |
| 124l | —CH$_3$ | —CH$_3$ | isobutyl CH$_3$/CH$_3$ | 123l | J | MS (ES$^+$): 543.3 |
| 124m | —C(=O)C(CH$_3$)$_3$ | —CH$_3$ | sec-butyl CH$_3$/CH$_3$ | 123m | J | $^1$HNMR (DMSO-d$_6$): δ 10.67 (s, 1H), 9.19 (bs, 2H), 8.88 (bs, 2H), 8.71 (t, J=5.6 Hz, 1H), 8.25 (d, J=1.8 Hz, 1H), 8.07 (dd, J=1.8 and 8.1 Hz, 1H), 7.73 (m, 4H), 7.65 (s, 1H), 7.50 (d, J=8 Hz, 1H), 7.45 (s, 1H), 6.73 (dd, J=11 and 17.5 Hz, 1H), 6.03 (d, J=17.5 Hz, 1H), 5.49 (d, J=11 Hz, 1H), 3.56 (s, 3H), 3.09 (t, J=6.5 Hz, 2H), 1.85 (m, 1H), 1.37 (s, 9H), 0.89 (d, J=6.8 Hz, 6H); MS (ES−): 597.3 and (ES$^+$): 599.5 |
| 125a | —CH$_3$ | —H | sec-butyl CH$_3$/CH$_3$ | 124a | I-2 | $^1$HNMR (DMSO): δ 13.40 (bs, 1H), 9.26 and 9.03 (2s, 4H), 8.53–8.49 (t, J=6 Hz, 1H), 8.02 (d, J=1.28 Hz, 1H), 7.71–7.53 (m, 6H), 7.0–6.9 (m, 2H), 6.5 (s, 1H), 5.89 (d, J=17.6 Hz, 1H), 5.33 (d, J=12.4 Hz, 1H), 3.77 (s, 3H), 3.04–2.99 (m, 2H), 1.85–1.75 (m, 1H), 0.86–0.84 (d, J=76.8 Hz, 6H); MS (ES$^+$): 515.3 |
| 125b | —C$_2$H$_5$ | —H | sec-butyl CH$_3$/CH$_3$ | 124b | I-2 | $^1$HNMR (DMSO): δ 9.17 and 8.92 (s, 3H), 8.67–8.63 (m, 1H), 8.28 (s, 1H), 7.95–7.93 (m, 1H), 7.83 (s, 1H), 7.73 (s, 5H), 7.29 (d, J=8.1 Hz, 1H), 7.02 (dd, J=17.7 Hz, 11.3 Hz, 1H), 6.82 (s, 1H), 6.00 (d, 17.7 Hz, 1H), 5.38 (d, 11.3 Hz, 1H), 4.14–4.06 (m, 2H), 3.11–3.04 (q, J=6.8 Hz, 2H), 1.89–1.80 (m, 1H), 1.35 (t, J=6.8 Hz, 3H), 0.88 (d, J=6.8 Hz, 6H); MS (ES$^+$): 529.2 |

-continued

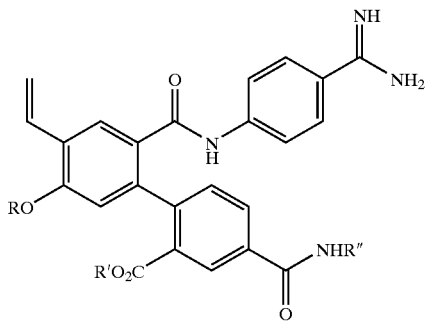

| Cpd. No. | —R | —R' | R" | Starting From | Method Used | Analytical Data |
|---|---|---|---|---|---|---|
| 125c | —CH(CH₃)₂ | —CH₃ | sec-butyl (CH(CH₃)CH₂CH₃) | 124c | I-2 | ¹HNMR (DMSO): δ 13.74 (s, 1H), 8.99 (s, 3H), 8.59–8.41 (m, 1H), 7.95 (s, 1H), 7.69 (s, 1H), 7.65–7.53 (m, 6H), 7.06-6.91 (m, 2H), 6.53 (s, 1H), 5.89 (d, J=17.7 Hz, 1H), 5.32 (d, J=11.5 Hz, 1H), 4.62–4.54 (m, 1H), 3.03–2.99 (m, 2H), 1.87–1.71 (m, 1H), 1.25 (d, J=6.1 Hz, 6H), 0.85 (d, J=6.8 Hz, 6H); MS (ES⁻): 541.2 |
| 125d | —CH₃ | —H | isobutyl (CH₂CH(CH₃)₂) | 124d | I-2 | ¹HNMR (DMSO-d₆): δ 8.9 (d, J=33.74, 4H), 8.08 (d, J=7.91 Hz, 1H), 7.81 (s, 1H), 7.51 (s, 1H), 7.41 (s, 4H), 6.78 (s, 1H), 6.3 (s, 2H), 5.70 (d, J=7.78 Hz, 1H), 5.15 (d, J=11.8 Hz, 2H),) 3.82 (m, J=20.34 Hz, 2H), 3.56 (bs, 3H) 0.92 (d, 6H); MS (ES+) 501.3 |
| 125e | —CH₃ | —H | 2-methylpentyl branched | 124e | I-2 | ¹HNMR (DMSO-d₆): δ 9.05 (s, 2H), 8.85 (s, 2H), 7.96 (d, J=9.04 Hz, 1H), 7.88 (s, 1H), 6,86 (m, J=17.8 Hz, 3H), 7.62 (m, 1H), 7.24 (d, J=7.8 Hz, 1H), 6.95 (d, J=7.8 Hz, 1H), 7.45 (m, J=28.63 Hz, 5H), 7.55 (s, 1H), 5.75 (d, J=17.5 Hz, 1H); 5.61 (d, J=11.11, 1H) 3.61 (s, 3H) 1.30 (bs, 3H) 1.05 (s, 4H) 0.66 (m, 6H); MS (ES+) 555.3 (100% M⁺¹) |
| 125f | —CH₃ | —H | n-pentyl | 124f | I-2 | ¹H NMR (DMSO-d₆): δ 12.7 (bs, 1H), 9.01 (bs, 2H), 8.87 (bs, 2H), 8.36 (t, J=6 Hz, 1H), 7.83 (s, 1H), 7.44 (m, 6H), 6.75 (m, 2H), 6.31 (d, J=2.2 Hz, 1H), 5.7 (d, J=17 Hz, 1H), 5.1 (d, J=11 Hz, 1H), 3.5 (s, 3H), 2.84 (m, 2H), 1.3 (m, 2H), 1.1 (m, 4H), 0.7 (m, 3H); MS (ES+) 529.4 |
| 125g | —CH₃ | —H | CH₂CF₃ | 124g | I-2 | ¹H NMR (DMSO): δ 9.22 (broad, 1H), 9.09 (s, 2H), 8.9 (s, 2H), 8.18 (s, 1H), 7.80 (m, 2H), 7.66 (m, 4H), 7.16 (s, 1H), 7.00 (dd, J=17.7, 11.1 Hz, 1H), 6.70 (s, 1H), 5.94 (d, J=17.7 Hz, 1H), 5.37 (d, J=10.9 Hz, 1H), 4.07 (m, 2H), 3.81 (s, 3H); MS (ES⁻) 539.3 |
| 125h | —CH₃ | —H | n-butyl | 124h | I-2 | ¹H NMR (DMSO): δ 9.03 (bs, 4H), 8.49 (bs, 1H), 8.04 (s, 1H), 7.65 (m, 6 H), 6.99 (m, 2H), 6.61 (s, 1H), 5.90 (d, J=17.5 Hz, 1H), 5.35 (d, J=11.5 Hz, 1H), 3.78 (s, 3H), 3.20 (m, 2H), 1.46 (m, 2H), 1.28 (m, 2H), 0.87 (t, J=7.3 Hz, 3H); MS (ES⁺) 515.4 |
| 125i | —CH₃ | —H | cyclopropylmethyl | 124i | I-2 | ¹H NMR (DMSO): δ 8.86 (s, 2H), 8.78 (s, 2H), 8.44 (broad, 1H), 7.89 (s, 1H), 7.53 (m, 2H), 7.43 (m, 4H), 6.86 (s, 1H), 6.78 (dd, J=17.5, 11.3 Hz, 1H), 6.44 (s, 1H), 5.71 (d, J=17.5 Hz, 1H), 5.14 (d, J=11.1 Hz, 1H), 3.59 (s, 3H), 2.89 (m, 2H), 0.79 (m, 1H), 0.20 (m, 2H), 0.01 (m, 2H); MS (ES⁻) 513.4 |
| 125j | —CH₃ | —H | cyclopentylmethyl | 124j | I-2 | ¹H NMR (DMSO): δ 13.14 (br s, 1H), 8.84 (m, 3H), 8.12 (d, J=7.3 Hz, 1H), 7.79 (s, 1H), 7.40 (m, 8H), 6.74 (m, 2H), 6.33 (s, 1H), 5.66 (d, J=19.2 Hz, 1H), 5.10 (d, J=11.7 Hz, 1H), 3.94 (m, 1H), 3.54 (s, 3H), 1.66–0.93 (m, 8H); MS (ES⁺) 527.4 |

-continued

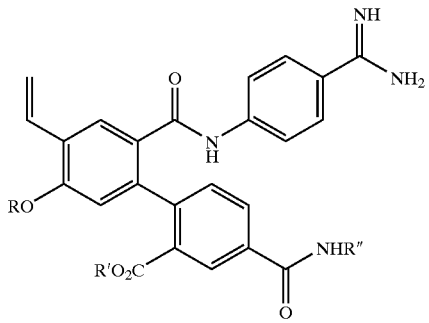

| Cpd. No. | —R | —R' | R" | Starting From | Method Used | Analytical Data |
|---|---|---|---|---|---|---|
| 125k | —CH$_3$ | —H | CH$_2$CH$_2$CH$_3$ | 124k | I-2 | $^1$H NMR (DMSO): δ 9.25 (m, 4H), 8.73 (t, J=5.7 Hz, 1H), 8.28 (s, 1H), 7.86 (m, 7H), 6.84 (s, 1H), 6.10 (d, J=17.7 Hz, 1H), 5.55 (d, J=11.3 Hz, 1H), 3.99 (s, 3H), 3.43 (qui, J=6.2 Hz, 2H), 1.28 (t, J=7.2 Hz, 3H); MS (ES$^+$): 487.2 |
| 125l | —CH$_3$ | —H | CH$_2$CH(CH$_3$)CH$_2$CH$_3$ (with CH$_3$) | 124l | I-2 | $^1$H NMR (DMSO): δ 8.91 (m, 4H), 8.38 (t, J=5.5 Hz, 1H), 7.96 (s, 1H), 7.53 (m, 5H), 6.86 (m, 2H), 6.52 (s, 1H), 5.77 (d, J=17.7 Hz, 1H), 5.21 (d, J=11.5 Hz, 1H), 3.65 (s, 3H), 2.94 (m, 1H), 1.57–0.56 (m, 11H); MS (ES$^+$): 529.3 |
| 125m | —CH$_3$ | —H | CH$_2$C(O)C(CH$_3$)$_3$ | 124m | I-2 | $^1$HNMR (DMSO-d$_6$): δ 10.07 (bs, 1H), 9.05 (bs, 2H), 8.98 (bs, 2H), 8.49 (t, J=5.6 Hz, 1H), 7.96 (s, 1H), 7.62 (m, 5 H), 7.06 (s, 1H), 7.03 (s, 1H), 6.94 (dd, J=11 and 18 Hz, 1H), 5.78 (d, J=18 Hz, 1H), 5.26 (d, J=11 Hz, 1H), 3.02 (t, J=5.7 Hz, 2H), 1.81 (m, 1H), 0.85 (d, J=6.8 Hz, 6H); MS (ES–): 499.2 and (ES$^+$) 501.3 |

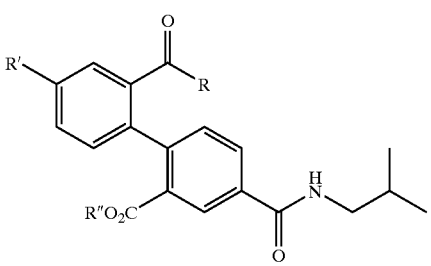

| Cpd. No. | —R | —R' | —R" | Starting From | Method Used | Analytical Data |
|---|---|---|---|---|---|---|
| 133a | N-methylpiperazinyl-tetrahydropyrimidinyl | —H | —CH$_3$ | 132 | A-5 | MS (ES$^+$): 506.4 |
| 133b | (methylamino)phenyl-imidazolinyl | —H | —CH$_3$ | 132 | J | MS (ES$^+$): 499.3 |
| 133c | N-methyl-(2-trifluoromethylbenzyl)amino | —H | —CH$_3$ | 132 | A-5 | Characterized in the next step |

-continued

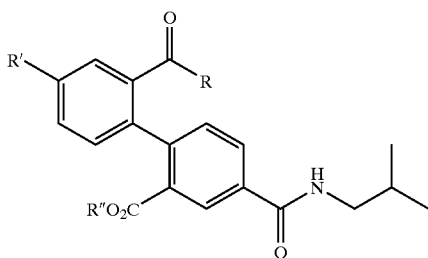

| Cpd. No. | —R | —R' | —R" | Starting From | Method Used | Analytical Data |
|---|---|---|---|---|---|---|
| 133d | [4-CF3-phenyl-NH-CH2-] | —H | —CH3 | 132 | A-5 | Characterized in the next step |
| 133e | [4-CF3-benzyl-NH-CH2-] | —H | —CH3 | 132 | A-5 | Characterized in the next step |
| 133f | [3-CF3-benzyl-NH-CH2-] | —H | —CH3 | 132 | A-5 | Characterized in the next step |
| 133g | [3-CF3-phenyl-NH-CH2-] | —H | —CH3 | 132 | A-5 | Characterized in the next step |
| 133h | [3-F-phenyl-NH-CH2-] | —H | —CH3 | 132 | A-5 | Characterized in the next step |
| 133i | [morpholino-CH2-] | —H | —CH3 | 132 | A-5 | Characterized in the next step |
| 133j | [2-F-phenyl-NH-CH2-] | —H | —CH3 | 132 | A-5 | Characterized in the next step |
| 133k | [4-(2-pyrimidinyl)piperazin-1-yl-CH2-] | —H | —CH3 | 132 | J | MS (ES+): 502.3 |
| 133l | [5-(indol-NH-CH2-)] | —H | —CH3 | 132 | J | MS (ES+): 470.2 |
| 133m | [cyclohexyl-NH-CH2-] | —H | —CH3 | 132 | J | MS (ES+): 437.3 |

-continued

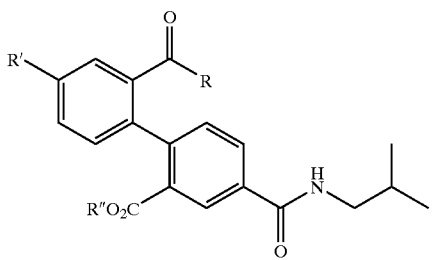

| Cpd. No. | —R | —R' | —R" | Starting From | Method Used | Analytical Data |
|---|---|---|---|---|---|---|
| 133n | [2-(methylamino)-6-methoxybenzothiazole] | —H | —CH₃ | 132 | J | MS (ES⁺): 518.2 |
| 133o | [4-methyl-1-(pyridin-2-yl)piperazine] | —H | —CH₃ | 132 | J | MS (ES⁺): 501.3 |
| 133p | [6-(methylamino)-1H-indazole] | —H | —CH₃ | 132 | J | MS (ES⁺): 469.1 |
| 133q | [5-(methylamino)-1H-indazole] | —H | —CH₃ | 132 | J | MS (ES⁻): 469.1; MS (ES⁺): 471.2 |
| 133r | [4-aminobenzyl methylamine] | —H | —CH₃ | 132 | A-5 | Characterized in the next step |
| 133s | [2-(methylamino)benzyl alcohol] | —H | —CH₃ | 132 | A-5 | MS (ES⁺): 483.2 (M + Na) |
| 133u | [2-(methylamino)pyridine] | —H | —CH₃ | 132 | A-5 | MS (ES⁺): 432.2 |
| 133v | [4-(methylamino)pyridine] | —H | —CH₃ | 132 | A-5 | MS (ES⁺): 432.2 |
| 133w | [3-(methylamino)phenol] | —H | —CH₃ | 132 | A-5 | MS (ES⁺): 447.2 |
| 133x | [2-(methylaminomethyl)pyridine] | —H | —CH₃ | 132 | A-5 | Characterized in the next step |

-continued

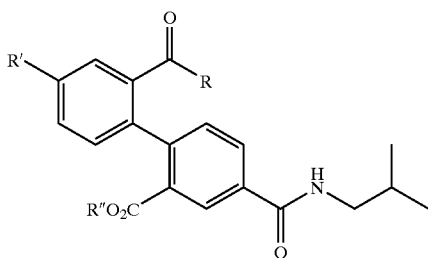

| Cpd. No. | —R | —R' | —R" | Starting From | Method Used | Analytical Data |
|---|---|---|---|---|---|---|
| 133y | NH-CH2-(3-pyridyl) | —H | —CH3 | 132 | A-5 | MS (ES+): 446.3 |
| 133z | NH-CH2-(4-pyridyl) | —H | —CH3 | 132 | A-5 | MS (ES+): 446.2 |
| 133aa | NH-(4-(2-hydroxyethyl)phenyl) | —H | —CH3 | 132 | A-4 | MS (ES+): 475.3 |
| 133ab | NH-(3,4-dihydroxymethylphenyl) | —H | —CH3 | 132 | J | MS (ES+): 499.3 (M + Na) |
| 133ac | NH-(1-methylbenzimidazol-2-yl) | —H | —CH3 | 132 | A-4 | MS (ES−): 483.2; MS (ES+): 485.2 |
| 133ad | NH-(4-(imidazol-1-yl)phenyl) | —H | —CH3 | 132 | A-4 | MS (ES−): 497.2; MS (ES+): 495.2 |
| 133ae | NH-CH2-(1H-benzimidazol-2-yl) | —H | —CH3 | 132 | A-4 | MS (ES−): 483.2; MS (ES+): 485.2 |
| 133af | NH-(4-acetoxyphenyl) | —H | —CH3 | 132 | J | MS (ES+): 511.3 (M + Na)+; MS (ES−): 487.3 |
| 133ag | NH-(4-hydroxy-3-methylphenyl) | —H | —CH3 | 132 | J | MS (ES−): 451.3 |
| 133ai | NH-(2-NHBoc-1H-benzimidazol-5-yl) | —H | —CH3 | 132 | J | MS (ES−): 584.4 |

-continued

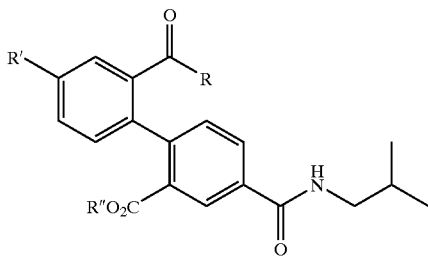

| Cpd. No. | —R | —R' | —R" | Starting From | Method Used | Analytical Data |
|---|---|---|---|---|---|---|
| 134a | N-methylpiperazine-tetrahydropyrimidine | —H | —H | 133a | I-2 | $^1$HNMR (DMSO-$d_6$): δ 13.13 (bs, 1H), 8.76 (t, J=6 and 5Hz, 1H), 8.32 (m, 2H), 8.02 (dd, J=1.9 and 8.1 Hz, 1H), 7.42 (m, 4H), 7.25 (m, 1H), 3.62–3.19 (m, 12H), 3.11 (t, J=6.8 Hz, 2H), 1.87 (m, 1H), 1.76 (m, 2H), 0.90 (d, J=6.8 Hz, 6H); MS (ES−) 490.3; (ES+) 492.3 |
| 134b | N-methyl-4-(imidazolinyl)aniline | —H | —H | 133b | I-2 | $^1$HNMR (DMSO-$d_6$): δ 13.82 (bs, 1H), 10.57 (bs, 2H), 8.50 (t, J=6 and 5 Hz, 1H), 7.99 (d, J=1.5 Hz, 1H), 7.83 (s, 1H), 7.8 (s, 1H), 7.59 (m, 4H), 7.46 (m, 2H), 7.03 (m, 1H), 6.92 (d, J=7.9 Hz, 1H), 3.89 (s, 4H), 3.02 (t, J=6.8 Hz, 2H), 1.81 (m, 1H), 0.8 (d, J=6.8 Hz, 6H); MS (ES$^-$): 483.3; MS (ES$^+$): 485.4 |
| 134c | N-methyl-2-(trifluoromethyl)benzylamine | —H | —H | 133c | I-2 | $^1$HNMR (DMSO-$d_6$): δ 8.71 (t, J=5.5 Hz, 1H), 8.40 (t, J=5.3 Hz, 1H), 8.30 (s, 1H), 8.00 (d, J=7.8 Hz, 1H), 7.63 (d, J=4.3 Hz, 2H), 7.40 (d, J=7.4 Hz, 4H), 7.27 (d, J=8.1 Hz, 1H), 7.18 (s, 1H), 6.91 (d, J=7.1 Hz, 1H), 4.42 (b, 2H), 3.13 (t, J=6.5 Hz, 2H), 1.93 (m, 1H), 0.91 (d, J=6.8 Hz, 6H); MS (ES−) 497.3 |
| 134d | N-methyl-4-(trifluoromethyl)aniline | —H | —H | 133d | I-2 | $^1$HNMR (DMSO-$d_6$): δ 10.45 (s, 1H), 8.63 (s, 1H), 8.27 (s, 1H), 7.93 (d, J=8.1 Hz, 1H), 7.67 (t, J=6.8 Hz, 2H), 7.55 (m, 2H), 7.27 (m 3H), 7.12 (m, 2H), 3.06 (t, J=6 Hz, 2H), 1.82 (m, 1H), 0.86 (d, J=6.8 Hz, 6H); MS (ES−) 483.3 |
| 134e | N-methyl-4-(trifluoromethyl)benzylamine | —H | —H | 133e | I-2 | $^1$HNMR (DMSO-$d_6$): δ 12.92 (bs, 1H), 8.71 (t, J=5.8 Hz, 1H), 8.49 (t, J=6.2 Hz, 1H), 8.32 (s, 1H), 8.01 (d, J=7.8 Hz, 1H), 7.52 (m, 5H), 7.27 (d, J=7.9 Hz, 1H), 7.18 (m, 1H), 7.08 (d, J=8.2 Hz, 2H), 4.32 (d, J=4.2 Hz, 2H), 3.12 (t, J=6.5 Hz, 2H), 1.88 (m, 1H), 0.91 (d, J=6.8 Hz, 6H); MS(ES−) 498.2 |
| 134f | N-methyl-3-(trifluoromethyl)benzylamine | —H | —H | 133f | I-2 | $^1$HNMR (DMSO-$d_6$): δ 8.66 (t, J=5.7 Hz, 1H), 8.27 (s, 1H), 7.92 (d, J=8.1 Hz, 1H), 7.45 (m, 7H), 7.18 (m, 3H), 4.32 (d, J=5.9 Hz, 2H), 3.12 (t, J=6 Hz, 2H), 1.89 (m, 1H), 0.91 (d, J=6.8 Hz, 6H); MS (ES−) 497.2 |
| 134g | N-methyl-3-(trifluoromethyl)aniline | —H | —H | 133g | I-2 | $^1$HNMR (DMSO-$d_6$): δ 13.1 (s, 1H), 9.58 (s, 1H), 8.65 (s, 1H), 8.29 (s, 1H), 7.98 (d, J=5.9 Hz, 1H), 7.75 (d, J=5.2 Hz, 2H), 7.30 (d, J=8 Hz, 2H), 7.12 (d, J=12.0 Hz, 1H), 7.12 (m, 4H), 3.06 (t, J=6 Hz, 2H), 1.85 (m, 1H), 0.86 (d, J=6.8 Hz, 6H); MS (ES−) 483.2 |
| 134h | N-methyl-3-fluoroaniline | —H | —H | 133h | I-2 | $^1$HNMR (DMSO-$d_6$): δ 10.31 (s, 1H), 8.65 (t, J=6.2 Hz, 1H), 8.31 (s, 1H), 7.98 (d, J=7.9 Hz, 1H), 7.66 (m, 1H), 7.53 (m, 3H), 7.27 (m, 4H), 6.85 (m, 1H), 3.09 (t, J=6.5 Hz, 2H), 1.86 (m, 1H), 0.89 (d, J=6.8 Hz, 6H); MS (ES−) 433.1 (M$^{-1}$) |
| 134i | morpholine | —H | —H | 133i | I-2 | $^1$HNMR (DMSO-$d_6$): δ 8.71 (t, J=5.7 Hz, 1H), 8.31 (s, 1H), 8.01 (d, J=7.9 Hz, 1H), 7.46 (m, 2H), 7.39 (m, 2H), 7.24 (s, 1H), 3.38 (b, 8H), 3.11 (t, J=6.5 Hz, 2H), 1.86 (m, 1H), 0.91 (d, J=6.8 Hz, 6H); MS (ES−) 409.3 |

-continued

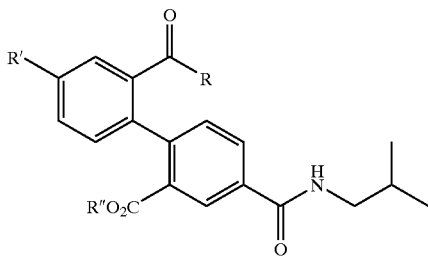

| Cpd. No. | —R | —R' | —R" | Starting From | Method Used | Analytical Data |
|---|---|---|---|---|---|---|
| 134j | (2-fluoro-N-methylanilino) | —H | —H | 133j | I-2 | ¹HNMR (DMSO-d$_6$): δ 9.61 (s, 1H), 8.67 (t, J=5.5 Hz, 1H), 8.32 (s, 1H), 7.98 (d, J=7.9 Hz, 1H), 7.71 (m, 2H), 7.54 (m, 2H), 7.29 (d, J=7.9 Hz, 1H), 7.04 (m, 4H), 3.10 (t, J=6.5 Hz, 2H), 1.86 (m, 1H), 0.89 (d, J=6.8 Hz, 6H); MS (ES−) 433.3 |
| 134k | 4-(pyrimidin-2-yl)piperazin-1-yl | —H | —H | 133k | I-2 | ¹HNMR (DMSO-d$_6$): δ 8.59 (t, J=6 and 5 Hz, 1H), 8.3 (d, J=5 Hz, 2H), 8.18 (s, 1H), 7.86 (d, J=8 Hz, 1H), 7.36 (m, 5H), 6.6 (t, J=4.7 Hz, 1H), 4.0 (m, 1H), 3.75 (m, 2H), 3.37 (m, 5H), 3.07 (t, J=6.8 Hz, 2H), 1.81 (m, 1H), 0.85 (d, J=6.8 Hz, 6H) |
| 134l | (1H-indol-5-yl)methylamino | —H | —H | 133l | I-2 | ¹HNMR (DMSO-d$_6$): δ 10.92 (bs, 1H), 8.55 (t, J=6 and 5 Hz, 1H), 8.14 (s, 1H), 7.76 (d, J=7 Hz, 1H), 7.68 (m, 1H), 7.62 (m, 1H), 7.45 (m, 2H), 7.24 (t, J=2.6 Hz, 1H), 7.19 (s, 1H), 7.15 (s, 1H), 7.10 (m, 2H), 6.95 (dd, J=1.5 and 8.7 Hz, 1H), 6.28 (s, 1H), 3.04 (t, J=6.8 Hz, 2H), 1.82 (m, 1H), 0.86 (d, J=6.8 Hz, 6H); MS (ES−) 454.3; (ES+) 456.3 |
| 134m | cyclohexyl-methylamino | —H | —H | 133m | I-2 | ¹HNMR (DMSO-d$_6$): δ 13.30 (bs, 1H), 8.62 (t, J=6 and 5 Hz, 1H), 8.18 (s, 1H), 7.87 (d, J=7.9 Hz, 1H), 7.42 (m, 3H), 7.09 (m, 2H), 3.03 (m, 1H), 3.1 (t, J=6.8 Hz, 2H), 1.86 (m, 1H), 1.4 (m, 4H), 1.09 (m, 1H), 0.89 (d, J=6.8 Hz, 6H); MS (ES−) 421.2; (ES+) 423.2 |
| 134n | (6-methoxybenzothiazol-2-yl)methylamino | —H | —H | 133n | I-2 | ¹HNMR (DMSO-d$_6$): δ 15.89 (bs, 1H), 8.56 (t, J=6 and 5 Hz, 1H), 8.06 (s, 1H), 7.67 (m, 2H), 7.54 (d, J=8.8 Hz, 1H), 7.48 (m, 4H), 7.05 (m, 1H), 6.96 (m, 2H), 3.77 (s, 3H), 3.03 (t, J=6.8 Hz, 2H), 1.81 (m, 1H), 0.84 (d, J=6.8 Hz, 6H); MS (ES−) 502.3; (ES+) 504.3 |
| 134o | 4-(pyridin-2-yl)piperazin-1-yl | —H | —H | 133o | I-2 | ¹HNMR (DMSO-d$_6$): δ 13.07 (bs, 1H), 8.63 (t, J=6 and 5 Hz, 1H), 8.26 (s, 1H), 8.05 (d, J=4 Hz, 1H), 7.94 (d, J=8 Hz, 1H), 7.43 (m, 5H), 7.28 (m, 1H), 6.72 (d, J=8.8 Hz, 1H), 6.62 (dd, J=5.5 and 6.5 Hz, 1H), 3.34 (m, 8H), 3.07 (t, J=6.8 Hz, 2H), 1.82 (m, 1H), 0.85 (d, J=6.8 Hz, 6H); MS (ES−) 486.3; (ES+) 488.3 |
| 134p | (1H-indazol-6-yl)methylamino | —H | —H | 133p | I-2 | ¹HNMR (DMSO-d$_6$): δ 12.94 (bs, 1H), 10.20 (bs, 1H), 8.63 (t, J=6 and 5 Hz, 1H), 8.28 (d, J=1.5 Hz, 1H), 7.96 (m, 2H), 7.92 (d, J=8.3 Hz, 1H), 7.68 (m, 1H), 7.52 (m, 2H), 7.4 (m, 1H), 7.3 (m, 2H), 7.24 (m, 1H), 3.08 (t, J=6.8 Hz, 2H), 1.84 (m, 1H), 0.88 (d, J=6.8 Hz, 6H); MS (ES−) 455.2; (ES+) 479.2 (M + Na) |
| 134q | (1H-indazol-5-yl)methylamino | —H | —H | 133q | I-2 | ¹HNMR (DMSO-d$_6$): δ 12.84 (bs, 1H), 10.45 (bs, 1H), 8.62 (t, J=6 and 5 Hz, 1H), 8.27 (d, J=,1.5 Hz, 1H), 8.01 (s, 1H), 7.93 (s, 2H), 7.9 (d, J=1.5 Hz, 1H), 7.69 (m, 1H), 7.57 (d, J=8.7 Hz, 1H), 7.52 (m, 2H), 7.29 (d, J=8 Hz, 1H), 7.23 (m, 1H), 7.02 (dd, J=1.5 and 8.7 Hz, 1H), 3.07 (t, J=6.8 Hz, 2H), 1.83 (m, 1H), 0.87 (d, J=6.8 Hz, 6H), MS (ES−) 455.2; (ES+) 479.3 (M + Na) |

-continued

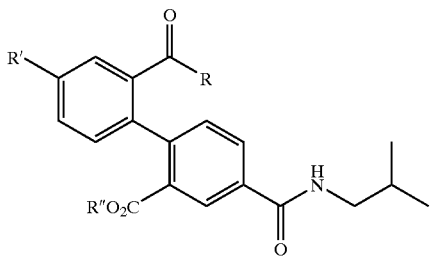

| Cpd. No. | —R | —R' | —R" | Starting From | Method Used | Analytical Data |
|---|---|---|---|---|---|---|
| 134r | | —H | —H | 133r | I-2 | ¹HNMR (DMSO-d$_6$): δ 8.64 (t, J=5.5 Hz, 1H), 8.16 (s, 1H), 7.87 (d, J=7.1 Hz, 1H), 7.50 (m, 1H), 7.40 (d, J=4.1 Hz, 2H), 7.19 (b, 3H), 7.07 (m, 2H), 6.51 (m, 2H), 6.35 (d, J=7.8 Hz, 2H), 3.97 (d, J=5.6 Hz, 2H), 3.13 (t, J=6.5 Hz, 2H), 1.90 (m, 1H), 0.91 (d, J=6.8 Hz, 6H) |
| 134s | ![](methylamino-2-hydroxymethylphenyl) | —H | —H | 133s | I-2 | ¹HNMR (DMSO-d$_6$): δ 9.53 (bs, 1H), 8.67 (t, J=4.7 Hz, 1H), 8.32 (s, 1H), 7.99 d, J=8.1 Hz, 1H), 7.70 (d, J=7.6 Hz, 1H), 7.52 (m, 2H), 7.46 (d, J=11.5 Hz, 1H), 7.32 (m, 3H), 7.18 (m, 3H), 4.33 (s, 2H), 3.10 (t, J=6.5 Hz, 2H), 1.86 (m, 1H), 0.89 (d, J=6.8 Hz, 6H); MS (ES−) 445.2 |
| 134t | —OH | —H | —H | 132 | I-2 | ¹HNMR (DMSO-d$_6$): δ 12.57 (b, 1H), 8.69 (t, J=5.6 Hz, 1H), 8.36 (s, 1H), 7.99 (d, J=7.9 Hz, 1H), 7.92 (d, J=7.7 Hz, 1H), 7.57 (t, J=7.5 Hz, 1H), 7.46 (t, J=7.7 Hz, 1H), 7.23 (d, J=5.2 Hz, 1H), 7.17 (d, J=7.5 Hz, 1H), 3.12 (t, J=6.5 Hz, 2H), 1.88 (m, 1H), 0.91 (d, J=6.8 Hz, 6H); MS (ES−) 340.2 |
| 134u | | —H | —H | 133u | I-2 | ¹HNMR (DMSO-d$_6$): δ 8.56 (t, J=5.0 Hz, 1H), 8.16 (d, J=7.0 Hz, 2H), 7.94 (d, J=8.4 Hz, 1H), 7.75 (d, J=7.4 Hz, 1H), 7.63 (m, 2H), 7.46 (m, 2H), 7.21 (b, 1H), 7.07 (s, 2H), 6.99 (t, J=5.1 Hz, 1H), 3.05 (t, J=6.5 Hz, 2H), 1.83 (m, 1H), 0.86 (d, J=6.8 Hz, 6H); MS (ES−) 416.3 |
| 134v | | —H | —H | 133v | I-2 | ¹HNMR (DMSO-d$_6$): δ 8.60 (t, J=5.6 Hz, 1H), 8.32 (d, J=5.3 Hz, 2H), 8.11 (s, 1H), 7.78 (d, J=7.7 Hz, 1H), 7.65 (d, J=5.5 Hz, 1H), 7.55 (m, 2H), 7.43 (d, J=4.5 Hz, 2H), 7.14 (m, 3H), 3.06 (t, J=6.5 Hz, 2H), 1.83 (m, 1H), 0.86 (d, J=6.8 Hz, 6H); MS (ES−) 416.2 |
| 134w | | —H | —H | 133w | I-2 | ¹HNMR (DMSO-d$_6$): δ 10.10 (bs, 1H), 9.31 (s, 1H), 8.65 (t, J=5.7 Hz, 1H), 8.27 (s, 1H), 7.93 (d, J=8.1 Hz, 1H), 7.62 (d, J=5.3 Hz, 1H), 7.48 (m, 2H), 7.28 (s, 1H), 7.20 (d, J=12.0 Hz, 1H), 7.09 (s, 1H), 6.98 (d, J=7.0 Hz, 1H), 6.81 (d, J=7.3 Hz, 1H), 6.37 (t, J=7.6 Hz, 1H), 3.09 (t, J=6.5 Hz, 2H), 1.85 (m, 1H), 0.90 (d, J=6.8 Hz, 6H); MS (ES−) 431.1 |
| 134x | | —H | —H | 133x | I-2 | ¹HNMR (DMSO-d$_6$): δ 10.28 (bs, 1H), 8.63 (t, J=5.3 Hz, 1H), 8.34 (d, J=4.7 Hz, 1H), 8.06 (s, 1H), 7.82 (d, J=6.6 Hz, 1H), 7.53 (m, 1H), 7.42 (m, 2H), 7.34 (t, J=8.6 Hz, 1H), 7.18 (s, 1H), 7.07 (d, J=2.7 Hz, 2H), 6.10 (b; 1H), 4.43 (b; 1H), 4.12 (b, 1H), 3.12 (t, J=6.5 Hz, 2H), 1.89 (m, 1H), 0.90 (d, J=6.8 Hz, 6H); MS (ES+) 432.3, (ES−) 430.2 |
| 134y | | —H | —H | 133y | I-2 | ¹HNMR (DMSO-d$_6$): δ 9.79 (bs, 1H), 8.62 (t, J=6.0 Hz, 1H), 8.31 (d, J=4.5 Hz, 1H), 8.20 (s, 1H), 8.08 (s, 1H), 7.78 (d, J=2.1 Hz, 1H), 7.51 (m, 1H), 7.42 (m, 2H), 7.06 (m, 3H), 6.88 (m, 1H), 4.02 (b, 2H), 3.13 (t, J=6.5 Hz, 2H), 1.90 (m, 1H), 0.93 (d, J=6.8 Hz, 6H); MS (ES+) 432.3, (ES−) 430.3 |

-continued

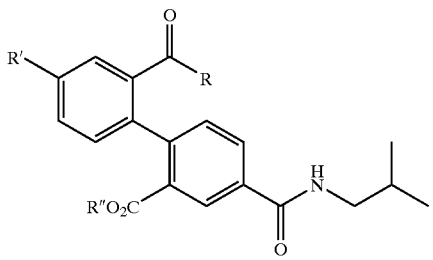

| Cpd. No. | —R | —R' | —R" | Starting From | Method Used | Analytical Data |
|---|---|---|---|---|---|---|
| 134z | NH-CH2-pyridin-4-yl | —H | —H | 133z | I-2 | $^1$HNMR (DMSO-$d_6$): δ 10.71 (bs, 1H), 8.64 (t, J=5.9 Hz, 1H), 8.21 (d, J=5.2 Hz, 2H), 8.05 (s, 1H), 7.81 (d, J=7.7 Hz, 1H), 7.51 (m, 1H), 7.42 (m, 2H), 7.18 (s, 1H), 7.04 (t, J=1.4 Hz, 2H), 6.51 (b, 2H), 4.41 (b, 1H), 4.01 (b, 1H), 3.13 (t, J=6.5 Hz, 2H), 1.91 (m, 1H), 0.91 (d, J=6.8 Hz, 6H); MS (ES+) 432.2, (ES−) 430.2 |
| 134aa | NH-(4-(2-hydroxyethyl)phenyl) | —H | —H | 133aa | I-2 | $^1$HNMR (DMSO-$d_6$): δ 10.02 (bs, □1H), 8.65 (t, J=5.7 Hz, 1H), 8.26 (s, 1H), 7.94 (d, J=7.7 Hz, 1H), 7.66(d, J=5.8 Hz, 1H), 7.51 (m, 2H), 7.36 (d, J=8.4 Hz, 2H), 7.29 (d, J=7.9 Hz, 1H), 7.22 (d, J=5.5 Hz, 1H), 7.07 (d, J=8.3 Hz, 2H), 4.57 (t, J=9.0 Hz, 1H), 3.51 (m, 2H), 3.09 (t, J=6.5 Hz, 2H), 2.62 (t, J=6.6 Hz, 2H), 1.85 (m, 1H), 0.90 (d, J=6.8 Hz, 6H), MS (ES−) 459.2 |
| 134ab | NH-(4-hydroxy-3-hydroxymethylphenyl) | —H | —H | 133ab | I-2 | $^1$HNMR (DMSO-$d_6$): δ 9.05 (s, 1H), 8.70 (t, J=5.7 Hz, 1H), 8.56 (s, 1H), 8.36 (s, 1H), 8.12 (m, 2H), 7.79 (m, 1H), 7.60 (m, 1H), 7.44 (s, 2H), 7.09 (m, 2H), 6.56 (d, J=8.9 Hz, 1H), 4.89 (t, J=4.4 Hz, 1H), 4.38 (d, J=5.6 Hz, 2H), 3.11 (t, J=6.5 Hz, 2H), 1.84 (m, 1H), 0.90 (d, J=6.8 Hz, 6H), MS (ES−) 461.1 |
| 134ac | NH-(1-methylbenzimidazol-2-yl) | —H | —H | 133ac | I-2 | $^1$HNMR (DMSO-$d_6$): δ 8.60 (t, J=6 and 5 Hz, 1H), 8.13 (s, 2H), 7.85 (d, J=2 Hz, 1H), 7.46 (m, 4H), 7.36 (d, J=7.7 Hz, 1H), 7.16 (m, 4H), 7.10 (m, 1H), 3.17 (s, 3H), 3.08 (t, J=6.8 Hz, 2H), 1.85 (m, 1H), 0.89 (d, J=6.8 Hz, 6H), MS (ES−) 469.2; (ES+) 471.3 |
| 134ad | NH-(4-(imidazol-1-yl)phenyl) | —H | —H | 133ad | I-2 | $^1$HNMR (DMSO-$d_6$): δ 8.55 (t, J=6 and 5 Hz, 1H), 8.10 (s, 2H), 7.73 (d, J=7.2 Hz, 1H), 7.54 (m, 4H), 7.46 (m, 5H), 7.08 (m, 3H), 3.04 (t, J=6.8 Hz, 2H), 1.82 (m, 1H), 0.86 (d, J=6.8 Hz, 6H), MS (ES−) 481.1; (ES+) 483.3 |
| 134ae | NH-CH2-(1H-benzimidazol-2-yl) | —H | —H | 133ae | I-2 | $^1$HNMR (DMSO-$d_6$): δ 9.66 (bs, 1H), 8.54 (t, J=6 and 5 Hz, 1H), 8.12 (s, 2H), 7.77 (dd, J=8 and 2 Hz, 1H), 7.6 (dd, J=7 and 2 Hz, 1H), 7.45 (m, 5H), 7.10 (m, 4H), 4.36 (bs, 2H), 3.09 (t, J=6.8 Hz, 2H), 1.86 (m, 1H), 0.89 (d, J=6.8 Hz, 6H), MS (ES−) 469.2; (ES+) 471.3 |
| 134af | NH-(4-hydroxyphenyl) | —H | —H | 133af | I-2 | $^1$HNMR (DMSO-$d_6$): δ 9.76 (s, 1H), 9.17 (s, 1H), 8.63 (t, J=5.0 Hz, 1H), 8.29 (s, 1H), 7.90 (d, J=1.6 Hz, 1H), 7.60 (s, 1H), 7.51 (d, J=8 Hz 1H), 7.30 (d, J=3.6 Hz, 2H), 7.28 (d, J=8.2 Hz, 1H), 7.22 (t, 3H), 6.60 (d, J=8.9 Hz, 1H), 3.06 (t, J=6 Hz, 2H), 1.85 (m, 1H), 0.86 (d, J=6.8 Hz, 6H); MS (ES−) 431.2 |
| 134ag | NH-(4-hydroxy-3-methylphenyl) | —H | —H | 133ag | I-2 | $^1$HNMR (DMSO-$d_6$): δ 9.64 (s, 1H), 9.06 (s, 1H), 8.66 (t, J=5.6 Hz, 1H), 8.29 (s, 1H), 7.95 (d, J=7.9 Hz, 1H), 7.63 (m, 1H), 7.50 (m, 2H), 7.29 (d, J=3.1 Hz, 1H), 7.20 (d, J=8.9 Hz, 1H), 7.11 (m, 1H), 7.03 (m, 1H), 6.60 (d, J=8.9 Hz, 1H), 3.08 (t, J=6 Hz, 2H), 2.05 (s, 3H), 1.85 (m, 1H), 0.86 (d, J=6.8 Hz, 6H); MS (ES−) 445.2, MS (ES+) 469.3 (M + Na) |

-continued

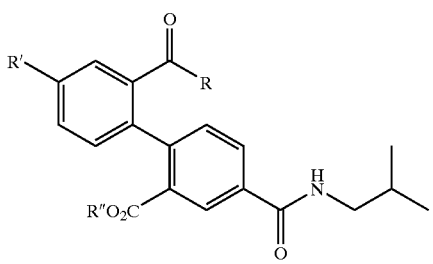

| Cpd. No. | —R | —R' | —R" | Starting From | Method Used | Analytical Data |
|---|---|---|---|---|---|---|
| 134ai | 5-(methylamino)-2-amino-benzimidazole | —H | —H | 133ai | I-2, S | MS (ES+): 472.2; MS (ES−): 470.2 |
| 135a | NH-CH2CH2CH2-imidazole | —CH=CH2 | —CH3 | 30f | A-4 | MS (ES+): 489.3 |
| 135b | NH-CH2CH2-imidazole | —CH=CH2 | —CH3 | 30f | A-4 | MS (ES+): 475.3; MS (ES−): 473.3 |
| 135c | NH-(5-NHBoc-pyridin-2-yl) | —CH=CH2 | —CH3 | 30f | J | MS (ES+): 573.5; MS (ES−): 571.3 |
| 135d | NH-(2-amino-pyrimidin-5-yl) | —CH=CH2 | —CH3 | 30f | A-4 | MS (ES−): 472.2 |
| 135e | NH-(3-chlorophenyl) | —CH=CH2 | —CH3 | 30f | J | MS (ES−): 489.1 |
| 135f | NH-(4-carbamoylphenyl) | —CH=CH2 | —CH3 | 30f | J | MS (ES−): 498.1 |
| 135g | NH-(4-CH2CN-phenyl) | —CH=CH2 | —CH3 | 30f | J | MS (ES−): 494.3 |
| 135h | NH-(4-CH2NHBoc-phenyl) | —CH=CH2 | —CH3 | 30f | J | MS (ES−): 584.2 |
| 136a | NH-CH2CH2CH2-imidazole | —CH=CH2 | —H | 135a | I-2 | ¹HNMR (DMSO-d6): δ 8.66 (t, J=.55 Hz, 1H), 8.35 (t, J=4 and 6.4 Hz, 1H), 8.28 (d, J=2 Hz, 1H), 7.95 (dd, J=7.9 and 2 Hz, 1H), 7.69 (s, 1H), 7.59 (m, 2H), 7.25 (d, J=8.1 Hz, 2H), 7.15 (m, 2H), 6.93 (s, 1H), 6.88 (dd, J=17.7 and 11.5 Hz, 1H), 5.95 (d, J=17.7 Hz, 1H), 5.37 (d, J=11.5 Hz, 1H), 3.76 (t, J=6.8 Hz, 2H), 3.10 (t, J=6.4 Hz, 2H), 2.96 (m, 2H), 1.86 (m, 1H), 1.67 (m, 2H), 0.89 (d, J=6.8 Hz, 6H); MS (ES−) 473.3; (ES+) 475.3 |

-continued

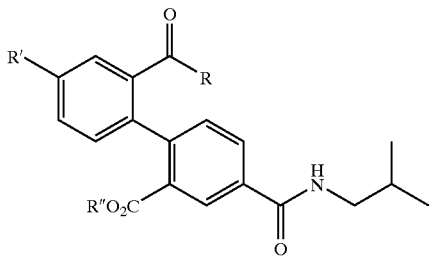

| Cpd. No. | —R | —R' | —R" | Starting From | Method Used | Analytical Data |
|---|---|---|---|---|---|---|
| 136b | [imidazole-ethyl-NH] | —CH=CH₂ | —H | 135b | I-2 | ¹HNMR (DMSO-d₆): δ 8.64 (t, 1H), 8.51 (s, 1H), 8.21 (s, 1H), 7.88 (d, J=7.8 Hz, 1H), 7.74 (s, 1H), 7.56 (s, 2H), 7.15 (m, 2H), 6.80 (t, 2H), 5.90 (d, J=17 Hz, 1H), 5.36 (d, J=11.0 Hz, 1H), 3.18 (m, 2H), 3.06 (t, J=6 Hz, 2H), 2.43 (m, 2H), 1.85 (m, 1H), 0.86 (d, J=6.8 Hz, 6H); MS (ES+) 461.2, MS (ES−) 459.2 |
| 136c | [2-aminopyridin-5-yl-NH] | —CH=CH₂ | —H | 135c | I-2, S | ¹HNMR (DMSO-d₆/D₂O): δ 8.71 (t, 1H), 8.27 (d, J=3 Hz, 1H), 8.21 (d, J=3 Hz, 1H), 7.96 (q, 1H), 7.79 (q, 1H), 7.72 (s, 1H), 7.63 (d, J=8 Hz 1H), 7.30 (d, J=6 Hz, 1H), 7.24 (d, J=7 Hz, 1H), 6.87 (q, 2H), 6.00 (d, J=8 Hz, 1H), 5.41 (d, J=8 Hz, 1H), 3.06 (t, J=6 Hz, 2H), 1.85 (m, 1H), 0.86 (d, J=6.8 Hz, 6H); MS (ES+) 459.2 |
| 136d | [2-aminopyrimidin-5-yl-NH] | —CH=CH₂ | —H | 135d | I-2 | ¹HNMR (DMSO-d₆): δ 12.86 (bs, 1H), 9.17 (s, 1H), 8.65 (t, J=6 Hz, 1H), 8.29 (d, J=2 Hz, 1H), 8.26 (s, 2H), 7.97 (dd, J=8 and 2 Hz, 1H), 7.76 (s, 1H), 7.63 (d, 8 Hz, 1H), 7.31 (d, J=8 Hz, 1H), 7.24 (d, J=8 Hz, 1H), 6.86 (dd, J=10.7 and 17.5 Hz, 1H), 6.49 (s, 1H), 5.99 (d, J=17.5 Hz, 1H), 5.40 (d, J=10.7 Hz, 1H), 3.10 (t, J=6.8 Hz, 2H), 1.86 (m, 1H), 0.89 (d, J=6.8 Hz, 6H); MS (ES−) 458.2, (ES+) 460.3 |
| 136e | [3-chlorophenyl-NH] | —CH=CH₂ | —H | 135e | I-2 | ¹HNMR (DMSO-d₆): δ 12.72 (s, broad, 1H), 8.65 (t, J=5.7 Hz, 1H), 8.29 (s, 1H), 7.93 (d, J=7.9 Hz, 1H), 7.74 (m, 2H), 7.65 (d, J=6 Hz 1H), 7.42 (d, J=7.9 Hz, 1H), 7.24 (m, 3H), 7.11 (m, 1H), 6.84 (q, J=11.1, 17.8 Hz, 1H), 5.97 (d, J=18 Hz, 1H), 5.58 (d, 1H), 5.41 (d, 1H), 3.08 (t, J=6 Hz, 2H), 1.85 (m, 1H), 0.86 (d, J=6.8 Hz, 6H); MS (ES−) 475.1 |
| 136f | [4-carbamoylphenyl-NH] | —CH=CH₂ | —H | 135f | I-2 | ¹HNMR (DMSO-d₆): δ 8.67 (t, J=6.06 Hz, 1H), 8.28 (s, 1H), 7.90 (d, J=7.7 Hz, 1H), 7.67 (m, 4H), 7.32 (m, 5H), 7.09 (d, J=7.9 Hz 1H), 6.89 (q, J=10.9 & 18.0 Hz, 1H), 5.99 (d, J=17.5 Hz, 1H), 5.42 (d, J=11 Hz, 1H), 3.08 (t, J=6.3 Hz, 2H), 1.88 (m, 1H), 0.87 (d, J=6.8 Hz, 6H); MS (ES−) 484.2 |
| 136g | [4-cyanomethylphenyl-NH] | —CH=CH₂ | —H | 135g | I-2 | ¹HNMR (DMSO-d₆): δ 10.38 (s, 1H), 8.66 (t, J=6.06 Hz, 1H), 8.29 (s, 1H), 7.95 (d, J=6.1 Hz, 1H), 7.75 (s, 1H), 7.63 (d, 2H), 7.43 (d, 2H), 7.26 (m, 3H), 7.00 (d, J=7.7 Hz, 1H), 6.85 (q, J=10.9 & 18.0 Hz, 1H), 5.98 (d, J=17.5 Hz, 1H), 5.40 (d, J=11 Hz, 1H), 3.98 (s, 2H), 3.08 (t, J=6.3 Hz, 2H), 1.86 (m, 1H), 0.88 (d, J=6.8 Hz, 6H); MS (ES−) 480.2 |
| 136h | [4-aminomethylphenyl-NH] | —CH=CH₂ | —H | 135h | S, I-2 | ¹HNMR (DMSO-d₆): δ 8.55 (t, J=6.06 Hz, 1H), 8.02 (s, 1H), 7.60 (m, 4H), 7.21 (t, J=7.1, 2H), 6.99 (m, 2H), 6.83 (d, J=6.8 Hz, 1H), 6.81 (q, J=10.9 & 18.0 Hz, 1H), 5.92 (d, J=17.5 Hz, 1H), 5.35 (d, J=11 Hz, 1H), 3.89 (s, 2H), 3.03 (t, J=6.3 Hz, 2H), 1.36 (m, 1H), 0.86 (d, J=6.8 Hz, 6H) |

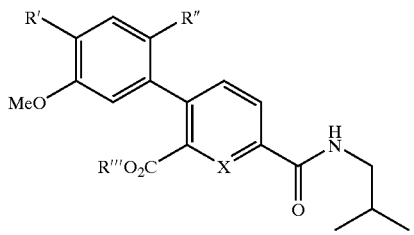

| Cpd. No. | —R' | —R" | R'" | X | Starting From | Method Used | Analytical Data |
|---|---|---|---|---|---|---|---|
| 117n | —OBn | —CHO | —CH$_3$ | N | 116 + 220a | D-2 | MS (ES$^+$): 477.2 |
| 118n | —OBn | —CO$_2$H | —CH$_3$ | N | 117n | E | Characterized at the next step |
| 119n | —OBn | —CO$_2$MEM | —CH$_3$ | N | 118n | F | Characterized at the next step |
| 120n | —OH | —CO$_2$MEM | —CH$_3$ | N | 119n | G | Characterized at the next step |
| 121n | —OSO$_2$CF$_3$ | —CO$_2$MEM | —CH$_3$ | N | 120n | B-2 | Characterized at the next step |
| 122n | —CH=CH$_2$ | —CO$_2$MEM | —CH$_3$ | N | 121n | D-3 | Characterized at the next step |
| 123n | —CH=CH$_2$ | CO$_2$H | —CH$_3$ | N | 122n | I-1 | MS (ES$^-$): 411.1 |
| 124n | —CH=CH$_2$ | ![acetamidobenzamidine] | —CH$_3$ | N | 123n | J | MS (ES$^+$): 530.3 |
| 125n | —CH=CH$_2$ | ![acetamidobenzamidine] | H | N | 124n | I-2 | 1H NMR (DMSO-d6 +H2O): 8.24 (d, J=7.7 Hz, 1H), 8.0–7.9 (m, 2H), 7.81 (s, 4H), 7.14–6.94 (m, 2H), 6.08 (d, J=17.3 Hz, 1H), 5.48 (d, J=12.05 Hz, 1H), 3.87 (s, 3H), 3.20 (d, J=6.4 Hz, 2H), 2.04–1.75 (1H, m), 0.92 (d, J=6.4 Hz, 6H). MS (ES+): 516.34. |
| 189f | —OH | —CHO | —CH$_3$ | CH | 117a | AL | MS (ES$^+$): 386.4. |
| 189g | —OH | —CHO | —CH$_3$ | N | 117n | AL | MS (ES$^+$): 387.38 |
| 189h | —OSO$_2$CF$_3$ | —CHO | —CH$_3$ | CH | 189f | B-2 | MS (ES$^+$): 518.2 |
| 189i | —OSO$_2$CF$_3$ | —CHO | —CH$_3$ | N | 189g | B-2 | MS (ES$^+$): 541.1 (M + Na) |
| 189j | —CH=CH$_2$ | —CHO | —CH$_3$ | CH | 189h | D-3 | MS (ES$^+$): 418.3 (M + Na) |
| 189k | —CH=CH$_2$ | —CHO | —CH$_3$ | N | 189i | D-3 | MS (ES$^+$): 397.3 |
| 189l | —CH=CH$_2$ | ![ethylaminobenzamidine] | H | CH | 189j | AE-3 | $^1$HNMR (DMSO-d$_6$): δ 8.63 (t, J=5 Hz, 1H), 8.56 (bs, 4H), 8.33 (s, 1H), 7.90 (d, J=8 Hz, 1H), 7.61 (m, 1H), 7.50 (s, 1H), 7.47 (2, 1H), 7.41 (s, 1H), 7.30 (d, J=7.2 Hz, 1H), 6.94 (dd, J=11 & 17.5 Hz, 1H), 6.67 (m, 3H), 5.62 (d, J=17.5 Hz, 1H), 5.20 (d, J=11 Hz, 1H), 4.01 (m, 2H), 3.73 (s, 3H), 3.09 (t, J=6.5 Hz, 2H), 1.86 (m, 1H), 0.80 (d, J=6.5 Hz, 6H); MS (ES$^+$) 501.46 |
| 189m | —CH=CH$_2$ | ![ethylaminobenzamidine] | H | N | 189k | AE-3 | $^1$H NMR (DMSOd6 +H2O): 8.20 (d, J=7.9 Hz, 1H), 8.04 (d, J=7.9 Hz, 1H), 7.67–7.45 (m, 4H), 6.94 (dd, J=17.3 and 11.1 Hz, 1H), 6.5 (d, J=8.3 Hz, 1H), 5.73 (d, J=17.9 Hz, 1H), 5.28 (d, J=11.3 Hz, 1H), 4.01 (s, 2H), 3.76 (s, 3H), 3.18 (d, J=6.9 Hz, 2H), 2.0–1.76 (m, 1H), 0.91 (d, J=6.6 Hz, 6H); MS (ES+): 502.34 |
| 189n | —CH=CH$_2$ | ![ethylaminopyridylamidine] | H | CH | 189j | AE-3 | $^1$HNMR [DMSO/DCl (1 drop)]: δ 8.34 (m, 3H), 8.3 (d, J=8.3 Hz, 1H), 8.02 (d, J=7.7 Hz, 1H), 7.69 (bs, 1H), 7.43 (d, J=8 Hz, 1H), 6.98 (dd, J=11 & 17 Hz, 1H), 6.75 (s, 1H), 5.88 (d, J=17 Hz, 1H), 5.32 (d, J=11 Hz, 1H), 4.40 (m, 2H), 3.77 (s, 3H), 3.09 (d, J=7 Hz), 1.87 (m, 1H), 0.89 (d, J=7 Hz, 6H); MS (ES$^+$) 502.39 |

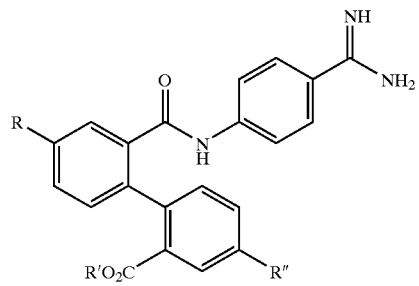

| Cpd. No. | —R | —R' | —R" | Starting From | Method Used | Analytical Data |
|---|---|---|---|---|---|---|
| 148a | 2-methylfuran | —CH₃ | -NHC(O)CH₂CH(CH₃)₂ | 147a | J | ¹H NMR (DMSO-d₆): δ 10.65 (s, 1 H), 10.15 (s, 1 H), 9.19 (s, 2 H), 8.88 (s, 2 H), 8.10 (d, J = 2.1 Hz, 1 H), 7.92 (s, 1 H), 7.93–7.75 (m, 6 H), 7.31 (dd, J = 8.4 and 23.9 Hz, 1 H), 7.12 (d, J = 3.5 Hz, 1 H), 6.67 (m, 1 H), 3.53 (s, 3 H), 2.20 (d, J = 7.0 Hz, 2 H), 2.07 (m, 1 H), 0.94 (d, J = 6.3 Hz, 6 H). |
| 148b | 2-methylthiophene | —CH₃ | -NHC(O)CH₂CH(CH₃)₂ | 147b | J | ¹H NMR (DMSO-d₆): δ 10.65 (s, 1 H), 10.09 (s, 1 H), 9.17 (s, 1 H), 8.83 (s, 1 H), 8.10 (d, J = 2.0 Hz, 1 H), 7.85 (d, J = 2.0 Hz, 2 H), 7.81 (d, J = 2.0 and 7.9 Hz, 2 H), 7.76 (m, 5 H), 7.66 (d, J = 3.9 Hz, 1 H), 7.62 d, J = 4.9 Hz, 1 H), 7.31 (d, J = 7.9 Hz, 1 H), 7.26 (d, J = 7.9 Hz, 1 H), 7.19 (t, J = 3.9 Hz, 1 H), 3.53 (s, 1 H), 2.19 (d, J = 6.9 Hz, 2 H), 2.06 (m, J = 6.9 Hz, 1 H), 0.92 (d, J = 6.9 Hz, 6 H); MS (ES⁺): 555.67 |
| 148c | —CH=CH₂ | —CH₃ | -NHC(O)CH₂CH(CH₃)₂ | 147c | J | Characterized in the next step |
| 149a | 2-methylfuran | —H | -NHC(O)CH₂CH(CH₃)₂ | 148a | I-2 | MS (ES⁺): 525.3 |
| 149b | 2-methylthiophene | —H | -NHC(O)CH₂CH(CH₃)₂ | 148b | I-2 | ¹H NMR (DMSO-d₆): δ 13.95 (s, 1 H), 9.79 (s, 1 H), 8.87 (s, 4 H), 7.76 (s, 1 H), 7.65 (m, 8 H), 7.46 (dd, J = 2.1 and 8.4 Hz, 1 H), 7.16 (t, J = 4.2 Hz, 1 H), 7.04 (d, J = 7.7 Hz, 1 H), 6.76 (d, J = 8.4 Hz, 1 H), 2.13 (d, J = 7.0 Hz, 2 H), 2.03 (m, J = 6.3 and 7.0 Hz, 1 H), 0.90 (d, J = 6.3 Hz, 6 H); MS (ES⁺): 541.62 |
| 149c | —CH=CH₂ | —H | -NHC(O)CH₂CH(CH₃)₂ | 148c | I-2 | MS (ES⁺): 485.6 |
| 175 | —H | —CH₂ | -NHC(O)CH(CH₃)₂ (ethyl amide) | 174 | J | ¹H NMR (DMSO-d₆): δ 8.81 (m, 4 H), 8.37 (t, J = 6.0 Hz, 1 H), 7.74–7.23 (m, 11 H), 4.31 (d, J = 6.2 Hz, 2 H), 3.51 (s, 3 H), 2.44 (m, 1 H), 1.04 (d, J = 7.0 Hz, 6 H); MS (ES⁺): 473.3 |
| 176 | —H | —H | -NHC(O)CH(CH₃)₂ (ethyl amide) | 175 | I-2 | ¹H NMR (DMSO-d₆): δ 13.79 (br s, 1 H), 9.03 (m, 3 H), 8.25 (m, 1 H), 7.78–7.35 (m, 7 H), 6.99 (m, 2 H), 6.79 (m, 1 H), 4.20 (br s, 2 H), 3.51 (s, 3 H), 2.39 (m, 1 H), 1.00 (d, J = 6.8 Hz, 6 H); MS (ES⁺): 459.3 |
| 182 | —H | —CH₃ | -N(Boc)CH₂CH(CH₃)₂ (ethyl) | 178 | J | ¹H NMR (DMSO-d₆): δ 8.96 (m, 2 H), 7.79–7.38 (m, 9 H), 7.29 (dd, J = 7.5 and 1.7 Hz, 2 H), 4.42 (s, 2 H), 3.50 (s, 3 H), 2.97 (s, 2 H), 1.87 (m, 1 H), 1.36 (m, 9 H), 0.81 (d, J = 6.8 Hz, 6 H); MS (ES⁺): 559.5 |

-continued

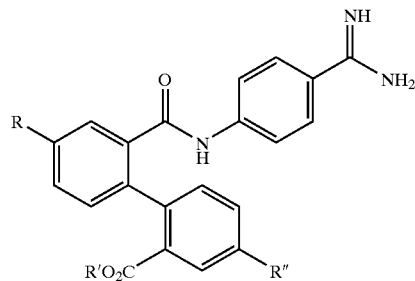

| Cpd. No. | —R | —R' | —R" | Starting From | Method Used | Analytical Data |
|---|---|---|---|---|---|---|
| 183 | —H | —H |  | 182 | I-2, S | ¹H NMR (DMSO-d₆): δ 9.11 (m, 4 H), 7.86 (s, 1 H), 7.66 (m, 5 H), 7.49 (m, 2 H), 7.38 (m, 1 H), 7.08 (m, 2 H), 4.12 (s, 2 H), 2.59 (m, 2 H), 1.87 (m, 1 H), 0.81 (d, J = 6.6 Hz, 6 H); MS (ES⁺): 445.32 |

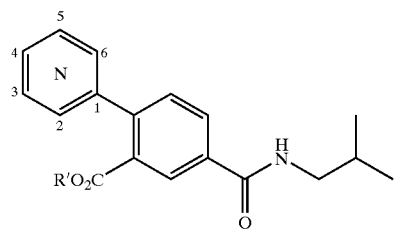

| Cpd. No. | N (in Ring With Respect to Phenyl) | —R | —R' | Starting From | Method Used | Analytical Data |
|---|---|---|---|---|---|---|
| 151 | 3 | —CHO | —CH₃ | 150+ 3a | D-9 | MS (ES⁻): 339.3 |
| 152 | 3 | —CO₂H | —CH₃ | 151 | E | ¹H NMR (CDCl₃): δ 8.69 (t, J = 5.8 Hz, 1 H), 8.50 (d, J = 4.9 Hz, 1 H), 8.33 (d, J = 1.7 Hz, 1 H), 8.24 (s, 1 H), 8.01 (dd, J = 7.9, 1.9 Hz, 1 H), 7.53 (d, J = 5.1 Hz, 1 H), 7.34 (d, J = 8.1 Hz, 1 H), 3.56 (s, 3 H), 3.12 (m, 2 H), 1.87 (m, 1 H), 0.91 (d, J = 6.6 Hz, 6 H) |
| 153 | 3 | 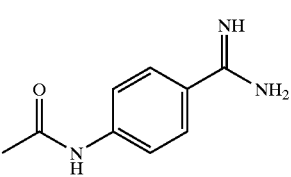 | —CH₃ | 152 | J | ¹H NMR (CD₃OD): δ 8.75 (d, J = 4.7 Hz, 2 H), 8.55 (s, 1 H), 8.42 (d, J = 1.9 Hz, 1 H), 8.07 (dd, J = 8.1, 1.9, 1 H), 7.74 (m, 3 H), 7.70 (d, J = 5.1 Hz, 1 H), 7.51 (d, J = 8.1 Hz, 1 H), 3.69 (s, 3 H), 3.21 (m, 2 H), 1.94 (m, 1 H), 0.98 (d, J = 6.6 Hz, 6 H); MS (ES⁺): 474 |
| 154 | 3 | (same as above) | —H | 153 | I-2 | ¹H NMR (DMSO): δ 11.18 (s, 1 H), 9.31 (s, 2 H), 9.10 (s, 2 H), 8.92 (d, J = 5.1 Hz, 1 H), 8.78 (m, 2 H), 8.43 (d, J = 1.5 Hz, 1 H), 8.07 (dd, J = 7.9, 1.3 Hz, 1 H), 7.97 (d, J = 5.3 Hz, 1 H), 7.82 (d, J = 8.7 Hz, 2 H), 7.72 (d, J = 8.8 Hz, 2 H), 7.50 (d, J = 7.9 Hz, 1 H), 3.10 (t, J = 6.0 Hz, 2 H), 1.86 (m, 1 H), 0.89 (d, J = 6.6 Hz, 6 H); MS (ES⁺) 460 |
| 156 | 4 | —CHO | —CH₃ | 155+ 3a | D-9 | MS (ES⁺): 341.4 |
| 157 | 4 | —CO₂H | —CH₃ | 156 | E | ¹H NMR (CDCl₃): δ 8.80 (s, 1 H), 8.46 (d, J = 5.1 Hz, 1 H), 8.29 (s, 1 H), 7.85 (d, J = 7.9 Hz, 1 H), 7.13 (d, J = 7.9 Hz, 1 H), 7.00 (d, J = 5.1 Hz, 1 H), 6.83 (bs, 2 H), 3.45 (s, 3 H), 3.15 (m, 2 H), 1.84 (m, 1 H), 0.90 (d, J = 6.6 Hz, 6 H); MS (ES⁻): 355.2 |

-continued

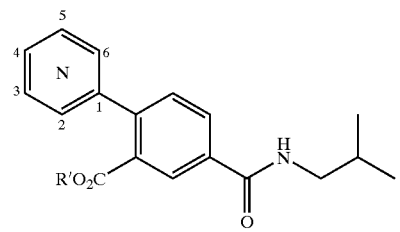

| Cpd. No. | N (in Ring With Respect to Phenyl) | —R | —R' | Starting From | Method Used | Analytical Data |
|---|---|---|---|---|---|---|
| 158 | 4 | (structure: 4-acetamidophenyl amidine, linked via C=O) | —CH₃ | 157 | J | ¹H NMR (CD₃OD): δ 8.85 (s, 1 H), 8.75 (d, J = 5.3 Hz, 1 H), 8.41 (d, J = 1.9 Hz, 1 H), 8.07 (dd, J = 8.1, 2.1, 1 H), 7.74 (s, 4 H), 7.48 (d, J = 8.1 Hz, 1 H), 7.45 (d, J = 5.1 Hz, 1 H), 3.69 (s, 3 H), 3.21 (m, 2 H), 1.94 (m, 1 H), 0.97 (d, J = 6.8 Hz, 6 H); MS (ES⁻): 472.4 |
| 159 | 4 | (structure: 4-acetamidophenyl amidine, linked via C=O) | —H | 158 | I-2 | ¹H NMR (DMSO): δ 10.97 (s, 1 H), 9.24 (s, 2 H), 8.96 (s, 3 H), 8.79 (m, 2 H), 8.40 (d, J = 1.8 Hz, 1 H), 8.06 (d, J = 7.7 Hz, 1 H), 7.77 (s, 4 H), 7.52 (m, 1 H), 7.38 (d, J = 7.5 Hz, 1 H), 3.10 (m, 2 H), 1.85 (m, 1 H), 0.89 (d, J = 5.3, 6 H); MS (ES⁺) 460.2 |

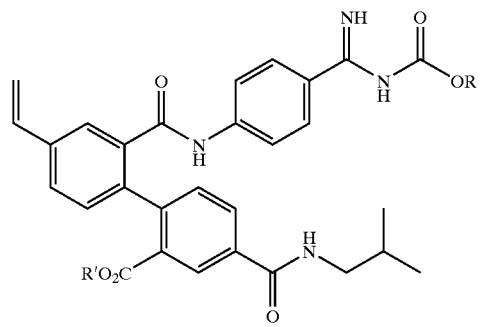

| Cpd. No. | —R | —R' | Starting From | Method Used | Analytical Data |
|---|---|---|---|---|---|
| 161a | —CH₃ | —CH₃ | 31f | AB-2 | ¹H NMR (DMSO-d6): δ 10.55 (s, 1H), 9.00 (bs, 2H), 8.68 (t, J=5.8 Hz, 1H), 8.24 (d, J=1.9 Hz, 1H), 8.04 (d, J=8.1 Hz, 1H), 7.91 (d, J = 8.8 Hz, 2H), 7.77 (d, J=1.3 Hz, 1H), 7.67 (m, 3H), 7.40 (d, J=7.9 Hz, 1H), 7.29 (d, J=7.9 Hz, 1H), 6.90 (dd, J=17.7, 11.0 Hz, 1H), 6.03 (d, J=17.7 Hz, 1H), 5.42 (d, J=11.0 Hz, 1H), 3.61 (s, 3H), 3.56 (s, 3H), 3.10 (t, J=6.4 Hz, 2H), 1.85 (m, 1H), 0.90 (d, J=6.5 Hz, 6H); MS (ES+): 557.3 |
| 161b | —C₂H₅ | —CH₃ | 31f | AB-2 | ¹H NMR (DMSO-d6): δ 10.54 (s, 1H), 9.20 (bs, 4H), 8.67 (t, J=6 Hz, 1H), 8.24 (1H), 8.02 (1H), 7.91 (2H), 7.77 (1H), 7.66 (m, 3H), 7.40 (1H), 7.29 (1H), 6.88 (dd, J=17.3, 10.7 Hz, 1H), 6.03 (d, J=17.3 Hz, 1H), 5.42 (d, J=10.7 Hz, 1H), 3.56 (s, 3H), 3.5 (m, 3H), 3.09 (2H), 1.85 (m, 1H), 0.89 (6H); MS (ES+): 571.3 |
| 161c | —CH₂C₆H₅ | —CH₃ | 31f | AB-2 | ¹H NMR (DMSO-d6): δ 10.54 (s, 1H), 9.20 (bs, 2H), 8.68 (t, J=5.8 Hz, 1H), 8.24 (d, J=1.9 Hz, 1H), 8.03 (d, J=8.1 Hz, 1H), 7.92 (d, J = 8.8 Hz, 2H), 7.77 (s, 1H), 7.68 (m, 4H), 7.36 (m, 6H), 6.89 (dd, J = 17.7, 11.2 Hz, 1H), 5.05 (s, 2H), 6.03 (a, J=17.7 Hz, 1H), 5.42 (d, J = 11.2, Hz, 1H), 3.56 (s, 3H), 3.09 (t, J=6.6 Hz, 2H), 1/84 (m, 1H), 0.89 (d, J=6.6 Hz, 6H); MS (ES+): 633.3 |

-continued

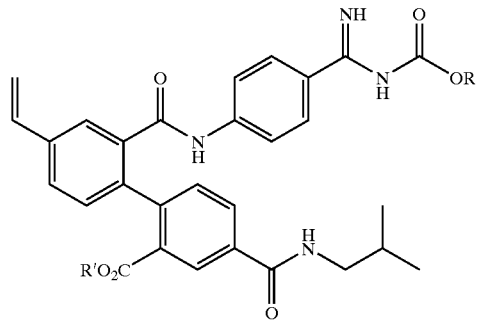

| Cpd. No. | —R | —R' | Starting From | Method Used | Analytical Data |
|---|---|---|---|---|---|
| 161d | —C(CH₃)₃ | —CH₃ | 31f | AB-2 | MS (ES+): 599.3 and 499.3 |
| 161e | —CH₂—CCl₃ | —CH₃ | 31f | AB-2 | ¹H NMR (DMSO-d6): δ □ 10.59 (s, 1H), 9.24 (s, 2H), 8.68 (t, J=5.6 Hz, 1H), 8.24 (d, J=1.8 Hz, 1H), 8.03 (dd, J=8.9, 1.9 Hz, 1H), 7.96 (d, J=8.9 Hz, 2H), 7.79 (d, J=1.5 Hz, 1H), 7.69 (m, 3H), 7.41 (d, J = 8.1 Hz, 1H), 7.29 (d, J=8.0 Hz, 1H), 6.89 (dd, J=17.7, 11.1 Hz, 1H), 6.03 (d, J=17.7 Hz, 1H), 5.42 (d, J=11.1 Hz, 1H), 4.88 (s, 2H), 3.56 (s, 3H), 3.10 (t, J=6.6 Hz, 2H), 1.85 (m, 1H), 0.89 (d, J=6.6 Hz, 6H); MS (ES+): 674.97 |
| 161f | 4-methoxybenzyl | —CH₃ | 31f | AB-2 | ¹H NMR (DMSO-d6): δ □ 10.58 (s, 1H), 9.15 (s, 2H), 8.69 (t, J=5.4 Hz, 1H), 8.25 (d, J=1.8 Hz, 1H), 8.04 (dd, J=8.1, 1.9 Hz, 1H), 7.95 (d, J=8.9 Hz, 2H), 7.78 (s, 1H), 7.68 (m, 3H), 7.40 (d, J=8.0 Hz, 1H), 7.29 (d, J=8.0 Hz, 1H), 7.07 (d, J=8.8 Hz, 2H), 6.93 (d, J=8.8 Hz, 2H), 6.89 (dd, J=17.7, 11.1 Hz, 1H), 6.03 (d, J=17.7 Hz, 1H), 5.42 (d, J=11.1 Hz, 1H), 3.75 (s, 3H), 3.57 (s, 3H), 3.10 (t, J=6.6 Hz, 2H), 1.85 (m, 1H), 0.89 (d, J=6.6 Hz, 6H); MS (ES+): 649.3 |
| 161g | 4-fluorobenzyl | —CH₃ | 31f | AB-2 | ¹H NMR (DMSO-d6): δ 10.59 (s, 1H), 9.19 (s, 2H), 8.68 (t, J=5.7 Hz, 1H), 8.25 (d, J=1.8 Hz, 1H), 8.03 (dd, J=8.1, 1.9 Hz, 1H), 7.95 (d, J = 8.9 Hz, 2H), 7.78 (d, J=1.7 Hz, 1H), 7.70 (m, 3H), 7.41 (d, J=8.1 Hz, 1H), 7.29 (d, J=7.9 Hz, 1H), 7.20 (m, 4H), 6.90 (dd, J=17.9, 11.1 Hz, 1H), 6.03 (d, J=17.9 Hz, 1H), 5.42 (d, J=11.1 Hz, 1H), 3.57 (s, 3H), 3.10 (t, J=6.8 Hz, 2H), 1.85 (m, 1H), 0.89 (d, J=6.6 Hz, 6H); MS (ES+): 637.5 |
| 161h | ethyl acetoxymethyl | —CH₃ | 31f | AB-1 | ¹H NMR (DMSO-d6): δ 10.58 (s, 1H), 9.00 (bs, 2H), 8.68 (t, J=5.9 Hz, 1H), 8.24 (d, J=1.9 Hz, 1H), 8.03 (d, J=8.1 Hz, 1H), 7.94 (d, J = 8.9 Hz, 2H), 7.78 (d, J=1.5 Hz, 1H), 7.68 (m, 3H), 7.40 (d, J=8.1 Hz, 1H), 7.29 (d, J=8.1 Hz, 1H), 6.89 (dd, J=17.5, 11.0 Hz, 1H), 6.03 (d, J=17.5 Hz, 1H), 5.71 (s, 2H), 5.42 (d, J=11.0 Hz, 1H), 3.56 (s, 3H), 3.10 (t, J=6.2 Hz, 2H), 2.07 (s, 3H), 1.85 (m, 1H), 0.89 (d, J=6.6 Hz, 6H); MS (ES+): 615.3 |
| 161i | ethyl pivaloyloxymethyl | —CH₃ | 31f | AB-1 | ¹H NMR (DMSO-d6): δ 10.57 (s, 1H), 9.22 (s, 2H), 8.67 (t, J=5.9 Hz, 1H), 8.24 (d, J=1.9 Hz, 1H), 8.03 (dd, J=8.1, 1.9 Hz, 1H), 7.94 (d, J = 8.9 Hz, 2H), 7.78 (d, J=1.5 Hz, 1H), 7.69 (m, 3H), 7.41 (d, J=7.9 Hz, 1H), 7.29 (d, J=7.9 Hz, 1H), 6.89 (dd, J=17.7, 11.1 Hz, 1H), 6.03 (d, J=17.7 Hz, 1H), 5.73 (s, 2H), 5.42 (d, J=11.1 Hz, 1H), 3.56 (s, 3H), 3.09 (t, J=6.6 Hz, 2H), 1.85 (m, 1H), 1.14 (s, 9H), 0.89 (d, J=6.7 Hz, 6H); MS (ES+): 657.52 |
| 161j | 1-(acetoxy)ethyl | —CH₃ | 31f | AB-1 | ¹H NMR (DMSO-d6): δ □ 10.57 (s, 1H), 9.24 (s, 1H), 9.17 (s, 1H), 8.68 (t, J=6.2 Hz, 1H), 8.25 (s, 1H), 8.04 (d, J=8.2 Hz, 1H), 7.94 (d, J = 7.5 Hz, 2H), 7.67 (s, 1H), 7.67 (m, 3H), 7.40 (d, J=7.9 Hz, 1H), 7.29 (d, J=7.9 Hz, 1H), 6.90 (dd, J=17.8, 11.1 Hz, 1H), 6.71 (q, J=5.5 Hz, 1H), 6.03 (d, J=17.7 Hz, 1H), 5.42 (d, J=11.1 Hz, 1H), 3.56 (s, 3H), 3.10 (t, J=6.6 Hz, 2H), 2.00 (s, 3H), 1.85 (m, 1H), 1.43 (d, J=5.5 Hz, 3H), 0.89 (d, J=6.7 Hz, 6H); MS (ES+): 629.4 |
| 162a | —CH₃ | —H | 161a | I-2 | ¹H NMR (DMSO-d6): δ 9.04 (bs, 3H), 8.57 (t, J=5.4 Hz, 1H), 8.16 (s, 1H), 7.86 (d, J=8.5 Hz, 2H), 7.79 (d, J=7.9 Hz, 1H), 7.72 (s, 1H), 5.97 (d, J=17.7 Hz, 1H), 5.37 (d, J=11.0 Hz, 1H), 7.58(m, 3H), 7.12(d, J=8.0Hz, 2H), 6.87(dd, J=17.7, 11.0Hz, 1H), 5.97 (d, J =17.7 Hz, 1H), 5.37 (d, J =11.0 Hz, 1H), 3.59 (s, 3H), 3.05 (t, J=6.6 Hz, 2H), 1.83 (m, 1H), 0.87 (d, J=6.6 Hz, 6H); (ES+): 543.38 |

-continued

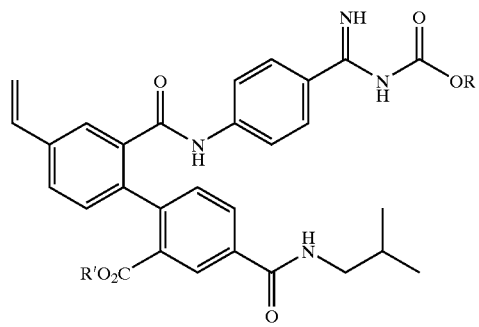

| Cpd. No. | —R | —R' | Starting From | Method Used | Analytical Data |
|---|---|---|---|---|---|
| 162b | —C$_2$H$_5$ | —H | 161b | I-2 | $^1$H NMR (DMSO-d6): δ 12.8 (bs, 1H), 10.8 (bs, 1H), 9.20 (bs, 2H), 8.68 (t, J=5.9 Hz, 1H), 8.24 (d, J=1.9 Hz, 1H), 7.91 (m, 3H), 7.77 (d, J=1.5 Hz, 1H), 7.64 (m, 3H), 7.28 (d, J=8.1 Hz, 1H), 7.22 (d, J=8.1 Hz, 1H), 6.87 (dd, J=17.7, 11.4 Hz, 1H), 6.01 (d, J=17.7 Hz, 1H), 5.42 (d, J=11.4 Hz, 1H), 4.05 (q, J=7.2 Hz, 2H), 3.08 (t, J=6.4 Hz, 2H), 1.84 (m, 1H), 1.21 (t, J=7.2 Hz, 3H), 0.88 (d, J=6.6 Hz, 6H); MS (ES$^-$): 555.2 |
| 162c | —CH$_2$C$_6$H$_5$ | —H | 161c | I-2 | $^1$H NMR (DMSO-d6): δ 12.7 (bs, 1H), 10.75 (bs, 1H), 9.15 (b, 2H), 8.63 (t, J=5.8 Hz, 1H), 8.27 (bs, 1H), 7.90 (d, J=8.3 Hz, 2H), 7.77 (s, 1H), 7.43–7.15 (m, 8H), 7.40 (d, J=8.1 Hz, 1H), 7.29 (d, J=8.1 Hz, 1H), 6.87 (dd, J=17.4, 11.0 Hz, 1H), 6.03 (d, J=17.5 Hz, 1H), 5.71 (s, 2H), 5.42 (d, J=11.0 Hz, 1H), 5.09 (s, 2H), 3.08 (t, J=6.4 Hz, 2H), 1.85 (m, 1H), 0.88 (d, J=6.6 Hz, 6H); MS (ES + 1): 619.2 |
| 162d | —C(CH$_3$)$_3$ | —H | 161d | I-2 | $^1$H NMR (DMSO-d6): δ 12.6 (bs, 1H), 11.0 (bs, 1H), 9.04 (b, 2H), 8.62 (t, J=5.4 Hz, 1H), 8.24 (s, 1H), 7.86 (m, 3H), 7.77 (s, 1H), 7.62 (m, 3H), 7.24 (d, J=8.2 Hz, 1H), 7.20 (d, J=8.0 Hz, 1H), 6.87 (dd, J = 17.2, 11.0 Hz, 1H), 6.00 (d, J=17.7 Hz, 1H), 5.40 (d, J=11.0 Hz, 1H), 3.07 (t, J=6.3 Hz, 2H), 1.84 (m, 1H), 1.44 (s, 9H), 0.88 (d, J=6.6 Hz, 6H); MS (ES + 1): 585.4 |

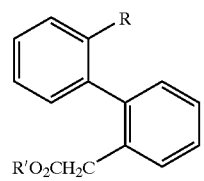

| Cpd. No. | —R | —R' | Starting From | Method Used | Analytical Data |
|---|---|---|---|---|---|
| 164 | —CHO | —CH$_3$ | 163 + 130 | D-2 | $^1$HNMR (DMSO-d$_6$): δ 9.58 (s, 1 H), 7.91 (dd, J = 1.2, 8.0 Hz, 1 H), 7.71 (dt, J=1.2 and 7.4 Hz, 1 H), 7.58 (t, J=7.4 Hz, 1 H), 7.41 (m, 2 H), 7.38 (m, 1 H), 7.32 (d, J=8 Hz, 1 H), 7.24 (d, J=7.4 Hz, 1 H), 3.52 (q, J=16 and 26 Hz, 2 H), 3.35 (s, 3 H); MS (ES+): 255.32 |
| 165 | —CO$_2$H | —CH$_3$ | 164 | E | Characterized in the next step |
| 166 | 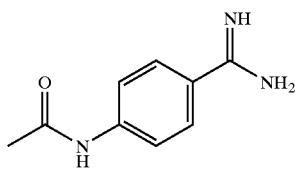 | —CH$_3$ | 165 | J | $^1$HNMR (DMSO-d$_6$): δ 10.34 (s, 1 H), 9.18 (s, 2 H), 8.92 (s, 2 H), 7.72–7.5 (m, 7 H), 7.34–7.14 (m, 5 H), 3.60 (q, J=17 & 40 Hz, 2 H), 3.48 (s, 3 H); MS (ES+) 388.67 |

US 6,936,719 B2

287                                                                                                    288

-continued

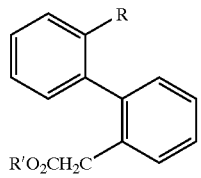

| Cpd. No. | —R | —R' | Starting From | Method Used | Analytical Data |
|---|---|---|---|---|---|
| 167 | ![4-acetamidobenzamidine] | —H | 166 | I-2 | ¹HNMR (DMSO-d₆): δ 11.74 (bs, 1 H), 9.90 (s, 1 H), 8.79 (bs, 2 H), 7.64 (m, 1 H), 7.50 (m, 7 H), 7.33 (d, J=8.6 Hz, 1 H), 7.26 (d, J=7.4 Hz, 1 H), 7.12 (t, J=7.4 Hz, 1 H), 7.02 (t, J=7.4 Hz, 1 H), 6.89 (d, J=6.8 Hz, 1 H), 3.83 (d, J=15 Hz, 2 H); MS (ES+) 374.79 |

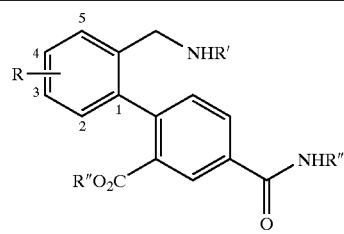

| Cpd. No. | —R | —R' | —R" | —R"' | Starting From | Method Used | Analytical Data |
|---|---|---|---|---|---|---|---|
| 188a | —CH=CH₂ (4) | 4-methylbenzamidine | CH(CH₃)CH₂CH₃ | —H | 187a | AE-3 | MS (ES+): 485.4 (100% M⁺¹) |
| 188b | —CH=CH₂ (4) | 4-methylbenzamidine | CH₂CF₃ | —H | 187b | AE-3 | ¹HNMR (DMSO-d₆/D₂O): δ 8.5 (d, J=2 Hz, 1 H), 8.17 (dd, J=8 Hz, 2 H), 7.65 (s, 1 H), 7.63 (s, 1 H), 7.54 (d, J=8 Hz, 1 H), 7.49 (bs, 2 H), 7.14 (d, J=7.7 Hz, 1 H), 6.78 (dd, J=11 and 17 Hz, 1 H), 6.62 (d, J = 9 hz, 1 H), 5.83 (d, J=17 hz, 1 H), 5.33 (d, J=11 hz, 1 H), 4.17 (d, J = 9 hz, 1 H), 4.12 (s, 2 H); MS (ES+): 497.3 |
| 188c | —CH=CH₂ (4) | 4-methylbenzamidine | CH₂CF₃ | —H | 187c | AE-3 | ¹HNMR (DMSO-d₆/D₂O): δ 8.6 (m, 3 H), 8.3 (m, 3 H), 7.9 (d, J = 7.9 Hz, 1 H), 7.45 (d, J=8.8 Hz, 1 H), 7.3 (m, 3 H), 7.1 (m, 1 H), 7.0 (d, J=8.1 Hz, 1 H), 6.6 (dd, J=6 and 28 Hz, 1 H), 6.4 (d, J=8.8 Hz, 2 H), 5.7 (d, J=17 Hz, 1 H), 5.15 (d, J=11 Hz, 1 H), 3.9 (m, 2 H), 3.25 (m, 2 H), 1.1 (t, J=& Hz, 3 H); MS (ES+): 443.3 |
| 188d | —CH=CH₂ (4) | 4-methylbenzamidine | CH(CH₃)CH₂CH₃ | H | 187d | AE-3 | ¹HNMR (DMSO-d₆): δ 8.8 (m, 2 H), 8.7 (m, 1 H), 8.4 (m, 2 H), 8.1 (m, 1 H), 7.6 (m, 2 H), 7.5 (m, 3 H), 7.3 (m, 1 H), 7.2 (m, 1 H), 6.8 (m, 1 H), 6.6 (m, 2 H), 5.8 (m, 1 H), 5.3 (m, 1 H), 4.1 (m, 2 H), 3.31 (m, 1 H), 3.2 (m, 1 H), 1.7 (m, 1 H), 1.6 (m, 1 H), 1.3 (m, 1 H), 1.0 (m, 6 H); MS (ES+): 485 |

-continued

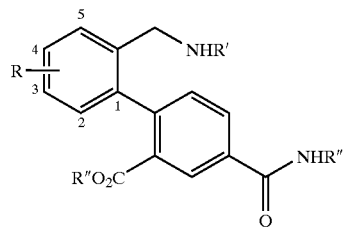

| Cpd. No. | —R | —R' | —R" | —R"' | Starting From | Method Used | Analytical Data |
|---|---|---|---|---|---|---|---|
| 189a | —OCH₃ (3) | 4-methylbenzamidine | sec-butyl | —H | 74 | AE-4, I-2 | ¹HNMR (DMSO-d₆): δ 8.60 (t, J = 6 Hz, 1 H), 8.39 (bs, 2 H), 8.28 (bs, 1 H), 7.78 (m, 1 H), 7.56 (m, 1 H), 7.43 (dd, J=5.8 Hz, 3.8 Hz, 2 H), 7.18 (m, 2 H), 6.80 (m, 3 H), 6.51 (bs, 1 H), 4.10 (m, 1 H), 3.85 (m, 1 H), 3.70 (s, 3 H), 3.17 (t, J=6 Hz, 2 H), 1.80 (m, 1 H), 0.89 (d, J=6.8 Hz, 6 H); MS (ES⁺) 475.2 |
| 189b | —OBn (4) | 4-methylbenzamidine | sec-butyl | —H | 184a | AE-3 | ¹HNMR (DMSO-d₆/D₂O): δ 8.24 (d, J=1.5 Hz, 1 H), 7.86 (d, J=7 Hz, 1 H), 7.49 (m, 2 H), 7.36 (m, 4 H), 7.26 (d, J=8.3 Hz, 1 H), 6.94 (m, 3 H), 6.66 (d, J=8.7 Hz, 2 Hz, 2 H), 5.03 (s, 2 H), 4.06 (q, J=16 and 21 Hz, 2 H), 3.02 (d, J=7 Hz, 2 H), 1.86 (m, 1 H), 0.89 (d, J=6.8 Hz, 6 H); MS (ES-): 549.2 and (ES⁺) 551.4 |
| 189c | —OH (4) | 4-methylbenzamidine | sec-butyl | —H | 189b | G | ¹HNMR (DMSO-d₆): δ 11.3 (bs, 1 H), 9.07 (s, 1 H), 8.46 (t, J=6 Hz, 1 H), 8.27 (bs, 2 H), 8.15 (bs, 2 H), 7.66 (d, J=7.7 Hz, 1 H), 7.36 (d, J = 8.5 Hz, 2 H), 7.03 (d, J=8.1 Hz, 1 H), 6.77 (m, 2 H), 6.68 (d, J=8.3 Hz, 2 Hz, 2 H), 6.6 (s, 1 H), 6.47 9d, J=8.2 Hz, 1 H), 4.05 (d, J=14 Hz, 1 H), 3.09 (d, J=14 Hz, 1 H), 3.01 (t, J=7 Hz, 2 H), 1.79 (m, 1 H), 0.82 (d, J=6.8 Hz, 6 H); MS (ES-): 459.2 and (ES⁺) 461.4 |
| 189d | —H | 4-methylbenzamidine | sec-butyl | —H | 131 | AE-3 | MS (ES⁺): 445.4; MS (ES⁻): 443.3 |
| 189e | —H | 6-methylpyridyl-3-amidine | sec-butyl | —H | 131 | AE-3 | MS (ES⁺): 446.46; MS (ES⁻): 444.45 |

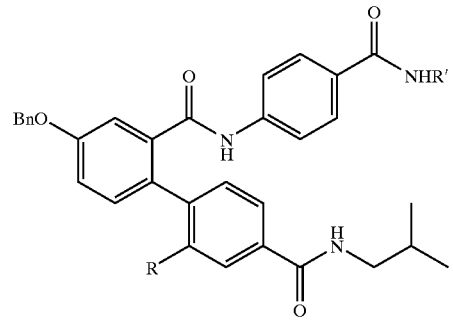

| Cpd. No. | —R | —R' | Starting From | Method Used | Analytical Data |
|---|---|---|---|---|---|
| 205 | ![acetamide](O=C-NH2 attached) | —Boc | 204 | A-4 | $^1$HNMR (DMSO-d$_6$): δ 11.04 (s, 0.6 H), 10.97 (bs, 0.4 H), 8.66 (t, J=5.6 Hz, 0.6 H), 8.56 (t, J=5.6 Hz, 0.4 H), 8.22 (s, 1 H), 8.11 (d, J=2 Hz, 0.6 H), 8.03 (d, J=2 Hz, 0.4 H), 7.94 (dd, J=2 and 8 Hz, 1 H), 7.82 (m, 4 H), 7.40 (m, 8 H), 7.18 (m, 2 H), 7.04 (m, 2 H), 5.21 (s, 0.8 H), 5.11 (s, 1.2 H), 3.11 (t, J=6.2 Hz, 1.2 H), 3.06 (t, J=6.2 Hz, 0.8 H), 1.84 (m, 1 H), 1.43 (s, 5.4 H), 1.42 (s, 3.6 H), 0.91 (d, J=6.8 Hz, 3.6 H), 0.88 (d, J=6.8 Hz, 2.4 H); MS (ES+): 665.5 |
| 206 | —CH$_2$OH | —Boc | 204 | A-6 | $^1$HNMR (DMSO-d$_6$): δ 12.15 (bs, 1 H), 11.07 (bs, 1 H), 10.69 (s, 1 H), 10.38 (bs, 1 H), 8.68 (t, J=5.6 Hz, 1 H), 8.12 (d, J=1.7 Hz, 1 H), 8.00 (dd, 1.8, 8 Hz, 1 H), 7.68 (m, 4 H), 7.46–7.30 (m, 6 H), 7.16 (d, J=2.8 Hz, 1 H), 7.01 (d, J = 8.5 Hz, 1 H), 6.86 (dd, J=8.5 and 2.8 Hz, 1 H), 5.07 (s, 2 H), 4.30 (d, J=7.4 Hz, 2 H), 3.15 (t, J=6.2 Hz, 2 H), 1.86 (m, 1 H), 1.53 (s, 9 H), 0.89 (d, J=6.8 Hz, 6 H); MS (ES–): 649.4 |
| 207 | —CH$_2$OH | —H | 206 | S-2 | $^1$HNMR (DMSO-d$_6$/D$_2$O): δ 10.66 (s, 1 H), 9.19 (bs, 2 H), 8.86 (bs, 2 H), 8.69 (t, J=5.5 Hz, 1 H), 8.13 (d, J=2 Hz, 1 H), 8.02 (dd, J=8 and 2 Hz, 1 H), 7.72 (m, 4 H), 7.38 (m, 6 H), 7.17 (d, J=2.6 Hz, 1 H), 7.03 (d, J=8.5 Hz, 1 H), 6.87 (dd, J=8.5 and 2.5 Hz, 1 H), 5.39 (t, J=4.7 Hz, 1 H), 5.08 (s, 2 H), 4.30 (m, 2 H), 3.13 (t, J=6.5 Hz, 2 H), 1.87 (m, 1 H), 0.91 (d, J=6.5 Hz, 6 H); MS (ES$^+$) 551.4 |
| 208 | ![acetamide] | —H | 205 | S-2 | $^1$HNMR (DMSO-d$_6$): δ 11.26 (s, 0.6 H), 11.20 (bs, 0.4 H), 9.15 (bs, 1.2 H), 9.11 (bs, 0.8 H), 8.84 (bs, 1.2 H), 8.82 (bs, 0.8 H), 8.67 (t, J=5.6 Hz, 0.6 H), 8.58 (t, J=5.6 Hz, 0.4 H), 8.3 (s, 1 H), 8.12 (d, J=2 Hz, 0.6 H), 8.04 (d, J=2 Hz, 0.4 H), 7.96 (dd, J=2 and 8 Hz, 1 H), 7.84 (m, 1 H), 7.70 (m, 2 H), 7.57 (m, 3 H), 7.40 (m, 4 H), 7.22 (m, 2 H), 7.02 (m, 2 H), 5.21 (s, 0.8 H), 5.11 (s, 1.2 H), 3.12 (t, J=6.5 Hz, 1.2 H), 3.06 (t, J=6.5 Hz, 0.8 H), 1.84 (m, 1 H), 0.90 (d, J=6.5 Hz, 3.6 H), 0.86 (d, J=6.5 Hz, 2.4 H); MS (ES+): 564.5 |

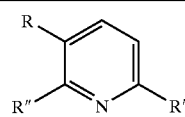

| Cpd. No. | —R | —R' | —R" | Starting From | Method Used | Analytical Data |
|---|---|---|---|---|---|---|
| 217 | —OCH$_3$ | —C(O)CH$_2$NHCH(CH$_3$)CH$_3$ (isobutylamide acetyl) | —Br | 216 | A-3 | $^1$H NMR (DMSO-d$_6$): δ 8.48 (t, J=6.2 Hz, 1 H), 8.06 (d, J=8.3 Hz, 1 H), 7.69 (d, J=8.5 Hz, 1 H), 4.01 (s, 3 H), 3.15 (t, J=6.5 Hz, 2 H), 1.91 (m, 1 H), 0.91 (d, J=6.6 Hz, 6 H); MS (ES$^+$): 287.1 |
| 218 | —OCH$_3$ | —C(O)CH$_2$NHCH(CH$_3$)CH$_3$ | —CH=CH$_2$ | 217 | D-12 | $^1$H NMR (CDCl$_3$): δ 8.08 (m, 2 H), 7.20 (m, 2 H), 6.39 (dd, J=2.0 and 17.3 Hz, 1 H), 5.53 (dd, J=2.0 and 10.9 Hz, 1 H), 4.01 (s, 3 H), 3.15 (t, J = 6.5 Hz, 2 H), 1.91 (m, 1 H), 0.91 (d, J=6.6 Hz, 6 H) |

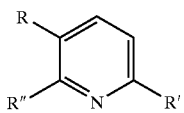

| Cpd. No. | —R | —R' | —R" | Starting From | Method Used | Analytical Data |
|---|---|---|---|---|---|---|
| 219 | —OH | CH₃CH(CH₃)CH₂NHC(O)CH₃ (isobutyl acetamide group) | —CO₂CH₃ | 218 | E-2, V-3, W-2 | $^1$H NMR (DMSO-$d_6$): δ 11.05 (s, 1 H), 8.48 (t, J = 6.2 Hz, 1 H) 8.06 (d J=8.7 Hz, 1 H) 7.53 (d, J=8.5 Hz, 1 H), 3.90 (s, 3 H), 3.12 (t, J=6.6 Hz, 2 H), 1.85 (m, 1 H), 0.86 (d, J=6.6 Hz, 6 H); MS (ES$^+$): 253.2 |
| 220 | —OSO₂CF₃ | CH₃CH(CH₃)CH₂NHC(O)CH₃ | —CO₂CH₃ | 219 | B-2 | MS (ES$^+$): 407.2 (M + Na)$^+$ |
| 237 | acetamidine (C(=NH)NH₂ with CH₃) | —NH₂ | —H | 236 | AF-1 | MS (ES$^+$): 137.1 |

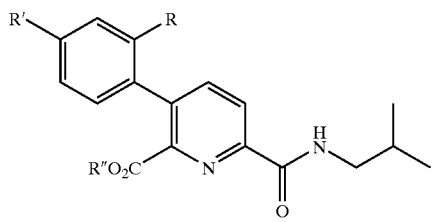

| Cpd. No. | —R | —R' | —R" | Starting From | Method Used | Analytical Data |
|---|---|---|---|---|---|---|
| 221 | —CHO | —OBn | —CH₃ | 220 + 6 | D-2 | $^1$H NMR (CDCl₃): δ 9.77 (s, 1 H), 8.40 (d, J=7.9 Hz, 1 H), 8.13 (d, J = 6.8 Hz, 1 H), 7.83 (d, J=7.9 Hz, 1 H), 7.61 (d, J=2.60 Hz, 1 H), 7.20 (m, 5 H), 7.21 (m 1 H), 7.18 (d, J=8.3 Hz, 1 H), 5.18 (s, 2 H), 3.72 (s, 3 H), 3.35 (q, J=5.8 Hz, 2 H), 1.96 (m, 1 H), 1.01 (d, J=6.8 Hz,6 H); MS (ES$^+$): 447.4 |
| 222 | —CO₂H | —OBn | —CH₃ | 221 | E | MS (ES$^-$): 461.3 |
| 223 | —CO₂MEM | —OBn | —CH₃ | 222 | F | MS (ES$^+$): 573.33 (M + Na)$^+$ |
| 224 | —CO₂MEM | —OH | —CH₃ | 223 | G | MS (ES$^+$): 461.36 |
| 225 | —CO₂MEM | —OSO₂CF₃ | —CH₃ | 224 | B-2 | MS (ES$^+$): 615.58 (M + Na)$^+$ |
| 226 | —CO₂MEM | —CH=CH₂ | —CH₃ | 225 | D-3 or D-12 | MS (ES$^-$): 381.35 [(M-MEM)-1] |
| 227 | —CO₂H | —CH=CH₂ | —CH₃ | 226 | I-1 | MS (ES$^-$): 381.35 |
| 228 | 4-acetamidobenzamidine group | —CH=CH₂ | —CH₃ | 227 | J | MS (ES$^+$): 500.35 |

-continued

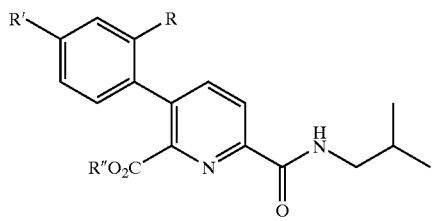

| Cpd. No. | —R | —R' | —R" | Starting From | Method Used | Analytical Data |
|---|---|---|---|---|---|---|
| 229 | 4-(acetamido)benzamidine | —CH=CH₂ | —H | 228 | I-2 | MS (ES⁺): 486.32 |
| 245 | —CHO | —OH | —CH₃ | 221 | AD | MS (ES⁺): 357.40 |
| 246 | —CHO | —OSO₂CF₃ | —CH₃ | 245 | B-2 | Characterized in the next step |
| 247 | —CHO | —CH=CH₂ | —CH₃ | 246 | D-3 | MS (ES⁺): 367.42 |
| 248 | 4-(ethylamino)benzamidine | —CH=CH₂ | —H | 247 | AE-3 | MS (ES⁺): 472.39 |
| 249 | 4-(acetamido)benzamidine | —OBn | —CH₃ | 222 | J | MS (ES⁺): 580.4 |
| 250 | 4-(acetamido)benzamidine | —OBn | —H | 249 | I-2 | MS (ES⁺): 566.4<br>MS (ES⁻): 564.3 |
| 251 | 4-(acetamido)benzamidine | —OH | —H | 250 | G | MS (ES⁺): 476.3<br>MS (ES⁻): 474.2 |
| 252 | 6-(ethylamino)pyridine-3-carboxamidine | —CH=CH₂ | —H | 247 | AE-3 | MS (ES⁺): 473.44<br>MS (ES⁻): 471.43 |

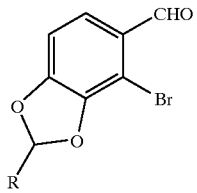

| Cpd. No. | —R | Starting From | Method Used | Analytical Data |
|---|---|---|---|---|
| 231b | —CO₂CH₃ | 230 | AG-3 | ¹H NMR (CDCl₃): δ 10.17 (d, J=0.75 Hz, 1 H), 7.62 (d, J=8.3 Hz, 1 H), 6.94 (dd, J=8.3, 0.75 Hz, 1 H), 6.51 (s, 1 H), 3.90 (s, 3 H) |

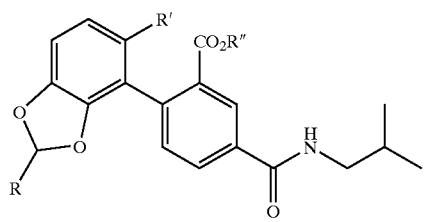

| Cpd. No. | —R | —R' | —R" | Starting From | Method Used | Analytical Data |
|---|---|---|---|---|---|---|
| 232a | —H | —CHO | —CH₃ | 231a + 6a | D-6 or D-7 | ¹HNMR (CDCl₃): δ 9.64 (s, 1 H), 8.44 (d, J = 2 Hz, 1 H), 8.02 (dd, J=8 and 2 Hz, 1 H), 7.60 (d, J=8.3 Hz, 1 H), 7.40 (d, J=8 Hz, 1 H), 6.96 (d, J=8 Hz, 1 H), 6.32 (t, J=6 and 5 Hz, 1 H), 6.01 (s, 2 H), 3.72 (s, 3 H), 3.33 (t, J = 6.5 Hz, 2 H), 1.93 (m, 1 H), 1.00 (d, J=6.8 Hz, 6 H); MS (ES⁺): 384.3 and 406.3 (M + Na)⁺ |
| 232b | —CO₂H | —CHO | —CH₃ | 231b + 6a | D-6 or D-7 | ¹HNMR (DMSO-d₆): δ 9.87 (s, 1 H), 9.49 (s, 1 H), 8.64 (d, J=2 Hz, 1 H), 8.3 (s, 1 H), 7.97 (d, J=8 Hz, 1 H), 7.43 (dd, J=8 and 2.6 Hz, 1 H), 7.35 (m, 2 H), 6.94 (m, 1 H), 6.05 (s, 0.4 H), 5.98 (s, 0.6 H), 3.55 (s, 1.8 H), 3.52 (s, 1.2 H), 3.02 (t, J=6.5 Hz, 2 H), 1.78 (m, 1 H), 0.81 (d, J=6.6 Hz, 6 H); MS (ES⁻): 426.2 |
| 233a | —H | —CO₂H | —CH₃ | 232a | E | ¹HNMR (DMSO-d₆): δ 12.29 (bs, 1 H), 8.69 (t, J=5.5 Hz, 1 H), 8.38 (d, J=2 Hz, 1 H), 8.03 (dd, J=8 and 2 Hz, 1 H), 7.58 (d, J=8.5 Hz, 1 H), 7.36 (d, J=8 Hz, 1 H), 7.00 (d, J=8.5 Hz, 1 H), 6.02 (s, 2 H), 3.64 (s, 3 H), 3.12 (t, J = 6.5 Hz, 2 H), 1.87 (m, 1 H), 0.91 (d, J=6.8 Hz, 6 H); MS (ES⁻): 398.2 |
| 233b | —CO₂H | —CO₂H | —CH₃ | 232b | E | ¹HNMR (DMSO-d₆): δ 8.64 (t, J=5.5 Hz, 1 H), 8.38 (d, J=4 Hz, 1 H), 8.00 (dd, J=8.5 and 4 Hz, 1 H), 7.59 (dd, J=8.5 and 4 Hz, 1 H), 7.30 (dd, J=8 and 2.5 Hz, 1 H), 6.52 (s, 0.5 H), 6.48 (s, 0.5 H), 3.60 (s, 1.5 H), 3.58 (s, 1.5 H), 3.08 (t, J=6.5 Hz, 2 H), 1.84 (m, 1 H), 0.88 (d, J=6.8 Hz, 6 H) |
| 234a | —H | 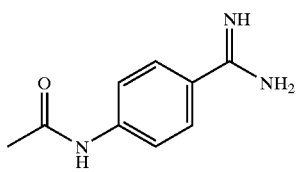 | —CH₃ | 233a | J | MS (ES⁺): 517.4 |

-continued

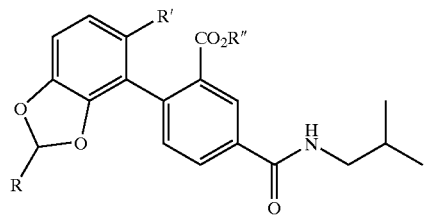

| Cpd. No. | —R | —R' | —R" | Starting From | Method Used | Analytical Data |
|---|---|---|---|---|---|---|
| 234b | —CO$_2$H | | —CH$_3$ | 233b | J | $^1$HNMR (DMSO-d$_6$): δ 12.41 (bs, 1 H), 11.09 (s, 1 H), 10.96 (s, 1 H), 9.22 (bs. 2 H), 8.96 (bs, 2 H), 8.70 (m, 1 H), 8.38 (dd, J=2 and 13 Hz, 1 H), 8.04 (d, J=8 Hz, 1 H), 7.82 (m, 4 H), 7.65 (dd, J=8 and 5 Hz, 1 H), 7.39 (dd, J = 8 and 2.5 Hz, 1 H), 7.11 (dd, J=8.5 and 1.7 Hz, 1 H), 6.05 (s, 1 H), 3.67 (s, 1.5 H), 3.50 (s, 1.5 H), 3.10 (t, J=6.5 Hz, 2 H), 1.88 (m, 1 H), 0.90 (d, J=6.8 Hz, 6 H) |
| 235a | —H | | —H | 234a | I-2 | $^1$HNMR (DMSO-d$_6$ + DCl one drop): δ 8.34 (d, J=2 Hz, 1 H), 7.97 (dd, J=8 and 2 Hz, 1 H), 7.75 (m, 4 H), 7.33 (dd, J=3.8 and 8.1 Hz, 2 H), 7.04 (d, J=8.1 Hz, 1 H), 6.01 (d, J=6 Hz, 2 H), 3.07 (t, J=6.5 Hz, 2 H), 1.83 (m, 1 H), 0.86 (d, J=6.8 Hz, 6 H); MS (ES−) 501.3; (ES+) 503.3 |

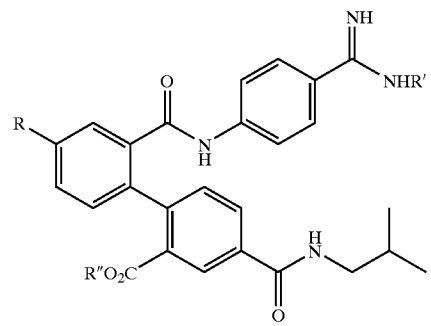

| Cpd. No. | —R | —R' | —R" | Starting From | Method Used | Analytical Data |
|---|---|---|---|---|---|---|
| 240 | —CH(OH)—CH$_2$OH | —Boc | —CH$_3$ | 161d | L | $^1$H NMR (DMSO-d6): δ 10.47 (s, 1H), 9.07 (s, 2H), 8.72 (t, J = 5.7 Hz, 1H), 8.29 (d, J = 2 Hz, 1H), 8.08 (dd, J = 8.0, 2 Hz, 1H), 7.95 (s, 1H), 7.92 (s, 1 H), 7.67 (m, 2 H), 7.62 (d, J = 6.5 Hz, 1 H), 7.46 (d, J = 8 Hz, 1H), 7.31 (d, J = 8 Hz, 1H), 5.50 (d, J = 4.5 Hz, 1H), 4.91 (t, J = 5.7 Hz, 1H), 4.74 (m, 1 H), 4.25 (s, 1 H), 3.63 (s, 3H), 3.15 (t, J = 6.4 Hz, 2H), 1.91 (m, 1H), 1.50 (s, 9 H), 0.95 (d, J = 6.7 Hz, 6H) |
| 241 | —CHO | —Boc | —CH$_3$ | 240 | M | $^1$H NMR (DMSO-d6): δ 10.69 (s, 1H), 10.17 (s, 1 H), 9.10 (bs, 2 H), 8.72 (t, J = 5.7 Hz, 1H), 8.30 (d, J = 1.5 Hz, 1H), 8.22 (d, J = 1.5 Hz, 1H), 8.22 (dd, J = 1.5 and 8 Hz, 1 H), 8.07 (dd, J = 1.5 and 8 Hz, 1 H), 7.89 (s, 1H), 7.86 (s, 1 H), 7.65 (s, 1 H), 7.62 (s, 1 H), 7.57 (d, J = 8 Hz, 1H), 7.44 (d, J = 8 Hz, 1H), 3.57 (s, 3H), 3.11 (t, J = 6.4 Hz, 2H), 1.85 (m, 1H), 1.44 (s, 9 H), 0.89 (d, J = 6.7 Hz, 6H) |
| 242 | —CH(OH)—CH=CH$_2$ | —Boc | —CH$_3$ | 241 | AG | MS (ES$^+$): 629.39 |
| 243 | —CH(OH)—CH=CH$_2$ | —H | —CH$_3$ | 242 | S | MS (ES$^+$): 529.38 |
| 244 | —CH(OH)—CH=CH$_2$ | —H | —H | 243 | I-2 | MS (ES$^−$): 515.35 |

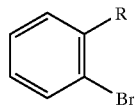

| Cpd. No. | —R | Starting From | Method Used | Analytical Data |
|---|---|---|---|---|
| 254 | propyl-NH—C6H4—C(=NH)NH2 | 253 | AE-3 | MS (ES+): 318.2, 320.2 |
| 255 | propyl-NH—C6H4—C(=NH)NHBoc | 254 | R | MS (ES+): 418 |

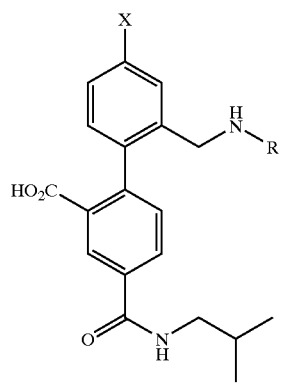

| Cpd. No. | X | —R | Starting From | Method Used | Analytical Data |
|---|---|---|---|---|---|
| 258a | H | 3-F-4-(C(=NH)NH2)-phenyl | 131 | AE-3 | 1HNMR (DMSO-d6): δ 11.71 (bs, 1 H), 8.57 (t, J = 5.5 Hz, 1 H), 8.44 (s, 1 H), 8.34 (s, 1 H), 7.80 (dd, J = 1.5, 7.5 Hz, 1 H), 7.45 (d, J = 12.8 Hz, 1 H), 7.20 (m, 5 H), 6.96 (m, 1 H), 4.13 (m, 2 H), 3.09 (t, J = 6.8 Hz, 2 H), 1.87 (m 1 H), 0.87 (d, J = 6.8 Hz, 6 H); MS (ES+) 463.62. |
| 258b | —CH=CH2 | 3-HO-4-(C(=NH)NH2)-phenyl | 187a | AE-3 | 1HNMR (DMSO-d6): δ 10.01 (s, 1 H), 8.73 (s, 2 H), 8.39 (d, J = 2 Hz, 1 H), 8.33 (s, 1 H), 8.07 (dd, J = 7.7 & 2 Hz, 1 H), 7.78 (m, 2 H), 7.60 (m, 2 H), 7.40 (m, 2 H), 7.05 (m, 2 H), 6.7 (dd, J = 11 & 17.5, 1 H), 6.34 (t, J = 6 Hz, 1 H), 6.26 (d, J = 8 Hz, 1 H), 5.73 (d, J = 17.5 Hz, 1 H), 5.24 (d, J = 11 Hz, 1 H), 4.11 (t, J = 5.5 Hz, 2 H), 3.11 (t, J = 6 Hz, 2 H), 1.87 (m, 1 H), 0.90 (t, J = 6.6 Hz, 6 H); MS (ES+) 487.35. |
| 258c | —CH=CH2 | 3-allyl-4-(C(=NH)NH2)-phenyl | 187a | AE-3 | 1HNMR (DMSO-d6): δ 8.78 (s, 2 H), 8.73 (t, J = 5.5 Hz, 1 H), 8.40 (d, J = 2 Hz, 1 H), 8.37 (s, 2 H), 8.08 (s, 1 H), 7.48–7.32 (m, 5 H), 7.28 (d, J = 7.5 Hz, 1 H), 6.68 (m, 1 H), 6.55 (t, J = 5.5 Hz, 1 H), 6.30 (d, J = 8.6 Hz, 1 H), 6.01 (m, 1 H), 5.71 (d, J = 17.5 Hz, 1 H), 5.23 (d, J = 11 Hz, 1 H), 5.11 (m, 2 H), 4.13 (d, J = 5.3 Hz, 2 H), 3.11 (t, J = 6.5 Hz, 2 H), 1.87 (m, 1 H), 0.91 (d, J = 6.8 Hz, 6 H); MS (ES+) 511.41. |

-continued

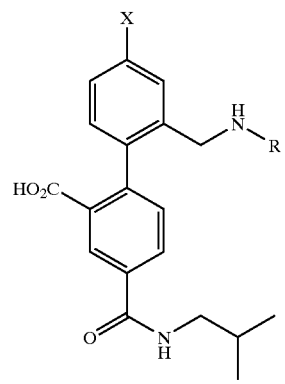

| Cpd. No. | X | —R | Starting From | Method Used | Analytical Data |
|---|---|---|---|---|---|
| 258d | —CH=CH₂ | 2-fluoro-4-methylbenzamidine | 187a | AE-3 | ¹HNMR (DMSO-d₆): δ 8.62 (t, J = 5.7 Hz, 2 H), 8.52 (s, 2 H), 8.31 (s, 1 H), 7.88 (s, 1 H), 7.68 (s, 1 H), 7.24 (m, 5 H), 7.00 (d, J = 6.1 Hz, 1 H), 6.72 (q, J = 11.2 Hz, 1 H), 6.48 (s, 1 H), 5.73 (d, J = 16.8 Hz, 1 H), 5.22 (d, J = 10.5 Hz, 1 H), 4.08 (m, 2 H), 3.10 (t, J = 6.1 Hz, 2 H), 1.86 (m, 1 H), 0.89 (d, J = 6.8 Hz, 6 H); MS (ES+) 489.39. |
| 258e | —CH=CH₂ | 5-methylpyridine-2-carboxamidine | 187a | AE-3 | ¹HNMR (DMSO-d₆): δ 8.61 (t, J = 5.3 Hz, 4 H), 8.32 (s, 1 H), 8.18 (s, 1 H), 7.89 (t, J = 8.5 Hz, 2 H), 7.70 (s, 1 H), 7.32 (d, J = 8.1 Hz, 1 H), 7.25 (m, 3 H), 6.97 (d, J = 7.5 Hz, 1 H), 6.68 (q, J = 17.8 & 10.9 Hz, 1 H), 5.67 (d, J = 17.6 Hz, 1 H), 5.18 (d, J = 10.9 Hz, 1 H), 4.24 (m, 2 H), 3.10 (t, J = 6.5 Hz, 2 H), 1.88 (m, 1 H), 0.90 (d, J = 6.8 Hz, 6 H); MS (ES+) 472.37. |
| 258f | —CH=CH₂ | 3-methoxy-4-methylbenzamidine | 187a | AE-3 | ¹HNMR (DMSO-d₆): δ 8.60 (s, 1 H), 8.38 (s, 2 H), 7.81 (s, 1 H), 7.30 (d, J = 7.7 Hz, 2 H), 7.17 (m, 4 H), 7.13 (d, J = 5.7 Hz, 1 H), 7.05 (m, 1 H), 6.69 (m, 2 H), 5.64 (d, J = 16.6 Hz, 1 H), 5.16 (d, J = 11.2 Hz, 1 H), 4.27 (m, 1 H), 3.91 (m, 4 H), 3.10 (t, J = 6.5 Hz, 2 H), 1.86 (m, 1 H), 0.90 (d, J = 6.6 Hz, 6 H); MS (ES⁺) 501.37. |
| 258g | —CH=CH₂ | 2-chloro-4-methylbenzamidine | 187a | AE-3 | ¹H NMR (DMSO-d₆): δ 13.84 (br s,2 H), 9.32 (s, 2 H), 9.11 (s, 2 H), 8.56 (t, J = 6.4 Hz, 1 H), 7.81–7.41 (m, 8 H), 7.11 (d, J = 7.9 Hz, 1 H), 6.86 (dd, J = 11.1 and 17.3 Hz, 1 H), 5.97 (d, J = 17.3 Hz, 1 H), 5.38 (d, J = 11.1 Hz, 1 H), 3.12 (m, 2 H), 1.87 (m, 1 H), 0.87 (d, J = 6.4 Hz, 6 H); MS (ES⁺): 520.5. |

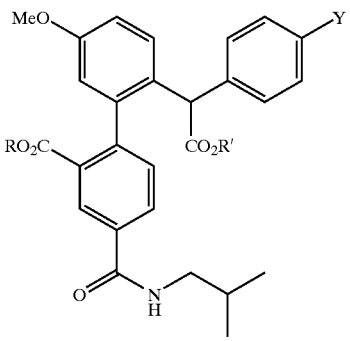

| Cpd. No. | R | R' | Y | Starting From | Method Used | Analytical Data |
|---|---|---|---|---|---|---|
| 259 | CH₃ | CH₃ | CN | 74 | AM | MS (ES⁺): 522.3 (M + Na) |
| 260 | H | H | ![NH/NH2 amidine] | 259 | AJ-1, I-2 | ¹HNMR (DMSO-d₆): δ 8.76 (bs, 2 H), 8.40 (bs, 2 H), 8.35 (m, 1 H), 8.08 (d, J = 7 Hz, 1 H), 7.87 (m, 1 H), 7.79 (d, J = 6 Hz, 1 H), 7.42–7.64 (m, 5 H), 7.30 (m, 1 H), 7.16 (m, 1 H), 7.05 (m, 1 H), 6.70 (t, J = 3.5 Hz, 1 H), 6.45 (m, 1 H), 3.86 (s, 1.5 H), 3.75 (s, 1.5 H), 3.10 (t, J = 6.7 Hz, 2 H), 1.88 (m, 1 H), 0.90 (d, J = 6.7 Hz, 6 H); MS (ES⁺) 519.35 |

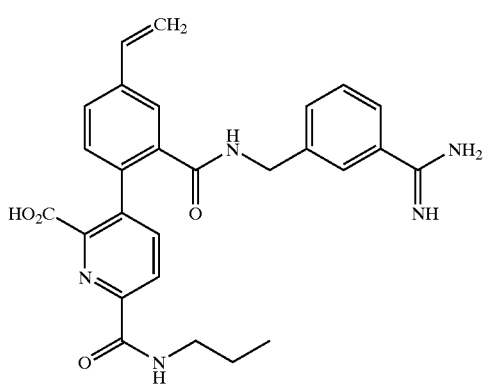

It was prepared as shown in Schemes 31 and 31a. Analytical data: ¹H NMR (DMSO-d₆): δ 13.05 (br s, 1H), 9.09 (s, 2H), 8.94 (s, 2H), 8.65 (m, 1H), 8.26–7.60 (m, 8H), 7.20 (m, 1H), 6.90 (dd, J=11.1 and 17.3 Hz, 1H), 6.00 (d, J=17.3 Hz, 1H), 5.40 (d, J=11.1 Hz, 1H), 3.25 (m, 2H), 1.59 (q, J=6.9 Hz, 2H), 0.92 (t, J=7.3 Hz, 3H); MS (ES⁻): 470.30.

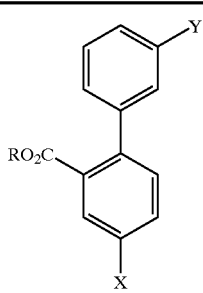

| Cpd. No. | X | Y | R | Starting From | Method Used | Analytical Data |
|---|---|---|---|---|---|---|
| 263a | H | CHO | CH₃ | 261 and 262a | D-1 | MS (ES⁺): 241.2 |

-continued

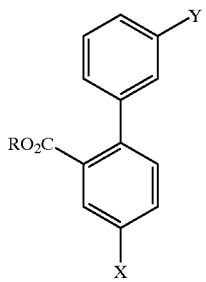

| Cpd. No. | X | Y | R | Starting From | Method Used | Analytical Data |
|---|---|---|---|---|---|---|
| 263b | isobutylamino-carbonyl | CHO | CH₃ | 261 and 3a | D-1 | MS (ES⁺): 340.3 |
| 264a | H | CO₂H | CH₃ | 263a | E | MS (ES⁻): 255.5 |
| 264b | isobutylamino-carbonyl | CO₂H | CH₃ | 263b | E | MS (ES⁺): 356.3 |
| 265a | H | 4-(amidino)phenyl-NHC(O)- | H | 264a | J, I-2 | ¹HNMR (DMSO-d₆, MSA salt): δ 10.39 (s, 1 H), 8.6 (s, 2 H0, 8.45 (s, 2 H), 7.12–7.65 (m, 4 H), 7.66–8.2 (m, 8 H), 2.35 (s, 3 H); MS (ES⁺) 360.33. |
| 265b | isobutylamino-carbonyl | 4-(amidino)phenyl-NHC(O)- | H | 264b | J, I-2 | ¹HNMR (DMSO-d₆): δ 13.01 (bs, 1 H), 10.74 (s, 1 H), 9.22 (s, 2 H), 8.88 (s, 2 H), 8.61 (t, J = 5.5 Hz, 1 H), 8.1 (dd, J = 8.2 and 2 Hz, 1 H), 8.02 (m, 3 H), 7.86 (m, 1 H), 7.83 (s, 1 H), 7.61 (m, 3 H), 3.19 (t, J = 6.7 Hz, 2 H), 2.32 (s, 3 H), 1.82 (m, 1 H), 0.92 (d, J = 6.59 Hz, 6 H); MS (ES⁺) 459.29. |
| 266a | H | 4-(amidino)phenyl-NHEt | H | 263a | AE-3 | ¹HNMR (DMSO-d₆ MSA salt): δ 8.75 (s, 2H), 8.40 (s, 2 H), 7.15–7.75 (m, 12 H), 4.40 (s, 2 H), 2.5 (s, 3 H); MS (ES⁺) 346.37. |
| 266b | isobutylamino-carbonyl | 4-(amidino)phenyl-NHEt | H | 263b | AE-3 | ¹HNMR (DMSO-d₆): δ 8.77 (s, 2 H), 8.39 (s, 2 H), 8.22 (s, 1 H), 7.6–7.2 (m, 10 H), 6.7 (d, J = 4.8 Hz, 2 H), 4.4 (b, 2 H), 2.99 (m, 2 H), 2.49 (s, 3 H), 1.88 (m, 1 H), 0.88 (d, J = 6.58 Hz, 6 H); MS (ES⁺) 445.32. |

The following non-limiting examples are presented to further illustrate the present invention.

2'-[({4-[Amino(imino)methyl]phenyl}amino)carbonyl]-4-[(isobutylamino)carbonyl]-4'-thien-2-yl-1,1'-biphenyl-2-carboxylic acid 2'-[({4-[Amino(imino)methyl]phenyl}amino)carbonyl]-4-[(isobutylamino)carbonyl]-4'-thien-3-yl-1,1'-biphenyl-2-carboxylic acid 2'-[({4-[Amino(imino)methyl]phenyl}amino)carbonyl]-4-[(isobutylamino)carbonyl]-1,1':4',1"-terphenyl-2-carboxylic acid 2'-[({4-[Amino(imino)methyl]phenyl}amino)carbonyl]-4'-(3-furyl)-4-[(isobutylamino)carbonyl]-1,1'-biphenyl-2-carboxylic acid 2'-[({4-[Amino(imino)methyl]phenyl}amino)carbonyl]-4-[(isobutylamino)carbonyl]-4'-pyridin-4-yl-1,1'-biphenyl-2-carboxylic acid 2'-[({4-[Amino(imino)methyl]phenyl}amino)carbonyl]-4-[(isobutylamino)carbonyl]-4'-(1H-pyrrol-2-yl)-1,1'-biphenyl-2-carboxylic acid 2'-[({4-[Amino(imino)methyl]phenyl}amino)carbonyl]-4'-[2-(hydroxymethyl)thien-3-yl]-4-[(isobutylamino)carbonyl]-1,1'-biphenyl-2-carboxylic acid 2'-[({4-[Amino(imino)methyl]phenyl}amino)carbonyl]-4'-[3-(hydroxymethyl)thien-2-yl]-4-[(isobutylamino)carbonyl]-1,1'-biphenyl-2-carboxylic acid 2'-[({4-[Amino(imino)methyl]phenyl}amino)carbonyl]-4-[(isobutylamino)carbonyl]-4'-vinyl-1,1'-biphenyl-2-carboxylic acid 4'-Allyl-2'-[({4-[amino(imino)methyl]phenyl}amino)carbonyl]-4-[(isobutylamino)carbonyl]-1,1'-biphenyl-2-carboxylate 2'-[({4-[Amino(imino)methyl]phenyl}amino)carbonyl]-4-[(isobutylamino)carbonyl]-4'-(1,3-thiazol-2-yl)-1,1'-biphenyl-2-carboxylic acid 2'-[({4-[Amino(imino)methyl]phenyl}amino)carbonyl]-4'-[3-(hydroxymethyl)-2-furyl]-4-[(isobutylamino)carbonyl]-1,1'-biphenyl-2-carboxylic acid 2'-[({4-[Amino(imino)methyl]phenyl}amino)carbonyl]-4-[(isobutylamino)carbonyl]-4'-prop-1-ynyl-1,1'-biphenyl-2-carboxylic acid 2'-[({4-[Amino(imino)methyl]phenyl}amino)carbonyl]-4'-(3-hydroxy-3-methylbut-1-ynyl)-4-[(isobutylamino)carbonyl]-1,1'-biphenyl-2-carboxylic acid 2'-[({4-[Amino(imino)methyl]phenyl}amino)carbonyl]-4-[(3-methylbutanoyl)amino]-4'-vinyl-1,1'-biphenyl-2-carboxylic acid 2'-[({4-[Amino(imino)methyl]phenyl}amino)carbonyl]-4'-(4-hydroxybut-1-ynyl)-4-[(isobutylamino)carbonyl]-1,1'-biphenyl-2-carboxylic acid 2'-[({4-[Amino(imino)methyl]phenyl}amino)carbonyl]-4-[(isobutylamino)carbonyl]-4'-[(1E)-3-methylbuta-1,3-dienyl]-1,1'-biphenyl-2-carboxylic acid 2'-[({4-[Amino(imino)methyl]phenyl}amino)carbonyl]-4'-(3-hydroxyprop-1-ynyl)-4-[(isobutylamino)carbonyl]-1,1'-biphenyl-2-carboxylic acid 2'-[({4-[Amino(imino)methyl]phenyl}amino)carbonyl]-4'-(2-furyl)-4-[(propylamino)carbonyl]-1,1'-biphenyl-2-carboxylic acid 2'-[({4-[Amino(imino)methyl]phenyl}amino)carbonyl]-4-[(sec-butylamino)carbonyl]-4'-(2-furyl)-1,1'-biphenyl-2-carboxylic acid 2'-[({4-[Amino(imino)methyl]phenyl}amino)carbonyl]-4'-(2-furyl)-4-{[(2,2,2-trifluoroethyl)amino]carbonyl}-1,1'-biphenyl-2-carboxylic acid 2'-[({4-[Amino(imino)methyl]phenyl}amino)carbonyl]-4'-(2-furyl)-4-{[(4-hydroxybutyl)amino]carbonyl}-1,1'-biphenyl-2-carboxylic acid 2'-[({4-[Amino(imino)methyl]phenyl}amino)carbonyl]-4-[(ethylamino)carbonyl]-4'-(2-furyl)-1,1'-biphenyl-2-carboxylic acid 2'-[({4-[Amino(imino)methyl]phenyl}amino)carbonyl]-4-[(isobutylamino)carbonyl]-5'-methoxy-4'-vinyl-1,1'-biphenyl-2-carboxylic acid 2'-[({4-[Amino(imino)methyl]phenyl}amino)carbonyl]-4-[(isobutylamino)carbonyl]-4'-(thien-2-ylmethyl)-1,1'-biphenyl-2-carboxylic acid 2-{3-[({4-[Amino(imino)methyl]phenyl}amino)carbonyl]pyridin-4-yl}-5-[(isobutylamino)carbonyl]benzoic acid 2'-[({4-[Amino(imino)methyl]phenyl}amino)carbonyl]-4-[(cyclopentylamino)carbonyl]-4'-vinyl-1,1'-biphenyl-2-carboxylic acid 2'-[({4-[Amino(imino)methyl]phenyl}amino)carbonyl]-5'-ethoxy-4-[(isobutylamino)carbonyl]-4'-vinyl-1,1'-biphenyl-2-carboxylic acid Methyl 2'-[({4-[({[(acetyloxy)methoxy]carbonyl}amino)(imino)methyl]phenyl}amino)carbonyl]-4-[(isobutylamino)carbonyl]-4'-vinyl-1,1'-biphenyl-2-carboxylate Methyl 2'-[({4-[{[(benzyloxy)carbonyl]amino}(imino)methyl]phenyl}amino) carbonyl]-4-[(isobutylamino)carbonyl]-4'-vinyl-1,1'-biphenyl-2-carboxylate N$^1$-{4-[Amino(imino)methyl]phenyl}-N8-isobutyl-6-oxo-6H-benzo[c]chromene-1,8-dicarboxamide 2'-[({4-[Amino(imino)methyl]phenyl}amino)methyl]-4-[(isobutylamino)carbonyl]-4'-vinyl-1,1'-biphenyl-2-carboxylic acid 2'-({[4-(4,5-Dihydro-1H-imidazol-2-yl)phenyl]amino}carbonyl)-4-[(isobutylamino)carbonyl]-1,1'-biphenyl-2-carboxylic acid 2'-[({4-[Amino(imino)methyl]phenyl}amino)carbonyl]-4-[(isobutylamino)carbonyl]-5'-thien-2-yl-1,1'-biphenyl-2-carboxylic acid 2'-[({4-[Amino(imino)methyl]phenyl}amino)carbonyl]-5'-(2-amino-2-oxoethoxy)-4-[(isobutylamino)carbonyl]-1,1'-biphenyl-2-carboxylic acid 2'-[({4-[Amino(imino)methyl]phenyl}amino)carbonyl]-4'-ethoxy-4-[(isobutylamino)carbonyl]-1,1'-biphenyl-2-carboxylic acid 2-{5-[({4-[Amino(imino)methyl]phenyl}amino)carbonyl]-1,3-benzodioxol-4-yl}-5-[(isobutylamino)carbonyl]benzoic acid 2'-[1-({4-[Amino(imino)methyl]phenyl}amino)ethyl]-4-[(isobutylamino)carbonyl]-1,1'-biphenyl-2-carboxylic acid 3-[2-[({4-[Amino(imino)methyl]phenyl}amino)carbonyl]-4-(benzyloxy)phenyl]-6-[(isobutylamino)carbonyl]pyridine-2-carboxylic acid 3-[2-(4-Carbamimidoyl-phenylcarbamoyl)-4-vinyl-phenyl]-6-isobutylcarbamoyl-pyridine-2-carboxylic acid 2'-[(5-Carbamimidoyl-pyridin-2-ylamino)-methyl]-4-isobutylcarbanoyl-4'-vinyl-biphenyl-2-carboxylic acid 2'-{[4-(N-Hydroxycarbamimidoyl)-phenylamino]-methyl}-4-isobutylcarbamoyl-4'-vinyl-biphenyl-2-carboxylic acid 2'-{[4-(N-Hydroxycarbamimidoyl)-phenylamino]-methyl}-4-isobutylcarbamoyl-4'-vinyl-biphenyl-2-carboxylic acid methyl ester 3-{2-[(4-Carbamimidoyl-phenylamino)-methyl]-4-vinyl-phenyl}-6-isobutylcarbamoyl-pyridine-2-carboxylic acid Methyl 3-{2-[({4-[(hydroxyamino)(imino)methyl]phenyl}amino)methyl]-4-vinylphenyl}-6-[(isobutylamino)carbonyl]pyridine-2-carboxylate Methyl 3-{2-[({4-[(hydroxyamino)(imino)methyl]phenyl}amino)carbonyl]-4-vinylphenyl}-6-[(isobutylamino)carbonyl]pyridine-2-carboxylate N$^2$-Hydroxy-3-{2-[({4-[(hydroxyamino)(imino)methyl]phenyl}amino)carbonyl]-4-vinylphenyl}-N6-isobutylpyridine-2,6-dicarboxamide 3-{2-[({4-[(Hydroxyamino)(imino)methyl]phenyl}amino)carbonyl]-4-vinylphenyl}-6-[(isobutylamino)carbonyl]pyridine-2-carboxylic acid 2'-[({4-[Amino(imino)methyl]phenyl}amino)methyl]-4-[(isobutylamino)carbonyl]-5'-methoxy-4'-vinyl-1,1'-biphenyl-2-carboxylic acid 2'-[({4-[Amino(imino)methyl]phenyl}amino)(carboxy)methyl]-4-[(isobutylamino)carbonyl]-5'-methoxy-1,1'-biphenyl-2-carboxylic acid 2'-[({5-[(Hydroxyamino)(imino)methyl]pyridin-2-yl}amino)methyl]-4-[(isobutylamino)carbonyl]-4'-vinyl-1,1'-biphenyl-2-carboxylic acid 2'-[({4-[Amino(imino)methyl]phenyl}amino)carbonyl]-4-{[(3-carboxypropyl)amino]carbonyl}-4'-(2-furyl)-1,1'-biphenyl-2-carboxylic acid 2'-[({4-[Amino(imino)methyl]phenyl}amino)carbonyl]-4-{[(3-carboxypropyl)amino]carbonyl}-4'-vinyl-1,1'-biphenyl-2-carboxylic acid 3-{2-[({4-[Amino(imino)methyl]phenyl}amino)methyl]-5-methoxy-4-vinylphenyl}-6-[(isobutylamino)carbonyl]pyridine-2-carboxylic acid 3-{2-[({4-[Amino(imino)methyl]phenyl}amino)carbonyl]-5-methoxy-4-vinylphenyl}-6-[(isobutylamino)carbonyl]pyridine-2-carboxylic acid 2'-(4-Carbamimidoyl-phenylcarbamoyl)-4-(2-carboxy-ethylcarbamoyl)-4'-ethyl-biphenyl-2-carboxylic acid 2'-[({5-[Amino(imino)methyl]pyridin-2-yl}amino)methyl]-4-[(isobutylamino)carbonyl]-5'-methoxy-4'-vinyl-1,1'-biphenyl-2-carboxylic acid 2'-[({6-[Amino(imino)methyl]pyridin-3-yl}amino)methyl]-4-[(isobutylamino)carbonyl]-4'-vinyl-1,1'-biphenyl-2-carboxylic acid 3'-[({4-[Amino(imino)methyl]phenyl}amino)carbonyl]-4-[(isobutylaminoicarbonyl]-1,1'-biphenyl-2-carboxylic acid 3'-[({4-[Amino(imino)methyl]phenyl}amino)methyl]-4-[(isobutylamino)carbonyl]-1,1'-biphenyl-2-carboxylic acid 4-{[(2-Aminoethyl)amino]carbonyl}-2'-[({4-[amino(imino)methyl]phenyl}amino)carbonyl]-4'-vinyl-1,1'-biphenyl-2-carboxylic acid 2'-[({4-[Amino(imino)methyl]phenyl}amino)carbonyl]-4-{[(2,3-dihydroxypropyl)amino]carbonyl}-4'-vinyl-1,1'-biphenyl-2-carboxylic acid 2'-(4-Carbamimidoyl-phenylcarbamoyl)-4-(2-carbamoyl-ethylcarbamoyl)-4'-ethyl-biphenyl-2-carboxylic acid Biological Assay Methods In Vitro Assay for Inhibition of TF/FVIIa To assess the inhibition of the test compounds against the target enzyme, TF/FVIIa, an amidolytic assay based upon the absorbance of p-Nitroanalide (pNA) at $OD_{405}$ was utilized. The $IC_{50}$ of the test compounds was determined by using KC4A data reduction software (Bio-Tek Instruments) to interpolate percent inhibition from observed Vmax values.

TF/FVIIa assay reactions were performed in a 200 μL mixture containing 4 nM FVIIa, 10 nM lipidated tissue factor, in an assay buffer containing 100 mM Tris, pH 7.2, 150 mM NaCl, 5 mM calcium chloride, 0.1% bovine serum albumin (BSA), and 10% dimethyl sulfoxide (DMSO). TF and FVIIa were allowed to equilibrate at room temperature for 15 minutes. Test compounds dissolved in DMSO were incubated at varied concentrations with TF/FVIIa for 10 minutes, followed by addition of 500 □M substrate Spectrozyme-FVIIa. Reactions were incubated for 5 minutes at room temperature prior to measuring the change in $OD_{405}$ run for 10 minutes at 21 second intervals with a Powerwave $_x$ (Bio-Tek Instruments) microplate reader.

In Vitro Assay for Human Thrombin

This colorimetric assay was used to assess the ability of the test compounds to inhibit the human thrombin enzyme. $IC_{50}$ of the test compounds was determined by using KC4A data reduction software (Bio-Tek Instruments) to interpolate percent inhibition from observed Vmax values.

Thrombin assay reactions were performed in a 200 μL mixture containing human thrombin at (1 U/mL) in an assay buffer containing 100 mM HEPES, 10 mM calcium chloride, and 10% DMSO, pH 7.5. Test compounds dissolved in DMSO were added to thrombin enzyme reactions at varied concentrations, followed by the addition of substrate Nα-Benzoyl-Phe-Val-Arg-p-Nitroanilide at a final concentration of 1 mM. Reactions were incubated for 5 minutes at room temperature prior to measuring the change in $OD_{405}$ nm for 10 minutes at 21 second intervals with a Powerwave $_x$ (Bio-Tek Instruments) microplate reader.

In Vitro Assay for Human Trypsin

This enzymatic assay was employed to evaluate the ability of the test compounds to inhibit human pancreatic trypsin. $IC_{50}$ of the test compounds was determined by using KC4A data reduction software (Bio-Tek Instruments) to interpolate percent inhibition from observed Vmax values.

Trypsin assay reactions were performed in a 200 μL mixture containing human pancreatic trypsin at 1 μg/mL in an assay buffer containing 200 mM triethanolamine (TEA), 10 mM calcium chloride, 10% DMSO, pH 7.8. Test compounds dissolved in DMSO were added to trypsin enzyme reactions at varied concentrations, followed by the addition of substrate Nα-Benzoyl-L-Arginine p-Nitroanilide (L-BAPNA) at a final concentration of (0.25 mg/mL). Reactions were incubated for 5 minutes at room temperature prior to measuring the change in $OD_{405}$ nm for 10 minutes at 21 second intervals with a Powerwave $_x$ (Bio-Tek Instruments) microplate reader.

Biological Data $IC_{50}$ Values of Some Selected Compounds on Different Serine Protease Enzymes

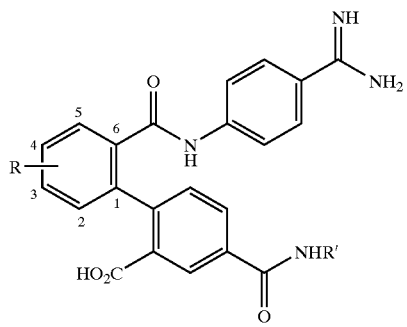

| R (With Respect to Phenyl Ring) | R' | TF/FVIIa | Trypsin | Thrombin |
|---|---|---|---|---|
| 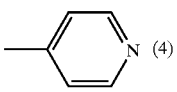 (4) | 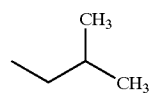 | ++ | + | + |

-continued

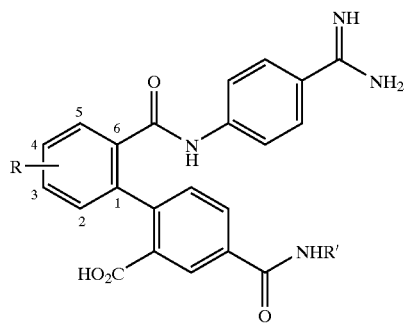

| R (With Respect to Phenyl Ring) | R' | TF/FVIIa | Trypsin | Thrombin |
|---|---|---|---|---|
| 5-(hydroxymethyl)-2-thienyl (4) | isobutyl (CH(CH3)CH2CH3) | ++ | + | + |
| 2-thiazolyl (4) | isobutyl | ++ | + | + |
| 2-methyl-3-butyn-2-ol (4) | isobutyl | ++ | − | − |
| phenoxy (3) | isobutyl | + | − | − |
| 2-thienyl (3) | isobutyl | ++ | − | − |
| 2-furyl (4) | propargyl (CH2C≡CH) | +++ | ++ | + |
| allyl (CH2CH=CH2) (4) | 2-methylhexyl branched | +++ | ++ | + |
| 2-furyl (4) | (CH2)5CO2H | +++ | ++ | + |
| allyl (4) | isobutyl | +++ | ++ | + |

IC$_{50}$ values: + means > 1 μM; ++ means > 100 nM; +++ means < 100 nM

A comparison of Examples with R group and without R group illustrates the greatly-enhanced activity achieved pursuant to the present invention.

Compounds of the present invention are useful as inhibitors of trypsin-like serine protease enzymes such as thrombin, factor VIIa, TF/FVIIa, and trypsin.

These compounds may be employed to inhibit the coagulation cascade and prevent or limit coagulation.

These compounds may be used to inhibit the formation of emboli or thromboli in blood vessels.

These compounds may be used to treat thrombolymphangitis, thrombosinusitis, thromboendocarditis, thromboangitis, and thromboarteritis.

These compounds may be used to inhibit thrombus formation following angioplasty. These may be used in combination with other antithrombolytic agents such as tissue plasminogen activators and their derivatives, streptokinase and its derivatives, or urokinase and its derivatives to prevent arterial occlusion following thrombolytic therapy.

These compounds may also be used in metastatic diseases, or for any disease where inhibition of coagulation is indicated.

These compounds may be used as diagnostic reagents in vitro for inhibiting clotting of blood in the tubes.

These compounds may be used alone or in combination with other compounds such as heparin, aspirin, or warfarin and any other anticoagulant agents.

These compounds may be used as anti-inflammatory agents.

According to a further aspect of the invention, compounds may be employed in preventing ex vivo coagulation such as that encountered in the extracorporeal perfusion of blood through for example artificial valves, prothesis, stents or catheters. According to this aspect of the invention the extracorporeal device may be coated with the compositions of the invention resulting in a lower risk of clot formation due to extrinsic pathway activation.

Dosage and Formulation

The compounds of this invention can be administered by any means that produces contact of the active agent's site of action with factor VIIa and other serine proteases in the body of a human, mammal, bird, or other animal. They can be administered by any conventional means, such as oral, topical, transdermal, parenteral, subcutaneous, intraperitoneal, intrapulmonary, and intranasal, available for use in conjunction with pharmaceuticals, either as individual therapeutic agents or in a combination of therapeutic agents. Parenteral infusion includes intramuscular, intravenous, and intraarterial. They can be administered alone, but generally administered with a pharmaceutical carrier elected on the basis of the chosen route of administration and standard pharmaceutical practice.

The dosage administered will, or course, vary depending upon known factors, such as the pharmacodynamic characteristics of the particular agent and its mode and route of administration; the age, health and weight of the recipient; the nature and extent of the symptoms, the kind of concurrent treatment; the frequency of treatment; and the effect desired. A daily dosage of active ingredient can be expected to be about 0.0001 to 1000 milligram (mg) per kilogram (kg) of body weight, with the preferred dose being 0.1 to about 30 mg/kg.

Dosage forms (compositions suitable for administration) contain from about mg to about 500 mg of compound per unit. In these pharmaceutical compositions, the compound of the present invention will ordinarily be present in an amount of about 0.5–95% by weight based on the total weight of the composition.

The daily dose of the compounds of the invention that is to be administered can be a single daily dose or can be divided into several, for example, two, three or four, part administrations. The pharmaceutical compositions or medicaments of the invention can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

Gelatin capsules contain a compound of the present invention and powdered carriers, such as lactose, starch, cellulose derivatives, biocompatible polymers, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated to mask by unpleasant taste and protect the tablet from the atmosphere, or enteric coated for selective disintegration in the gastrointestinal tract.

Liquid dosage forms for oral administration can contain coloring and flavoring to increase patient acceptance. They may also contain buffering agents, surfactants and preservatives. Liquid oral products can be developed to have sustained-release properties. They may also contain cyclodextrin derivatives to enhance the solubility of the active ingredient and to promote its oral uptake.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and, if necessary, buffering agents. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in Remington's Pharmaceutical Sciences, Mack Publishing Company and in the Handbook of Pharmaceuticals Excipients, American Pharmaceutical Association, both standard reference texts in this field.

Useful pharmaceutical dosage forms for administration of the compounds according to the present invention can be illustrated as follows:

Hard Shell Capsules

A large number of unit capsules are prepared by filling standard two-piece hard gelatin capsules each with 100 mg of powdered 1500 mg of lactose, 50 mg of cellulose, and 6 mg of magnesium stearate.

Soft Gelatin Capsules

A mixture of active ingredient in a digestible oil such as soybean oil, cottonseed oil, or olive oil is prepared and injected by means of a positive displacement pump into molten gelatin to form soft gelatin capsules containing 100 mg of the active ingredient. The capsules are washed and dried. The prodrug can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg of colloidal silicon dioxide, 5 mg of magnesium stearate, 275 mg of microcystalline cellulose, 11 mg of starch, and 9.98 mg of lactose. Appropriate aqueous and non-aqueous coatings may be applied to increase palatability improve elegance and stability or delay absorption.

Immediate Release Tablets/Capsules

These are solid oral dosage forms made by conventional and novel processes. These units are taken orally without water for immediate dissolution and delivery of the medication. The drug is mixed containing ingredient such as sugar, gelatin, pectin, and sweeteners. These liquids are solidified into solid tablets or caplets by freeze drying and solid thermoelastic sugars and polymers or effervescent components to produce porous matrices intended for immediate release, without the need of water.

Moreover, the compounds of the present invention can be administered in the form of nose drops, metered dose nasal or buccal inhalers. The drug is delivered from a nasal solution as a fine mist or from a powder as an aerosol.

In another embodiment of the invention, a compound of the invention can be used in an assay to identify the presence of factor VIIa and other serine protease or to isolate factor VIIa and other serine protease in a substantially purified form. For example, the compound of the invention can be labeled with, for example, a radioisotope, and the labeled compound is detected using a routine method useful for detecting the particular label. In addition, a compound the invention can be used advantageously as a probe to detect the location or amount of factor VIIa and other serine protease activity in vivo, in vitro or ex vivo.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. The foregoing description of the invention illustrates and describes the present invention. Additionally, the disclosure shows and describes only the preferred embodiments of the invention but, as mentioned above, it is to be understood that the invention is capable of use in various other combinations, modifications, and environments and is capable of changes or modifications within the scope of the inventive concept as expressed herein, commensurate with the above teachings and/or the skill or knowledge of the relevant art. The embodiments described hereinabove are further intended to explain best modes known of practicing the invention and to enable others skilled in the art to utilize the invention in such, or other, embodiments and with the various modifications required by the particular applications or uses of the invention. Accordingly, the description is not intended to limit the invention to the form disclosed herein. Also, it is intended that the appended claims be construed to include alternative embodiments.

What is claimed is:
1. Compound having the structure (I) shown below:

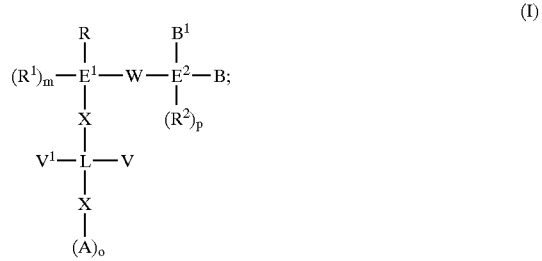

pharmaceutically acceptable salts thereof;
Each $E^1$ is a 5 to 7 membered saturated or unsaturated carbon ring, bicyclic saturated or unsaturated carbon ring, or 1–8 hydrocarbon chain which may be substituted with one or more hetero groups selected from N, O, S, S(O), and S(O$_2$) which may be saturated or unsaturated; wherein L is pyridine ring
R is —CH=CH—$R^2$, —C≡C—$R^2$, —C($R^2$)=CH$_2$, —C($R^2$)=C($R^3$), —CH=N$R^2$, —C($R^2$)=N—$R^3$, 4–7 membered saturated or unsaturated carbon ring system with or without substitution, 4–7 membered saturated or unsaturated hetero ring system with or without substitution, or chain of 2 to 8 carbon atoms having 1 to 5 double or triple bonds with substitutions selected from $R^1$, $R^2$, or $R^3$, these R, $R^1$, $R^2$, or $R^3$ do not include —($C_{2-4}$ alkenyl)-CO$_2$—$C_{1-8}$ alkyl, —($C_{2-4}$ alkenyl)-CO$_2$—$C_{1-8}$ alkyl-phenyl, and —($C_{2-4}$ alkenyl)-CO$_2$—$C_{1-8}$ alkyl-O—$C_{1-4}$ alkyl;
$R^1$ is H, —R, —NO$_2$, —CN, -halo, —N$_3$, —$C_{1-8}$ alkyl, —(CH$_2$)$_n$CO$_2R^2$, —$C_{2-8}$ alkenyl-CO$_2R^2$, —O(CH$_2$)$_n$CO$_2R^2$, —C(O)NR$^2R^3$, —P(O)(OR$^2$)$_2$, alkyl substituted tetrazol-5-yl, —(CH$_2$)$_n$O(CH$_2$)$_n$ aryl, —NR$^2R^3$, —(CH$_2$)$_n$ OR$^2$, —(CH$_2$)$_n$ SR$^2$, —N(R$^2$)C(O)R$^3$, —S(O$_2$)NR$^2R^3$, —N(R$^2$)S(O$_2$)R$^3$, —(CHR$^2$)$_n$ NR$^2R^3$, —C(O)R$^3$, (CH$_2$)$_n$ N(R$^3$)C(O)R$^3$, —N(R$^2$)CR$^2R^3$ substituted or unsubstituted (CH$_2$)$_n$-cycloalkyl, substituted or unsubstituted (CH$_2$)$_n$-phenyl, or substituted or unsubstituted (CH$_2$)$_n$-heterocycle which may be saturated or unsaturated;
m is 1 except that when $E^1$ is a cyclic ring of more than 5 atoms, then m is 1 or higher, depending upon the size of the ring;
$R^2$ is H, -halo, -alkyl, -haloalkyl, —(CH$_2$)$_n$-phenyl, —(CH$_2$)$_{1-3}$-biphenyl, —(CH$_2$)$_{1-4}$-Ph-N(SO$_2$—$C_{1-2}$-alkyl)$_2$, —CO(CHR$^1$)$_n$—OR$^1$, —(CHR$^1$)$_n$-heterocycle, —(CHR$^1$)$_n$—NH—CO—R$^1$, —(CHR$^1$)n-NH—SO$_2R^1$, —(CHR$^1$)$_n$-Ph-N(SO$_2$—$C_{1-2}$-alkyl)$_2$, —(CHR$^1$)$_n$—C(O)(CHR$^1$)—NHR$^1$, —(CHR$^1$)$_n$—C(S)(CHR$^1$)—NHR$^1$, —(CH$_2$)$_n$O(CH$_2$)$_n$CH$_3$, —CF$_3$, —$C_{2-5}$ acyl, —(CHR$^1$)$_n$OH, —(CHR$^1$)$_n$CO$_2R^1$, —(CHR$^1$)$_n$—O-alkyl, —(CHR$^1$)$_n$—O—(CH$_2$)$_n$—O-alkyl, —(CHR$^1$)$_n$—S-alkyl, —(CHR$^1$)$_n$—S(O)-alkyl, —(CHR$^1$)$_n$—S(O$_2$)-alkyl, —(CHR$^1$)$_n$—S(O$_2$)—NHR$_3$, —(CHR$^3$)$_n$—N$_3$, —(CHR$^3$)$_n$NHR$^4$, 2 to 8 carbon atom alkene chain having 1 to 5 double bonds, 2 to 8 carbon atom alkyne chain having 1 to 5 triple bonds, substituted or unsubstituted-(CHR$^3$)n heterocycle, or substituted or unsubstituted-(CHR$^3$)$_n$ cycloalkyl which may be saturated or unsaturated;
When n is more than 1, the substitutions $R^1$ and $R^3$ may be same or different;
$R^3$ is H, —OH, —CN, substituted alkyl, —$C_{2-8}$ alkenyl, substituted or unsubstituted cycloalkyl, —N(R$^1$)R$^2$, or 5–6 membered saturated substituted or unsubstituted hetero ring.

—NR²R³ may form a ring system having 4 to 7 atoms or may be bicyclic ring; wherein said ring system may be of carbon or hetero atoms and further it may saturated or unsaturated and also may be substituted or unsubstituted;

W is a direct bond, —CHR²—, —CH=CR²—, —CR²=CH—, —CR²=CR²—, —C≡C—, —O—CHR²—, —CHR²—O—, —N(R²)—C(O)—, —C(O)—N(R²)—, —N(R²)—CH—(R³)—, —CH₂—N(R²)—, —CH(R¹)—N(R²)—, —S—CHR²—, —CHR²—S—, —S(O₂)—N(R²)—, —C(O)N(R²)—(CHR²)n-, —C(R¹R²)n-NR²—, —N(R²)—S(O₂)—, —R²C(O)NR²—, —R²NC(O)NR²—, —CONR²CO—, —C(=NR²)NR²—, —NR²C(=NR²)NR², —NR²O—, —N=NCHR²—, or —C(O)NR²SO₂—;

E² is 5 to 7 membered saturated or unsaturated carbon ring, 5 to 7 membered saturated or unsaturated hetero ring, bicyclic ring system, $C_{1-8}$ alkyl, $C_{2-8}$ alkenyl, $C_{2-8}$ alkynyl, alkylaryl, aralkyl, aralkenyl, aralkynyl, alkoxy, alkylthio, or alkylamino;

each X individually is a direct bond, substituted or unsubstituted $C_{1-4}$ methylene chain, O, S, NR², S(O), S(O₂), or N(O) containing one or two $C_{1-4}$ substituted or unsubstituted methylene chains; X at different places may be same or different;

B is H, -halo, —CN, —NH₂, —(CH₂)ₙ—C(=NR⁴)NHR⁵, —(CH₂)ₙ—NHR⁴, —(CH₂)ₙNHC(=NR⁴)NR⁵, —(CH₂)ₙ—OR⁴, $C_{1-8}$ substituted or unsubstituted alkyl, substituted or unsubstituted ring system having 4 to 7 carbon or hetero atoms which may be saturated or unsaturated;

B¹ is selected from B; B¹ and B may be same or different;

There may be more than one similar or different R² groups present on E², when E² is a cyclic of more than 5 atoms; p is 1 except that when E² is a cyclic ring of more than 5 atoms; p is 1 or higher depending upon the size of the ring;

n is 0–4;

A is selected from R¹;

o is 1 except that when L is a cyclic ring of more than 5 atoms, o is 1 or higher depending upon the size of the ring;

Each V and V¹ individually is selected from R¹ and N-alkyl substituted carboxamidyl (—CONHR) where the alkyl group may be straight, branched, cyclic, or bicyclic; N,N-disubstituted carboxamidyl of the formula —CONR₁R₂ where R₁ and R₂ may be substituted or unsubstituted alkyl or aryl and may be the same or different; mono- or disubstituted sulfonamides of the formula SO₂NHR or —SO₂NR₁R₂; and methylene- or polymethylene chain-extended variants thereof;

Each R⁴ and R⁵ individually is H, —(CH₂)ₙOH, —C(O)OR⁶, —C(O)SR⁶, —(CH₂)ₙ C(O)NR⁷R⁸, —O—C(O)—O—R⁷, an amino acid or a dipeptide;

Each R⁶ is H, R⁷, —C(R⁷)(R⁸)—(CH₂)ₙ—O—C(O)—R⁹, —(CH₂)ₙ—C(R⁷)(R⁸)—O—C(O)R⁹, —(CH₂)ₙ—C(R⁷)(R⁸)—O—C(O)—O—R⁹, or —C(R⁷)(R⁸)—(CH₂)ₙ—O—C(O)—O—R⁹; and Each R⁷, R⁸ and R⁹ individually is H, alkyl, substituted alkyl, aryl, substituted aryl, alkenyl, substituted alkenyl, alkynyl, substituted alkynyl, heterocycle, substituted heterocycle, alkylaryl, substituted alkylaryl, cycloalkyl, substituted cycloalkyl, or CH₂CO₂alkyl.

2. The compound of claim 1 represented by the structure:

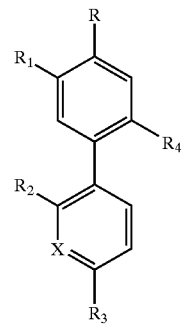

Wherein U is selected from the group consisting of

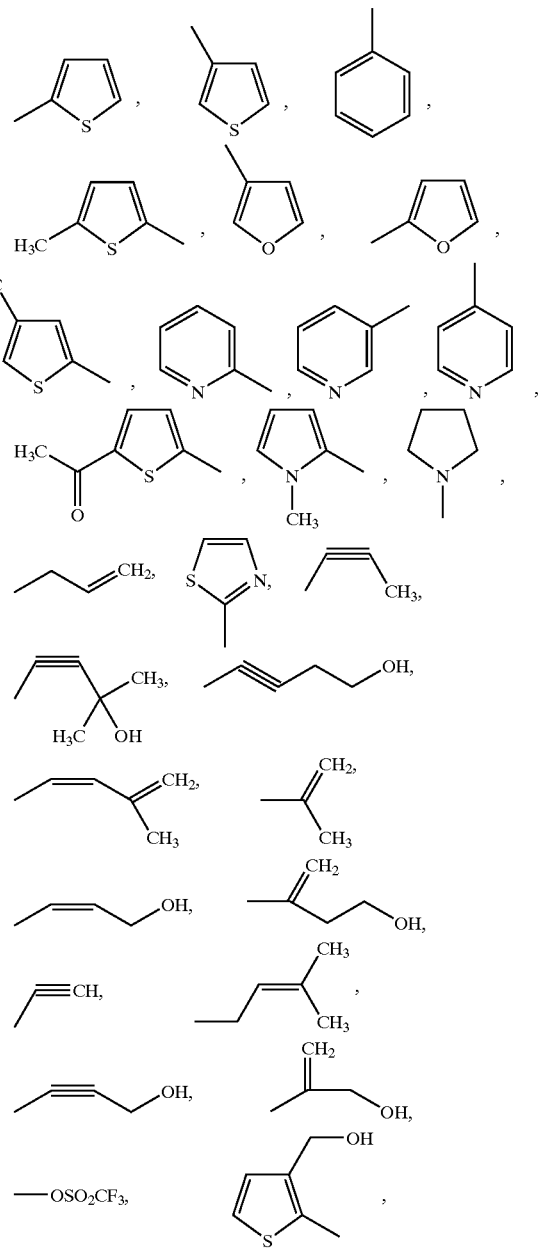

-continued

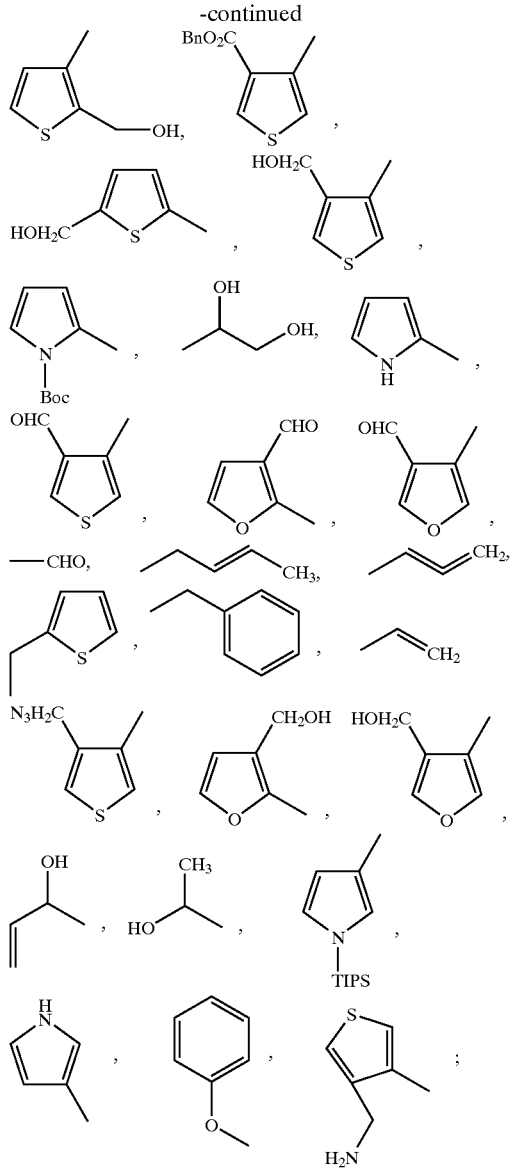

$R^1$ is selected from the group consisting of H, OH, OCH$_3$, CHO, OSO$_2$CF$_3$, OCH$_2$—CH$_2$—OAc, O—CH$_2$—CH$_2$—OH, OCH$_2$CO$_2$C$_2$H$_5$, OCH$_2$CO$_2$H, CO$_2$H, CH$_2$OH, OCH(CH$_3$)$_2$, OC(O)(CH$_3$)$_3$, OCH$_2$CONH$_2$,

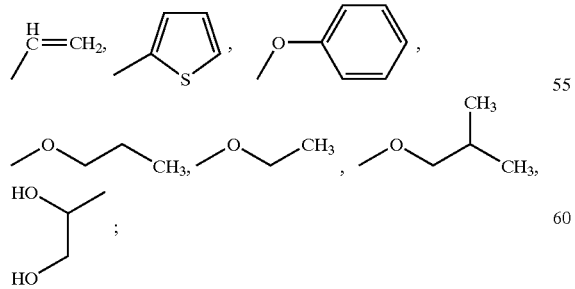

$R_2$ is selected from the group consisting of CO$_2$-alkyl, CO$_2$-aryl, CO$_2$-arylalkyl, CO$_2$H, CH$_2$CO$_2$—alkyl, CH$_2$OH, CONH$_2$;

$R_3$ is selected from the group consisting of H, C(O)—NH—R$_5$, CO$_2$MEM, CO$_2$H,

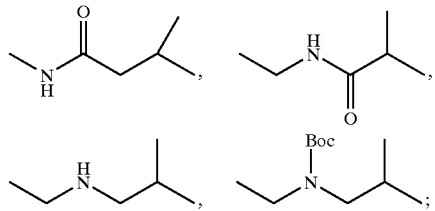

$R_4$ is selected from the group consisting of C(O)NH—R$_6$, —CH(R$_7$)—NH—R$_6$, CO$_2$H, CHO, CO$_2$MEM, —CH(R$_7$)—O—R$_6$, —CH$_2$—CH$_2$—NH—R$_6$ $R_5$ is selected from the group consisting of

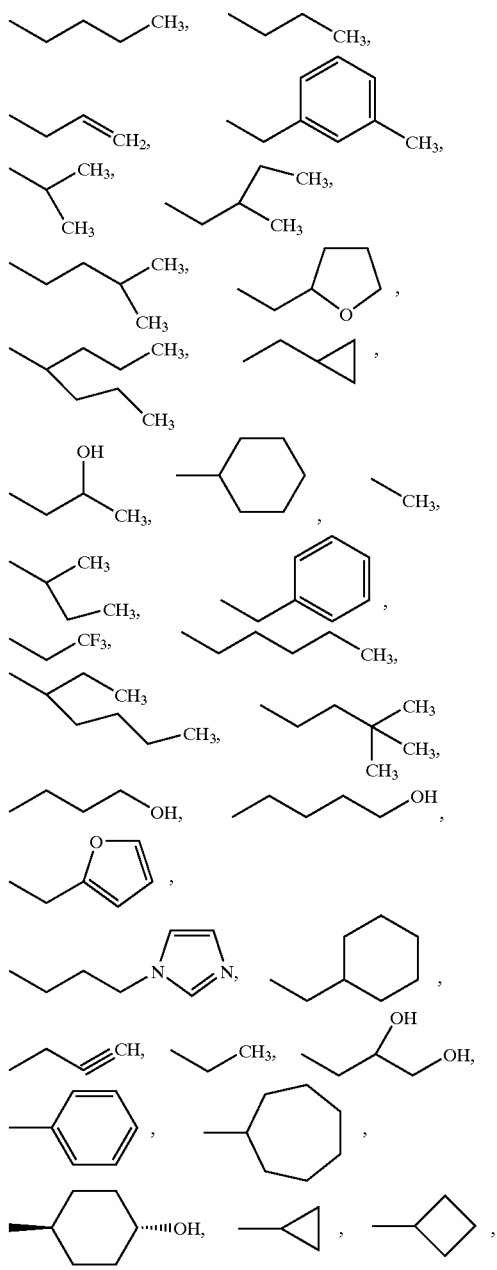

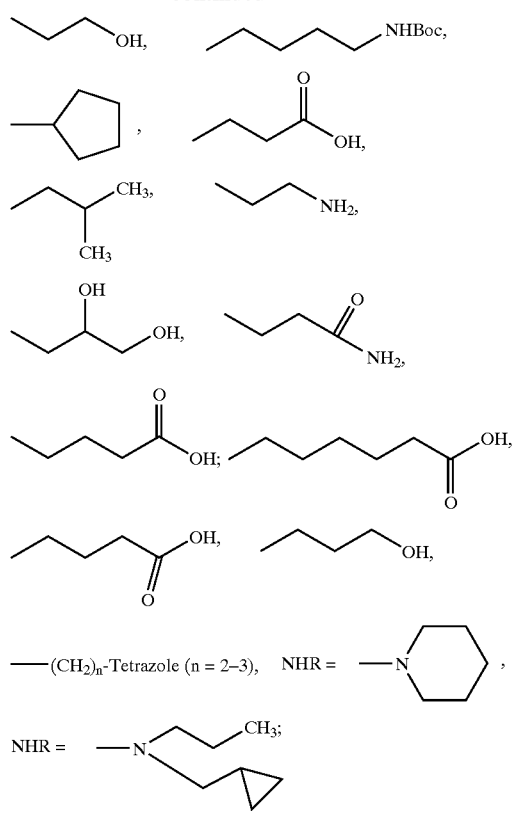
R$_6$ is selected from the group consisting of
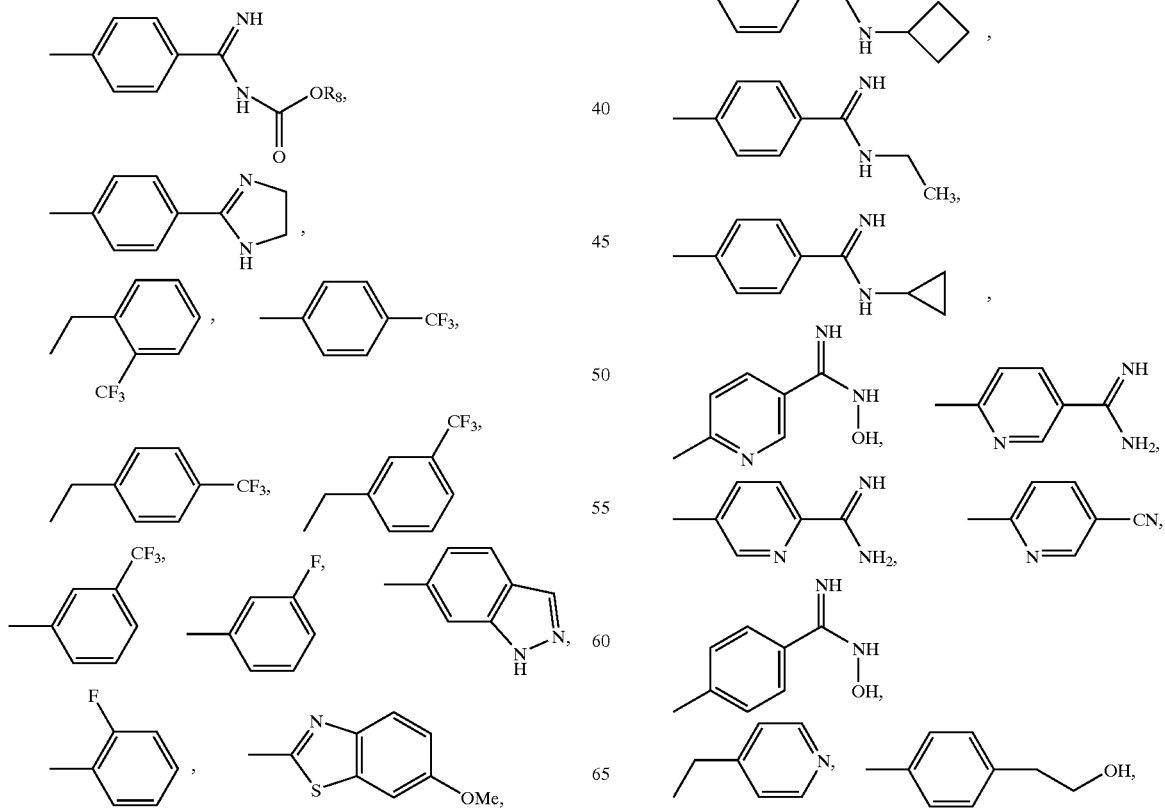

-continued

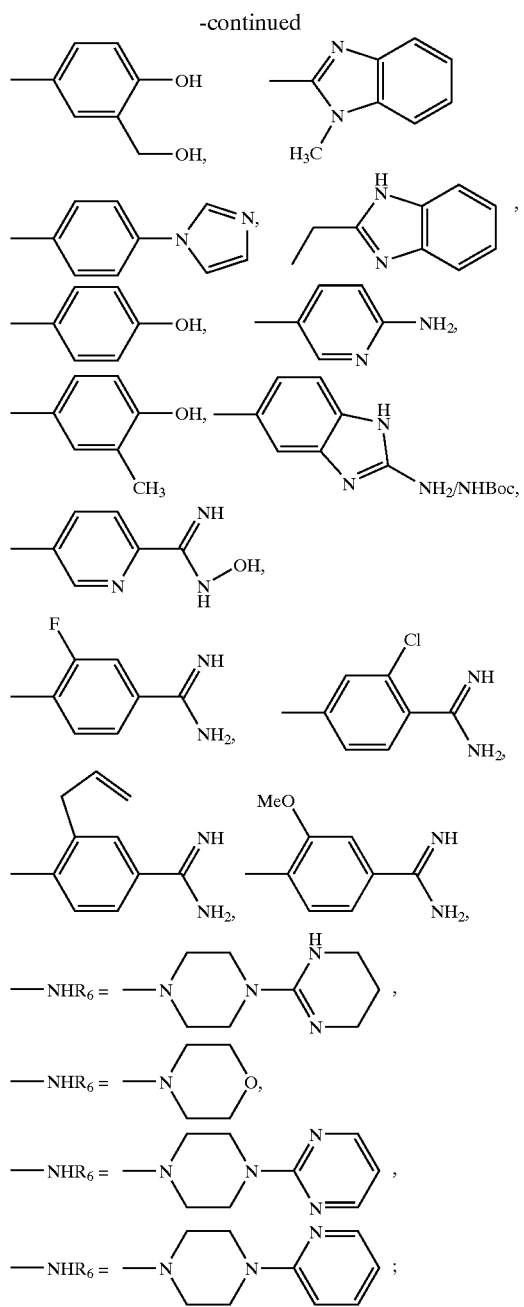

$R_7$ is selected from the group consisting of H, $CH_3$, —$(CH_2)_n$—$CO_2H$, —$(CH_2)_n$—$CO_2$-alkyl wherein n=0–3;

$R_8$ selected from the group consisting of —$CH_2$—$CCl_3$, —$CH_3$, $C_2H_5$, $CH_2C_6H_5$, $C(CH_3)_3$, -continued

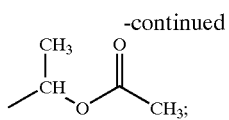

and X is N;
and pharmaceutically acceptable salts thereof; and prodrug thereof.

3. The compound of claim 1 represented by the structure:

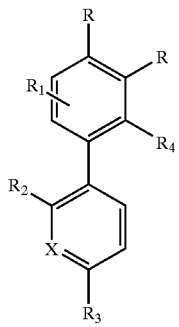

Wherein R is selected from the group consisting of

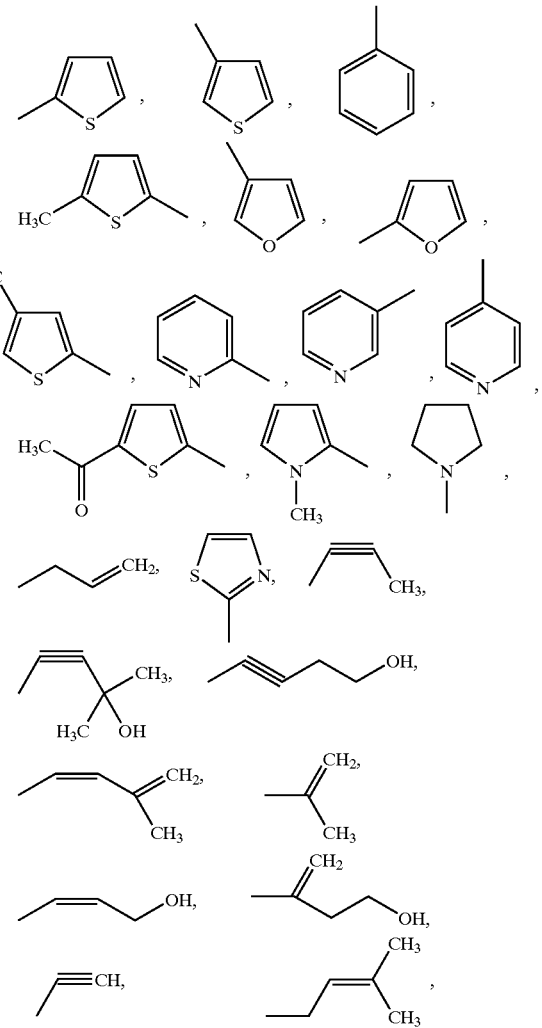

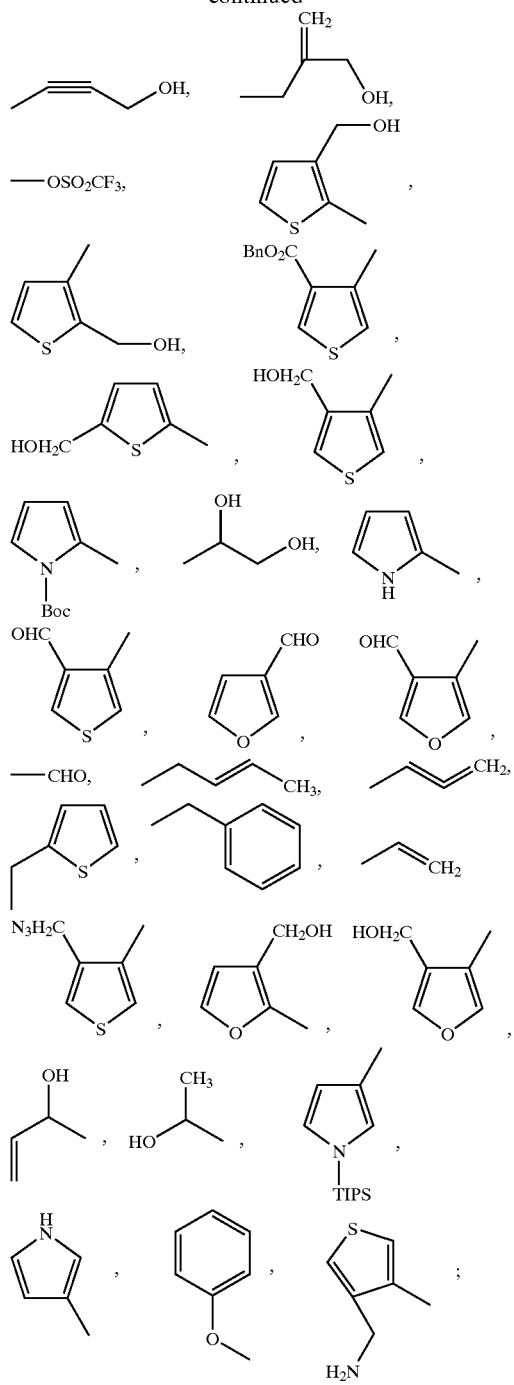

$R_1$ is selected from the group consisting of H, OH OCH$_3$, CHO, OSO$_2$CF$_3$, OCH$_2$—CH$_2$—OAc, O—CH$_2$—CH$_2$—OH, OCH$_2$CO$_2$C$_2$H$_5$, OCH$_2$CO$_2$H, CO$_2$H, CH$_2$OH, OCH(CH$_3$)$_2$, OC(O)(CH$_3$)$_3$, OCH$_2$CONH$_2$,

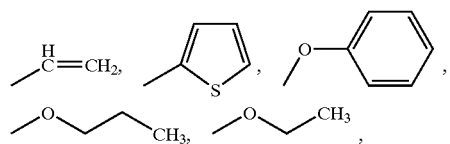

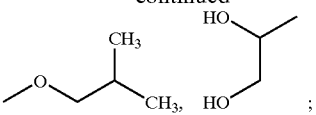

$R_2$ is selected from the group consisting of CO$_2$-alkyl, CO$_2$-aryl, CO$_2$-arylalkyl, CO$_2$H, CH$_2$CO$_2$-alkyl, CH$_2$OH, CONH$_2$;

$R_3$ is selected from the group consenting of H, C(O)—NH—R$_5$, CO$_2$MEM, CO$_2$H,

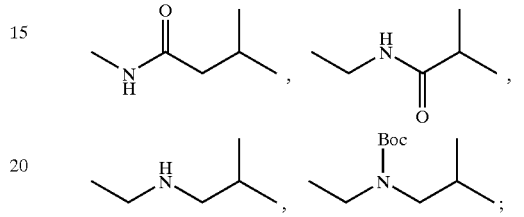

$R_4$ is selected from the group consisting of C(O)NH—R$_6$, —CH(R$_7$)—NH—R$_6$, CO$_2$H, CHO, CO$_2$MEM, —CH(R$_7$)—O—R$_6$, —CH$_2$—CH$_2$NH—R$_6$ $R_5$ is selected from the group consisting of

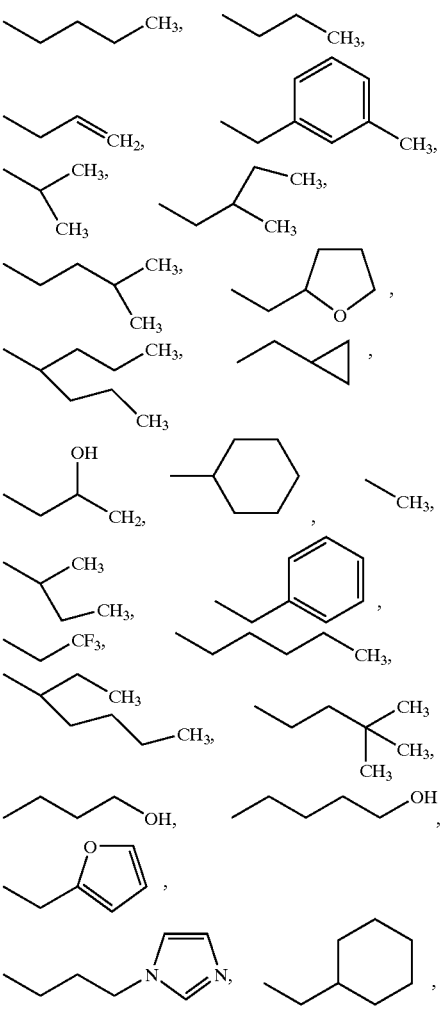

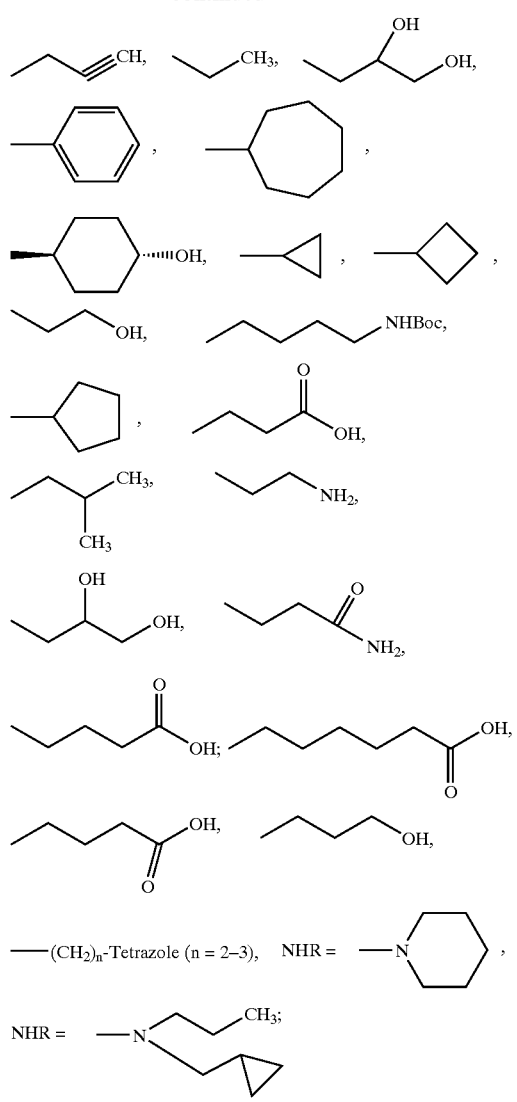
$R_6$ is selected from the group consisting of
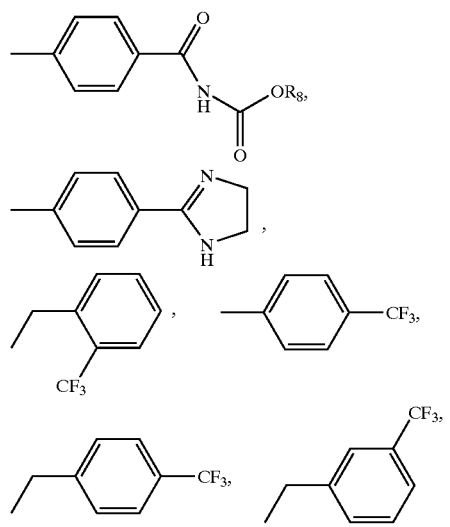
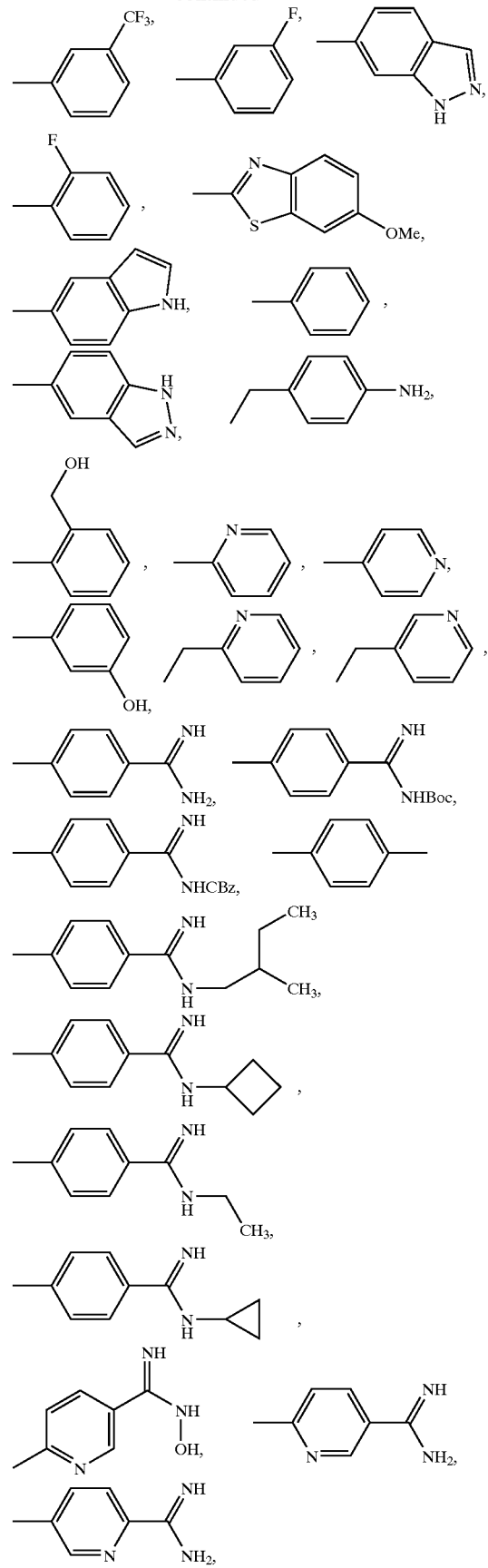

-continued
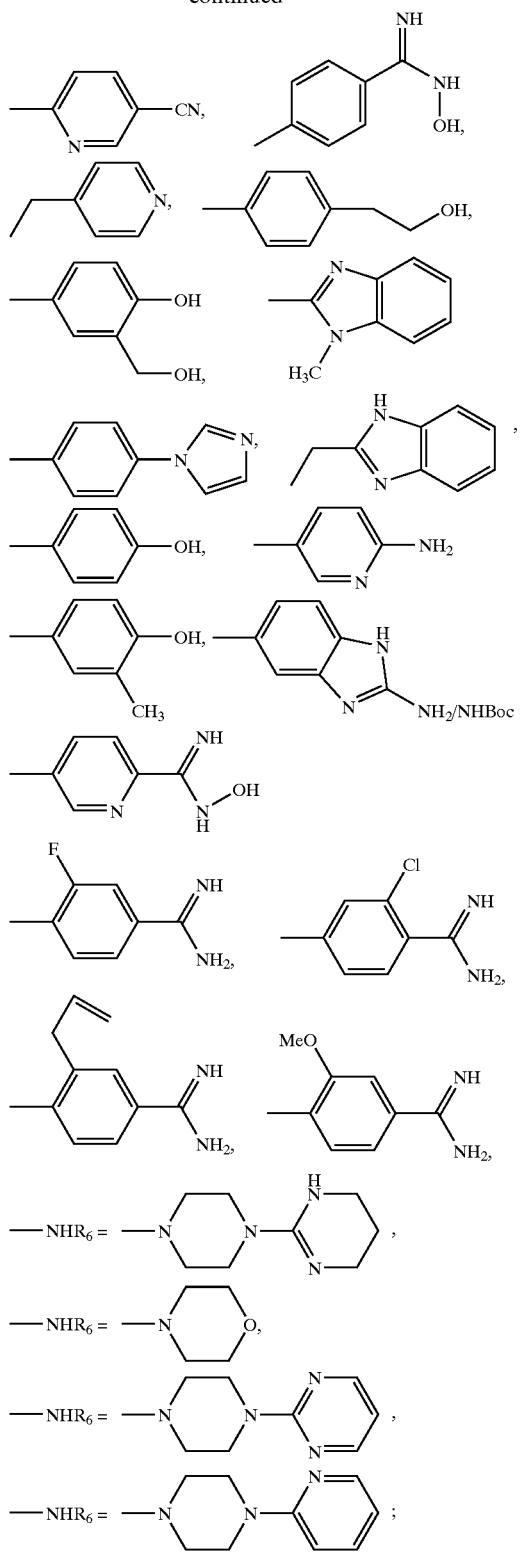
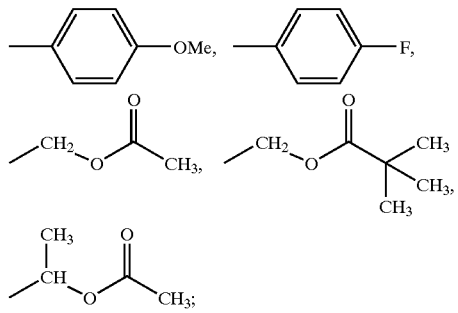
and X is N;
and pharmaceutically acceptable salts thereof; and prodrug thereof.
4. The compound of claim 1 represented by the structure:
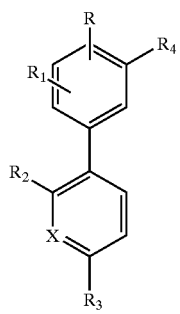
Wherein R is selected from the group consisting of
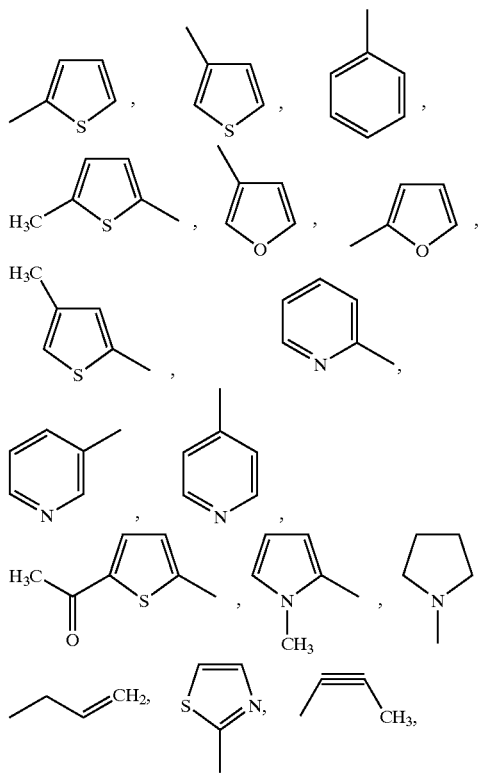
$R_7$ is selected from the group consisting of H, $CH_3$, —$(CH_2)_n$—$CO_2H$, —$(CH_2)_n$—$CO_2$-alkyl wherein n=0–3;
$R_8$ is selected from the group consisting of —$CH_2$—$CCl_3$, —$CH_3$, $C_2H_5$, $CH_2C_6H_5$, $C(CH_3)_3$,

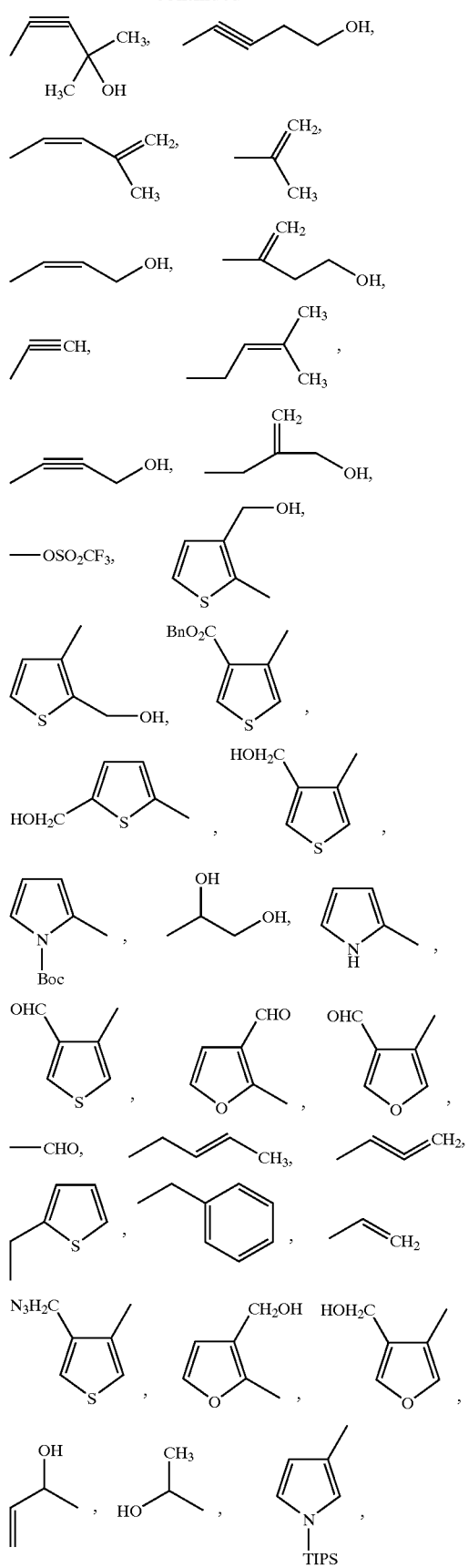

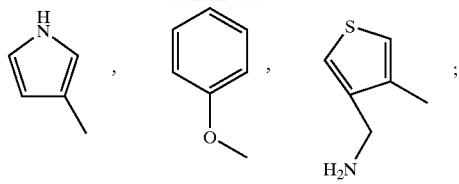

$R_1$ is selected from the group consisting of H, OH, $OCH_3$, CHO, $OSO_2CF_3$, $OCH_2$—$CH_2$—OAc, O—$CH_2$—$CH_2$—OH, $OCH_2CO_2C_2H_5$, $OCH_2CO_2H$, $CO_2H$, $CH_2OH$, $OCH(CH_3)_2$, $OC(O)(CH_3)_3$, $OCH_2CONH_2$,

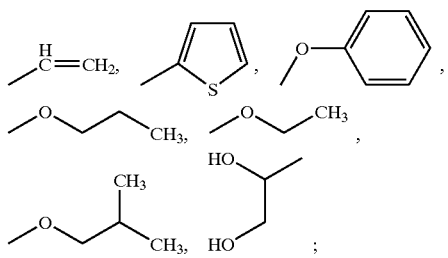

$R_2$ is selected from the group consisting of $CO_2$-alkyl, $CO_2$-aryl, $CO_2$-arylalkyl, $CO_2H$, $CH_2CO_2$-alkyl, $CH_2OH$, $CONH_2$;

$R_3$ is selected from the group consenting of H, C(O)—NH—$R_5$, $CO_2MEM$, $CO_2H$,

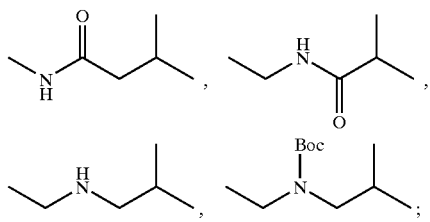

$R_4$ is selected from the group consisting of C(O)NH—$R_6$, —CH($R_7$)—NH—$R_6$, $CO_2H$, CHO, $CO_2MEM$, —CH($R_7$)—O—$R_6$, —$CH_2$—$CH_2$—NH—$R_6$ $R_5$ is selected from the group consisting of

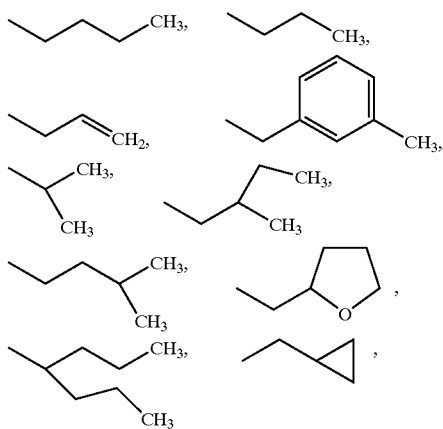

335
-continued
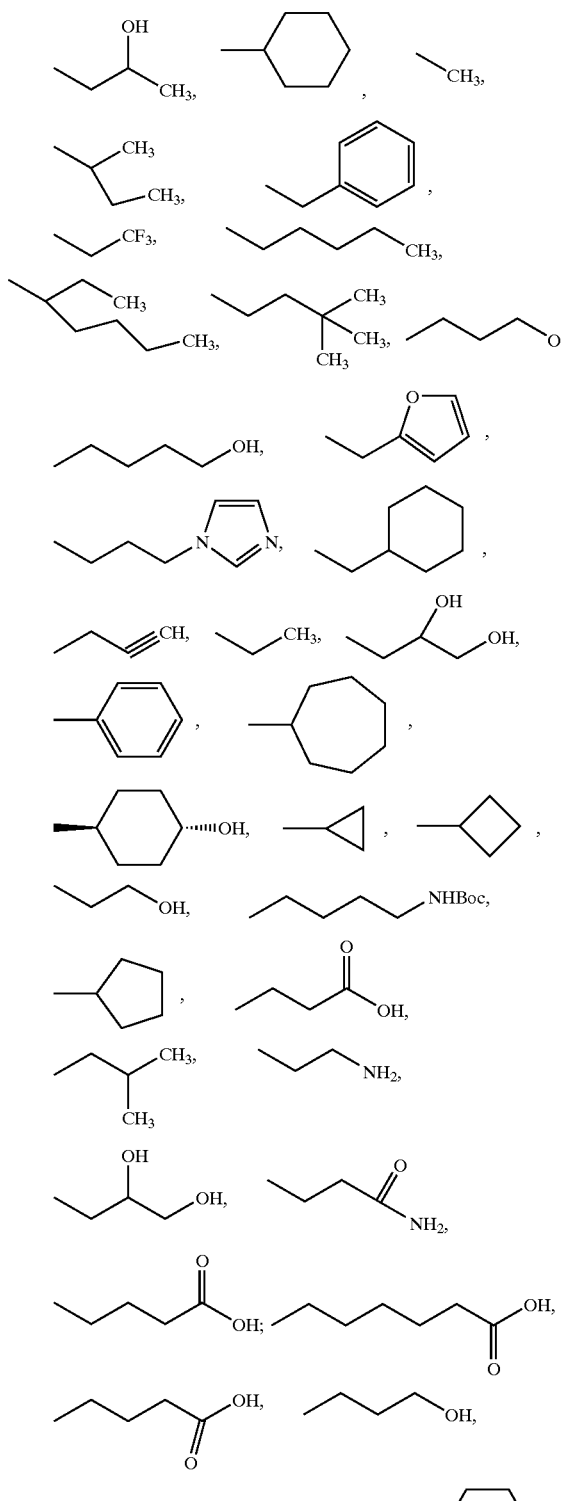
—(CH$_2$)$_n$-Tetrazole (n = 2–3), NHR = 
NHR = 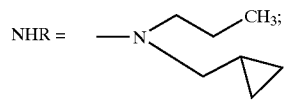
336
R$_6$ is selected from the group consisting of
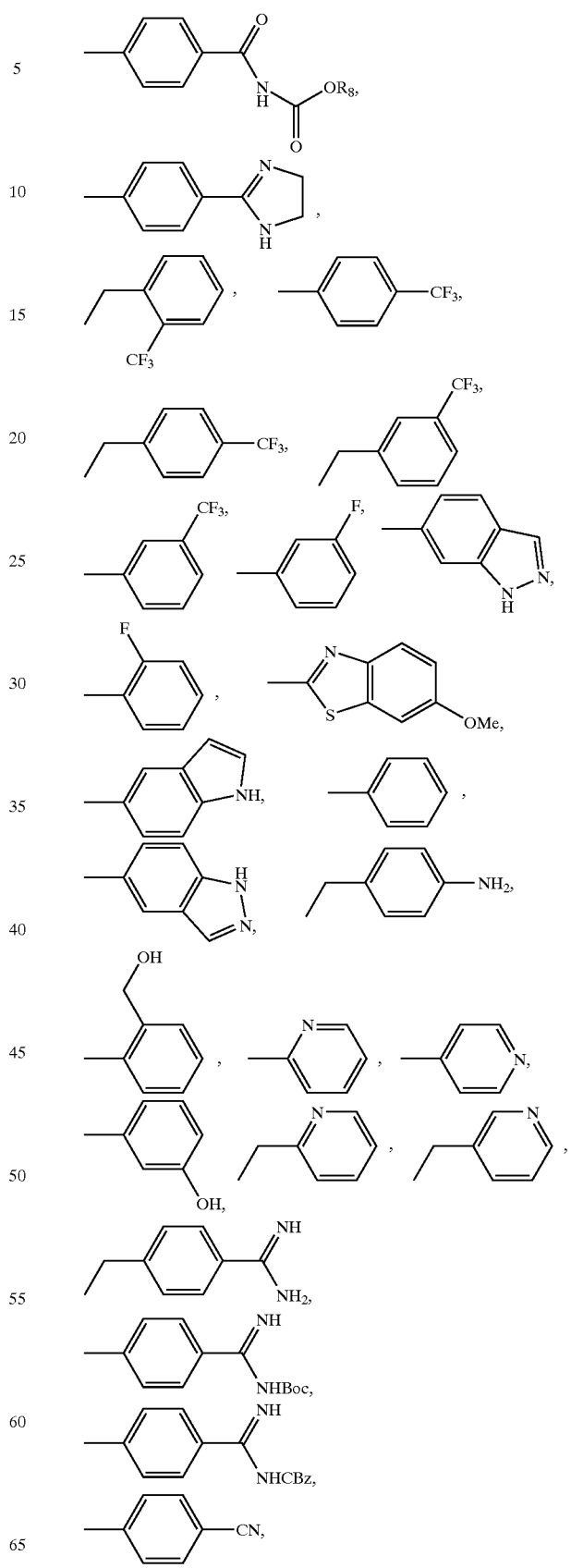

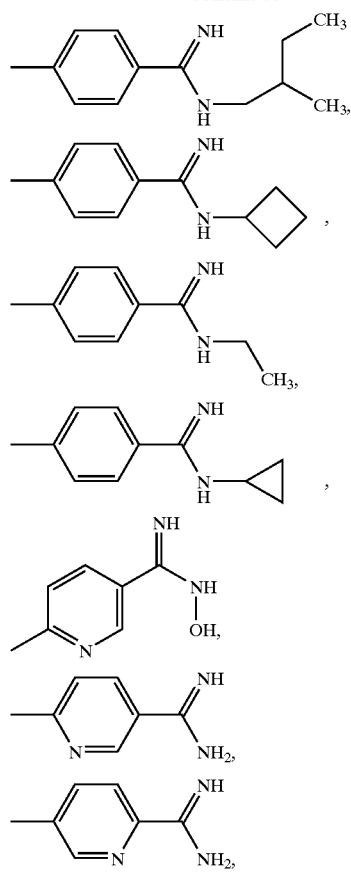

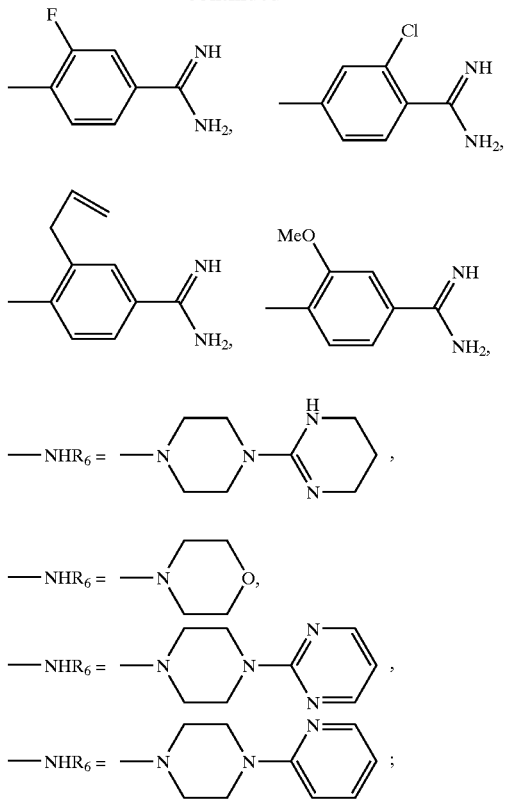

$R_7$ is selected from the group consisting of H, $CH_3$, $-(CH_2)_n-CO_2H$, $-(CH_2)_n-CO_2$-alkyl wherein n=0–3;

$R_8$ is selected from the group consisting of $-CH_2-CCl_3$, $-CH_3$, $C_2H_5$, $CH_2C_6H_5$, $C(CH_3)_3$,

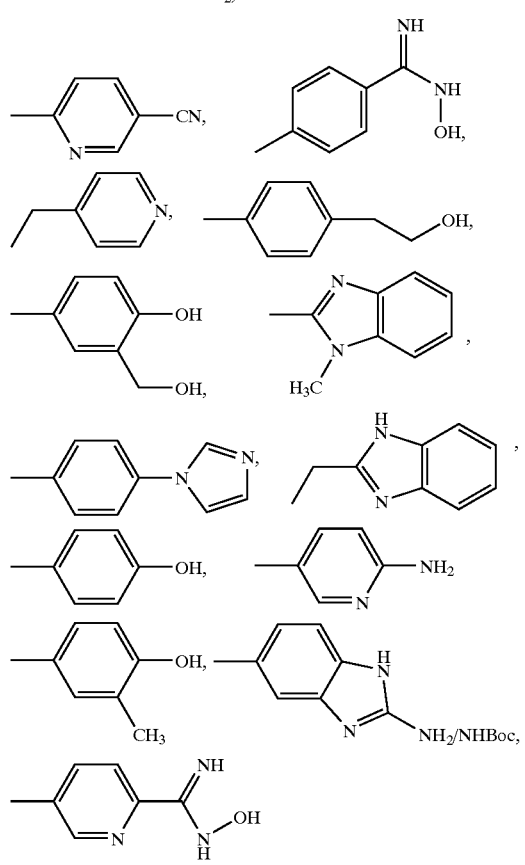

and X is N;

and pharmaceutically acceptable salts thereof; and prodrug thereof.

5. A pharmaceutical composition containing at least one compound according to claim 1.

6. A method for inhibiting the coagulation cascade and preventing or limiting coagulation by administering to a patient an effective amount of at least one compound according to claim 1.

7. A method for inhibiting the formation of emboli or thromboli in blood vessels by administering to a patient an effective amount of at least one compound according to claim 1.

8. A method for treating at least one condition selected from the group consisting of thrombolymphangitis thrombosinusitis, thromboendocarditis, thromboangitis, unstable angina, and thromboarteritis which comprises administering to a patient an effective amount of at least one compound according to claim 1.

9. A method for inhibiting thrombus formation following angioplasty which comprises administering to a patient an effective amount of at least one compound according to claim 1.

10. A method for preventing arteria occlusion following thrombolytic therapy which comprises administering to a patient an effective amount of at least one compound according to claim 1 and an effective amount of at least another antithrombolytic agent.

11. The method of claim 10 wherein said other antithrombolytic agent is selected from the group consisting of tissue plasminogen activators, streptokinase and urokinase, and functional derivatives thereof.

12. A method of claim 6 which further comprises administering a further anticoagulant agent to said patient.

13. The method of claim 12 wherein said further anticoagulant agent is selected from the group consisting of heparin, aspirin, and warfarin.

14. A method for treating a patient in need of an anti-inflammatory agent which comprises administering to said patient an effective amount of at least one of the compounds according to claim 1.

15. A method for inhibiting in vitro clotting of blood which comprises contacting said blood with at least one compound according to claim 1.

16. The method of claim 15 which comprises inhibiting said blood in tubes.

17. The compound of claim 1 represented by the structure;

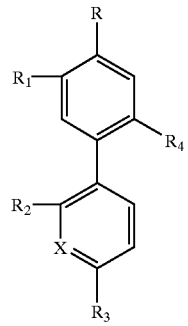

wherein R=CH=CH$_2$; R$_1$=H; R$_2$=CO$_2$H; R$_3$=C(O)NHCH$_2$ CH(CH$_3$)$_2$; X=N and R$_4$=

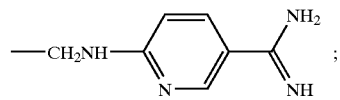

pharmaceutically acceptable salts thereof and prodrugs thereof.

18. The compound of claim 3 wherein R=CH=CH$_2$; R$_1$=OCH$_3$; R$_2$=CO$_2$H; R$_3$=C(O)NHR$_5$; R$_5$=CH$_2$Cyclopropyl; R$_4$=C(O)NHR$_6$ and

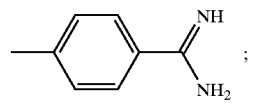

pharmaceutically acceptable salts thereof and prodrugs thereof.

* * * * *

UNITED STATES PATENT AND TRADEMARK OFFICE
CERTIFICATE OF CORRECTION

PATENT NO. : 6,936,719 B2
APPLICATION NO. : 10/738027
DATED : August 30, 2005
INVENTOR(S) : Yarlagadda S. Babu et al.

Page 1 of 4

It is certified that error appears in the above-identified patent and that said Letters Patent is hereby corrected as shown below:

Columns 320-326:
Replace Claim 2 in its entirety with Claim 2 as filed by applicant (shown below):

2. The compound of claim 1 represented by the structure:

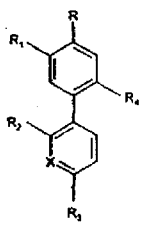

Wherein R is selected from the group consisting of

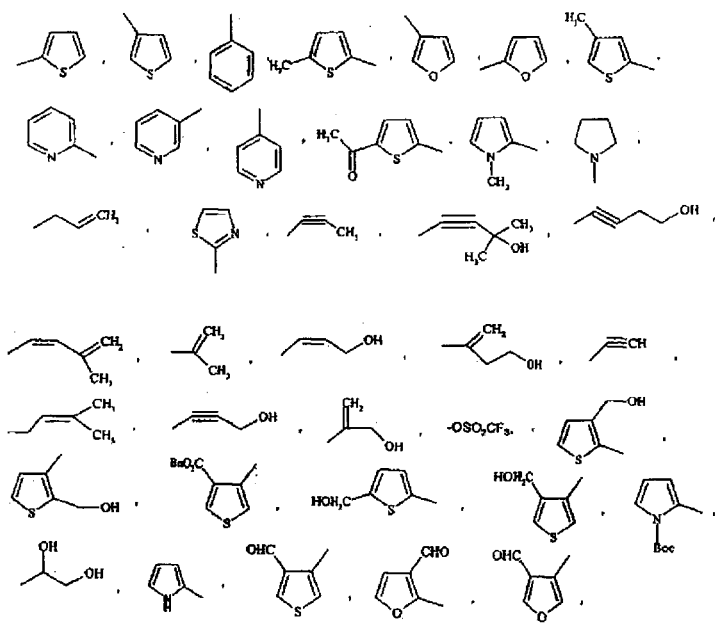

Signed and Sealed this
Twenty-second Day of January, 2013

David J. Kappos
*Director of the United States Patent and Trademark Office*

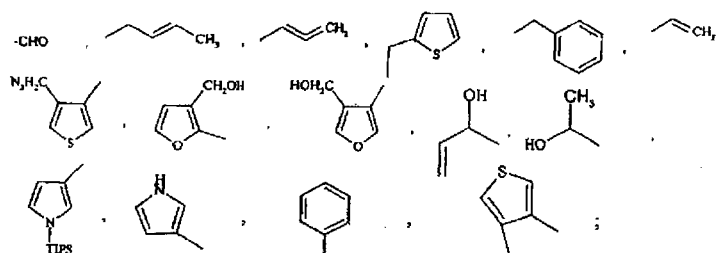

$R_1$ is selected from the group consisting of H, OH, $OCH_3$, CHO, $OSO_2CF_3$, $OCH_2$-$CH_2$-OAc, O-$CH_2$-$CH_2$-OH, $OCH_2CO_2C_2H_5$, $OCH_2CO_2H$, $CO_2H$, $CH_2OH$, $OCH(CH_3)_2$, $OC(O)(CH_3)_3$, $OCH_2CONH_2$,

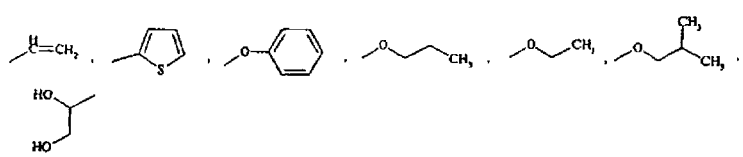

$R_2$ is selected from the group consisting of $CO_2$-alkyl, $CO_2$-aryl, $CO_2$-arylalkyl, $CO_2H$, $CH_2CO_2$-alkyl, $CH_2OH$, $CONH_2$;

$R_3$ is selected from the group consisting of H, C(O)-NH-$R_5$, $CO_2MEM$, $CO_2H$,

$R_4$ is selected from the group consisting of C(O)NH-$R_6$, -CH($R_7$)-NH-$R_6$, $CO_2H$, CHO, $CO_2MEM$, -CH($R_7$)-O-$R_6$, -$CH_2$-$CH_2$-NH-$R_6$ $R_5$ is selected from the group consisting of

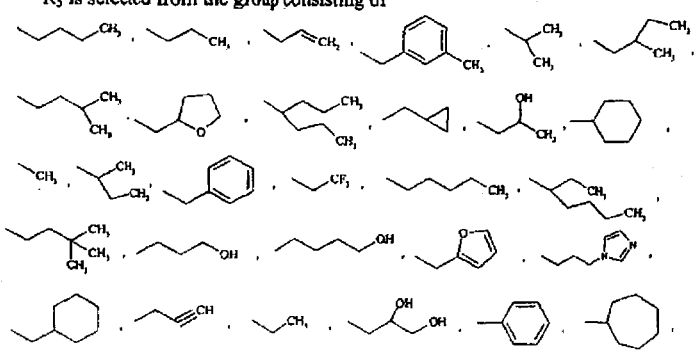

CERTIFICATE OF CORRECTION (continued)
U.S. Pat. No. 6,936,719 B2

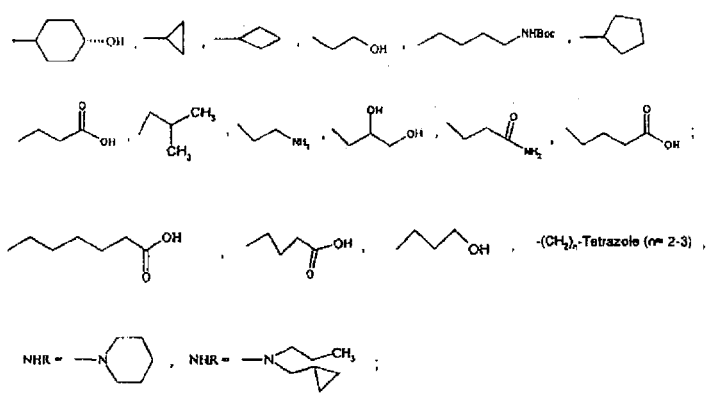

R₆ is selected from the group consisting of

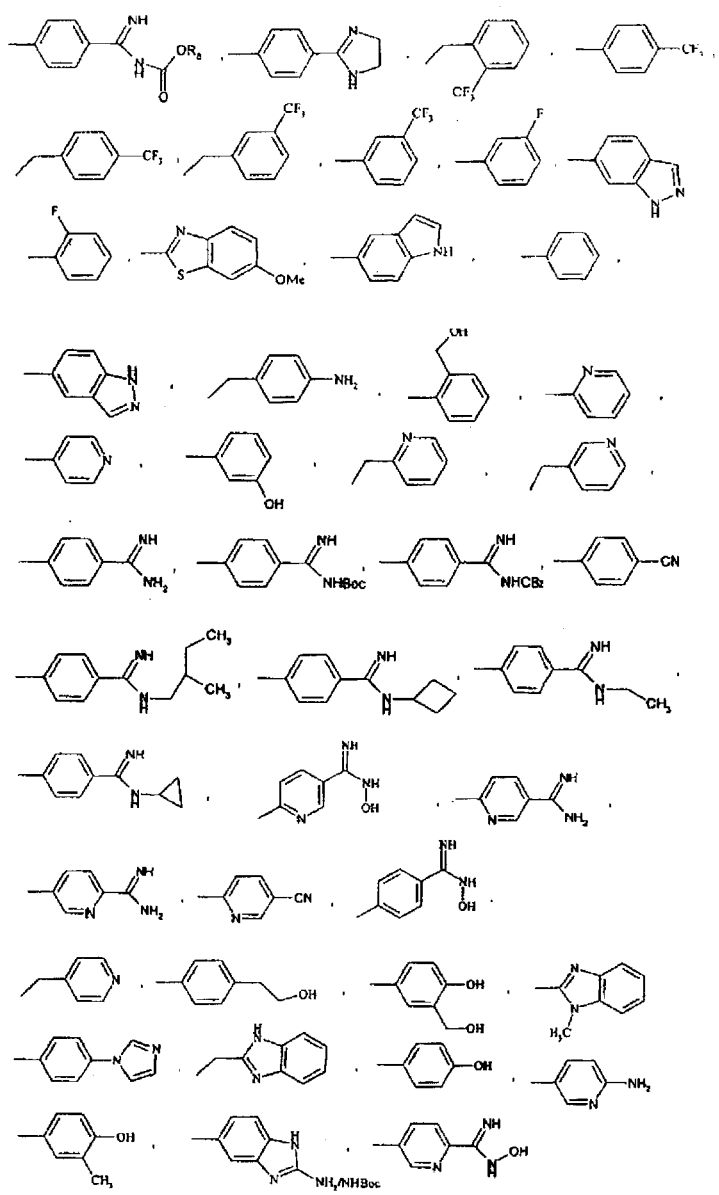

CERTIFICATE OF CORRECTION (continued)
U.S. Pat. No. 6,936,719 B2

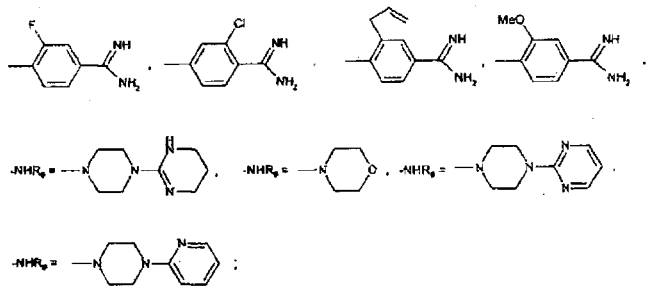

R$_7$ is selected from the group consisting of H, CH$_3$, -(CH$_2$)$_n$-CO$_2$H, -(CH$_2$)$_n$-CO$_2$-alkyl wherein n = 0-3;

R$_8$ is selected from the group consisting of -CH$_2$-CCl$_3$, -CH$_3$, C$_2$H$_5$, CH$_2$C$_6$H$_5$, C(CH$_3$)$_3$,

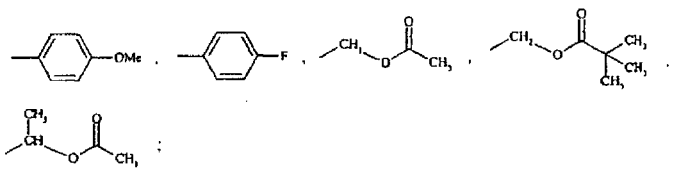

and X is N; and pharmaceutically acceptable salts thereof; and prodrugs thereof.

Column 340:
Replace Claim 18 in its entirety with Claim 18 as filed by applicant (shown below):

18. The compound of claim 2 wherein R= CH=CH$_2$; R$_1$ =OCH$_3$; R$_2$ =CO$_2$H; R$_3$ = C(O)NHR$_5$; R$_5$ =CH$_2$Cyclopropyl; R$_4$ = C(O)NHR$_6$ and R$_6$ = 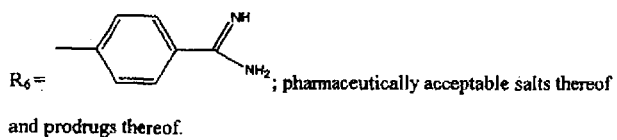 ; pharmaceutically acceptable salts thereof and prodrugs thereof.